United States Patent
TenBrink et al.

[19]

[11] Patent Number: 5,877,317

[45] Date of Patent: Mar. 2, 1999

[54] HETEROCYCLIC COMPOUNDS FOR THE TREATMENT OF CNS AND CARDIOVASCULAR DISORDERS

[75] Inventors: Ruth E. TenBrink, Richland; Michael D. Ennis, Portage, both of Mich.; Robert A. Lahti, Columbia, Md.

[73] Assignee: Pharmacia & Upjohn Company, Kalamazoo, Mich.

[21] Appl. No.: 663,094

[22] PCT Filed: Nov. 30, 1994

[86] PCT No.: PCT/US94/13284

§ 371 Date: Jul. 24, 1996

§ 102(e) Date: Jul. 24, 1996

[87] PCT Pub. No.: WO95/18118

PCT Pub. Date: Jul. 6, 1995

Related U.S. Application Data

[63] Continuation of Ser. No. 279,974, Jul. 25, 1994, abandoned, which is a continuation-in-part of Ser. No. 175,218, Dec. 28, 1993, abandoned.

[51] Int. Cl.[6] .................. A61K 31/495; C07D 405/06; C07D 405/14; C07F 7/10
[52] U.S. Cl. .................. 544/295; 544/229; 544/375; 544/376; 544/364; 540/575; 546/148; 546/196; 546/202; 546/282.7; 546/283.1; 435/140; 514/218; 514/253; 514/320; 514/324; 514/319; 514/337; 514/345; 514/352
[58] Field of Search .................. 514/253; 544/376; 544/375, 229, 295, 364

[56] References Cited

U.S. PATENT DOCUMENTS

| | | | |
|---|---|---|---|
| 3,467,675 | 9/1969 | Petersen et al. | 544/146 |
| 3,549,656 | 12/1970 | Petersen et al. | 544/146 |
| 4,066,648 | 1/1978 | Oka et al. | 544/402 |
| 4,130,646 | 12/1978 | Vogt et al. | 424/250 |
| 4,179,510 | 12/1979 | McCall | 514/253 |
| 4,556,656 | 12/1985 | McCall | 514/227 |
| 4,994,486 | 2/1991 | Schoenleber et al. | 514/456 |
| 5,032,598 | 7/1991 | Baldwin et al. | 514/318 |
| 5,120,843 | 6/1992 | McCall et al. | 544/123 |
| 5,137,911 | 8/1992 | Cebazat et al. | 514/452 |
| 5,140,040 | 8/1992 | DeBernardis et al. | 514/422 |
| 5,215,989 | 6/1993 | Baldwin et al. | 514/252 |

FOREIGN PATENT DOCUMENTS

| | | |
|---|---|---|
| 9180251 | 9/1991 | Australia . |
| 300908 | 1/1989 | European Pat. Off. . |
| 404197 | 12/1990 | European Pat. Off. . |
| 9015056 | 12/1990 | European Pat. Off. . |
| 458387 | 11/1991 | European Pat. Off. . |
| 1552004 | 9/1979 | United Kingdom .......... C07D 311/76 |
| 8808424 | 11/1988 | WIPO . |
| 9218089 | 10/1992 | WIPO . |
| 93/16057 | 8/1993 | WIPO . |
| 94/00441 | 1/1994 | WIPO . |

OTHER PUBLICATIONS

Abstract for NL 8001981 (Oct. 7, 1980), Upjohn Co.
Abstract for JP61–083180 (Apr. 26, 1986), Morishita Pharm.
Abstract for JP51–125287 (Nov. 1, 1976), Takeda Chemical.
Abstract for JP57–159713 (Oct. 1, 1982), Yamato.
Abstract for DE 3409612 (Sep. 19, 1985), Boehringer Ingelheim.
Abstract for EP 494817 (Jul. 15, 1992), Adir & Cie.
Abstract for EP 428437 (May 22, 1991), Adir & Cie.
Abstract for EP 490772 (Jun. 17, 1992), Adir & Cie.
Abstract for EP457686 (Nov. 21, 1991), Adir & Cie.
Perrone et al. J. Med. Chem., 37, 99–104 (1994).
Ratsner et al Collection Czechoslov. Chem. Commun., 43, 1760–77 (1978).
Pol. J. Pharmacol. Pharm., 36(6), 697–703 (1984), Mistal et al.
J. Med. Chem., 25(1), 75–81 (1982)., McCall et al.

*Primary Examiner*—Emily Bernhardt
*Attorney, Agent, or Firm*—Bruce Stein

[57] ABSTRACT

Novel aromatic bicyclic amines of formula (I)

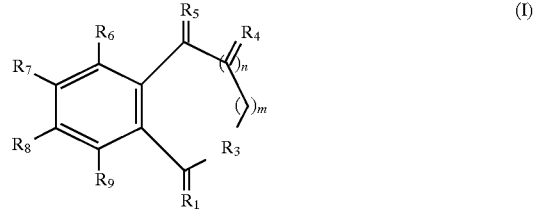

are useful in treating central nervous system disorders and cardiac arrhythmias and cardiac fibrillation.

22 Claims, No Drawings

HETEROCYCLIC COMPOUNDS FOR THE TREATMENT OF CNS AND CARDIOVASCULAR DISORDERS

This application is the continuation (national phase) of International Application No. PCT/US94/13284, International Filing Date 30 Nov. 1994, which was a continuation of U.S. patent application Ser. No. 08/279,974, filed 25 Jul. 1994, abandoned which was a continuation-in-part of U.S. patent application Ser. No. 08/175,218, filed 28 Dec. 1993, abandoned.

BACKGROUND OF THE INVENTION

1. Field of the Invention

The invention relates to Isochroman-alkyl-piperazinyl-aryl compounds useful as anti-psychotic agents.

2. Description of the Related Art

Chromans (also known as 1-benzopyrans, where the oxygen atom is attached to the aromatic ring) and isochromans (also known as 2-benzopyrans, where the oxygen atom is not attached to the aromatic ring) are known in the art, as are aryl-piperazines (or aminopiperidines). Chromans and aryl piperazines linked together with an alkyl chain are also known. European Patent 300,908 discloses (1-benzopyran)]-alkyl-(piperazinyl or aminopiperidine)-aryls useful as anti-arrythmics and anti-fibrillatory agents. The compounds of this invention require -alkyl-piperazinyl (or aminopiperidinyl)-aryl at carbon 1 of an 2- benzopyran ring which are useful for CNS and cardiovascular disorders.

Various isochromans, thioisochromans, benzoxepines, and benzothiepines with hydroxy, alkoxy, or o-methylenedioxy substitution on their aromatic rings, and linked to aryl piperazines(piperidines) by alkyl chains are known. These compounds are disclosed as being useful as antipsychotics and hypotensives. The compounds of this invention do not permit oxygen substitution on the aromatic ring of the isochroman, thioisochroman, benzoxepin, or benzothiepin ring system for their usefulness in CNS and cardiovascular disorders.

Another group of isochromans, thioisochromans, benzoxepines and benzothiepines with hydroxy, alkoxy, or o-methylenedioxy functionality attached to their aromatic rings, and linked to aryl piperazines(piperidines) by alkyl chains are known, useful as antipsychotics and hypotensives. The compounds of this invention do not permit oxygen substitution on the aromatic ring of the isochroman, thioisochroman, benzoxepin, or benzothiepin ring system for their usefulness in CNS and cardiovascular disorders.

U.S. Pat. No. 4,179,510 and the many divisionals thereof discloses isochromanalkyl-piperazinyl (or aminopiperidinyl)-aryls requiring oxygen as a substituent on the isochroman aromatic ring. These compounds are disclosed as being useful as hypotensive and antipsychotic agents.

Also disclosed are isochroman-, isothiochroman-, 2-benzoxepin-, and -2-benzothiepin-alkyloxyethanols as being useful for preparing the above compounds. More specifically 7,8-dimethoxybenzoxepines are disclosed as are 1-[(6,7-dimethoxyisochroman)alkyl]-4-(aryl)piperazines. Further disclosed are 2-benzoxepine-alkyl-piperazine (aminopiperidine)-aryls, 2-benzothiepins and 2-benzoxepines all requiring an oxygen atom as a substituent on the aromatic ring and useful for the same purposes.

Dutch Patent 8,001,981 discloses 1-(2-chlorophenyl)-4-[2-(1,3,4,5-tetrahydro-7,8-dimethoxy-2-benzoxepin-1-yl)ethyl]piperazine useful as an antipsychotic agent.

International Patent Publication WO 9218089 discloses isochroman-alkyl-piperazinyl (aminopiperidinyl)-aryls, with the requirement that oxygen be present on the aromatic ring of the isochroman which are useful in sensitizing cells against multi-drug resistance.

International Patent Publication WO 8808424 discloses isochromans-alkyl-piperazinyl (or aminopiperidinyl)-aryls, with the requirement that oxygen be present on the aromatic ring of the isochroman, useful in the treatment of head injury, spinal trauma, and stroke.

International Patent Publication WO 9015056 and U.S. Pat. No. 5,140,040 disclose isochromans, tetralins, and dihydroanaphthalenes substituted with various alkyl amines for the treatment of glaucoma, depression, hypertension, congestive heart failure and vascular spastic conditions.

U.S. Pat. No. 4,994,486 discloses isochroman-alkyl-amines for treating psychoses, Parkinson's disease, and addictive behavior.

Japanese Patent 61083180 discloses isochroman-alkyl-(alkyl)amines as antiulcer agents.

European Patent 404,197 discloses isochroman-alkyl-piperazine-alkyl-keto (alcohol)-aryls with bronchodilator and antiallergy activity.

Japanese Patent 51125287 (J 52083846) discloses isochroman-alkyl-amines(piperazine) with antidepressive, analgesic, diuretic, antiinflammatory, and anti-asthma activity.

German Patent DE 2,624,693 and Great Britain Patent GB 1552004 discloses isochroman-alkyl-amines including aryl piperazines as analgesics, hypotensives, antidepressants, diuretics, antiinflammatories, muscle relaxants, and vasodilators. The compounds differ from the compounds of this invention in that oxygen substitution is required on the isochroman aromatic ring.

Japanese Patent 57159713 discloses isochroman- and tetralin-(no alkyl spacer)-piperazine-aryls as antiallergics. The compounds of this invention require at least one carbon as a linker.

U.S. Pat. Nos. 3,549,656 and 3,467,675 and Belgium Patent 678,035 disclose phthalan-, isochroman-, and isochromen-alkylene-amines for the treatment of depression.

European Patent 458,387 and U.S. Pat. No. 5,137,911 disclose isochroman-alkylene-piperazine-alkylene-aryls useful as blood platelet aggregation inhibitors, as intracellular calcium antagonists, and for treating cardiac dysrhythmias, angina pectoris, stroke, and myocardial infarction.

German Patent DE 3,409,612 discloses dimethoxyisochroman- and benzoxepine-alkyl-aminoalkyls for prophylaxis of coronary heart disease or hypertension.

Japanese Patent 6 1083180 discloses isochroman-alkyl-amines useful for treating ulcers. European Patent 457,686 discloses phthalan and indane alkyl aminopiperidinyl ureas or carbamates for the treatment of stress, pain, and schizophrenia.

Similar compounds include the indanes, indenes, tetralins, dihydronaphthalenes, benzocycloheptanes, benzocycloheptenes. European Patent 494,817 discloses indane-, tetralin-, and benzocycloheptane-alkyl-piperazine-benzisoxazoles and -benzothiazoles as dopamine and serotonin antagonists for the treatment of pain, depression, anxiety, psychosis, and schizophrenia. European Patent 428,437 discloses indane-alkyl-piperidine-benzisoxazoles for the treatment of schizophrenia and depression. European Patent 490,772 discloses tetralin(dihydronaphthalene)-alkyl-piperazine-aryls for the treatment of anxiety, depression, migraine, stress, and diabetes. The aryl group attached to piperazine must have an oxygen-containing ring fused to the benzene ring. U.S. Pat. No. 4,130,646 discloses tetralin-, dihydronaphthalene-, indane-, indene- substituted at the 2-position with -methylene-piperazine-aryl, as tranquillizers with sedative, muscle relaxant, and neuroleptic activity. AU 9180251 discloses tetralin- and dihydronapthalen-alkyl (or alkene)- piperidine(or pyrrolidine, tetrahydropyridine)-alkyl (alkylphenyl) useful for treating stress, hypertension, migraine, anxiety, depression, schizophrenia, and pain. *Pol. J. Pharmacol. Pharm.*, 36(6), 697–703 (1984) discloses indane-alkyl-piperazine-phenyl where phenyl is optionally meta-substituted with chlorine, having serotoninolytic properties.

*J. Med. Chem.*, 25(1), 75–81 (1982) discloses 6,7-dimethoxyisochroman-alkyl-piperazinyl-aryl type compounds which have hypotensive activity.

U.S. Pat. Nos. 5,032,598 and 5,215,989 generically encompass the isochromans and tetralins of the present invention if the variable substituents are appropriately chosen.

International Publication No. WO 88/08424 and U.S. Pat. No. 5,120,843 disclose a dialkoxyisochroman containing a substituted pyridinylpiperazinylethyl side chain. However, the compounds of the present invention do not permit alkoxy substitution. TO AVOID U-79,129

International Publication No. WO 94/00441 discloses tetralins containing a substituted aryl or heteroarylpiperazinyl side chain with an alkyl linker where the alkyl linker contains three or four carbon atoms, having serotoninergic, dopaminergic and adrenergic activity. The compounds of the present invention have less than three carbon atoms in the alkyl linking group. Further, there is no disclosure of any type of isochroman type compounds.

*J. Med. Chem.*, 37, 99–104 (1994) discloses dihydronaphthalene-propyl-aryl piperazines with mixed serotonergic and dopaminergic activity. The compounds of the present invention have a two carbon linker.

*Collection Czechoslov. Chem. Commun.*, 43, 1760–77 (1978) discloses tetralins which have a piperazinyl group attached directly to the tetralin moiety whereas the claimed compounds do not permit the piperazinyl group to be directly attached to the tetralin.

International Patent Publication No. WO 93/16057 discloses tetralins in which the piperazinyl substituent is attached directly to the tetralin which is not permitted in the claimed invention. This document discloses chromans but not isochromans.

U.S. Pat. No. 3,146,235 discloses a ketone on the tetralin portion of the molecule; the claimed compounds do not have this substitution. In addition, U.S. Pat. No. 3,146,235 discloses a 1-carbon linker between the tetralin and the nitrogen of the piperazine portion of the molecule; the claimed compounds disclose a 2-carbon linker.

Czechosolvican Patant 193,303 discloses compounds with no carbon linker between the tetralin and the nitrogen of the piperazine portion of the molecules, whereas the claimed compounds have a two carbon linker. The compounds of Czech. 193,303 are useful as antimicrobials, the claimed compounds are useful for CNS (schizophrenia, etc.) and cardiovascular diseases (fibrillation and arrhythmias).

Great Britain patent 1,434,854 discloses monocyclic heterocyclics containing sulfur (specifically thiophene) attached by a carbon linker of one to four carbons to one nitrogen of a piperazine ring; the second nitrogen of the piperazine ring is attached by a carbon linker of one to four carbons to an aryl group. The present invention discloses only bicyclic heterocyclics (with or without sulfur), linked to the first nitrogen of a piperazine ring by a two carbon linker and a direct attachment (no carbon linker) between the second nitrogen of the piperazine ring and an aryl group.

It has long been known that strong bases can induce racemization at chiral centers adjacent ($\alpha$-position) to carbonyl compounds by deprotonation followed by protonation, the chiral center racemized in LVI is not adjacent to the carbonyl, but rather it is the $\beta$-position.

SUMMARY OF INVENTION

Disclosed are aromatic bicyclic amines of formula (I)

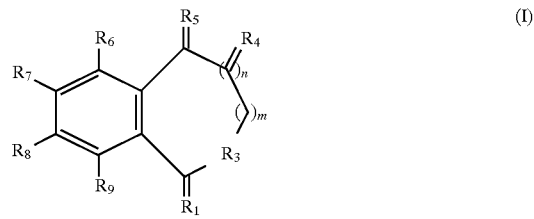

where m is 0 or 1;
where n is 0 or 1;
where $R_1$ (1) is $\alpha$-$R_{1-1}$:$\beta$-$R_{1-2}$ where one of $R_{1-1}$ or $R_{1-2}$ is —H or $C_1$–$C_6$ alkyl and the other of $R_{1-1}$ or $R_{1-2}$ is —$CR_{10-1}R_{10-2}$—$CR_{11}$—$R_2$—Ar/Het
where $R_{10-1}$ and $R_{10-2}$ are the same or different and are —H or $C_{1-C6}$ alkyl,
where $R_{11}$ is =O or $R_{11-1}$:$R_{11-2}$ where $R_{11-1}$ and $R_{11-2}$ are the same or different and are —H or $C_{1-C6}$ alkyl;
where $R_2$ is selected from the group consisting of

where $R_{2-1}$ and $R_{2-2}$ are —H or $C_1$–$C_6$ alkyl,
where $R_{2-3}$ is nitrogen (N—) or methine (HC—),
where q is 1 or 2,

where $R_{2-4}$ is:
—H,
$C_1$–$C_6$ alkyl,
$C_3$–$C_7$ cycloalkyl,
—$C_1$–$C_3$ alkyl-[$C_3$–$C_7$ cycloalkyl],
where s is 0, 1 or 2,

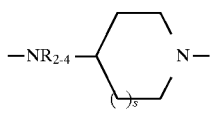

where $R_{2-4}$ and s are as defined above;

where $R_3$ is —O— or —S—;

where $R_4$ is $\alpha$-$R_{4-1}$:$\beta$-$R_{4-2}$ where one of $R_{4-1}$ and $R_{4-2}$ is:
—H,
$C_1$–$C_6$ alkyl and where the other of $R_{4-1}$ or $R_{4-2}$ is
—H,
$C_1$–$C_6$ alkyl,
—φ,
—OH,
—O—($C_1$–$C_3$)alkyl;

where $R_5$ is is $\alpha$-$R_{5-1}$:$\beta$-$R_{5-2}$ where one of $R_{5-1}$ and $R_{5-2}$ is:
—H,
$C_1$–$C_6$ alkyl, and where the other of $R_{5-1}$ or $R_{5-2}$ is
—H,
$C_1$–$C_6$ alkyl,
—φ,
—OH,
—O—($C_1$–$C_3$)alkyl;

and when n is 1, one of $R_{4-1}$ or $R_{4-2}$ and one of $R_{5-1}$ or $R_{5-2}$ can be taken together with the carbon atoms to which they are attached to form a carbon ring of 5-, 6- or 7-members;

where $R_6$ is —H
—F,
—Cl,
—Br,
—I,
—CO—$NR_{6-1}R_{6-2}$ where $R_{6-1}$ and $R_{6-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{6-1}R_{6-2}$ where $R_{6-1}$ and $R_{6-2}$ are as defined above,
—$CF_3$,
—φ optionally substituted with one or two
—F,
—Cl,
—Br,
—I,
—CO—$NR_{6-1}R_{6-2}$ where $R_{6-1}$ and $R_{6-2}$ are as defined above,
—$NR_{6-1}R_{6-2}$ where $R_{6-1}$ and $R_{6-2}$ are as defined above,
—$NO_2$,
—C≡N,
—N($R_{6-1}$)—CO—$R_{6-2}$ where $R_{6-1}$ and $R_{6-2}$ are as defined above,
—O—$SO_2$—$CF_3$,
$C_1$–$C_4$ alkyl,
—Si($CH_3$)$_3$, and where $R_6$ and one of $R_{5-1}$ or $R_{5-2}$ are taken together with the carbon atoms to which they are attached to form a carbon ring of 5-, 6- or 7-members;

where $R_7$ is —H
—F,
—Cl,
—Br,
—I,
—CO—$NR_{7-1}R_{7-2}$ where $R_{7-1}$ and $R_{7-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{7-1}R_{7-2}$ where $R_{7-1}$ and $R_{7-2}$ are as defined above,
—$CF_3$,
—φ optionally substituted with one or two
—F,
—Cl,
—Br,
—I,
—CO—$NR_{7-1}R_{7-2}$ where $R_{7-1}$ and $R_{7-2}$ are as defined above,
—$NR_{7-1}R_{7-2}$ where $R_{7-1}$ and $R_{7-2}$ are as defined above,
—$NO_2$,
—C≡N,
—N($R_{7-1}$)—CO—$R_{7-2}$ where $R_{7-1}$ and $R_{7-2}$ are as defined above,
—O—$SO_2$—$CF_3$,
$C_1$–$C_4$ alkyl,
—Si($CH_3$)$_3$;

where $R_8$ is —H
—F,
—Cl,
—Br,
—I,
—CO—$NR_{8-1}R_{8-2}$ where $R_{8-1}$ and $R_{8-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{8-1}R_{8-2}$ where $R_{8-1}$ and $R_{8-2}$ are as defined above,
—$CF_3$,
—φ optionally substituted with one or two
—F,
—Cl,
—Br,
—I,
—CO—$NR_{8-1}R_{8-2}$ where $R_{8-1}$ and $R_{8-2}$ are as defined above,
—$NR_{8-1}R_{8-2}$ where $R_{8-1}$ and $R_{8-2}$ are as defined above,
—$NO_2$,
—C≡N,
—N($R_{8-1}$)—CO—$R_{8-2}$ where $R_{8-1}$ and $R_{8-2}$ are as defined above,
—O—$SO_2$—$CF_3$,
$C_1$–$C_4$ alkyl,
—Si($CH_3$)$_3$;

where $R_9$ is —H
—F,
—Cl,
—Br,
—I,
—CO—$NR_{9-1}R_{9-2}$ where $R_{9-1}$ and $R_{9-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{9-1}R_{9-2}$ where $R_{9-1}$ and $R_{9-2}$ are as defined above,
—$CF_3$,
—φ optionally substituted with one or two
—F, —Cl,
—Br,
—I,
—CO—NR$_{9\text{-}1}$R$_{9\text{-}2}$ where R$_{9\text{-}1}$ and R$_{9\text{-}2}$ are as defined above,
—NR$_{9\text{-}1}$R$_{9\text{-}2}$ where R$_{9\text{-}1}$ and R$_{9\text{-}2}$ are as defined above,
—NO$_2$,
—C≡N,
—N(R$_{9\text{-}1}$)—CO—R$_{9\text{-}2}$ where R$_{9\text{-}1}$ and R$_{9\text{-}2}$ are as defined above,
—O—SO$_2$—CF$_3$,
C$_1$–C$_4$ alkyl,
—Si(CH$_3$)$_3$;

with the proviso that not more than two of R$_6$, R$_7$, R$_8$ and R$_9$ are other than —H;

where Ar/Het is
—φ optionally substituted with one or two R$_{Ar/Het\text{-}1}$ where R$_{Ar/Het\text{-}1}$ is selected from the group consisting of
—F,
—Cl,
—Br,
—I,
—CO—NR$_{Ar/Het\text{-}2}$R$_{Ar/Het\text{-}3}$ where R$_{Ar/Het\text{-}2}$ and R$_{Ar/Het\text{-}3}$ are the same or different and are:
—H,
C$_1$–C$_6$ alkyl,
C$_3$–C$_7$ cycloalkyl,
—C$_1$–C$_3$ alkyl-[C$_3$–C$_7$ cycloalkyl],
—SO$_2$—NR$_{Ar/Het\text{-}2}$R$_{Ar/Het\text{-}3}$ where R$_{Ar/Het\text{-}2}$ and R$_{Ar/Het\text{-}3}$ are as defined above,
—OH,
—SH,
C$_1$–C$_6$ alkyl,
C$_3$–C$_6$ cycloalkyl,
—O—R$_{Ar/Het\text{-}4}$ where R$_{Ar\text{-}Het\text{-}4}$ is
—C$_1$–C$_6$ alkyl,
—CH$_2$—(C$_3$–C$_6$ cycloalkyl),
—CH$_2$—φ,
—(C$_3$–C$_6$ cycloalkyl),
—SO$_2$—CF$_3$,
—CH$_2$—CF$_3$,
—CF$_3$,
—CO—R$_{Ar/Het\text{-}2}$ where R$_{Ar/Het\text{-}2}$ is as defined above,
—CO—OR$_{Ar/Het\text{-}2}$ where R$_{Ar/Het\text{-}2}$ is as defined above,
—C≡N,
—NO$_2$,
—NR$_{Ar/Het\text{-}2}$—CO—R$_{Ar/Het\text{-}3}$ where R$_{Ar/Het\text{-}2}$ and R$_{Ar/Het\text{-}3}$ are as defined above,
—S—(C$_1$–C$_6$ alkyl),
—NR$_{ArHet\text{-}2}$R$_{Ar/Het\text{-}3}$ where R$_{Ar/Het\text{-}2}$ and R$_{Ar/Het\text{-}3}$ are as defined above,
2-, 3- and 4-pyridinyl optionally substituted with one or two R$_{Ar/Het\text{-}1}$ where R$_{AR/Het\text{-}1}$ is as defined above,
2-, 4-, 5- pyrimidinyl optionally substituted with one or two R$_{Ar/Het\text{-}1}$ where R$_{Ar/Het\text{-}1}$ is as defined above, and enantiomers and diastereomers thereof where such exist and pharmaceutically acceptable salts thereof.

Also disclosed is a process for the preparation of a compound of the formula

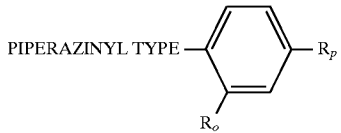

where R$_p$ is —H, —CO—NH$_2$ or —SO$_2$—NH$_2$;
where R$_o$ is —H, —CO—NH$_2$ or —SO$_2$—NH$_2$ with the provisos
(1) that one of R$_p$ and R$_o$ must be —H
(2) but only one of R$_p$ and R$_o$ can be —H;
where PIPERAZINYL TYPE is selected from the group consisting of

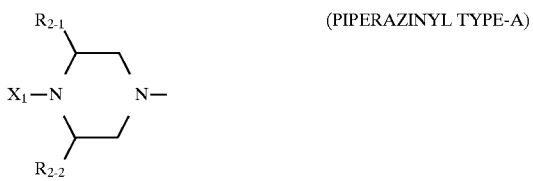

where R$_{2\text{-}1}$ is —H or C$_1$–C$_6$ alkyl,
where R$_{2\text{-}2}$ is —H or C$_1$–C$_6$ alkyl,
where X$_1$ is —H, benzyl, benzyloxycarbonyl or t-butyloxycarbonyl,

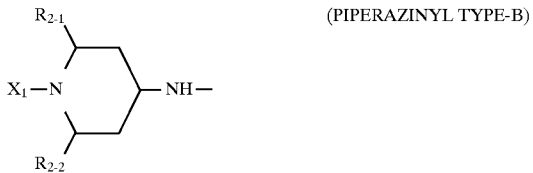

where R$_{2\text{-}1}$, R$_{2\text{-}2}$ and X$_1$ are as defined above,

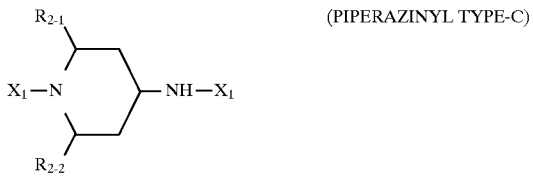

where R$_{2\text{-}1}$, R$_{2\text{-}2}$ and X$_1$ are as defined above, which comprises contacting piperazine type compound of the formula

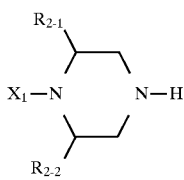

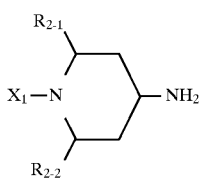

-continued

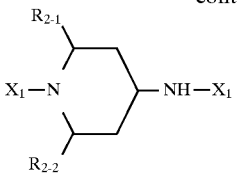

where $R_{2-1}$, $R_{2-2}$ and $X_1$ are as defined above with a halophenyl compound of the formula

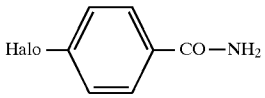

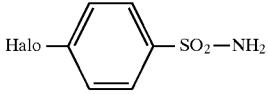

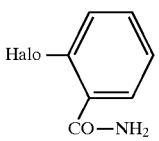

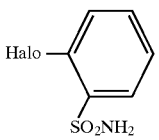

where halo is —F or —Cl in the presence of water at a temperature of about 40° to about 110°.

Further disclosed is 2-[2-(isochroman-1-yl)ethyl]-6,7-dimethoxy-1,2,3,4-tetrahydroisoquinoline and pharmaceutical acceptable salts thereof.

Disclosed is a process for preparing optically pure (−)-(isochroman-1-yl)acetic acid (LV) which comprises contacting optically impure (±)-(isochroman-1-yl)acetic acid ester (LIV) with *Pseudomonas cepaica* lipase in an aqueous media in the pH range of about 5 to about 8 and in a temperature range of about 20° to about 35°.

Also disclosed is a process for racemization of (+)-(isochroman-1-yl)acetic acid (LVI) to the corresponding optically impure mixture of (+)-(isochroman-1-yl)acetic acid (LVI) and (−)-(isochroman-1-yl)acetic acid (LV) which comprises:

(1) contacting the (+)-(isochroman-1-yl)acetic acid with base having a p$K_a$ of greater than 11 and
(2) quenching the reaction mixture of step (1) with a proton donor.

Disclosed is use of aromatic bicyclic amines of formula (I)

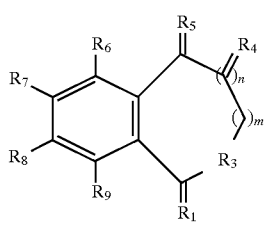

where m is 0 or 1;
where n is 0 or 1;
where $R_1$ (1) is $\alpha$-$R_{1-1}$:$\beta$-$R_{1-2}$ where one of $R_{1-1}$ or $R_{1-2}$ is —H or $C_1$–$C_6$ alkyl and the other of $R_{1-1}$ or $R_{1-2}$ is —$CR_{10-1}R_{10-2}$—$CR_{11}$—$R_2$—Ar/Het where $R_{10-1}$ and $R_{10-2}$ are the same or different and are —H or $C_1$–$C_6$ alkyl,
where $R_{11}$ is =O or $R_{11-1}$:$R_{11-2}$ where $R_{11-1}$ and $R_{11-2}$ are the same or different and are —H or $C_1$–$C_6$ alkyl;
where $R_2$ is selected from the group consisting of

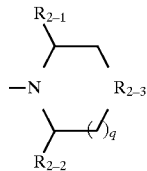
(XXV-A)

where $R_{2-1}$ and $R_{2-2}$ are —H or $C_1$–$C_6$ alkyl,
where $R_{2-3}$ is nitrogen (N—) or methine (HC—),
where q is 1 or 2,

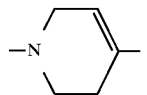
(XXV-B)

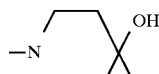
(XXV-C)

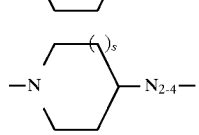
(XXV-D)

where $R_{2-4}$ is:
—H,
$C_1$–$C_6$ alkyl,
$C_3$–$C_7$ cycloalkyl,
—$C_1$–$C_3$ alkyl-[$C_3$–$C_7$ cycloalkyl],
where s is 0, 1 or 2,

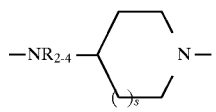
(XXV-E)

where $R_{2-4}$ and s are as defined above;
where $R_3$ is —$CH_2$—;
where $R_4$ is $\alpha$-$R_{4-1}$:$\beta$-$R_{4-2}$ where one of $R_{4-1}$ and $R_{4-2}$ is:
—H,
$C_1$–$C_6$ alkyl, and where the other of $R_{4-1}$ or $R_{4-2}$ is
—H,
$C_1$–$C_6$ alkyl,
—$\phi$,
—OH,
—O—($C_1$–$C_3$)alkyl;
where $R_5$ is is $\alpha$-$R_{5-1}$:$\beta$-$R_{5-2}$ where one of $R_{5-1}$ and $R_{5-2}$ is:
—H,
$C_1$–$C_6$ alkyl, and where the other of $R_{5-1}$ or $R_{5-2}$ is
—H,
$C_1$–$C_6$ alkyl,
—$\phi$,
—OH,
—O—($C_1$–$C_3$)alkyl;
and when n is 1, one of $R_{4-1}$ or $R_{4-2}$ and one of $R_{5-1}$ or $R_{5-2}$ can be taken together with the carbon atoms to which they are attached to form a carbon ring of 5-, 6- or 7-members;
where $R_6$ is —H
—F,
—Cl, —Br,
—I,
—CO—$NR_{6-1}R_{6-2}$ where $R_{6-1}$ and $R_{6-2}$ are the same or different and are
   —H,
   $C_1$–$C_6$ alkyl,
   $C_3$–$C_7$ cycloalkyl,
   —$C_1$–$C_3$ alkyl-[$C_3$–$C_7$ cycloalkyl],
—SO—$NR_{6-1}R_{6-2}$ where $R_{6-1}$ and $R_{6-2}$ are as defined above,
—$CF_3$,
—φ optionally substituted with one or two
   —F,
   —Cl,
   —Br,
   —I,
   —CO—$NR_{6-1}R_{6-2}$ where $R_{6-1}$ and $R_{6-2}$ are as defined above,
—$NR_{6-1}R_{6-2}$ where $R_{6-1}$ and $R_{6-2}$ are as defined above,
—$NO_2$,
—C≡N,
—N($R_{6-1}$)—CO—$R_{6-2}$ where $R_{6-1}$ and $R_{6-2}$ are as defined above,
—O—$SO_2$—$CF_3$,
$C_1$–$C_4$ alkyl,
—$Si(CH_3)_3$;
and where $R_6$ and one of $R_{5-1}$ or $R_{5-2}$ are taken together with the carbon atoms to which they are attached to form a carbon ring of 5-, 6- or 7-members;
where $R_7$ is —H
   —F,
   —Cl,
   —Br,
   —I,
   —CO—$NR_{7-1}R_{7-2}$ where $R_{7-1}$ and $R_{7-2}$ are the same or different and are
      —H,
      $C_1$–$C_6$ alkyl,
      $C_3$–$C_7$ cycloalkyl,
      —$C_1$–$C_3$ alkyl-[$C_3$–$C_7$ cycloalkyl],
   —SO—$NR_{7-1}R_{7-2}$ where $R_{7-1}$ and $R_{7-2}$ are as defined above,
   —$CF_3$,
   —φ optionally substituted with one or two
      —F,
      —Cl,
      —Br,
      —I,
      —CO—$NR_{7-1}R_{7-2}$ where $R_{7-1}$ and $R_{7-2}$ are as defined above,
   —$NR_{7-1}R_{7-2}$ where $R_{7-1}$ and $R_{7-2}$ are as defined above,
   —$NO_2$,
   —C≡N,
   —N($R_{7-1}$)—CO—$R_{7-2}$ where $R_{7-1}$ and $R_{7-2}$ are as defined above,
   —O—$SO_2$—$CF_3$,
   $C_1$–$C_4$ alkyl,
   —$Si(CH_3)_3$;
where $R_8$ is —H
   —F,
   —Cl,
   —Br,
   —I,
   —CO—$NR_{8-1}R_{8-2}$ where $R_{8-1}$ and $R_{8-2}$ are the same or different and are
      —H,
      $C_1$–$C_6$ alkyl,
      $C_3$–$C_7$ cycloalkyl,
      —$C_1$–$C_3$ alkyl-[$C_3$–$C_7$ cycloalkyl],
   —SO—$NR_{8-1}R_{8-2}$ where $R_{8-1}$ and $R_{8-2}$ are as defined above,
   —$CF_3$,
   —φ optionally substituted with one or two
      —F,
      —Cl,
      —Br,
      —I,
      —CO—$NR_{8-1}R_{8-2}$ where $R_{8-1}$ and $R_{8-2}$ are as defined above,
   —$NR_{8-1}R_{8-2}$ where $R_{8-1}$ and $R_{8-2}$ are as defined above,
   —$NO_2$,
   —C≡N,
   —N($R_{8-1}$)—CO—$R_{8-2}$ where $R_{8-1}$ and $R_{8-2}$ are as defined above,
   —O—$SO_2$—$CF_3$,
   $C_1$–$C_4$ alkyl,
   —$Si(CH_3)_3$;
where $R_9$ is —H
   —F,
   —Cl,
   —Br,
   —I,
   —CO—$NR_{9-1}R_{9-2}$ where $R_{9-1}$ and $R_{9-2}$ are the same or different and are
      —H,
      $C_1$–$C_6$ alkyl,
      $C_3$–$C_7$ cycloalkyl,
      —$C_1$–$C_3$ alkyl-[$C_3$–$C_7$ cycloalkyl],
   —SO—$NR_{9-1}R_{9-2}$ where $R_{9-1}$ and $R_{9-2}$ are as defined above,
   —$CF_3$,
   —φ optionally substituted with one or two
      —F,
      —Cl,
      —Br,
      —I,
      —CO—$NR_{9-1}R_{9-2}$ where $R_{9-1}$ and $R_{9-2}$ are as defined above,
   —$NR_{9-1}R_{9-2}$ where $R_{9-1}$ and $R_{9-2}$ are as defined above,
   —$NO_2$,
   —C≡N,
   —N($R_{9-1}$)—CO—$R_{9-2}$ where $R_{9-1}$ and $R_{9-2}$ are as defined above,
   —O—$SO_2$—$CF_3$,
   $C_1$–$C_4$ alkyl,
   —$Si(CH_3)_3$;
with the proviso that not more than two of $R_6$, $R_7$, $R_8$ and $R_9$ are other than —H;
where Ar/Het is
   —φ optionally substituted with one or two $R_{Ar/Het-1}$ where $R_{Ar/Het-1}$ is selected from the group consisting of
      —F,
      —Cl,
      —Br,
      —I,
      —CO—$NR_{Ar/Het-2}R_{Ar/Het-3}$ where $R_{Ar/Het-2}$ and $R_{Ar/Het-3}$ are the same or different and are:
         —H,
         $C_1$–$C_6$ alkyl,
         $C_3$–$C_7$ cycloalkyl,
         —$C_1$–$C_3$ alkyl-[$C_3$–$C_7$ cycloalkyl],
      —$SO_2$—$NR_{Ar/Het-2}R_{Ar/Het-3}$ where $R_{Ar/Het-2}$ and $R_{Ar/Het-3}$ are as defined above, —OH,
—SH,
$C_1$–$C_6$ alkyl,
$C_3$–$C_6$ cycloalkyl,
—O—$R_{Ar/Het-4}$ where $R_{Ar/Het-4}$ is
  —$C_1$–$C_6$ alkyl,
  —$CH_2$—($C_3$–$C_6$ cycloalkyl),
  —$CH_2$—φ,
  —($C_3$–$C_6$ cycloalkyl),
  —$SO_2$—$CF_3$,
  —$CH_2$—$CF_3$,
—$CF_3$,
—CO—$R_{Ar/Het-2}$ where $R_{Ar/Het-2}$ is as defined above,
—CO—$OR_{Ar/Het-2}$ where $R_{Ar/Het-2}$ is as defined above,
—C≡N,
—$NO_2$,
—$NR_{Ar/Het-2}$—CO—$R_{Ar/Het-3}$ where $R_{Ar/Het-2}$ and $R_{Ar/Het-3}$ are as defined above,
—S—($C_1$–$C_6$ alkyl),
—$NR_{Ar/Het-2}R_{Ar/Het-3}$ where $R_{Ar/Het-2}$ and $R_{Ar/Het-3}$ are as defined above,
2-, 3- and 4-pyridinyl optionally substituted with one or two $R_{Ar/Het-1}$ where $R_{Ar/Het-1}$ is as defined above,
2-, 4-, 5- pyrimidinyl optionally substituted with one or two $R_{Ar/Het-1}$ where $R_{Ar/Het-1}$ is as defined above, and where $R_1$ (2) is $R_{1-3}$:$R_{1-4}$ and $R_3$ is —$CR_{3-1}$:$R_{3-2}$— where one of $R_{1-3}$ or $R_{1-4}$ is taken together with one of $R_{3-1}$ and $R_{3-2}$ to form a second bond between the carbon atoms to which $R_1$ and $R_{3-1}$ and $R_{3-2}$ are attached,
  where the other of $R_{1-3}$ and $R_{1-4}$ is —$CR_{10-1}R_{10-2}$—($CR_{11}$)$_p$—$R_2$—Ar/Het
where $R_{10-1}$, $R_{10-2}$, $R_{11}$, p, $R_2$ and Ar/Het are as defined above,
  where the other of $R_{3-1}$ and $R_{3-2}$ is —H and
  where m, n, $R_2$, $R_4$, $R_5$, $R_6$, $R_7$, $R_8$, $R_9$ are as defined above;
where $R_1$ (3) is =C[—H][—$CR_{11}$—$R_2$—Ar/Het][—H]
  where $R_{11}$, $R_2$ and Ar/Het are as defined above and
  where m, n, $R_2$, $R_4$, $R_5$, $R_6$, $R_7$, $R_8$, $R_9$ are as defined above; and
where $R_1$ (4) is =C[—$CR_{11}$—$R_2$—Ar/Het][—H] where $R_{11}$, $R_2$ and Ar/Het are as defined above,
  where m, n, $R_2$, $R_4$, $R_5$, $R_6$, $R_7$, $R_8$, $R_9$ are as defined above;
with the proviso that when m=0, n=0 and $R_3$ is —$CH_2$—, Ar/Het is not —φ or halo substituted —φ;
enantiomers and diastereomers thereof where such exist and pharmaceutically acceptable salts thereof to prepare a medicament to treat humans who are in need of treatment for psychosis, paraphrenia, psychotic depression, mania, schizophrenia, schizophreniform disorders, vascular headaches, migraine headaches, anxiety, drug addiction, convulsive disorders, spectrum disorders, personality disorders, attention deficit disorders in children and adults, post traumatic stress syndrome, dysthymia and extrapyramidal motor side effects of other antipsychotic (neuroleptic) drugs.

Disclosed are aromatic bicyclic amines selected from the group consisting of:
4-[2-(indan-1-yl)ethyl]-1-(4-methoxyphenyl)piperazine,
4-[2-(1,2,3,4-tetrahydronaphthalen-1-yl)ethyl]-1-(4-methoxyphenyl)piperazine,
4-[2-(indan-1-yl)ethyl]-1-(4-hydroxyphenyl)piperazine,
4-[2-(1,2,3,4-tetrahydronaphthalen-1-yl)ethyl]-1-(4-hydroxyphenyl)piperazine,
4-[2-(indan-1-yl)ethyl]-1-[(4-trifluoromethanesulfonyloxy)phenyl]piperazine,
4-[2-(1,2,3,4-tetrahydronaphthalen-1-yl)ethyl]-1-[(4-trifluoromethanesulfonyloxy)phenyl]piperazine,
4-[2-(indan-1-yl)ethyl]-1-(4-methoxycarbonyl)phenylpiperazine,
4-[2-(indan-1-yl)ethyl]-1-(4-aminocarbonylphenyl)piperazine,
4-[2-(indan-1-yl)ethyl]-1-(4-cyanophenyl)piperazine,
(E)-4-[1-(1,2,3,4-tetrahydronaphthenyl)methylidenemethyl]-1-(4-methoxyphenyl)piperazine,
4-[2-(3,4-dihydronaphthalen-1-yl)ethyl]-1-(4-methoxyphenyl)piperazine,
4-[2-(inden-1-yl)ethyl]-1-(4-hydroxyphenyl)piperazine,
4-[2-(inden-1-yl)ethyl]-1-(4-aminocarbonylphenyl)piperazine,
4-[1-methyl-2-(1,2,3,4-tetrahydronaphthalen-1-yl)ethyl]1-(4-methoxyphenyl)piperazine,
4-[2-(inden-1-yl)ethyl]-1-(4-methoxyphenyl)piperazine,
4-[4-[2-(1,2,3,4-tetrahydro-1-naphthalenyl)ethyl]-1-piperazinyl]benzamide,
4-[4-[2-(1,2,3,4-tetrahydro-1-naphthalenyl)ethyl]-1-piperazinyl]benzenesulfonamide,
4-[4-[2-(3,4-dihydro-1-naphthalenyl)ethyl]-1-piperazinyl]benzamide,
4-[4-[2-(3,4-dihydro-1-naphthalenyl)ethyl]-1-piperazinyl]benzenesulfonamide,
4-[4-[2-(inden-1-yl)ethyl]piperazin-1-yl]benzenesulfonamide and
4-[4-[2-(indan-1-yl))ethyl]piperazin-1-yl]benzenesulfonamide.

DETAILED DESCRIPTION OF THE INVENTION

CHART A discloses the aromatic bicyclic amines (I) and further sets forth the compounds where the non-aromatic ring contains 5- (m=0, n=0), 6- (m or n=0 and the other of m and n=1) and 7-members (m=1, n=1). It is preferred that m is 0 and n is 1. The 5-member ring compounds are known as phthalans, thiophthalans, indanes and indenes. The 6-member ring compounds are known as 2-benzopyrans or isochromans, thioisochromans, tetralins and dihydronaphthalenes. The 7-member ring compounds are known as 2-benzoxepines and 2-benzothiopins. $R_3$ can be —O—, —S—, —$CH_2$— or —CH=. When $R_3$ is —O— the aromatic bicyclic amines (I) are known as phthalins, isochromans and 2-benzoxepins. When $R_3$ is —S— the aromatic bicyclic amines (I) are known as thiophthalans, isothiochromans and 2-thiobenzoxepins. When $R_3$ is —$CH_2$— the aromatic bicyclic amines (I) are known as indans, tetralins and 1,2-benzocycloheptenes and when $R_3$ is —CH= the aromatic bicyclic amines (I) are known as indenes, 1,2-dihydronaphthalenes and 1,2-benzo-1,3-cycloheptadienes. It is preferred that $R_3$ is —O— or —$CH_2$—.

$R_1$ provides four situations, no double bonds, an endocyclic double bond, and the two isomeric exocyclic double bonds "E" and "Z". It is preferred that $R_1$ is $R_{1-1}$:$R_{1-2}$ where one is —H and other is —$CR_{10-1}R_{10-2}$—$CR_{11}$—$R_2$—Ar/Het (no double bonds). It is preferred that $R_{10}$ is —H:—H. It is preferred that $R_{11}$ is —H:—H or —H:$C_1$ alkyl; it is more preferred that $R_{11}$ be —H:—H. It is preferred that Ar/Het be —CO—$NH_2$, —$SO_2$—$NH_2$, $C_1$ alkoxy and —F; it is more preferred that Ar/Het be —φ substituted with —CO—$NH_2$ or —$SO_2$—$NH_2$. It is preferred that $R_3$ is —O— or —$CH_2$—. It is preferred that $R_4$ (when present) is α-$R_{4-1}$:β-$R_{4-2}$ where $R_{4-1}$ and $R_{4-2}$ are —H or $C_1$ alkyl; it is preferred that $R_4$ is —H:—H. It is preferred that $R_5$ is α-$R_{5-1}$:β-$R_{5-2}$ where $R_{5-1}$ and $R_{5-2}$ are —H or $C_1$ alkyl; it is more preferred that $R_5$ is —H:—H. It is preferred that $R_6$ is —H, —Br or —CO—NH$_2$; it is more preferred that $R_6$ is —H. It is preferred that $R_7$ is —H, —F, —Cl, —Br or —CO—NH$_2$; it is more preferred that $R_7$ is —H or —CO—NH$_2$. It is preferred that $R_8$ is —H, —Br or $C_1$ alkyl; it is more preferred that $R_8$ is —H. It is preferred that $R_9$ is —H. It is preferred that the aromatic bicyclic amines (I) be selected from the group consisting of the compounds of EXAMPLES 1–27, 30–51, 58, 61, 70–78, 80, 81, 85, 87–89, 91–110. It is more preferred that the aromatic bicyclic amines (I) be selected from the group consisting of the compounds of EXAMPLES 2, 3, 7, 48, 49, and 109. It is even more preferred that the aromatic bicyclic amine (I) be the compound of EXAMPLE 49 either as the free base or as the methanesulfonate salt.

The invention, for the most part, is the aromatic bicyclic amines (I) themselves. In most all cases the aromatic bicyclic amines (I) are readily prepared by methods well known to those skilled in the art, including the best method of preparation. Because this is the case, it will not be stated for each step that it is performed by a method known to those skilled in the art but will be incorporated by reference from this statement. Where this is not the case the reaction step will be explained in detail. New chemistry includes the preparation of the $R_2$—Ar/Het group when Ar/Het is substituted by two specific groups —CO—NH$_2$ and —SO—NH2 in the para and ortho positions of the phenyl ring (CHART B). Further, new chemistry includes the emzymatic resolution of the optically impure ethyl(isochroman-1-yl) acetate. In addition, new chemistry is a method of transforming the undesired enantiomer ethyl (+)-(isochroman-1-yl)acetate to the racemic form ethyl (±)-(isochroman-1-yl) acetate whereby it can again be resolved into its optically pure form.

CHART B discloses a procedure to prepare the —R$_2$—Ar/Het portion of the aromatic bicyclic amines (I) when the Ar group is —ϕ or pyridyl and it is substituted in the ortho or para positions with an electronegative substituent such as —CO—NR$_{Ar/Het-2}$R$_{Ar/Het-}$3, —COOR$_{Ar/Het-2}$, —C≡N, —NO$_2$ or —SO$_2$—NR$_{ArHet-2}$R$_{Ar/Het-3}$. The appropriately substituted piperazine (II) is contacted with the appropriate halogenated aromatic compound (III), such as heating in a polar solvent such as water with a base (either excess piperazine (II) or diisopropylethylamine) at elevated temperature to form the desired aromatic piperazine (IV). It is preferred that the halo group be -F. EWG refers to electron withdrawing group and includes the substituents identified above. The preferred $R_2$ group is piperazinyl.

CHART C discloses a specific example where after the —R$_2$—Ar/Het is prepared with a para methoxy substituent, a second substituent (—Br) is added in the ortho position. The secondary nitrogen of 1-(4-methoxyphenyl)piperazine [alkoxy aromatic piperazine (V)] is protected by contacting it with an appropriate blocking group to form the protected alkoxy aromatic piperazine (VI). Suitable protecting groups include formate, benzyloxycarbonyl and acetyl; the preferred blocking group is formate. If the blocking group is formate, it can be added by refluxing the alkoxy aromatic piperazine (V) in neat ethyl formate. This protected alkoxy aromatic piperazine (VI) is then reacted with the appropriate reagent (bromine in the presence of sodium acetate and acetic acid) to introduce the desired substituent (—Br) and give the protected brominated compounds (VII) as is known to those skilled in the art. The protected brominated compounds (VII) then has the protecting group removed, by methods known to those skilled in the art, such as by reaction with aqueous hydrochloric acid followed by neutralization to give the bromoalkoxy compound (VIII).

CHART D discloses a known method for the preparation of $R_2$—Ar/Het groups, especially when $R_2$ is piperazine. The substituted nitrobenzene (IX) is reduced to the substituted aniline type compound (X) by reaction with reducing agents such as hydrogen and a palladium on carbon catalyst or Raney nickel catalyst, or alternatively in many cases the substituted aniline type compound (X) can be purchased commercially. The substituted aniline type compound (X) is then heated with bis(2-chloroethyl)amine hydrochloride with or without added base in solvents such as THF, toluene, ethylene glycol or chlorobenzene at elevated temperature to give the desired substituted aromatic piperazine (XI) in its salt form. To obtain the desired substituted aromatic piperazine (XI) as the free base, base is added and the free base of the desired substituted aromatic piperazine (XI) is isolated.

CHART E discloses the preferred methods of preparing the $R_2$—Ar/Het compounds when the $R_2$ group is piperidinyl or tetrahydropyridine. A piperidine ketone (XII) with a readily removable group, as discussed above such as benzyl (ϕ—CH$_2$—) attached to the piperidine nitrogen atom, is reacted with the appropriate Ar/Het-Grignard reagent (XIII) to produce the protected hydroxy piperidine (XIV) as is known to those skilled in the art. The protecting group can be removed by hydrogenolysis, as is known to those skilled in the art, to produce the hydroxy piperidine (XV), this is the group (XXV-C). Alternatively, the protected hydroxy piperidine (XIV) is dehydrated using aqueous hydrochloric acid to form the protected unsaturated piperidine (XVI), by means known to those skilled in the art following which the protecting group is removed most conveniently by using Olofson's reagent [Olofson et al, *J. Org. Chem.*, 49, 2081 and 2795 (1984) to give the tetrahydropyridine (XVII) which is the (XXV-B) group. Alternatively, instead of transforming the protected unsaturated piperidine (XVI) to the unsaturated piperidine (XVII), it first can have the unsaturation in the piperidine ring removed forming the protected Ar/Het-piperidine (XVIII) by hydrogenation using a palladium on carbon catalyst by means known to those skilled in the art. The protected Ar/Het-piperidine (XVIII) then has the protecting group removed preferably using Olofson's reagent (discussed above) to form the Ar/Het-piperidine (XIX), which is group (XXV-A) where $R_{2-3}$ is methane. Three different piperidinyl $R_2$ groups are produced following the procedures of CHART E.

CHART F discloses the preparation of a specific $R_2$—Ar/Het group where the Ar/Het group is —ϕ substituted with —O—R$_{Ar/Het-}$4. The hydroxy phenyl piperazine (XXI) has its free piperazinyl nitrogen atom protected by reaction with a group such as di-tert-butyl dicarbonate, (CH$_3$)$_3$—C—O—CO—O—CO—O—C—(CH$_3$)$_3$, (XX) to form the protected hydroxy phenyl piperazine (XXII) as is known to those skilled in the art. The protected hydroxy phenyl piperazine (XXII) then has the hydroxy functionality on the phenyl ring transformed into the desired —O—R$_{Ar/Het-}$4 substituent as is known to those skilled in the art, such as the method of Camps et al, *Synthesis* 727 (1980) to give the protected oxygenated substituted phenyl piperazine (XXIII). Finally, the protecting group of the protected oxygenated substituted phenyl piperazine (XXIII) is removed by known means, such as trifluoroacetic acid or hydrochloric acid/methanol to give the desired oxygenated substituted phenyl piperazine (XXIV) after treatment with base and isolation of the resulting salt.

CHART G discloses the preparation of $R_2$—Ar/Het groups where the $R_2$ group is piperidinyl of the type (XXV- D). A protected piperidine ketone (XXV) is reacted with a substituted amine (XVI) in a reductive amination in the presence of sodium cyanoborohydride in methanol or hydrogen and palladium on carbon catalyst to give the protected amino substituted piperidine (XVII) as is known to those skilled in the art. This protected amino substituted piperidine (XVII) is then reacted with the appropriate halogenated (substituted) phenyl group in the presence of added base such as diisopropylethylamine or excess protected amino substituted piperidine (XXVII) to form the tertiary amine—protected phenyl substituted amino substituted piperidine (XXVIII) as is known to those skilled in the art which has the protecting group removed by methods known to those skilled in the art, such as hydrogenolysis, to give the desired phenyl substituted amino substituted piperidine (XIX).

CHART H discloses an alternate process to prepare the protected phenyl substituted amino substituted piperidine (XXVIII) which is similar to the process of CHART D in the first step in that it reduces the substituted nitrobenzene (IX) to the corresponding substituted aniline type compound (X) in the same manner as discussed with regard to CHART D. The substituted aniline type compound (X) is then reacted with the protected piperidine ketone using sodium cyanoborohydride (NaCNBH$_3$) and methanol or hydrogen and palladium on carbon catalyst to form a protected piperidine substituted amine (XXX) in a manner similar to that described for CHART G with regard to the reaction of the protected piperidine ketone (XXV) with the substituted amine (XXVI). At this point the secondary nitrogen group is alkylated with an $R_{2-4}$-halo group, or the nitrogen is reductively aminated with sodium cyanoborohydride or hydrogen and palladium on carbon catalyst and an aldehyde such that $R_{2-4}$ is formed to give the protected amino substituted piperidine (XXXVIII) which has the protecting group removed by methods such as hydrogenolysis to give the desired phenyl substituted amino substituted piperidine (XXIX).

Whereas CHART G disclosed the preparation of $R_2$—Ar/Het groups where the $R_2$ group is piperidinyl of the type (XXV-D), CHART I discloses a preparation of $R_2$—Ar/Het groups where the $R_2$ group is piperidinyl of the type (XXV-E). The substituted aniline type compound (X) is reacted with hydroxy aldehydes of the same or differing chain length in the presence of sodium cyanoborohydride and an alcohol (preferably methanol) or hydrogen and palladium on carbon catalyst to form the di-(hydroxyethyl)phenylamine (XXXI) by methods known to those skilled in the art. The hydroxy groups are replaced with leaving groups, preferably bromine or O-tosyl, to form the dialkylated aniline (XXXII). The dialkylated aniline (XXXII) is then cyclized to form the Ar/Het piperidine ketone (XXXIII) by the method of *Bull. Chem. Soc. Japan*, 57, 1637 (1984). The Ar/Het piperidine ketone (XXXIII) is then transformed into the Ar/Het piperidinyl amine (XXXIV) in the same manner as the protected piperidine ketone (XXV) was transformed into the protected amino substituted piperidine (XXVII) in CHART G by reaction with the substituted amine NH$_2$—R$_{2-4}$ (XXVI).

CHART J discloses the preparation of intermediates useful in the synthesis of the aromatic bicyclic ring system. More specifically, CHART J discloses a method of preparation when $R_5$ is not ≠—H:—H. The appropriately substituted ($R_6$, $R_7$, $R_8$ and/or $R_9$) phenylacetic acids (most of which are commercially available) is converted to the corresponding ester (XXXVI) by a number of common routes, such as acid/alcohol or alcohol and condensing agent. The ester (XXXVI) is alkylated by methods known in the art, e.g. such as treatment in THF with a base such as lithium diisopropylamide followed by an alkylating agent such as iodomethane or iodoethane to give the substituted ester (XXXVII). The substituted ester (XXXVII) can be hydrolyzed under standard aqueous acidic or basic conditions to give the corresponding substituted acid (XXXIX). Alternatively, the substituted ester (XXXVII) can again be alkylated to form the disubstituted ester (XXXVIII) by the same method as stated for introduction of the first alkyl group. Hydrolysis of the disubstituted ester (XXXVIII) gives the substituted acid (XXXIX) containing two substituents ($R_{5-1}$ and $R_{5-2}$). The substituted acid (XXXIX) is converted to the corresponding substituted benzoyl halide (XL) by well known means, preferably by reaction with oxalyl chloride, neat, or with dichloromethane as solvent and catalytic DMF present. In the event that $R_{5-1}$ and $R_{5-2}$ are not the same, an asymmetric center is formed which will produce two enantiomers. If it is desirable to separate the more active isomer (enantiomer) from the less active enantiomer this is accomplished by reacting the substituted phenylacetic acid halide (XL) with the lithium salt of (S)-(–)-4-benzyl-2-oxazolidinone (Aldrich) or other chiral auxiliary to form the diastereomeric phenylacetamide (XLI) and diastereomeric phenylacetamide (XLII) by known means, [(*Aldrichimica Acta* 15, 23 (1982)]. The diastereomers so created are separated by chromatography. Reduction of the optically pure diastereomers with lithium aluminum hydride in THF or ether gives the (+)-alcohol (XLIII) and (–)-alcohol (XLIV).

CHART K discloses a method of introducing $R_4$ substitution whether or not $R_5$ is substituted, the conversion of the readily available substituted acid (XXXIX) starting material to intermediate alcohol (XLV) and $R_4$-alcohol (LI). When $R_4$ is —H:—H, the disubstituted acid (XXIX) is reduced with common reducing agents such as borane-THF or borane-methyl sulfide in THF or lithium aluminum hydride in THF or ether to the alcohol (XLV). When the disubstituted acid (XXXIX) contains a sensitive $R_6$, $R_7$, $R_8$ and/or $R_9$ group, borane-methyl sulfide is the preferred reducing agent. When $R_4$ is other than —H:—H, then it is preferable to transform the disubstituted benzylic acid (XXXIX) to the amide (XLVI) using a condensing agent such as diethylcyanophosphonate or dicyclohexylcarbodiimide and N,O-dimethylhydroxylamine hydrochloride. Treatment of the amide (XLVI) with the appropriate Grignard reagent (XLVII) in THF or ether as solvent gives the $R_{4-1}$-ketone (XLVIII). Reduction of the $R_{4-1}$-ketone (XLVIII) with reducing agents such as sodium borohydride in alcohol, borane-methyl sulfide in THF, or lithium aluminum hydride in THF or ether gives the $R_4$-alcohol (XLIX) where one of $R_{4-1}$ and/or $R_{4-2}$ are ≠—H. Should it be desired that both $R_{4-1}$ and $R_{4-2}$≠—H the $R_{4-1}$ ketone (XLVIII) is treated with a second Grignard reagent in ether or THF to give $R_{4-1}$-alcohol (LI).

CHART L discloses how the two alcohols (XLIII) and (XLIV) of CHART J and the three alcohols of CHART K, the alcohol (XLV), the $R_{4-1}$-alcohol (XLIX) and the $R_4$-alcohol (LI) can be converted to the thiol (LIII) intermediate to prepare aromatic bicyclic amines (I) where $R_3$ is —S—. First the alcohol (XLV, XLIX or LI) is transformed to the corresponding bromo compound (LII) by methods known to those skilled in the art, for example see J. March, Advanced Organic Chemistry, 2nd Ed., McGraw-Hill, 1977, pp. 391–392 or *J. Am. Chem. Soc.*, 68, 2103 (1946). The bromo compound (LII) is then converted to the thiol (LIII) by methods known to the art, e.g. J. March, Advanced Organic Chemistry, 2nd Ed.; McGraw-Hill, 1977, p. 374.

CHART M discloses an enzymatic resolution of the optically impure bicyclic ester (LIV). When the bicyclic ring system is formed an asymmetric center is created at $C_1$ which produces two enantiomers. It is desirable to separate the enantiomers and to do so at the stage of a convenient intermediate. If the optically impure bicyclic ester is contacted with the enzymes (lipase) derived from *Pseudomonas cepacia* by kinetic resolution takes place when the enzyme preferentially hydrolyzes the (−)-enantiomer of the ester to give the (−)-enantiomeric acid (LV) and the (+)-enantiomeric ester (LVI). It is preferred that the pH be in the range of about 5 to about 8 and the temperature be in the range of about 20° to about 35°. Further, it is preferred that 10% by weight be used of *Pseudomonas cepacia* lipase. The (−)-enantiomeric acid (LV) and the (+)-enantiomeric ester (LVI) are separated by acid/base extraction techniques or the (−)-enantiomeric acid (LV) can be preferentially crystallized from a mixture of the (−)-enantiomeric acid (LV) and (+)-enantiomeric ester (LVI). The enzymes from *Pseudomonas cepacia* are commercially available and are used in a weight/weight ratio of enzyme/ester of about 1/10 to about 1/1. The reaction is monitored by known means of removing an aliquot, acidifying and examining by HPLC. When the reaction is complete the reaction mixture is made basic with a base such as sodium hydroxide and the resulting mixture is extracted with a solvent such as ethyl acetate to remove the (+)-ester. Next the aqueous basic mixture is acidified with an acid such as hydrochloric acid, then extracted with a solvent such as ethyl acetate, ether or dichloromethane. The extracts are concentrated and crystallized to give the (−)-acid.

The undesired enantiomer, (+)-ethyl (isochroman-1-yl) acetate (LVI), recovered from the *Pseudomonas cepacia* mediated kinetic resolution of enantiomers, can be effectively recycled back to the racemic mixture for subsequent further treatment with the Pseodomonas lipase. This iterative process optimizes the overall yield of the desired (−)-isochroman-1-yl-acetic acid (LV). Suitable bases for this racemization are those with pKa's greater than 11, preferably greater than 12. Operable bases include alkali metal amide bases, alkali metal alkoxides, and alkali metal carbonates which can all induce this racemization. It is preferred that the base be alkali metal amide bases or alkali metal alkoxides; it is more preferred that the base be the alkali metal alkoxides, such as sodium or potassium t-butoxide or ethoxide. At the completion of the racemization, the reaction was quenched with a proton donor. Vitually any proton donor is operable, for example even water will quench the reaction. However, operationally water is not preferred because it will produce hydroxide which will hydrolyze the ester function. Usually the proton donor is an acid. Most common proton donors (hydrochloric acid, ammonium chloride) used to quench enolate anions can be used for this quenching, however, for ease of workup and purification, acetic acid or trifluoroacetic acid is preferred.

CHART N discloses a method of chemical resolution of the optically impure (racemic) bicyclic acid (LVII) by use of an amine such as R-(+)-α-methylbenzylamine (LVIII). The preferred enantiomer is known to be the S-(−) configuration. When the amine (LVIII) is reacted with the optically impure bicyclic acid (LVII) a diastereomeric salt pair is formed. The (−)-enantiomer of the optically impure bicyclic acid (LVII) preferentially crystallizes, leaving the (+)-enantiomer salt (LX) in solution. The crystals of the (−) crystalline bicyclic acid salt (LIX) are collected and recrystallized several times to provide the (−) crystalline bicyclic acid salt (LIX) highly enriched. A partitioning of the salt between an organic solvent such as dichloromethane and aqueous hydrochloric acid removes the (R)-(+)-α-methylbenzylamine (LVIII) in the aqueous layer and leaves the (−) crystalline bicyclic acid salt (LXI) in the organic phase. Removal of the solvent and recrystallization gives (−) crystalline bicyclic acid salt (LXI) in high enantiomeric excess. Addition of (S)-(−)-α-methylbenzylamine to the optically impure bicyclic acid (LVII) as above followed by crystallization and acidification by the method detailed above leads to enriched (+)-enantiomer.

CHART O discloses one of many useful routes to transform various alcohols (XLIII, XLIV, XLV, XLIX, LI and LIII) or thiols (LIII) to the aromatic bicyclic amines (I). The particular route chosen will depend on the availability of starting materials, the nature of the $R_6$, $R_7$, $R_8$ and/or $R_9$ groups and whether or not chiral (I) is desired. The particular alcohol that it is desired to start with (XLIII, XLIV, XLV, XLIX, LI and LIII) is treated with the halo acetal (LXII) such as 3-chloropropionaldehyde diethyl acetal (Aldrich) or bromoacetaldehyde diethyl acetal (Aldrich) in the presence of a Lewis acids such as titanium tetrachloride, methanesulfonic acid, tin tetrachloride and boron trifluoride-etherate in solvents such as dichloromethane and nitromethane (together or separately) to give the non-cyclized halide (LXIII). The non-cyclized halide (LXIII) is then reacted with a Lewis acid such as aluminum trichloride in dichloromethane or nitromethane to give the cyclized halide (LXIV). This can be accomplished without the isolation of the non-cyclized halide (LXIII) by using alcohol (XLIII, XLIV, XLV, XLIX, LI and LIII) and titanium tetrachloride in dichloromethane or nitromethane or both. Displacement of the halo group from the cyclized halide (LXIV) with the nitrogen nucleophile $R_2$—Ar/Het (LXV) in solvents such as dichloromethane, THF, DMF or ethylene glycol produces the 6-membered aromatic bicyclic amine (LXVI).

CHART P discloses two of many useful routes to transform various alcohols (XLIII, XLIV, XLV, XLIX, LI and LIII) or thiols (LIII) to the aromatic bicyclic amines (I). The particular route chosen will depend on the availability of starting materials, the nature of the $R_6$, $R_7$, $R_8$ and/or $R_9$ groups and whether or not chiral (I) is desired. The particular alcohol that it is desired to start with (XLIII, XLIV, XLV, XLIX, LI and LIII) is treated with the halo ketone (LXVII) such as chloroacetone (Aldrich) or 4-chloro-2-butanone (Pfaltz and Bauer) in the presence of a Lewis acids such as titanium tetrachloride, methanesulfonic acid, tin tetrachloride or boron trifluoride-etherate in solvents such as dichloromethane and nitromethane (together or separately) to give the non-cyclized $R_{1-1}$ halide (LXVIII). The non-cyclized $R_{1-1}$ halide (LXVIII) is then reacted with a Lewis acid such as aluminum trichloride in dichloromethane or nitromethane to give the cyclized $R_{1-1}$ halide (LXIX). This can be accomplished without the isolation of the non-cyclized halide (LXIII). Displacement of the halo group from the cyclized $R_{1-1}$ halide (LXIX) with the nitrogen nucleophile $R_2$—Ar/Het (LXV) in solvents such as dichloromethane, THF, DMF or ethylene glycol produces the 6-membered $R_{1-1}$ aromatic bicyclic amine (LXX).

CHART Q discloses a method of preparing aromatic bicyclic amines (I) when $R_{1-10}$ and $R_{10-2}$ are alkyl. One of the reactants of CHART Q is produced by the process set forth in CHART AA. The particular desired starting alcohol-acid (CXXII) is esterified by known methods to give the protected ester (CXXIII). The protected ester (CXXIII) is oxidized via Swern oxidation [(*Tetrahedron*, 34, 1651 (1978)]) to give a protected aldehyde (CXXXIV). The protected aldehyde (CXXXIV) is treated with alcohols (XLIII, XLIV, XLV, XLIX, LI and LIII) in the presence of Lewis acids such as titanium tetrachloride, methanesulfonic acid, tin tetrachloride or boron trifluoride etherate in solvents such as dichloromethane or nitromethane or mixtures thereof to give the $R_{10}$-bicyclic ester (II). The $R_{10}$-bicyclic ester (LXXI) is hydrolyzed by known means to give the $R_{10}$-bicyclic acid (LXXII). Condensation of the bicyclic acid (LXXII) with $R_2$—Ar/Het (LXV) using reagents such as diethylcyanophosphonate, dicyclocarbodiimide, or carbonyldiimidazole in solvents such as dichloromethane or DMF give the $AR_{10}$-bicyclic keto amine (LXXIII). Reduction of the amide bond of the $AR_{10}$-bicyclic keto amine (LXXIII) with borane-methyl sulfide in THF gives $AR_{10}$-bicyclic methylene amine (LXXIV).

CHART R discloses a method of preparing aromatic bicyclic amines (I) where $R_{11}$ is —H:—H. The desired alcohol (XLIII, XLIV, XLV, XLIX, LI and LIII) is converted to a bicyclic ester (LXXVII) by reaction with an acetal ester (LXXV), such as ethyl 3,3-diethoxypropionate (Aldrich) or a keto ester (LXXVI) in the presence of a Lewis acid, preferably titanium tetrachloride or stannic chloride, in dichloromethane or nitromethane (together or separately) to give the bicyclic ester (LXXVII). The bicyclic ester (LXXVII) is reduced with a reducing agent such as lithium aluminum hydride in THF or ether to give the bicyclic alcohol (LXXIX). Additionally, bicyclic esters (LVI-CHART M) can be reduced as for the bicyclic ester (LXXVII) to the corresponding alcohol (LXXIX). Alternatively, the bicyclic ester (LXXVII) can first be hydrolyzed under standard hydrolysis conditions such as aqueous sodium hydroxide, followed by acidification, to give the bicyclic acid (LXXVIII), then reduced with a reagent such as borane-dimethyl sulfide or borane-THF to give the bicyclic alcohol (LXXIX). Alternatively, the bicyclic acid (LV - CHART M) and bicyclic acid (LXI-CHART N) can be reduced as above for the bicyclic acid (LXXVIII) to the corresponding bicyclic alcohol (LXIX). The bicyclic alcohol (LXXIX) hydroxyl group (—OH) is converted to a to a leaving group such as O-methanesulfonate, O-p-toluenesulfonate, O-trifluoromethylsulfonate, or other groups known in the art, in solvents such as dichloromethane or THF to give the bicyclic oxygenated compound (LXXX) which is then transformed by known means such as displacement with a nitrogen nucleophile such as $R_2$—Ar/Het (LXV) in solvents such as dichloromethane, DMF, THF or ethylene glycol to give the bicyclic 11-methylene amine (LXXXI). When non-reducible R groups are present an alternative method can be to convert the bicyclic acid (LXXVIII) to the corresponding bicyclic 11-keto amine (LXGII) by reaction with $R_2$—Ar/Het (LLXV) using a condensation reagent such as dicyclohexylcarbodiimide, carbonyl diimidazole, or diethylcyanophosphonate in solvents such as dichloromethane and/or DMF. This is followed by reduction with borane-methyl sulfide in THF or borane-THF, or lithium aluminum hydride in ether or THF to give the desired bicyclic 11-methylene amine (LXXXI).

CHART S discloses a method of preparing compounds where $R_{11-1}$ is alkyl. The starting bicyclic acid (LXXVIII) is converted to the corresponding bicyclic amide (LXXXIII) by condensation with N,O-dimethoxyhydroxylamine hydrochloride using a coupling agent such as diethylcyanophosphonate, dicyclocarbodiimide, or carbonyldiimidazole. The bicyclic amide (LXXXIII) is then reacted with a Grignard reagent containing the desired $R_{11-1}$ with THF as solvent, to give the bicyclic $R_{11}$-keto compound (LXXXIV). A reductive amination of the $R_{11}$-keto compound (LXXXIV) following the general procedure of Borch et al, *J. Am. Chem. Soc.,* 93, 2897 (1971) or Barney et al, *Tet. Lett.* 5547 (1990) gives the desired bicyclic $R_{11}$-substituted compound (LXXXV). Alternatively, bicyclic $R_{11}$-keto compound (LXXXIV) is reacted with ammonium acetate or ammonia in methanol by the above literature procedures to give a bicyclic $R_{11}$-amino compound (LXXXIV-A). This bicyclic $R_{11}$-keto compound (LXXXIV) is then reacted with the dialkylated aniline (XXXII) (CHART I) in solvents such as methylene chloride, THF or DMF to give the bicyclic $R_{11}$-substituted compound (LXXXV).

CHART U and EXAMPLES 52–58 disclose a method for the preparation of the compounds where m and n is 0 and $R_3$ is —O—. The phthalide-3-acetic acid (XCI) is converted to the corresponding phthalic acid ester (XCII) by reaction in the corresponding alcoholic solution saturated with hydrogen chloride. The phthalic acid ester (XCII) is reduced to the hydroxy phthalan derivative (XCIII) using diisobutylaluminum hydride in tetrahydrofuran/methylene chloride at −78°, see *J. Am. Chem. Soc.,* 103, 3468 (1981). The lactol, hydroxy phthalan derivative (XCIII), is converted to the alkoxy phthalan derivative (XCIV), preferably the methoxy derivative in a solution of trimethylorthoformate/methanol in the presence of a catalytic amount of p-toluenesulfonic acid, see *Synthesis,* 38, (1974). The alkoxy phthalan derivative (XCIV) is converted to a phthalanyl ester (XCV) by reaction with reagents such as triethylsilane/trimethylsilyl trifluromethanesulfonate in methylene chloride, see *J. Am. Chem. Soc.,* 111, 4136 (1989). The phthalanyl ester (XCV) is then hydrolyzed in base, for example sodium hydroxide/methanol-water, to give the corresponding phthalan-1-acetic acid (XCVI). Next the phthalan-1-acetic acid (XCVI) is coupled with $R_2$—Ar/Het (LXV) using diethyl cyanophosphonate/-triethylamine in methylene chloride to give the coupled product, phthalan keto amine (XCVII), see *Tetrahedron Lett.,* 1595 (1973) or *Tetrahedron Lett.,* 2211 (1976). Finally, the phthalan keto amine (XCVII) has the ketone moiety reduced with a reducing agent such as borane or lithium aluminum hydride/aluminum chloride in THF to give the desired phthalan-1-ethylamine (XCVIII), see *J. Am. Chem. Soc.,* 88, 729 (1966). Alternatively, either the phthalanyl ester (XCV) or the phthalan-1-acetic acid (XCVI) is reduced to the phthalan alcohol (XCIX) by a reducing agent such as borane lithium aluminum hydride in tetrahydrofuran, using methods known to those skilled in the art. The phthalan alcohol (XCIX) is then converted into a phthalan derivative with a readily removable leaving group, where the readily removable leaving group is such as mesylate, tosylate, or halides [(C), $X_2$=—OMs, —OTs, —Cl, —Br, or —I). This phthalan derivative with a leaving group (C) is then coupled with $R_2$—Ar/Het (LXV) using diisopropylethylamine as the base and refluxing in ethylene glycol, to give the desired phthalan-1-ethyl amine (XCVIII).

CHART U and EXAMPLES 59–61 also disclose a method of preparing bicyclic compounds with the non-aromatic ring being 5-membered, where $R_3$ is —O— and where $R_5$ contains an alkoxy substituent (one of $R_{5-1}$ or $R_{5-2}$ is —O-alkyl). This method of preparation begins with hydrolysis of the ester of the alkoxy phthalan derivative (XCIV) with base such as sodium hydroxide/methanol-water to give the alkoxy phthalan acid (CI). This compound is coupled with $R_2$—Ar/Het (LXV), using diethyl cyanophosphonate/triethyl amine in methylene chloride to give the phthalan keto amine (CII). The phthalan keto amine (CII) has the ketone function reduced with a reducing agent such as lithium aluminum hydride/aluminum chloride to give the desired 1-alkoxyphthalan-3-ethylene amine (CIII).

Alternatively, either the alkoxy phthalan derivative (XCIV) or alkoxy phthalan acid (CI) is reduced with a reducing agent such as borane or lithium aluminum hydride to give the 1-alkoxyphthalan alcohol (CIV). This 1-alkoxyphthalan alcohol (CIV) then has the hydroxyl group converted into a leaving group such as mesylate, tosylate, or halides ($X_2$=—OMs, —OTs, —Cl, —Br, or —I) to give the 1-alkoxyphthalan derivative (CV), which is then coupled with $R_2$—Ar/Het (LXV) using diisopropylethylamine as the base and refluxing in ethylene glycol, to give the desired 1-alkoxyphthalan-3-ethylene amine (CIII).

CHART V and EXAMPLES 62–79 discloses a method of preparing the aromatic bicyclic amines (I) when the non-aromatic ring is either 5-, 6- or 7-membered, when $R_3$ is carbon and where the compound is saturated except for the aromatic ring. The keto bicyclic compound (CVI) is reacted with trialkylphosphonoacetate (preferably triethylphosphonoacetate) and sodium hydride in tetrahydrofuran to give a mixture of unsaturated bicyclic esters (CVII-A+CVII-B+CVII-C) by what is known as the Horner-Emmons reaction. The mixture of unsaturated bicyclic esters (CVII-A+CVII-B+CVII-C) is hydrogenated using palladium on carbon to give the bicyclic acetic acid ester (CVIII). The bicyclic acetic acid ester (CVIII) is hydrolyzed in base, preferably sodium hydroxide/methanol-water to give bicyclic acetic acid (CIX). The bicyclic acetic acid (CIX) is coupled with $R_2$/Ar/Het (LXV) as discussed above, using diethyl cyanophosphonate/triethylamine in methylene chloride to give the bicyclic keto amine (CXI) which is then reduced as discussed above to the bicyclic ethylene amine (CXII). Alternatively, the bicyclic acetic acid (CIX) can be converted to the corresponding bicyclic ethanol (CX) which has the hydroxy group replaced with a leaving group forming the bicyclic ethyl compound (CXIII), which then is converted to the desired bicyclic ethylene amine (CXII).

Once the bicyclic ring is formed with the side chain at $R_1$, —C($R_{10}$)—C($R_{11}$)—$R_2$—Ar/Het the nature of the side chain can be modified in a number of ways as is well known to those skilled in the art. For example, an amide product can be converted into 1-methyl derivatives by reacting the bicyclic keto amine (CXI) with methylmagnesium bromide followed by sodium cyanoborohydride treatment to yield methyl derivative (CXII), *J. Am. Chem Soc.*, 111, 2588 (1989). A $R_2$—Ar/Het compound where Ar/Het is a 4-methoxyphenyl compound (XCVIII, CXII) can be demethylated using lithium diphenylphosphine to give the phenolic derivative where $R_2$—Ar/Het is 1-(4-hydroxyphenyl)piperazine (EXAMPLE 72 and 73), *Tetrahedron Lett.*, 1071 (1976). The phenolic derivative can be reacted with triflic anhydride/pyridine in methylene chloride to give the triflate where $R_2$—Ar/Het is 1-(4-(trifluoromethanesulfonyloxy)phenyl)-piperazine (EXAMPLE 74 and 75), *J. Org. Chem.*, 38, 3673 (1973). The triflate can be reacted with carbon monoxide using palladium catalyst to give the methyl ester where $R_2$—Ar/Het is 1-(4-carbomethoxyphenyl)piperazine (EXAMPLE 76), *J. Chem. Soc., Chem. Commun.*, 904 (1987). The methyl ester can be reacted with formamide/sodium methoxide to give the carboxamide where $R_2$—Ar/Het— is —CO—$NH_2$ (EXAMPLE 77), *J. Org. Chem.*, 30, 2376 (1965). The carboxamide can be reacted with phosphorus oxychloride to give the nitrile ($R_2$—Ar/Het is —CN) (EXAMPLE 78), *Org. Synth., Coll.* Vol., 3, 535 (1955).

CHART W discloses a method of preparing the aromatic bicyclic amines (I) when the non-aromatic ring is either 5-, 6- or 7-membered, when $R_3$ is carbon and where the non-aromatic ring either contains unsaturation or has unsaturation attached directly to it at $C_1$. The mixture of unsaturated bicyclic esters (CVII-A+CVII-B+CVII-C) is hydrolyzed with base such as sodium hydroxide/methanol-water to give the corresponding mixture of carboxylic acids. This mixture is coupled with $R_2$—Ar/Het (LXV) using diethyl cyanophosphonate/triethylamine in methylene chloride, to give the mixture of unsaturated bicyclic keto amines (CXIV-A+CXIV-B+CXIV-C), *Tetrahedron Lett.*, 1595 (1973) and *Tetrahedron Lett.*, 2211 (1976). The products are separated by liquid chromatography. Each of the unsaturated bicyclic keto amines (CXIV-A, CXIV-B, and CXIV-C) is reduced with a reducing agent such as lithium aluminum hydride/aluminum chloride in tetrahydrofuran to give the corresponding unsaturated bicyclic amine (CXV-A, CXV-B, and CXV-C), *J. Am. Chem. Soc.*, 88, 729 (1966). Alternatively, the unsaturated bicyclic ester (CVII-B) is reduced with a reducing agent such as lithium aluminum hydride to give the unsaturated bicyclic alcohol (CXVI-B), see EXAMPLE 86. This alcohol is then converted into the unsaturated bicyclic with a leaving group (CXVII-BI), and then coupled with $R_2$—Ar/Het (LXV) as discussed above to give the unsaturated bicyclic amine (CXV-B), see EXAMPLE 87.

CHART X discloses the preparation of compounds where m and n are both 1. o-Halobenzoates (CXVIII) are subjected to palladium-catalyzed cross-coupling with the propargyl alcohol to give the o-substituted benzoate (CXIX). At this point, $R_5$-1 and $R_4$-1 are introduced via known alkyne-addition reactions to give the disubstituted olefinic alcohol (CXX), or the fully saturated system can be readily obtained by standard hydrogenation to provide the alcohol ester (CXXI). Carbonyl homologation using the lithium enolate of t-butyl acetate affords the β-carbonyl system (CXXII), which is subjected to the reductive cyclization procedure using triethylsilane/trimethylsilyl triflate, *J.Am. Chem. Soc.*, 111, 4136 (1989). The cyclized 7-member acid (CXIII) thus obtained is then coupled to $R_2$—Ar/Het (LXV) and the resulting amides reduced in a manner analogous to that shown in Charts Q, R, and S to provide the cyclized 7-member keto amine (CXXIV) and cyclized 7-member methylene amine (CXXV).

CHART Y discloses how once the bicyclic structure has been almost finalized it is possible to change substituents on the aromatic ring. In CHART Y, the substituent at $C_7$ has been changed from —Br to —CO—$NH_2$. The bromobicyclic amine (CXXVI) is transformed to the bicyclic 7-member amide (CXXVII) by standard metal-halogen exchange with t-butyl lithium followed by quenching of the resulting anion with trimethylsilyl isocyanate, *Tetrahedron Lett.*, 16, 981 (1975). While CHART Y discloses a particular transformation at a particular position it will be apparent to those skilled in the art that many other transformations can be performed at $C_6$-, $C_8$- and $C_9$-positions as well.

CHART Z discloses a preferred method of producing the compounds where $R_3$ is —O— and where m is 0 and n is 1. For the o-haloacetic acid (CXXVIII) it is preferred that $X_4$ be —Br. The o-haloacetic acid (CXXVIII) is reduced to give the corresponding o-halo alcohol (CXXIX) by reaction with borane or borane-methylsulfide. The o-halo alcohol (CXXIX) is transformed to the corresponding cinnamic ester (CXXX) by a Heck olefination preferably using ethyl acrylate and a palladium(O) catalyst. Using this reaction the hydroxy group does not have to be protected. The reaction can be performed neat or preferably with a solvent such as DMF at steam bath temperature (110°). The cinnamic ester (CXXX) is cyclized to give the important intermediate, the racemic aromatic bicyclic ester (CXXXI) by reaction with potassium t-butoxide (5 mole percent) in THF at 0°. Potassium is much preferred over lithium. The reaction is quenched by an acid such as acetic acid.

The above reaction is partially reversible. In this case it permits the transformation of the undesired (+)-aromatic bicyclic ester (CXXXI) by the Michael cyclization conditions with potassium t-butoxide via the cinnamic ester intermediate (CXXX) to racemic-aromatic bicyclic ester (CXXXI). Treating a 98/2 mixture of (+)/(−)-aromatic bicyclic ester (CXXXI) under the conditions described above produced a 1/1 racemic mixture. This racemic-aromatic bicyclic ester (CXXXI) can then be resolved by means discussed above to obtain additional desired (−)-aromatic bicyclic ester (CXXXI).

The aromatic bicyclic amines (I) contain an asymmetric center and therefore produce two enantiomers one "S" which is (−) and the other "R" which is (+). In some cases both enantiomers (+) and (−) are useful in the same way as the optically impure (racemic, ±) mixture. Hence, they may be utilized in the racemic form without separating them. However, if it is desired to utilize one of the enantiomers, the optically impure mixture can be resolved by means known to those skilled in the art. It is preferable to resolve the racemic mixture at the stage of the racemic bicyclic acid (LVII) using methods known to those skilled in the art, see for example, Optical Resolution Procedures for Chemical Compounds, Vol 1,: Amines and Related Compounds, Paul Newman, Optical Resolution Information Center, Manhattan College, Riverdale, N.Y., 10471, 1978 and the previous discussion of the relevant CHARTS. These optically pure compounds are then used in the same way as the racemic mixture. When used in this patent application the term aromatic bicyclic amines (I) refers to and includes both enantiomers as well as optically impure forms thereof, the most common of which is a racemic mixture (±, dl).

Some aromatic bicyclic amines (I) contain two asymmetric centers and therefore four enantiomers (SS, RR, SR, RS) exist producing two diastereomeric pairs of enantiomers, one SS,RR and the other SR,RS. The diastereomeric pairs of enantiomers can be readily separated by means known to those skilled in the art. When used in this patent application the term aromatic bicyclic amines (I) includes all four enantiomers as well as optically impure forms thereof, the most common of which is a racemic mixture (±).

The aromatic bicyclic amines (I) are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3—(CH_2)_n—COOH$ where n is 0 thru 4, $HOOC—(CH_2)$n-COOH where n is as defined above.

The aromatic bicyclic amines (I) of this invention posses selective pharmacological properties and are useful in treating humans who have a central nervous system disorders including psychosis, paraphrenia, psychotic depression, mania, schizophrenia, schizophreniform disorders. The aromatic bicyclic amines (I) are also useful in the treatment of vascular headaches, particularly migraine headaches. They are treated by administering to such human who is in need of treatment a central nervous system effective amount of a aromatic bicyclic amine (I). Other central nervous system disorders which can be treated with the aromatic bicyclic amines include anxiety, drug addiction, convulsive disorders, spectrum disorders, personality disorders, attention deficit disorders in children and adults, post traumatic stress syndrome and dysthymia. With regard to schizophrenia the bicyclic amines (I) are useful to treat psychotic, affective, psychomotor and vegative symptoms of schizophrenia as well as the extrapyramidal motor side effects of other antipsychotic (neuroleptic) drugs. This action will allow higher doses of the latter compounds to be used and greater antipsychotic efficacy to be obtained as a result of the reduction in dose limiting side effects. In addition to their central nervous system pharmacological activities, the compounds of this invention are also useful in treating cardiac arrhythmias and cardiac fibrillation.

In clinical practice the aromatic bicyclic amines (I) of the present invention will normally be administered orally, rectally or by injection in the form of pharmaceutical compositions containing the active ingredient either as a free base or as a pharmaceutically acceptable acid addition salt in association with one or more pharmaceutically acceptable carriers.

For therapeutical treatment of central nervous system disorders the suitable daily doses of the aromatic bicyclic amines (I) are from about 0.005 to about 50 mg/kg for oral application, preferably from about 0.1 to about 30 mg/kg, and from about 0.05 to about 10 mg/kg for parenteral application, preferably from about 0.03 to about 3 mg/kg. The use and administration to a patient to be treated in the clinic would be readily apparent to a person of ordinary skill in the art.

For purposes of treating cardiac arrhythmias and fibrillation, the aromatic bicyclic amines (I) will normally be given orally, rectally or by injection. The daily doses of the aromatic bicyclic amines (I) for cardiac purposes is from about 1 to about 300 mg/kg for oral administration, preferably from about 1 to about 50 mg/kg. When given parenterally the dose is from about 0.1 to about 100 mg/kg, preferably from about 0.5 to about 50 mg/kg.

The exact dosage and frequency of administration depends on the particular aromatic bicyclic amine (I) used, the particular condition being treated, the severity of the condition being treated, the age, weight, general physical condition of the particular patient, other medication the individual may be taking as is well known to those skilled in the art and can be more accurately determined by measuring the blood level or concentration of the aromatic bicyclic amine (I) in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3—C(=Z_1)$H. Groups $R_i$ and $R_j$ would represent monovalent variable substituents if attached to the formula $CH_3—CH_2—C(R_i)(R_j)—H$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent (X2) will be identified as being in the alpha (α) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(=$R_6$)- is defined to consist of two monovalent variable substituents, the two monovalent variable substituents are α-$R_{6-1}$:β-$R_{6-2}$, . . . α-$R_{6-9}$:β-$R_{6-10}$, etc, giving —C(α-$R_{6-1}$)(β-$R_{6-2}$)—, . . . —C(α-$R_{6-9}$)(β-$R_{6-10}$)—, etc. Likewise, for the bivalent variable $R_{11}$, —C(=$R_{11}$)—, two monovalent variable substituents are α-$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O— CO— . . . " means a lactone in which the carbonyl is bonded to $C_2$. However, when designated " . . . $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

When the term aromatic bicyclic amine (I) is used it includes a particular compound, enantiomers thereof and racemic forms thereof where such compounds exist and are pharmacologically useful as described herein.

All temperatures are in degrees Centigrade.

TLC refers to thin-layer chromatography.

HPLC refers to high pressure liquid chromatography.

THF refers to tetrahydrofuran.

DMSO refers to dimethylsulfoxide.

DMF refers to dimethylformamide.

Saline refers to an aqueous saturated sodium chloride solution.

IR refers to infrared spectroscopy.

NMR refers to nuclear (proton) magnetic resonance spectroscopy, chemical shifts are reported in ppm ($\delta$) downfield from tetramethylsilane.

TMS refers to trimethylsilyl.

—$\phi$ refers to phenyl ($C_6H_5$).

$[\alpha]_D^{25}$ refers to the angle of rotation of plant polarized light (specific optical rotation) at 25° with the sodium D line (5893A).

MS refers to mass spectrometry expressed as m/e or mass/charge unit. [M+H]+ refers to the positive ion of a parent plus a hydrogen atom. EI refers to electron impact. CI refers to chemical ionization. FAB refers to fast atom bombardment.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include mesylate, chloride, sulfate, phosphate, nitrate, citrate, $CH_3$—$(CH_2)_{n_1}$—$COO^{-1}$ where $n_1$ is 0 thru 4, $^{-1}OOC$—$(CH_2)_{n_1}$—$COO^{-1}$ where n is as defined above, $^{-1}OOC$—$CH$=$CH$—$COO^{-1}$, $\phi$—$COO^{-1}$, When solvent pairs are used, the ratios of solvents used are volume/volume (v/v).

When the solubility of a solid in a solvent is used the ratio of the solid to the solvent is weight/volume (wt/v).

THF is distilled from sodium or potassium metal and benzophenone prior to use. Other solvents were used as obtained from commercial suppliers.

mp are uncorrected.

The chemical structural formula for the EXAMPLEs below are set forth at the end of the EXAMPLE section and correspond to the EXAMPLEs in the following manner. E-x is the chemical structural formula for EXAMPLE x. Even though the EXAMPLE may have produced a particular salt form, the chemical structural formulas may identify the compound in its free (non-salt) form.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

[(3-Chloro-1-ethoxypropoxy)ethyl]benzene (LXIII)

3-Chloropropionaldehyde diethyl acetal (LXII, 30.66 g, 0.184 mol) is added to an ice-cooled solution of phenethyl alcohol (XLV, 20.44 g, 0.167 mol) in nitromethane (50 ml) is added and methanesulfonic acid (1.61 g, 0.0167 mol). After 30 min the ice bath is removed and the mixture is allowed to stir overnight. The mixture is then warmed in a water bath at approximately 40°–50° under reduced pressure for 10–20 min (no appreciable removal of nitromethane occurs but there is some further reaction observed). The mixture is partitioned between ethyl ether and saline, the layers are separated and the organic phase is dried over magnesium sulfate and concentrated under reduced pressure. The crude material is stored overnight in the refrigerator and then chromatographed on silica gel eluting with hexane and then ethyl acetate/hexane (2/98). The appropriate fractions are pooled and concentrated to give the title compound, NMR ($CDCl_3$) 1.20, 2.05, 2.87, 3.43–3.86, 4.69 and 7.24 $\delta$.

PREPARATION 2

1-(2-Chloroethyl)isochroman (LXIV)

Aluminum trichloride (17.44 g, 0.131 mol) is added, in aliquots over a period of 5–10 min, to an ice-cooled solution of [2-(3-chloro-1-ethoxypropoxy)ethyl]benzene (LXIII, PREPARATION 1, 28.87 g, 0.119 mol) in nitromethane (150 ml). After 30 min, hydrochloric acid (4N) is added and the mixture is partitioned between ether and saline. The organic phase, which contains nitromethane, is dried over magnesium sulfate and carefully concentrated under reduced pressure. The nitromethane/product mixture is then extracted six times with hexane and the hexane extracts are concentrated and chromatographed on silica gel eluting with ether/hexane (5/95). The appropriate fractions are pooled and concentrated to give the title compound, NMR ($CDCl_3$) 2.23, 2.36, 2.71, 2.97, 3.68, 3.79, 4.10, 4.93 and 7.06–7.23 $\delta$.

Example 1

1-(2-Chlorophenyl)-4-[2-(isochroman-1-yl)ethyl]piperazine hydrochloride (LXVI)

A mixture of 1-(2-chloroethyl)isochroman (LXIV, PREPARATION 2, 0.497 g, 2.53 mmol), 1-(2-chlorophenyl)piperazine dihydrochloride (XI, 0.952 g, 3.79 mmol), diisopropylethylamine (1.76 ml, 10.1 mmol) and ethylene glycol (5 ml) is heated at 100° for 16 hr. After cooling, the mixture is partitioned between ethyl acetate and saline. The organic phase is dried over magnesium sulfate, concentrated, and the residue chromatographed on silica gel eluting with methanol/dichloromethane (2/98) to give a material which is taken up in several mls of methanol. Methanol saturated with hydrochloric gas (6 ml) is added. After standing for several minutes, the mixture is concentrated under reduced pressure. Several mls of methanol are added back, followed by ether. The resulting solid is collected, washed with ether, and dried under vacuum to give the title compound; mp 197°–198°; MS ((m/z) 356; IR (mineral oil) 1093, 1481, 743, 2436 and 2426 $cm^{-1}$.

Example 2

1-(4-Fluorophenyl)-4-[2-(isochroman-1-yl)ethyl]piperazine dihydrochloride (LXVI)

Following the general procedure of EXAMPLE 1 and making non-critical variations but using 1-(1-fluorophenyl)

piperazine (XI) in place of 1-(2-chlorophenyl)-piperazine dihydrochloride (XI), the title compound is obtained, mp 195°–202°; MS (m/z) 340; IR (mineral oil) 2343, 1506, 1105, 1119 and 1237 cm$^{-1}$.

Example 3

1-[2-(Isochroman-1-yl)ethyl]-4-phenylpiperazine dihydrochloride (LXVI)

Following the general procedure of EXAMPLE 1 and making non-critical variations but using 1-phenylpiperazine hydrochloride (XI) in place of 1-(2-chlorophenyl)piperazine dihydrochloride (XI), the title compound is obtained, mp 178°–192° (decomp); MS (m/z) 322; IR (mineral oil) 2385, 2360, 1493, 1108 and 2210 cm$^{-1}$.

Example 4

1-[2-(Isochroman-1-yl)ethyl]-4-(2-pyridyl) piperazine dihydrochloride monohydrate (LXVI)

Following the general procedure of EXAMPLE 1 and making non-critical variations but using 1-(2-pyridyl) piperazine (XI) in place of 1-(2-chlorophenyl)piperazine dihydrochloride (XI), the title compound is obtained, mp 196°–201°; MS (m/z) 323; IR (mineral oil) 1612, 1438, 1637, 2380, 2433 and 1111 cm$^{-1}$.

Example 5

1-[2-(Isochroman-1-yl)ethyl]-4-phenylpiperidine hydrochloride (LXVI)

Following the general procedure of EXAMPLE 1 and making non-critical variations but using 4-phenylpiperidine (XIX) in place of 1-(2-chlorophenyl)-piperazine dihydrochloride (XI), the title compound is obtained, mp 195°–204°; MS (m/z) 321; IR (mineral oil) 2495, 2485, 696, 2534, 1109 and 756 cm$^{-1}$.

Example 6

1-(4-Chlorophenyl)-4-[2-(isochroman-1-yl)ethyl] piperazine dihydrochloride hemihydrate (LXVI)

Following the general procedure of EXAMPLE 1 and making non-critical variations but using 1-(4-chlorophenyl) piperazine dihydrochloride (XI) in place of 1-(2-chlorophenyl)piperazine dihydrochloride (XI), the desired product is obtained. It is chromatographed on silica gel eluting first with methanol/dichloromethane (2/98), and again from silica gel eluting with ethyl acetate/dichloromethane (1/1). The appropriate fractions are pooled and concentrated to give the title compound as the free base. The dihydrochloride salt is formed using hydrogen chloride gas in methanol to give the title compound, mp 189°–199°; MS (m/z) 356; IR (mineral oil) 2334, 2374, 2291, 1493, 1105, 1098, 1119 and 743 cm$^{-1}$.

Example 7

1-[2-(Isochroman-1-yl)ethyl]-4-(4-methoxyphenyl) piperazine dihydrochloride hemihydrate (LXVI)

Following the general procedure of EXAMPLE 1 and making non-critical variations but using 1-(4-methoxyphenyl)piperazine dihydrochloride (XI) in place of 1-(2-chlorophenyl)piperazine dihydrochloride (XI), the title compound is obtained, mp 201°–205°; MS (m/z) 352; IR (mineral oil) 1512, 2380, 1261, 1115, 1487, 1105 cm$^{-1}$.

Example 8

1-[2-(Isochroman-1-yl)ethyl]-4-(2-methoxyphenyl) piperazine dihydrochloride monohydrate (XI)

Following the general procedure of EXAMPLE 1 and making non-critical variations but using 1-(2-methoxyphenyl)piperazine (XI) in place of 1-(2-chlorophenyl)piperazine dihydrochloride (XI), the title compound is obtained, mp 196°–199°; MS (m/z) 352; IR (mineral oil) 1263, 764, 2363, 1450, 1119, 2381, 2302 and 1276 cm$^{-1}$.

Example 9

1-(4-Fluorophenyl)-4-[2-(isochroman-1-yl)methyl] piperazine dihydrochloride (LXVI)

Step 1: 1-(Bromomethyl)isochroman (LXIV, p=0)

A mixture of phenethyl alcohol (XLV, 1.20 g, 9.82 mmol), bromoacetaldehyde diethyl acetal (LXII, p=0, 2.13 g, 10.8 mmol), methanesulfonic acid (0.094 g, 0.98 mmol) and nitromethane (12 ml) is stirred overnight. TLC (ethyl ether/hexane, 5/95) indicated starting material still remained, so additional methanesulfonic acid (0.2 g) is added. After 5.5 hr the mixture is heated at 100° for 24 hr, at which time additional bromoacetaldehyde diethylacetal (1 ml) is added. Heating is continued for another 20 hr and then the reaction mixture is cooled and partitioned between ethyl ether, aq. sodium bicarbonate, and saline. The organic phase is separated and dried over magnesium sulfate, concentrated, and the residue chromatographed on silica gel eluting with ethyl ether/hexane (5/95). The appropriate fractions are pooled and concentrated to give the to give the mixed acetal (LXII). A solution of the mixed acetal (1.19 g, 4.36 mmol) in nitromethane (8 ml) is stirred at 0° and aluminum trichloride (0.64 g, 4.79 mmol) is added. After 25 min, hydrochloric acid (4N, 6 ml) is added and the mixture is partitioned between ether, hydrochloric acid (4N) and saline. The organic phase is dried over magnesium sulfate, concentrated, and chromatographed on silica gel eluting with ether/hexane (5/95). The appropriate fractions are pooled and concentrated to give 1-(bromomethyl) isochroman (LXIV), NMR (CDCl$_3$) 2.73, 3.01, 3.66, 3.85, 4.20, 5.03, 7.08, 7.16 and 7.23 δ.

Step 2: 1-(4-Fluorophenyl)-4-[2-(isochroman-1-yl) methyl]piperazine dihydrochloride (LXVI)

Following the general procedure of EXAMPLE 1 and making non-critical variations but using 1-(bromomethyl) isochroman (LXIV, Step 1) and 1-(4-fluorophenyl) piperazine (XI) and 1-(4-fluorophenyl) piperazine (XI), the title compound is obtained, mp 225°–229°; MS (m/z) 326; IR (mineral oil) 2278, 2266, 2198, 2336, 2246, 2365, 1514 and 748 cm$^{-1}$.

Example 10

1-(4-Fluorophenyl)-4-[2-(4,4-dimethylisochroman-1-yl)ethyl]piperazine dihydrochloride monohydrate (LXVI)

Step 1: 2-Methyl-2-phenylpropanol (XLV)

Ethyl 2-methyl-2-phenylpropionate LIII, 4.50 g, 23.5 mmol) is added to lithium aluminum hydride (0.908 g, 23.5 mmol) in dry ether (100 ml) cooled at 0°. After stirring for 2.5 hr, the mixture is quenched by adding, successively, water (1 ml), aqueous sodium hydroxide (15%, 1 ml) and water (3 ml). After stirring for several minutes, the solids are filtered off and washed well with ether. The filtrate is washed twice with saline and the organic phase is separated, dried over magnesium sulfate and concentrated to give 2-methyl-2-phenylpropanol (XLV), NMR (CDCl$_3$) 1.34, 3.62, 3.71, 7.22 and 7.31–7.41 6 δ.

Step 2: 1-(2-Chloroethyl)-4,4-dimethylisochroman (LXIV)

Methanesulfonic acid (0.21 g, 1.99 mmol) is added to a mixture of 3-chloropropionaldehyde diethyl acetal (LXII) and 2-methyl-2-phenylpropanol (XLV, Step I, 2.93 g, 19.9 mmol) in nitromethane (15 ml) cooled to 0°. After the addition the ice bath is removed and the reaction mixture is stirred overnight and then partitioned between ether and saline. The organic phase is separated and dried over magnesium sulfate, concentrated, and the residue chromatographed on silica gel eluting with a gradient of ethyl acetate/hexane (0.5/99.5 to 1/99 to 2/98). The appropriate fractions are pooled and concentrated to give the mixed acetal (LXIII). The mixed acetal (3.07 g, 11.3 mmol) is stirred at 0° in nitromethane (30 ml). Aluminum chloride (1.66 g, 12.4 mmol) is added over 10 min. The mixture is stirred an additional 25 min and then hydrochloric acid (4N, 4 ml) is added. The mixture is stirred for several minutes and then partitioned between dichloromethane, water, and aqueous sodium bicarbonate. The organic phase is separated, dried over sodium sulfate, concentrated and the residue chromatographed on silica gel (500 ml) eluting with an ethyl acetate/hexane gradient (0.5/99.5 to 2.5/97.5). The appropriate fractions are pooled and concentrated to give 1-(2-chloroethyl)-4,4-dimethylisochroman (LXIV), NMR (CDCl$_3$) 1.23, 1.30, 2.31, 3.52, 3.66, 3.64, 3.81, 4.96, 7.05, 7.14–7.25 and 7.34 δ.

Step 3: 1-(4-Fluorophenyl)-4-[2-(4,4-dimethylisochroman-1-yl)ethyl]piperazine dihydrochloride hydrate (LXVI)

Following the general procedure of EXAMPLE 1 and making non-critical variations but using 1-(2-chloroethyl)-4,4-dimethylisochroman (Step II, 0.362 g, 2.00 mmol) and 1-(4-fluorophenyl)piperazine (XI), the title compound is obtained, mp 238–°240°; MS (m/z) 368; IR (mineral oil) 1507, 2356, 1488, 1106, 1445, 2261, 1437, 1236, 761 and 1117 cm$^{-1}$.

Example 11

1-(4-Methoxyphenyl)-4-[2-(4,4-dimethylisochroman-1-yl)ethyl]piperazine dihydrochloride (LXVI)

Following the general procedure of EXAMPLE 1 and making non-critical variations but using 1-(2-chloroethyl)-4,4-dimethylisochroman (LXIV, EXAMPLE 10, Step II, 0.300 g, 1.33 mmol) and 1-(4-methoxyphenyl)piperazine (XI, 0.522 g, 2.00 mmol), the title compound is obtained as a dihydrochloride hemihydrate, mp 211°–219°; MS (m/z) 380; IR (mineral oil) 1512, 2377, 1261, 1116 and 1489 cm$^{-1}$.

Example 12

1-(2-Fluorophenyl)-4-[2-(isochroman-1-yl)ethyl]piperazine dihydrochloride (LXVI)

Following the general procedure of EXAMPLE 1 and making non-critical variations but using 1-(2-fluorophenyl)piperazine (XI, 0.496 g, 2.17 mmol) in place of 1-(2-chlorophenyl)piperazine dihydrochloride (XI), the title compound is obtained, mp 165°–169°; MS (m/z) 340; IR (mineral oil) 2351, 1448, 777, 2270, 1486, 2251, 758, 1241 and 1112 cm$^{-1}$.

Example 13

1-[3-(Trifluoromethyl)phenyl]-4-[2-(isochroman-1-yl)ethyl]piperazine dihydrochloride (LXVI)

Following the general procedure of EXAMPLE 1 and making non-critical variations but using 1-[3-(trifluoromethyl)phenyl]piperazine (XI, 0.29 ml, 1.92 mmole) in place of 1-(2-chlorophenyl)piperazine dihydrochloride (XI), the title compound is obtained, mp 216°–2190°; MS (m/z) 390; IR (mineral oil) 1114, 1309, 1168, 1295, 693 and 1321 cm$^{-1}$.

Example 14

1-[2-(Isochroman-1-yl)ethyl]-4-(2-methylphenyl)piperazine dihydrochloride (LXVI)

A mixture of 1-(2-chloroethyl)isochroman (LXIV, PREPARATION 2, 0.2466 g, 1.25 mmol), 1-(2-methylphenyl)piperazine dihydrochloride (XI, 0.5327 g, 2.14 mmol), diisopropylethylamine (0.98 ml, 5.63 mmol) and ethylene glycol (2.5 ml) is stirred under nitrogen at 100° for 3 days. The reaction mixture is cooled and partitioned between aqueous sodium bicarbonate and ethyl acetate. The combined organic phase is washed with saline, dried over magnesium sulfate and concentrated. The residue is chromatographed on silica gel eluting with methanol/dichloromethane (2/98). The appropriate fractions are pooled and concentrated to give the free base of the title compound. The dihydrochloride salt is formed using hydrochloric acid/methanol to give the title compound, mp 207.5°–210.5°; MS (m/z) 336; IR (mineral oil) 770, 2406, 2435, 2992, 2364 and 1489 cm$^{-1}$.

Example 15

1-(3-Chlorophenyl)-4-[2-(isochroman-1-yl)ethyl]piperazine dihydrochloride (LXVI)

Following the general procedure of EXAMPLE 1 and making non-critical variations but using 1-(3-chlorophenyl)piperazine dihydrochloride (XI, 0.5169 g (1.92 mmol) in place of 1-(2-chlorophenyl)piperazine dihydrochloride (XI), the title compound is obtained, mp 176.75°–179°; MS (m/z) 356; IR (mineral oil) 2269, 2295, 2166, 2130, 2200 and 1449 cm$^{-1}$.

Example 16

1-[2-(Isochroman-1-yl)ethyl]-4-(4-methylphenyl)piperazine dihydrochloride (LXVI)

Following the general procedure of EXAMPLE 1 and making non-critical variations but using 1-(4-methylphenyl)piperazine dihydrochloride (XI, 0.4701 g, 1.89 mmol) in place of 1-(2-chlorophenyl)piperazine dihydrochloride (XI), the title compound is obtained, mp 200°–205°; MS (m/z) 336; IR (mineral oil) 1104, 1119, 743, 1512, 2210 and 1487 cm$^{-1}$.

Example 17

1-[2-(Isochroman-1-yl)ethyl]-4-(3-methoxyphenyl)piperazine dihydrochloride (LXVI)

Following the general procedure of EXAMPLE 1 and making non-critical variations but using 1-(3-methoxyphenyl)piperazine dihydrochloride (XI, 0.5173 g, 1.95 mmol) in place of 1-(2-chlorophenyl)piperazine dihydrochloride (XI), the title compound is obtained (chromatography using methanol/dichloromethane, 1/99), mp 189.5°–193°; MS (m/z) 352; IR (mineral oil) 2373, 1460, 1512, 1048, 748 and 1291 cm$^{-1}$.

Example 18

1-(3,4-Dichlorophenyl)-4-[2-(isochroman-1-yl)ethyl] piperazine dihydrochloride (LXVI)

Following the general procedure of EXAMPLE 1 and making non-critical variations but using 1-(3,4-dichlorophenyl)piperazine (XI, 0.4427 g, 1.92 mmol) in place of 1-(2-chlorophenyl)piperazine dihydrochloride (XI), the title compound (purified by chromatography eluting with methanol/dichloromethane (1/99)) is obtained, MS (m/z) 390; IR (mineral oil) 1485, 1108, 2544, 763, 751 and 2450 cm$^{-1}$.

Example 19

1-[3-(Isochroman-1-yl)propyl]-4-(4-methoxyphenyl) piperazine dihydrochloride (XC)

A mixture of 1-(2-chloroethyl)isochroman (LXIV, PREPARATION 2, 0.9874 g, 5.02 mmol), sodium cyanide (0.3793 g, 7.74 mmol), sodium iodide (a few mg) and DMF (5 ml) is heated overnight at 856. Additional sodium cyanide (0.5826 g, 11.9 mmol) is then added in two portions, along with DMF (14 ml) and a few mgs of sodium iodide. The mixture is heated at 97° for another two days and then cooled and poured into water. The mixture is extracted several times with ethyl acetate and the combined organic phase is backwashed twice with water, followed by two saline washes, then dried over magnesium sulfate and concentrated to dryness. The crude product is chromatographed on silica gel eluting with ethyl acetate/hexane (10/90). The appropriate fractions are pooled and concentrated to give 1-(2-cyanoethyl)isochroman (LXVI), NMR (CDCl$_3$) 2.11, 2.27–2.72, 2.98, 3.77, 4.13, 4.86 and 7.17 δ.

A mixture of 1-(2-cyanoethyl)isochroman (LVI, 0.509 g, 2.72 mmol) and hydrochloric acid (6N, 4.6 ml) is heated overnight at 100°. The mixture is heated overnight again after addition of 1,4-dioxane (0.6 ml). Additional hydrochloric acid (6N) is added and the temperature is increased to 127° for 5 hr. After cooling, the mixture is partitioned between water and ether and the combined organic phase is dried with magnesium sulfate and concentrated to dryness to yield 3-(isochroman-1-yl)propionic acid (LXXVII), NMR (CDCl$_3$) 2.11, 2.27–2.60, 2.66, 2.97, 3.76, 4.12, 4.84 and 7.15 δ.

A mixture of 3-(isochroman-1-yl)propionic acid (LXXXVII, 0.5054 g, 2.45 mmol) in THF (2.8 ml) is added to an ice-cooled slurry of lithium aluminum hydride (0.1021 g, 2.69 mmol) in THF (3 ml). After the mixture had stirred for 30 min at 0°, it is quenched slowly with water (0.10 ml) water and allowed to stir for 15 min. An aqueous sodium hydroxide solution (15%, 0.10ml) is added and again the reaction stirred 15 min. After a final addition of water (0.3 ml) the solids are removed by filtration and washed with ether. The filtrate is washed with saline, dried over magnesium sulfate and concentrated to dryness. The crude product is chromatographed on silica gel eluting with methanol/dichloromethane (2/98). The appropriate fractions are pooled and concentrated to give 3-(isochroman-1-yl) propanol (LXXXVIII), NMR (CDCl$_3$) 1.73, 1.92, 2.11, 2.34, 2.68, 3.03, 3.66, 3.78, 4.17, 4.82 and 7.15 δ.

Methanesulfonyl chloride (0.07 ml, 0.904 mmol) is added to an ice-cooled mixture of 3-(isochroman-1-yl)propanol (LXXXVIII, 0.1575 g, 0.819 mmol) in pyridine (2.2 ml). The mixture is stirred for 4 hr at 0° and then stored overnight in the refrigerator. The mixture is then partitioned between dichloromethane and water and the combined organic phase is backwashed with water, dried with magnesium sulfate and concentrated to give 3-(isochroman-1-yl)propanol-O-methane sulfonate (LXXXIX), NMR (CDCl$_3$) 1.91, 2.08, 2.67, 3.00, 3.03, 3.76, 4.12, 4.30, 4.81 and 7.15 δ.

A mixture of 3-(isochroman-1-yl)propanol-O-methane sulfonate (LXXXIX, 0.1911 g, 0.707 mmol), 1-(4-methoxyphenyl)piperazine dihydrochloride (IX, 0.2566 g, 0.968 mmol), diisopropylethylamine (0.49 ml, 2.81 mmol) and ethylene glycol (1.4 ml) are stirred at 50° for 78 min. After cooling, the mixture is partitioned between ethyl acetate and aqueous sodium bicarbonate solution. The organic phase is backwashed with saline and then dried over magnesium sulfate. After concentration, the residue is chromatographed on silica gel eluting first with methanol/dichloromethane (1/99), followed by methanol/dichloromethane (3/97). The appropriate fractions are pooled and concentrated to give the free base of the title compound. The dihydrochloride salt is prepared using hydrogen chloride gas in methanol to give the title compound, mp 202°–206°; MS (m/z) 366; IR (mineral oil) 1512, 2396, 1262, 1027, 2501 and 2465 cm$^{-1}$.

Example 20

1-[2-(6-Fluoroisochroman-1-yl)ethyl]-4-(4-methoxyphenyl)piperazine dihydrochloride (LXVI)

Step 1: Borane-dimethyl sulfide complex (9.15 ml, 96.5 mmol) is added dropwise and then faster as gas evolution slowed, to an ice-cooled mixture of 3-fluorophenyl acetic acid (XXXIX, 4.96 g, 32.2 mmol) in THF (30 ml). After 2 hr methanol is added dropwise over the course of several hours. The solvents are then removed under reduced pressure and methanol is again added and removed under reduced pressure. The methanol addition/removal is repeated three times and then the residue is partitioned between dichloromethane and aqueous sodium bicarbonate. The organic layers are dried over sodium sulfate and concentrated to give 2-(3-fluorophenyl)ethanol (LXV), MS (m/z) 140; IR (neat) 1590, 1046, 1450, 1141, 782, 1488 and 691 cm$^{-1}$.

A mixture of 2-(3-fluorophenyl)ethanol (LXV, 4.53 g, 32.3 mmol), 3-chloropropionaldehyde diethyl acetal (LXII, 8.08 g, 48.5 mmol), dichloromethane (20 ml), methanesulfonic acid (0.93 g, 9.7 mmol) and 10.6 g of 4A molecular sieves is stirred at 20°–250 for 20 hr. The molecular sieves are then removed by filtration and the filtrate is partitioned between dichloromethane and aqueous sodium bicarbonate. The organic phase is dried over sodium sulfate, concentrated and the crude product is chromatographed on silica gel eluting with ether/hexane (10/90). The appropriate fractions are pooled and concentrated to give the mixed acetal (LXIII) containing a small amount of an impurity, NMR (CDCl$_3$) 1.17, 2.05, 2.88, 3.4–3.7, 3.83, 4.68, 6.88–7.02 and 7.24 δ.

Step 2 (Method 1): Aluminum trichloride (2.7 g, 20.1 mmol) is added to an ice-cooled mixture of the mixed acetal (LXIII, Step 1, 5.24 g, 20.1 mmol) in nitromethane (10 ml). After 1 hr ice is added and the mixture is partitioned between dichloromethane and hydrochloric acid (1N). The organic phase is washed with saline and dried over sodium sulfate. After concentration, the crude product is chromatographed on silica gel eluting with ethyl acetate/hexane (2.5/97.5) to give 1-(2-chloroethyl)-6-fluoroisochroman (LXIV).

Step 2 (Method 2): A solution of the mixed acetal (LXIII, Step 1, 0.141 g, 0.54 mmol) in nitromethane (2 ml) is warmed to 45° C. and titanium tetrachloride (1M in dichloromethane, 0.40 ml) is added as a bolus. After 10 min the mixture is partitioned between dichloromethane and aqueous sodium bicarbonate. The organic phase is separated and dried over sodium sulfate, concentrated and the crude product chromatographed on silica gel eluting with ethyl acetate/hexane (5/95). The appropriate fractions are pooled and concentrated to give 1-(2-chloroethyl)-6-fluoroisochroman (LXIV), NMR (CDCl$_3$) 2.20, 2.31, 2.70, 2.97, 3.5–3.85, 4.10, 4.40, 6.8–6.93, 7.04 δ.

Step 3: Following the general procedure of EXAMPLE 1 and making non-critical variations but using 1-(2-chloroethyl)-6-fluoroisochroman (LXIV, Step 2, 0.242 g, 1.22 mmol) and 1-(4-methoxyphenyl)piperazine dihydrochloride (XI, 0.484 g, 1.83 mmol), the title compound is obtained, mp 215°–218°; MS (m/z) 370; IR (mineral oil) 1512, 1115, 1501, 1261, 1246, 1487 cm$^{-1}$.

Example 21

1-[2-(6-Fluoroisochroman-1-yl)ethyl]-4-(4-fluorophenyl)piperazine dihydrochloride (LXVI)

Following the general procedure of EXAMPLE 1 and making non-critical variations but using 1-(2-chloroethyl)-6-fluoroisochroman (LXIV, EXAMPLE 20—Step 2, 0.167 g, 0.84 mmol) and 1-(4-fluorophenyl)piperazine dihydrochloride (XI, 0.227 g, 1.26 mmol), the title compound is obtained, mp 201°–204°; MS (m/z) 358; IR (mineral oil) 2346, 1501, 1507, 1117, 1245, 1113 cm$^{-1}$.

Example 22

1-[2-(6-Bromoisochroman-1-yl)ethyl]-4-(4-methoxyphenyl)piperazine dihydrochloride (LXI)

Following the general procedure of EXAMPLE 20, Step 1, and making non-critical variations 3-bromophenylacetic acid (XXXIX, 5.12 g, 23.8 mmol) is converted to 2-(3-bromophenyl)ethanol (XLV), NMR (CDCl$_3$) 1.41, 2.84, 3.86, 7.18, 7.37 δ.

Titanium tetrachloride (1M in methylene chloride, 51 ml) is added over a period of 10 min to an ice-cooled mixture of 2-(3-bromophenyl)ethanol (XLV, 4.34 g, 21.6 mmol) and ethyl 3,3-diethoxypropionate (LXXXV, 4.93 g, 25.9 mmol) in nitromethane (5 ml). After stirring for 10 min, the ice bath is removed and the mixture is allowed to stir at 20–250 for 5 hr, at which time it is poured onto ice/aqueous hydrochloric acid (~1N). The mixture is extracted with dichloromethane and backwashed with hydrochloric acid (0.5N)/saline and saline. The organic phase is separated dried over sodium sulfate, concentrated, and the residue chromatographed on silica gel eluting with ethyl acetate/hexane (5/95). The appropriate fractions are pooled and concentrated to give ethyl (6-bromoisochroman-1-yl)acetate (LXXVII), NMR (CDCl$_3$) 1.28, 2.66–2.87, 2.96, 3.768, 3.807, 4.11, 4.21, 5.19, 6.93 and 7.28 δ.

Sodium hydroxide (1N, 19.8 ml) is added to ethyl (6-bromoisochroman-1-yl)acetate (LXXVII, 3.96 g, 13.2 mmol) in ethanol (20 ml). The mixture is stirred for 2 hr, at which time the ethanol is removed under reduced pressure. The residue is acidified with hydrochloric acid (4N, approximately 6 ml) and extracted with ether. The organic phase is separated and is washed with dilute aqueous hydrochloric acid, dilute aqueous hydrochloric acid /saline, and saline, dried over magnesium sulfate, and concentrated under reduced pressure. The (6-bromoisochroman-1-yl)acetic acid (LXVIII) thus obtained is stirred at 0° with THF (20 ml) and borane-methyl sulfide (3.75 ml, 39.6 mmol) is added over several minutes. After stirring at 0° for 3.5 hr, the mixture is allowed to slowly warm to 20°–250 and methanol is added to quench excess borane, until no further gas evolution is observed. The mixture is then concentrated under reduced pressure and methanol is again added and removed under reduced pressure. This procedure is repeated twice and the residue is then partitioned between dichloromethane, aqueous sodium bicarbonate and saline. The organic phase is separated, dried over sodium sulfate and concentrated to give 2-(6-bromoisochroman-1-yl)ethanol (LXXIX), NMR (CDCl$_3$) 2.04, 2.21, 2.65, 3.02, 3.70–3.87, 4.17, 4.92, 6.93 and 7.28 δ.

Pyridine (0.044 ml, 0.54 mmol) is added to 2-(6-bromoisochroman-1-yl)ethanol (LXXIX, 0.0925 g, 0.36 mmol) and dichloromethane (2 ml). This is followed by methanesulfonyl chloride (0.036 ml, 0.47 mmol). The mixture is stirred overnight and then an additional pyridine (0.022 ml) and methanesulfonyl chloride (0.018 ml) are added. The mixture is stirred an additional 6.5 hr and then is partitioned between dichloromethane, hydrochloric acid (0.25N) and saline. The organic phase is separated, dried over sodium sulfate and concentrated under reduced pressure to give 0.128 g of 2-(6-bromoisochroman-1-yl)ethanol-O-mesylate (LXXX). This material is stirred at 600 for 3.5 hr with diisopropylethylamine (0.196 g, 1.52 mmol) and 1-(4-methoxyphenyl)piperazine dihydrochloride (XI, 0.172 g, 0.651 mmol) in ethylene glycol (2 ml). After cooling, the mixture is partitioned between dichloromethane and aqueous sodium bicarbonate. The organic phase is separated, dried over sodium sulfate and concentrated under reduced pressure. The residue is chromatographed on silica gel eluting with methanol/dichloromethane (2/98). The appropriate fractions are pooled and concentrated to give the free base of the product. The dihydrochloride salt is prepared using hydrochloric acid in methanol to give the title compound, mp 205°–208°; MS (m/z) 430, 432; IR (mineral oil) 1512, 2384, 1262, 1116, 1482 and 1105 cm$^{-1}$.

Example 23

1-[2-(6-Chloroisochroman-1-yl)ethyl]-4-(4-methoxyphenyl)piperazine dihydrochloride (LXXXI)

Borane-methyl sulfide (10.8 ml) is added to an ice-cooled solution of 3-chlorophenylacetic acid (XXXIX, 6.498g, 0.0381 mole) in THF (20 ml). The mixture is stirred for 1.5 hr in an ice/water bath, followed by an additional 30 min at 20°–250. The mixture is then cooled again at 0° and excess borane is cautiously quenched over several hours with the addition of methanol. The mixture is concentrated under reduced pressure, methanol is added to the residue, and the mixture is again concentrated under reduced pressure (repeated twice). The resulting material is partitioned between dichloromethane and saturated aqueous sodium bicarbonate. The combined organic phases are dried over magnesium sulfate and concentrated to give 3-chlorophenethyl alcohol (XLV), NMR (CDCl$_3$) 1.76, 2.82, 3.83 and 7.09–7.32 δ.

A mixture of 3-chlorophenethyl alcohol (XLV, 5.9055 g, 0.0398 mol), 3-chloropropionaldehyde diethyl acetal (LXII, 7.2 ml, 0.0430 mol) and nitromethane (3 ml) is cooled in an ice/water bath. Titanium tetrachloride (1M in dichloromethane, 88 ml, 0.088 mol) is added dropwise and the mixture is heated at 45° for 3 hr. After cooling, the mixture is poured onto ice/aqueous hydrochloric acid (1N) and extracted with dichloromethane. The combined organic layers are backwashed with hydrochloric acid (1N) and filtered through a pad of Celite topped with sodium sulfate. The filtrate is concentrated and chromatographed twice on silica gel eluting with ethyl acetate/hexane (5/95). The appropriate fractions are pooled and concentrated to give 6-chloro-1-(2-chloroethyl)isochroman (LXIV), NMR (CDCl$_3$) 2.23, 2.70, 2.93, 3.75, 4.09, 4.89, 7.01 and 7.16 δ.

Following the general procedure of EXAMPLE 1 and making non-critical variations but using 6-chloro-1-(2-chloroethyl)isochroman (LXIV, 0.2315 g, 0.972 mmol) and 1-(4-methoxyphenyl)piperazine dihydrochloride (XI, 0.3772 g, 1.00 mmol), the title compound is obtained, mp 203.5°–208°; MS (m/z) 386; IR (mineral oil) 1512, 2388, 1485, 1261, 1118 and 1105 cm$^{-1}$.

Example 24

1-[2-(6-Chloroisochroman-1-yl)ethyl]-4-(4-fluorophenyl)piperazine dihydrochloride (LXVI)

Following the general procedure of EXAMPLE 1 and making non-critical variations but using 6-chloro-1-(2-chloroethyl)isochroman (LXIV, EXAMPLE 23, 0.2041 g, 0.883 mmol) and 1-(4-fluorophenyl)piperazine (XI, 0.2205 g, 1.22 mmol), the title compound is obtained, mp 197°–198.5°; MS (m/z) 374; IR (mineral oil) 2344, 1506, 1105, 1486, 1119 and 1238 cm$^{-1}$.

Example 25

1-(4-Methoxyphenyl)-4-[2-(4-methylisochroman-1-yl)ethyl]-piperazine dihydrochloride, Isomer A (LXVI)

Step 1: Oxalyl chloride (12.5 ml, 0.1433 mol) is added to 2-phenylpropionic acid (XXXIX, 3.0 ml, 0.0220 mol) and the mixture is stirred (neat) for 38 min. The excess oxalyl chloride is then removed under reduced pressure. Dichloromethane is added to the residue and the resulting mixture is concentrated under reduced pressure to remove residual oxalyl chloride. Dichloromethane is added a final time and the solution concentrated under reduced pressure to give 2-phenylpropionic acid chloride (XL).

Step 2: A mixture of (4S)-(−)-4-benzyl-2-oxazolidinone (3.903 g, 22.0 mmol) in THF (23 ml) is cooled at −78° and butyl lithium (1.6M in hexane, 14.7 ml, 23.5 mmol) is added. The mixture is stirred for 50 min and then the portion of 2-phenylpropionic acid chloride (XL) from above, in THF (8 ml) is added dropwise to the mixture. The mixture is stirred for 1 hr at −78° and then allowed to warm to 20°–25°. Saturated aqueous sodium bicarbonate solution (100 ml) is added and the phases separated. The aqueous phase is washed with ether and the combined organic phases are then washed several times with saturated aqueous sodium bicarbonate followed by a saline wash. The organic phase is dried over magnesium sulfate and concentrated. The resulting diastereomers are separated on silica gel eluting with ethyl acetate/hexane (7/93) followed by ethyl acetate/hexane (12/88). The appropriate fractions are pooled and concentrated to give (4S)-4-(phenylmethyl)-3-(2-phenylpropionyl)-2-oxazolidinone (XLI, Isomer I, less polar isomer), NMR (CDCl$_3$) 1.55, 2.79, 3.35, 4.09, 4.58, 5.12 and 7.30 δ; and (4S)-4-(phenylmethyl)-3-(2-phenylpropionyl)-2-oxazolidinone (XLII, Isomer II, more polar isomer), NMR (CDCl$_3$) δ1.52, 2.58, 3.09, 4.08, 4.19, 4.75, 5.11, 6.95 and 7.31 δ.

Step 3: A mixture of (4S)-4-(phenylmethyl)-3-(2-phenylpropionyl)-2-oxazolidinone (XLI, Isomer I, 2.651 g, 8.57 mmol) in THF (10 ml) is added dropwise to a cooled slurry of lithium aluminum hydride (0.3518 g, 9.27 mmol) in THF (10 ml). After the mixture had stirred for 28 min at 0°, water (0.35 ml) is added and the mixture is stirred for 15 min. Sodium hydroxide (15% aqueous solution, 0.35 ml) is added and again the mixture is allowed to stir for 15 min. After the final addition of water (1.05 ml), the salts are removed by filtration and washed with ether. The combined filtrates are washed with saline, dried over magnesium sulfate and concentrated. The residue is chromatographed on silica gel eluting with ethyl acetate/hexane (15/85). The appropriate fractions are pooled and concentrated to give 2-phenylpropanol (XLIII, Isomer Ia), NMR (CDCl$_3$) 1.28, 1.35, 2.95, 3.71 and 7.26 δ.

Step 4: A mixture of 2-phenylpropanol (XLIII, Isomer Ia, 0.848 g, 6.23 mmol), 3-chloropropionaldehyde diethylacetal (LXII, 1.15 ml, 6.87 mmol), methanesulfonic acid (0.08 ml, 1.23 mmol) and nitromethane (1.9 ml) is stirred overnight at 20°–25°. The mixture is then poured into saline and extracted with ether. The combined organic phase is backwashed with saline, dried over magnesium sulfate, concentrated, and chromatographed on silica gel eluting first with hexane, followed by ethyl acetate/hexane (2/98). The appropriate fractions are pooled and concentrated to give the mixed acetal (LXIII) NMR (CDCl$_3$) 1.22, 1.25, 2.02, 2.97, 3.55, 4.65 and 7.24 Δ.

Step 5: A mixture of the mixed acetal (LXIII, 1.213 g, 4.76 mmol) and nitromethane (6.3 ml) is cooled at 0°. Aluminum trichloride (0.6988 g, 5.24 mmol) is added to the solution, in portions, over 5 min and the mixture is stirred for 1 hr. Additional aluminum trichloride (0.103 g, 0.771 mmol) is then added and the mixture stirred another hour, at which time hydrochloric acid (4N, 2.7 ml) is added. Additional water is added to help dissolve the salts and the mixture is extracted with ether several times. The combined organic phase is backwashed twice with hydrochloric acid (1N), once with saline, and then dried over magnesium sulfate and concentrated under reduced pressure. Material which remained at the origin as evidenced by thin layer chromatography (ethyl ether/hexane, 5/95) is removed by filtration through a silica gel plug using ether/hexane (5/95) followed by ether/hexane (10/90). The material from the product fractions is rechromatographed on a sized 40–60 micron silica gel column eluting with ether/hexane (1/99). The appropriate fractions are pooled and concentrated to give the less polar compound, 1-(2-chloroethyl)-4-methylisochroman (LXIV), Isomer III, NMR (CDCl$_3$) 1.33, 2.24, 2.40, 2.80, 3.65, 3.82, 4.90, 7.07, 7.19 δ; and the more polar diastereomer, 1-(2-chloroethyl)-4-methylisochroman, Isomer IV, NMR (CDCl$_3$) 1.25, 2.28, 2.97, 3.46, 3.66, 3.80, 4.03, 4.97, 7.06 and 7.22 δ.

Step 6: Following the general procedure of EXAMPLE 1 and making non-critical variations but using 1-(2-chloroethyl)-4-methyl-isochroman (LXIV, Isomer III, 0.0839 g, 0.398 mmol) and 1-(4-methoxyphenyl)piperazine dihydrochloride (XI, 0.1547 g, 0.583 mmol) the title compound (Isomer A) is obtained, mp 216°–218°; MS (m/z) 366; IR (mineral oil) 1512, 2345, 2376, 2407, 1261, 1126 cm$^{-1}$.

Example 26

1-(4-Methoxyphenyl)-4-[2-(4-methylisochroman-1-yl)ethyl]piperazine dihydrochloride, Isomer B (LXVI)

Following the general procedure of EXAMPLE 1 and making non-critical variations but using 1-(2-chloroethyl)-

4-methylisochroman (LXIV, EXAMPLE 25, Isomer IV, 0.0702 g, 0.333 mmol) and 1-(4-methoxyphenyl)piperazine dihydrochloride (XI, 0.1268 g, 0.478 mmol), the title compound (Isomer B) is obtained, mp 209°–211.5°; MS (m/z) 366; IR (mineral oil) 1513, 2344, 1261, 1448, 761, 1490 cm$^{-1}$.

Example 27

1-(4-Methoxyphenyl)-4-[2-(4-methylisochroman-1-yl)ethyl]piperazine dihydrochloride, Isomer C (LXVI) 1-(4-Methoxyphenyl)-4-[2-(4-methylisochroman-1-yl)ethyl]piperazine dihydrochloride, Isomer D (LXVI)

Following the general procedure of EXAMPLEs 25 and 26 and making non-critical variations but using (4S)-4-(phenylmethyl)-3-(2-phenylpropionyl)-2-oxazolidinone (XLII, Isomer II, EXAMPLE 25—Step 2) in place of Isomer I, a less polar compound Isomer C and a more polar compound Isomer D are obtained, Isomer C—mp 211.5°–215°; MS (m/z) 366; IR (mineral oil) 1512, 2376, 2345, 2406, 1261 and 1126 cm$^{-1}$; Isomer D—mp 210°–212.25°; MS (m/z) 366; IR (mineral oil) 1513, 2345, 1261, 761, 1489, 2214 cm$^{-1}$.

Example 29

2-[2-(Isochroman-1-yl)ethyl]-6,7-dimethoxy-1,2,3,4-tetrahydroisoquinoline hydrochloride (LXVI)

Following the general procedure of EXAMPLE 1 and making non-critical variations but using 6,7-dimethoxy-1,2,3,4-tetrahydroquinoline hydrochloride (0.430 g, 1.89 mmol) in place of 1-(2-chlorophenyl)piperazine, the title compound is obtained, mp=209°–211°; MS (m/z) 353; IR (mineral oil) 1228, 1124, 1520, 1116 and 2484 cm$^{-1}$.

Example 30

4'-[4-[2-(Isochroman-1-yl)ethyl]piperazin-1-yl] benzophenone dihydrochloride (LXVI)

Following the general procedure of EXAMPLE 1 and making non-critical variations but using 4'-piperazinoacetophenone (XI, 0.692 g, 2.88 mmol) in place of 1-(2-chlorophenyl)piperazine dihydrochloride (XI), the title compound is obtained, mp=128°–138°; MS (m/z) 364; IR (mineral oil) 1683, 1600, 1270, 1112, 1257, 1359 cm$^{-1}$.

Example 31

1-(2-Cyanophenyl)-4-[2-(isochroman-1-yl)ethyl] piperazine hydrochloride (LXVI)

Following the general procedure of EXAMPLE 1 and making non-critical variations but using 1-(2-cyanophenyl) piperazine (XI, 0.2956 g, 1.58 mmol) in place of 1-(2-chlorophenyl)piperazine dihydrochloride (XI), the title compound is obtained, mp 203°–204°; MS (m/z) 347; IR (mineral oil) 755, 2453, 1492, 1107, 746, 2526 cm$^{-1}$.

Example 32

1-[2-(Isochroman-1-yl)ethyl]-4-(2-pyrimidyl) piperazine dihydrochloride monohydrate (LXVI)

Following the general procedure of EXAMPLE 1 and making non-critical variations but using 1-(2 pyrimidyl) piperazine dihydrochloride (XI, 0.3433 g, 1.45 mmol) in place of 1-(2-chlorophenyl)piperazine dihydrochloride (XI), the title compound is obtained, mp=203°–204.25°; MS (m/z) at 324; IR (mineral oil) 1624, 1609, 1451, 2454, 1347 and 2539 cm$^{-1}$.

Example 33

1-(4-Methoxyphenyl)-4-[2-(7-methylisochroman-1-yl)ethyl]piperazine dihydrochloride (LXXXI)

Following the general process of EXAMPLE 22 and making non-critical variations but using 4-methylphenethyl alcohol (XLV) in place of 2-(3-bromophenyl)ethanol (XLV), the title compound is obtained, mp=204.5°–206°; MS (m/z) 366; IR 1522, 1274, 2140, 2120, 1446 and 2275 cm$^{-1}$.

Example 34

1-(4-Methoxyphenyl)-4-[2-(6-methylisochroman-1-yl)ethyl]piperazine dihydrochloride (LXXXI)

Following the general process of EXAMPLE 22 and making non-critical variations but using 3-methylphenethyl alcohol (XLV) in place of 2-(3-bromophenyl)ethanol (XLV), the title compound is obtained, mp=211.5°–213°; MS (m/z) 366; IR (mineral oil) 2389, 1512, 1114, 1262, 1438 and 1487 cm$^{-1}$.

Example 35

1-[2-(Isochroman-1-yl)ethyl]-4-(2-methylphenyl) piperidin-4-ol hydrochloride (LXVI)

Following the general procedure of EXAMPLE 1 and making non-critical variations but using 4-(2-methylphenyl)-4-hydroxypiperidine (XV, 0.3045 g, 1.59 mmol) in place of 1-(2-chlorophenyl)piperazine dihydrochloride (XI), the impure title compound is produced. It is purified by chromatography eluting with methanol/dichloromethane (3/97) containing approximately 5% ammonium hydroxide by volume. The appropriate fractions are pooled and concentrated. The concentration is followed by crystallization from ethyl acetate/hexane and then salt formation with hydrochloric acid/methanol gives the title compound, mp=190°–191°; MS (m/z) 351; IR (mineral oil) 1106, 754, 2574, 3377, 762 and 2597 cm$^{-1}$.

Example 36

4-(4-Trifluoromethylphenyl)-4-[2-(isochroman-1-yl) ethyl]piperidin-4-ol hydrochloride (LXVI)

Following the general procedure of EXAMPLE 1 and making non-critical variations but using 4-[4-(trifluoromethyl)phenyl]-4-hydroxypiperidine (XV, 0.368 g, 1.58 mmol) in place of 1-(2-chlorophenyl)piperazine dihydrochloride (XI) and after purification and crystallization from ethyl acetate/hexane, the title compound is obtained, mp 170°–173°; MS (m/z) 405; IR (mineral oil) 1116, 1334, 1166, 846, 1073, 1411 cm$^{-1}$.

Example 37

1-[2-(6-Bromoisochroman-1-yl)ethyl]-4-(2-bromo-4-methoxyphenyl)piperazine dihydrochloride (LXXXI)

A mixture of 1-(4-methoxyphenyl)piperazine (XI, 7.41 g) and ethyl formate (108 ml) is stirred at reflux for 3 hr. The mixture is then cooled, concentrated, and the residue chromatographed on silica gel eluting with methanol/dichloromethane (2/98). The appropriate fractions are pooled and concentrated to give 1-formyl-4-(4-methoxyphenyl)piperazine (VI), NMR (CDCl$_3$) δ3.05, 3.54, 3.71, 3.78, 6.88, 8.10.

Sodium acetate (VI, 9.702 g, 0.1182 mol) is added to a mixture of 1-formyl-4-(4-methoxyphenyl)piperazine (VI, 5.17 g, 23.5 mmol) and acetic acid (102 ml). When the sodium acetate had completely dissolved, a solution of bromine (7.912 g, 49.5 mmol) in acetic acid (9.5 ml) is added over 14 min. After 35 min the mixture is poured into water poured into water and extracted exhaustively with dichloromethane. The combined organic extracts are backwashed with water, followed by saturated sodium bicarbonate, dried over sodium sulfate and concentrated. The residue is chromatographed on silica gel eluting first with ethyl acetate/dichloromethane (10/90) and then ethyl acetate/dichloromethane (20/80). The appropriate fractions are pooled and concentrated to give 1-formyl-4-(2-bromo-4-methoxyphenyl)piperazine (VII), NMR (CDCl$_3$) 2.94, 3.55, 3.74, 3.78, 6.83, 6.97, 7.16 and 8.10 δ.

A mixture of 1-formyl-4-(2-bromo-4-methoxyphenyl)piperazine (VII, 3.92 g, 3.1 mmol) and hydrochloric acid (4N, 70 ml) is heated at 100° for 50 min. The mixture is then concentrated under reduced pressure to remove most of the aqueous hydrochloric acid. Saturated sodium bicarbonate is then cautiously added and the aqueous phase is extracted with dichloromethane. The combined organic phase is backwashed with saline, dried over magnesium sulfate, and concentrated to give 1-(2-bromo-4-methoxyphenyl)piperazine (VIII), NMR (CDCl$_3$) 2.55, 2.95, 3.08, 3.77, 6.83, 7.01, 7.14 δ.

Following the general procedure of EXAMPLE 22 and making non-critical variations but using 2-(6-bromoisochroman-1-yl)ethanol-O-mesylate (LXXX, EXAMPLE 22) and 1-(2-bromo-4-methoxyphenyl)piperazine (VIII, 2.11 g, 7.78 mmol), the title compound is obtained, mp 210°–220°; MS (m/z) 508, 510, 512; IR (mineral oil) 1488, 1479, 2380, 2356, 1115, 2308 cm$^{-1}$.

Example 38

1-[2-(Isochroman-1-yl)-2-methylpropyl]-4-(4-methoxyphenyl)piperazine dihydrochloride (LXXIV)

A mixture of 2,2-dimethyl-3-hydroxypropionic acid (CXXXII, 11.54 g, 97.7 mmol), methanol (150 ml) and methanol (25 ml) saturated with hydrochloric acid gas is stirred overnight at 20°–25°. The mixture is then concentrated under reduced pressure, ether is added, and again the mixture is concentrated. The residue is dissolved in ether and poured cautiously into a small amount of saturated sodium bicarbonate. The phases are separated and the aqueous phase is washed several times with ether. The combined organic phases are backwashed with saline, dried over magnesium sulfate, and concentrated under reduced pressure to give methyl 2,2-dimethyl-3-hydroxypropionate (CXXXII), NMR (CDCl$_3$) 1.20, 2.48, 3.56 and 3.71 δ.

A mixture of DMSO (18.7 ml, 0.2635 mol) and dichloromethane (425 ml) is cooled in a dry ice/acetone bath. Oxalyl chloride (12.0 ml, 0.1376 mol) is added and the mixture is stirred for 15 min. To this mixture is added dropwise, over 55 min, a mixture of methyl 2,2-dimethyl-3-hydroxypropionate (11.854 g (89.7 mmol) in dichloromethane (150 ml). The mixture is stirred in a dry ice/acetone bath for 55 min, after which time triethylamine (62 ml, 0.445 mol) is added. Additional dichloromethane (200 ml) is added. The mixture is allowed to warm to 12° and then is poured into water (100 ml). The phases are separated and the aqueous phase is extracted twice with dichloromethane. The combined organic extracts are backwashed twice with saline, dried with magnesium sulfate and concentrated. The residue is dissolved in hexane and the resulting salts are removed by filtration. The filtrate is dried over magnesium sulfate, concentrated, and the residue chromatographed on silica gel eluting with ethyl acetate/hexane (10/90). The appropriate fractions are pooled and concentrated to give methyl 2,2-dimethylmalonate semialdehyde (CXXXIV), NMR (CDCl$_3$) 1.36, 3.76 and 9.67 δ.

Titanium tetrachloride (1M in dichloromethane, 28 ml, 28.0 mmol) is added dropwise over 6 min to a mixture of phenethyl alcohol (XLV, 1.624 g, 13.3 mmol), methyl 2,2-dimethylmalonate semialdehyde (CXXIV, 1.884 g, 14.5 mmol) and nitromethane (5 ml) previously cooled to 0°. The mixture is heated at 40° for 80 min and then, after cooling, the mixture is concentrated and the residue is partitioned between 1N hydrochloric acid and ether. The phases are separated and the aqueous phase is washed twice with ether. The combined organic phases are backwashed with saline, dried over magnesium sulfate, and concentrated. The residue is chromatographed on silica gel eluting with ethyl acetate/hexane (5/95). The appropriate fractions are pooled and concentrated to give methyl 2-(isochroman-1-yl)-2-methylpropionate (LXXI), NMR (CDCl$_3$) 1.11, 2.52, 2.00, 3.56, 3.76, 4.13, 5.18, 6.96 and 7.14 δ.

Sodium hydroxide (1N, 12 ml) is added dropwise over several minutes, followed by a few mls of THF (to aid in solution) to a mixture of methyl 2-(isochroman-1-yl)-2-methylpropionate (LXXI, 1.833 g, 7.8 mmol) in ethanol (12 ml). The mixture is stirred overnight at 20°–25°, then at 47° for 2 hr, followed by stirring at 20°–25° over the weekend. Additional THF and sodium hydroxide (1N, 12 ml) are added and the mixture is stirred overnight at 20°–25° and then at 40° for 7 hr, followed by overnight at 20°–25°. Ethanol is then removed under reduced pressure and the resulting solids are dissolved in water. The aqueous phase is separated and washed twice with hexane to remove any unreacted starting material and the aqueous phase is then cooled in an ice/water bath and hydrochloric acid (4N, 6 ml) is added dropwise. The mixture is extracted three times with ether and the combined organic phases are backwashed with saline, dried over magnesium sulfate, and concentrated. Recrystallization from dichloromethane/hexane gives 2-(isochroman-1-yl)-2-methylpropionic acid (LXXII), mp 110.5°–115.75°.

Triethylamine (1 ml) is added dropwise to a mixture of 2-(isochroman-1-yl)-2-methylpropionic acid (LXXII, 0.502 g, 2.3 mmol), 1-(4-methoxyphenyl)piperazine dihydrochloride (XI, 0.668 g, 2.5 mmol), diethylcyanophosphonate (0.44 ml, 2.9 mmol), DMF (2.4 ml) and dichloromethane (2.4 ml). After the mixture had stirred for 2.5 hr, aqueous saturated sodium bicarbonate is added and the mixture is stirred for 70 min. The mixture is then partitioned between dichloromethane and saline, the phases separated and the organic phase is dried over magnesium sulfate and concentrated. The residue is chromatographed on silica gel eluting with methanol/dichloromethane (1/99). The appropriate fractions are pooled and concentrated to give a residue. Ethyl acetate and hexane are added and the solids are collected and dried to give 2-(isochroman-1-yl)-1-[4-(4-methoxyphenyl)piperazin-1-yl]-2-methylpropan-1-one (LXXIII), mp 119.5°–121°. Borane-methyl sulfide (1.1 ml)

is added to a mixture of 2-(isochroman-1-yl)-1-[4-(4-methoxyphenyl)piperazin-1-yl]-2-methylpropan-1-one (LXXIII, 0.397 g, 1.0 mmol) and THF (98 ml). The mixture is heated for 3.5 hr at 76° and then cooled in an ice/water bath. Hydrochloric acid (10%, 1.3 ml) is added, followed by methanol. The mixture is concentrated and methanol is again added and removed under reduced pressure. The methanol addition/removal is repeated twice more and the resulting material is partitioned between dichloromethane and saturated sodium bicarbonate. The combined organic phases are dried over magnesium sulfate, concentrated, and the residue chromatographed on silica gel eluting with ethyl acetate/hexane (5/95) followed by ethyl acetate/hexane (10/90). The appropriate fractions are pooled and concentrated to give the free base of the title compound.

Addition of hydrochloric acid/methanol and collection of the resulting salt gives the title compound, mp 203.5°–205°; MS (m/z) 380; IR (mineral oil) 1514, 1103, 1445, 1259, 1271 and 1496 cm$^{-1}$.

Example 39

1-(4-Hydroxyphenyl)-4-[2-(isochroman-1-yl)ethyl] piperazine dihydrochloride (LXVI)

Following the general procedure of EXAMPLE 1 and making non-critical variations but using 1-(4-hydroxyphenyl)piperazine (XI, 0.5371 g) in place of 1-(2-chlorophenylpiperazine dihydrochloride (XI), the title compound is obtained, mp 238°–241°; MS (m/z) 338; IR (mineral oil) 2546, 2455, 2521, 1505, 2491 and 2366 cm$^{-1}$.

Example 40

1-[2-(Isochroman-1-yl)ethyl]-4-(3,4-methylenedioxyphenyl)piperazine dihydrochloride 0.7 H$_2$O (LXVI)

Following the general procedure of EXAMPLE 1 and making non-critical variations but using 1-(3,4-methylenedioxyphenyl)piperazine hydrochloride (XI, 0.541 g) in place of 1-(2-chlorophenylpiperazine dihydrochloride (XI), the title compound is obtained, mp 201°–206°; MS (m/z) 366; IR (mineral oil) 1037, 2361, 2340, 1483, 1487 and 1440 cm$^{-1}$.

Example 41

1-[2-(Isochroman-1-yl)ethyl]-4-(4-pyridyl) piperazine dihydrochloride 0.8 H$_2$O (LXVI)

Following the general procedure of EXAMPLE 1 and making non-critical variations but using 1-(4-pyridyl) piperazine (XI, 0.3635 g) in place of 1-(2-chlorophenylpiperazine dihydrochloride (XI), the title compound is obtained, mp 231°–234°; MS (m/z) 323; IR (mineral oil) 1642, 1541, 1451, 3410, 3014 and 1274 cm$^{-1}$.

Example 42

1-[2-(Isochroman-1-yl)ethyl]-4-(4-methoxyphenyl) piperidine hydrochloride (LXVI)

Step 1: 4-Bromoanisole (13 ml, 0.1038 mol) in THF (13.5 ml) is added to a mixture of magnesium (2.24 g, 92.2 mmol) in dry THF (20 ml). When the magnesium is consumed the reagent mixture (XIII) is cooled in a ice/water bath and a mixture of 1-benzyl-4-piperidone (XII, 15 ml, 80.9 mmol) in THF (35 ml) is added dropwise over 21 minutes. The bath is then removed and the mixture stirred for 27 minutes, then poured into saturated aqueous sodium bicarbonate. The mixture is extracted several times with ether and the combined organic extracts are dried over magnesium sulfate, concentrated and the resulting material chromatographed on silica gel eluting with methanol/dichloromethane (4/96) containing ammonium hydroxide (0.4%). Impure fractions are combined and rechromatographed as above to give 1-benzyl-4-(4-methoxyphenyl)piperidin-4-ol (XIV), NMR (CDCl$_3$) 1.74, 2.14, 2.46, 2.78, 3.58, 3.80, 6.88, 7.31 and 7.44 δ.

Step 2: A mixture of 1-benzyl-4-(4-methoxyphenyl) piperidin-4-ol (XIV, Step 1, 8.37 g, 28.1 mmol) and concentrated hydrochloric acid/H$_2$O (1/1, 28 ml) is heated at 76° for 3 min. The resulting slurry is cooled and aqueous sodium hydroxide is added to make the mixture basic. The mixture is extracted several times with dichloromethane and the combined organic extracts are backwashed with saline, dried over magnesium sulfate, concentrated, and the resulting material chromatographed on silica gel eluting with methanol/dichloromethane (4/96). The appropriate fractions are pooled and concentrated to give 1-benzyl-1,2,3,6-tetrahydro-4-(4-methoxyphenyl)pyridine (XVI), MS (m/z) 279; IR (mineral oil) 1515, 738, 1030, 1258, 1250 and 1241 cm$^{-1}$.

Step 3: Palladium on carbon (10%, 0.0695 g) is added to a mixture of 1-benzyl-1,2,3,6-tetrahydro-4-(4-methoxyphenyl)pyridine (XVI, Step 2, 0.6843 g, 2.4 mmol) in methanol/hydrochloric acid and the mixture is shaken overnight under approximately 40 psi of hydrogen. Additional palladium on carbon and concentrated hydrochloric acid are added and the mixture is again shaken overnight under hydrogen. The palladium on carbon then is filtered off and the filtrate is concentrated. The residue is partitioned between dichloromethane and saturated sodium bicarbonate and the combined organic phases are backwashed with saturated sodium bicarbonate, dried over magnesium sulfate, and concentrated to give 1-benzyl-4-(4-methoxyphenyl)piperidine (XVIII), NMR (CDCl$_3$) 1.77, 2.07, 2.45, 3.00, 3.55, 3.78, 6.85, 7.16 and 7.31 δ.

Step 4: A mixture of 1-benzyl-4-(4-methoxy) phenylpiperidine (XVIII, Step 3, 0.4724 g, 1.7 mmol), dichloroethane (4.4 ml) and 1-chloroethylchloroformate (0.66 ml, 6.1 mmol) is refluxed overnight, then concentrated and the residue refluxed in methanol for 2 hours. After cooling, the solvent is removed and the resulting solids are slurried in dichloromethane. Ether is added and the solids are collected and then partitioned between dichloromethane and saturated sodium bicarbonate. The combined organic phases are backwashed with saline, dried over magnesium sulfate, and concentrated to give a residue which is chromatographed on silica gel eluting with methanol/dichloromethane (4/96) containing ammonium hydroxide (0.4%), followed by methanol/dichloromethane (6/94) containing ammonium hydroxide (0.4%). The appropriate fractions are pooled and concentrated to give 4-(4-methoxyphenyl)piperidine (XIX), NMR (CDCl$_3$) 1.66, 1.83, 2.06, 2.58, 2.76, 3.21, 3.79, 6.85 and 7.15 δ.

Step 5: Following the general procedure of EXAMPLE 1 and making non-critical variations but using 1-(4-methoxyphenyl)piperidine (XIX, Step 4, 0.215 g) in place of 1-(2-chlorophenyl)piperazine (XI), the title compound is obtained, mp 198°–200°; MS (m/z) 351; IR (mineral oil) 1515, 1252, 1108, 758, 2533 and 2503 cm$^{-1}$.

Example 43

1-[2-(Isochroman-1-yl)ethyl]-1,2,3,6-tetrahydro-4-(4-methoxyphenyl)pyridine hydrochloride 1.25 H$_2$O (LXVI)

A mixture of 1-benzyl-1,2,3,6-tetrahydro-4-(4-methoxyphenyl)pyridine (XVI, EXAMPLE 42—Step 2, 2.021 g, 7.2 mmol), dichloroethane (19 ml) and 1-chloroethylchloroformate (2.8 ml, 26.0 mmol) is refluxed overnight. The mixture is concentrated to about one third the original volume and methanol is added. The mixture is refluxed for 2 hr, then cooled and concentrated. The resulting solids are slurried in dichloromethane, ether is added, and the solids are collected and then partitioned between dichloromethane and saturated aqueous sodium bicarbonate. Some solids remained in the aqueous phase and are collected and combined with the organic fractions. Following chromatography on silica gel eluting with methanol/dichloromethane (0.5% ammonium hydroxide, 6/94), the appropriate fractions are pooled and concentrated to give 1,2,3,6-tetrahydro-4-(4-methoxypheny)pyridine (XVII).

Following the general procedure of EXAMPLE 1 and making non-critical variations but using 1,2,3,6-tetrahydro-4-(4-methoxyphenyl)pyridine (XVII, 0.207 g) in place of 1-(2-chlorophenyl)piperazine dihydrochloride (XI), the title compound is obtained, mp 143°–148.5°; MS (m/z) 349; IR (mineral oil) 1514, 1247, 1111, 1184, 1608 and 1282 $cm^{-1}$.

Example 44

1-(4-Ethoxyphenyl)-4-[2-(isochroman-1-yl)ethyl] piperazine dihydrochloride hydrate (LXXXI)

A mixture of 1-(4-hydroxyphenyl)piperazine (XXI, 2.086 g, 11.7 mmol), di-tert-butyl dicarbonate (XX, 2.555 g, 11.7 mmol), potassium carbonate (0.885 g, 6.4 mmol), THF (50 ml) and water (4 ml) is stirred at 20°–25° for 1 hr. The mixture is then poured into saline and the phases are separated. The aqueous phase is extracted three times with dichloromethane and the combined organic phases are backwashed with saline, dried over sodium sulfate and concentrated. The resulting material is chromatographed on silica gel eluting with acetone/hexane (25/75). The appropriate fractions are pooled and concentrated to give 1-(tert-butyloxycarbonyl)-4-(4-hydroxyphenyl)piperazine (XXII), (m/z) 278; IR (mineral oil) 1659, 1514, 1431, 1277, 1231 and 1446 $cm^{-1}$.

A mixture of 1-(tert-butyloxycarbonyl)-4-(4-hydroxyphenyl)piperazine (XXII, 0.602 g, 2.2 mmol) in dry THF (4 ml) is added to an ice-cooled slurry of sodium hydride (0.1013 g, 2.5 mmol-60% in oil) in THF (1 ml). DMF (15.3 ml) is added to solubilize the solids that had precipitated, after which ethyl iodide (0.34 ml, 4.3 mmol) is added. The ice/water bath is removed and the mixture stirred for five hr. Another portion of ethyl iodide (0.35 ml, 4.4 mmol) is added and the mixture is allowed to stir over the weekend at 20°–250, at which time it is concentrated and the resulting solids are partitioned between ethyl acetate and aqueous saturated sodium bicarbonate. The combined organic phases are dried over magnesium sulfate, concentrated, and the residue chromatographed on silica gel eluting with methanol/dichloromethane (1/99) containing ammonium hydroxide (0.5%), followed by methanol/dichloromethane (2/98) containing ammonium hydroxide (0.5%). The appropriate fractions are pooled and concentrated to give 1-(tert-butyloxycarbonyl)-4-(4-ethoxyphenyl) piperazine (XXIII). 1-(Tert-butyloxycarbonyl)-4-(4-ethoxyphenyl)piperazine (XXIII, 0.43 g) is dissolved in methanol and methanol saturated with hydrochloric acid gas is added. After stirring at 20°–25° for 5 hours the slurry is concentrated and ether is added. The solids are collected, washed with ether, and dried to give 1-(4-ethoxyphenyl) piperazine dihydrochloride (XXIV), MS (m/z) 206; IR (mineral oil) 1253, 1511, 2542, 2432, 1475 and 2622 $cm^{-1}$.

Triethylamine (0.48 ml) is added to a mixture of (−)-(isochroman-1-yl)acetic acid (LXI, EXAMPLE 45 Step 3, 0.2016 g, 1.05 mmol), DMF (1.1 ml), dichloromethane (1.1 ml), 1-(4-ethoxyphenyl)piperazine dihydrochloride (XXIV, 0.2997 g, 1.07 mmol) and diethyl cyanophosphonate (0.21 ml). After 2 hr, saturated sodium bicarbonate is added and the mixture is stirred for 2 hr and then extracted several times with dichloromethane. The combined organic phases are backwashed with saline, dried over magnesium sulfate, concentrated, and the residue chromatographed on silica gel eluting with methanol/dichloromethane (2/98). The appropriate fractions are pooled and concentrated to give a residue which upon crystallization from ethyl acetate/hexane gives 2-(isochroman-1-yl)-1-[4-(4-ethoxyphenyl)piperazin-1-yl]-2-methylpropan-1-one (LXXXII), MS (m/z) 380; IR (mineral oil) 1620, 1248, 1515, 1107, 1444 and 815 $cm^{-1}$.

Borane-methyl sulfide (0.8 ml, 0.08 mol) is added to a mixture of 2-(isochroman- 1-yl)-1-[4-(4-ethoxyphenyl) piperazin-1-yl]-2-methylpropan-1-one (LXXXII, 0.279 g, 0.73 mmol) in THF (5 ml). The mixture is heated at 76° for 3 hr, then cooled in an ice/water bath. Hydrochloric acid/water (10%, 0.95 ml) is added, followed by methanol. The mixture is concentrated and additional methanol is added and removed under reduced pressure. This is repeated two more times. The residue is partitioned between dichloromethane and aqueous saturated sodium bicarbonate and the combined organic phases are separated and dried over magnesium sulfate and concentrated. The residue is chromatographed on silica gel eluting with methanol/dichloromethane (2/98). The appropriate fractions are pooled and concentrated to give the free base of the title compound. The dihydrochloride salt is prepared by dissolving the material in methanol and adding methanol saturated with hydrochloric acid to give the title compound, mp 211°–212°; MS (m/z) 366; IR (mineral oil) 1510, 1117, 2329, 1257, 1475 and 2259 $cm^{-1}$.

Example 45

1-[2-[(−)-Isochroman-1-yl]-1,1-dimethylethyl]-4-(methoxyphenyl)piperazine, Isomer C (LXXXV) and 1-[2-[(−)-Isochroman-1-yl]-1,1-dimethylethyl]-4-(methoxyphenyl)-piperazine, Isomer D (LXXXV)

Step 1: Titanium tetrachloride (1M in methylene chloride, 90 ml, 90.0 mmol) is added over a period of 20 minutes to an ice-cooled mixture of phenethyl alcohol (XLV, 4.9 ml, 41.0 mmol), ethyl 3,3-diethoxypropionate (LXXV, 9.1 ml, 46.8 mmol) and nitromethane (17 ml). The mixture is stirred for 2 hr and then concentrated, diluted with ether, poured into ice/hydrochloric acid (1N), and allowed to stir. The phases are separated and the aqueous phase is extracted three times with ether. The combined organic phases are backwashed with saline, dried over magnesium sulfate and concentrated. The residue is chromatographed on silica gel eluting with ethyl acetate/hexane (10/90). The appropriate fractions are pooled and concentrated to give ethyl (±)-(isochroman-1-yl)acetate (LXXVII), NMR (CDCl$_3$) 1.28, 2.68–3.04, 3.82, 4.13, 4.22, 5.26, 7.05 and 7.16 δ.

Step 2: A mixture of ethyl (±)-(isochroman-1-yl)acetate (LXXVII, 7.00 g, 3.18 mmol), sodium hydroxide (1N, 48 ml) and ethanol (50 ml) is stirred at 20°–25° for 1.5 hr. Ethanol is then removed under reduced pressure and the aqueous mixture is cooled at 0° with stirring. Hydrochloric acid (4N, 12–13 ml) is added and the mixture is extracted with ether several times. The organic phases are washed with saline and dried over magnesium sulfate, concentrated, and the resulting material (combined with 0.47 g of (±)-(isochroman-1-yl)acetic acid from another run) chromatographed on silica gel eluting with methanol/ dichloromethane (4/96, containing 0.125% acetic acid). The appropriate fractions are pooled and concentrated to give the desired product. Crystallization from dichloromethane/hexane gives (±)-(isochroman-1-yl)acetic acid (LXXVIII), mp 76°–77°.

Step 3: Resolution of (±)-(Isochroman-1-yl)acetic acid

R-(+)-α-methylbenzylamine (LVIII, 4.80 g) is added to a cooled solution of (±)-(isochroman-1-yl)acetic acid (7.62 g) in dichloromethane (20ml). Ethyl acetate is added (40 ml) and the major portion of the dichloromethane is boiled off. The mixture is allowed to stand overnight, at which time the solids are collected. The solids are recrystallized twice from dichloromethane and ethyl acetate. This material (3.07 g) is then partitioned between dichloromethane and hydrochloric acid (1N). The organic phases are separated, dried, concentrated and crystallized from dichloromethane/hexane to give (−)-(isochroman-1-yl)acetic acid (LXI), [α] −132 °(0.98, methylene chloride).

Step 4: Diethylcyanophosphonate (1.0 ml) and triethylamine (1.75 ml) are added to (−)-(isochroman-1-yl)acetic acid (LXI, 1.15 g) and N,O-dimethylhydroxylamine hydrochloride in dichloromethane (20 ml). After stirring overnight, the mixture is partitioned between dichloromethane and aqueous sodium bicarbonate. The organic phases are separated, dried, concentrated and the residue chromatographed on silica gel eluting with ethyl acetate/hexane (50/50) to give the amide LXXXIII, [α] −104° (0.95, methylene chloride). This material is stirred at 0° and methyl magnesium bromide (3M in ether, 2.0 ml) is added. The ice bath is then removed and the mixture stirred for 25 min, at which time it is partitioned between ether and saline. The organic phase is separated, dried and concentrated and the residue chromatographed on silica gel eluting with ethyl ether/hexane (30/90) to give (−)-(isochroman-1-yl)acetone (LXXXIV), MS (m/z) 190.

Step 5: A mixture of (−)-(isochroman-1-yl)acetone (LXXXIV, 0.73 g), ammonium acetate (1.48 g), methanol (2.5 ml), and THF (2.5 ml) is stirred for 25 min and then acetic acid (1.5 ml) and sodium cyanoborohydride (0.48 g) are added. After stirring for 2 hr, the mixture is concentrated and the residue is stirred with dichloromethane and sodium hydroxide (4N). The mixture is extracted with dichloromethane and washed with saline/sodium hydroxide (1N). The organic phase is separated and dried over sodium sulfate to give 2-[(−)-isochroman-1-yl]-(±)-1-methylethylamine.

To a mixture of 2-[N-(2-hydroxyethyl)-N-(4-methoxyphenyl)amino]ethanol [XXXI, 1.0 g, prepared by the method of *J. Med. Chem.*, 35, 4264 (1992)], triethylamine (1.20 g) and dichloromethane (30 ml) are stirred at 0°, is added methanesulfonyl chloride (1.17 g). After stirring for 25 min the mixture is partitioned between dichloromethane and aqueous sodium bicarbonate. The organic phase is separated, dried over sodium sulfate and concentrated to dryness to give the bis-methanesulfonate (XXXII). 2-[(−)-Isochroman-1-yl]-(±)-1-methylethylamine (0.73 g) is added and the mixture is stirred with potassium carbonate (1.32 g) and acetonitrile (15 ml) at 80° for 10 hr and at 20°–250 for 12 hr. The mixture is then concentrated and the residue partitioned between dichloromethane, water and saline. The organic phase is dried, concentrated and the residue chromatographed on silica gel eluting with acetone/hexane (20/80). The appropriate fractions are pooled and concentrated to give the less polar Isomer C and the more polar Isomer D. Isomer C, mp 194°–198°; MS (m/z) 366; IR (mineral oil) 1515, 2390, 2375, 1257 and 1116 cm$^{-1}$; Isomer D, mp 215°–220°; MS (m/z) 366; IR (mineral oil) 2264, 1518, 2298, 2173 and 2203 cm$^{-1}$.

Example 46

1-[2-(Isochroman-1-yl)-1, 1-dimethylethyl]-4-(methoxyphenyl)piperazine (LXXXV, Isomers A) and 1-[2-(isochroman-1-yl)-1,1-dimethylethyl]-4-(methoxyphenyl)piperazine(LXXXV, Isomers B)

A mixture of (±)-3-(isochroman-1-yl)acetone (prepared in the same manner as for (−)-(isochroman-1-yl)acetone of EXAMPLE 45—Step 4, 0.56 g) and 1-(4-methoxyphenyl) piperazine (XI, 0.70 g) is stirred at reflux in dichloromethane for 1 hr. A solution of titanium tetrachloride (1M in dichloromethane, 14.6 ml) is added and the mixture is stirred for 3 hr. The solvent is then removed and the flask is cooled in an ice bath as sodium cyanoborohydride (0.92 g) and methanol are added. After stirring for 1 hr, the solvent is removed and aqueous sodium bicarbonate is added. The mixture is extracted with ether and washed with saline. After drying and concentration, the crude mixture is chromatographed on silica gel eluting with methanol/dichloromethane (2/98). The appropriate fractions are pooled and concentrated to give the less polar Isomer A and the more polar isomer B. Isomer A and Isomer B are each combined with material obtained from several previous experiments run by the same procedure and rechromatographed on silica gel eluting with acetone/hexane (20/80). The appropriate fractions are pooled and concentrated to give Isomers A and Isomers B. Isomers A, mp 198°–202°; MS (m/z) 366. Isomers B, mp 198°–206°; MS (m/z) 366.

Example 47

(±)-4-[4-[2-(Isochroman-1-yl)ethyl]piperazin-1-yl] benzamide (LXVI)

Step 1

A mixture of piperazine (II, 7.56 g) and 4-fluorobenzamide (III, 2.44 g) in water (10 ml) is heated at reflux for 27 hr. The mixture is then cooled, the solid collected and washed with water and dichloromethane, and dried to give 4-(piperazin-1-yl)benzamide (IV), mp 238°–243°; MS (m/z) 205; IR (mineral oil) 1609, 1255, 1665, 1389 and 3149 cm$^{-1}$.

Step 2

Following the general procedure of EXAMPLE 1 and making non-critical variations but using 4-(piperazin-1-yl) benzamide (IV, 4.17 g) in place of 1-(2-chlorophenyl) piperazine dihydrochloride (XI), the title compound is obtained, MS (m/z) 365.

Example 48

(−)-4-[4-[2-(Isochroman-1-yl)ethyl]piperazin-1-yl] benzamide dihydrochloride, maleate and methanesulfonate (LXXXI)

Borane-methyl sulfide (10.5 ml) in THF is added to an ice-cooled solution of (−)-(isochroman-1-yl)acetic acid (LXI, EXAMPLE 45—Step 3, 7.08 g, 36.8 mmol). After stirring for 20 min at 0°, the ice bath is removed and the solution is stirred at 20°–25° for another 1.7 hr. The reaction flask is then placed in an ice-water bath and methanol is added slowly until no further gas evolution occurs. The solvents are then removed under reduced pressure and methanol is again added and removed a second and third time. The residue is partitioned between dichloromethane, aqueous sodium bicarbonate and saline. The organic phase is separated, dried over sodium sulfate and concentrated to give (−)-2-(isochroman-1-yl)ethanol (LXXIX). This material is added to dimethylaminopyridine (0.22 g, 1.8 mmol), diisopropylethylamine (16.0 ml, 92 mmol) and THF (60 ml). The mixture is cooled in an ice-water bath and methanesulfonyl chloride (3.4 ml, 44.2 mmol) is added dropwise over several minutes. After stirring for 55 min at 0°, 4-(piperazin-1-yl)benzamide (IV, EXAMPLE 47 Step 1, 9.06 g, 44.2 mmol) and ethylene glycol (60 ml) are added. The mixture is heated at 80° overnight and then water is added and the resulting solid is collected and washed with water and toluene. After drying, the solid is passed through silica gel using methanol/dichloromethane (4/96) to give (−)-4-[4-[2-(isochroman-1-yl)ethyl]piperazin-1-yl] benzamide, MS (m/z) 365; IR (mineral oil) 1610, 1239, 1643, 1112, 1622 cm$^{-1}$.

The dihydrochloride salt is prepared by dissolving this material (free base) in methanol/dichloromethane, adding hydrochloric acid/methanol, and collecting the resulting solid, mp 175°–186°.

The maleate salt is prepared by dissolving the free base (1.38 g) in methanol/dichloromethane and adding maleic acid (0.44 g) which had been dissolved in a small amount of methanol, and collecting the solid which formed upon standing, mp 197°–198.5°.

The methanesulfonate salt is prepared by dissolving the free base (0.238 g) in methanol and adding methanesulfonic acid (0.063 g) and collecting the resulting solid to give the malate salt, mp 212°–217°.

Example 49

(−)-4-[4-[2-(Isochroman-1-yl)ethyl]piperazin-1-yl] benzenesulfonamide hydrochloride, maleate and methanesulfonate (LXXXI)

Step 1

A mixture of 4-fluorobenzenesulfonamide (III, 6.95 g) and piperazine (II, 17.1 g) in water (30 ml) is heated at 100° overnight. The solid is then collected, washed with water and toluene, and dried under reduced pressure to give 4-(piperazin-1-yl)benzenesulfonamide (IV), mp 219°–221°; MS (m/z) 241; IR (mineral oil) 1160, 822, 1332, 608, 1593 and 1137 cm$^{-1}$.

Step 2

To a cooled mixture of (−)-2-(isochroman-1-yl)ethanol (LXXIX, EXAMPLE 48, 10.6 g, 59.5 mmol), dimethylaminopyridine (Aldrich, 0.363 g, 2.98 mmol) and diisopropylethylamine (25.9 ml, 0.149 mol) in THF (65 ml) is added methanesulfonyl chloride (7.16 g, 62.5 mmol). After 20 min, 4-(piperazin-1-yl)benzenesulfonamide (IV, 15.08 g) and ethylene glycol (65 ml) are added and the temperature is raised to 100°. After stirring for 9.5 hr at 1000 the heating bath is turned off and the mixture is allowed to stir at 20°–25° for about another 6 hr. Water (175 ml) is then added to the mixture and the resulting solid is collected and washed with water (200 ml), toluene (75 ml), and ethyl ether (50 ml). The solid is dried under reduced pressure and then added to a silica gel column as a slurry in chloroform/methanol. The product is eluted from the column with methanol/chloroform (4/96) and the appropriate fractions are collected to give the title compound as the free base. After trituration with a mixture of hot chloroform/ethyl acetate/methanol, the solid is collected to give the title compound as the free base; mp 186.5°–187.5°.

The hydrochloride salt is prepared by dissolving a portion of the free base in methanol/dichloromethane and adding methanol saturated with hydrochloric acid gas (4 ml). The resulting slurry is concentrated under reduced pressure, ether is added, and the solids are collected by filtration to give the title compound as the monohydrochloride salt; mp 259°–261°; MS (m/z) 401; IR (mineral oil) 1151, 1595, 1108, 1317, 1102, 608 and 2585 cm$^{-1}$.

The maleate salt is prepared by dissolving the free base (0.98 g) in methanol/dichloromethane and adding maleic acid (0.28 g). Additional dichloromethane is added and the resulting solid collected and dried to give the title compound as the maleate salt, mp 107°–115°; MS (m/z) 401.

The methanesulfonate salt is prepared by dissolving the free base (0.50 g) in methanol/dichloromethane and adding methanesulfonic acid (0.119 g) dissolved in methanol. The solvents are removed under reduced pressure and methanol and ethyl acetate are added. The resulting crystals are collected and dried to give the methanesulfonate salt of the title compound, mp 217°–219°.

Example 50

(−)-1-[2-(Isochroman-1-yl)ethyl]-4-(4-isopropoxyphenyl)piperazine dihydrochloride (LXXXI)

A mixture of 4-isopropoxyaniline (X, 3.5 g, 23 mmol), bis(2-chloroethyl)amine hydrochloride (4.28 g, 24 mmol) and toluene (17.5 ml) are heated at 120° overnight. After cooling, the mixture is partitioned between dichloromethane and aqueous sodium bicarbonate. The combined organic phase is separated and dried over magnesium sulfate, concentrated and the residue chromatographed on silica gel eluting with methanol/dichloromethane (6/94 to 10/90). The appropriate fractions are pooled and concentrated to give 1-(4-isopropoxyphenyl)piperazine (XI).

A mixture of (−)-(isochroman-1-yl)acetic acid (LXI, EXAMPLE 45—Step 3, 0.216 g, 1.12 mmol), 1-(4-isopropoxyphenyl)piperazine (XI, 0.258 g, 1.17 mmol), triethylamine (0.21 ml, 1.51 mmol), diethylcyanophosphonate (0.23 ml, 1.52 mmol), DMF (1.2 ml) and dichloromethane (1.2 ml) are stirred for 2 hr. Aqueous sodium bicarbonate is then added and the mixture is stirred for approximately 1 hr. The phases are separated and the aqueous phase is extracted several times with dichloromethane. The organic phases are combined, dried over magnesium sulfate and concentrated. The concentrate is chromatographed on silica gel eluting with methanol/dichloromethane (2/98). The appropriate fractions are pooled and concentrated to give the amide (LXXXII) which is then taken up in THF (6 ml). Borane-methyl sulfide (1.1 ml) is added and the mixture is heated at 75° for 45 min and then cooled at 0°. Hydrochloric acid (10%, 1.3 ml) is carefully added, followed by methanol. The mixture is concentrated under reduced pressure and the methanol addition/removal is repeated two more times. The residue is partitioned between dichloromethane and aqueous sodium bicarbonate. The combined organic phases are dried over magnesium sulfate, concentrated and the residue chromatographed on silica gel (methanol/dichloromethane, 2/98) to give a material which is taken up in methanol and dichloromethane and treated with methanol/hydrochloric acid to give the title compound, mp 204°–205°.

Example 51

(±)-1-[2-(Isochroman-1-yl)ethyl]-4-(4-isopropoxyphenyl)piperazine (LXVI)

Following the general procedure of EXAMPLE 1 and making non-critical variations but using 1-(4- isopropoxyphenyl)piperazine (XI, EXAMPLE 50) in place of 1-(4-chlorophenyl)piperazine dihydrochloride, the title compound is obtained, MS (m/z) 380; IR (mineral oil) 1508, 2328, 1254, 1122 and 1445 cm$^{-1}$.

Example 52

Methyl Phthalide-3-acetate (XCII)

Phthalide-3-acetic acid (XCI, 9.6 g, 50 mmol) is dissolved in methanol (50 ml) saturated with anhydrous hydrochloric acid and the mixture is cooled to 0°–5° for 18 hr. The solvent is concentrated under reduced pressure, treated with sodium bicarbonate, and extracted with methylene chloride (800 ml). The organic phase is washed with saturated aqueous sodium bicarbonate, saline, dried over magnesium sulfate, filtered and concentrated to give the title compound, mp 62°–63°; NMR (CDCl$_3$, TMS) 7.94–7.50, 5.90, 3.77 and 2.92 δ.

Example 53

Methyl 3-(1-Hydroxy)phthalanyl Acetate (XCIII)

A mixture of methyl phthalide-3-acetate (XCII, EXAMPLE 52, 12.5 g, 60 mmol) in methylene chloride/THF (2/1, 300 ml) is cooled to −78° and treated with diisobutylaluminum hydride (1M) in toluene (120 ml) over 20 min. The mixture is stirred for 1 hr and quenched slowly with concentrated hydrochloric acid. The mixture is extracted with methylene chloride (2×800 ml) and the organic phase is washed with saline, dried (magnesium sulfate), filtered and concentrated under reduced pressure to give the title compound (impure—purified in the next step), NMR (CDCl$_3$, TMS) 7.92–7.14, 6.67, 5.88, 3.72 and 2.88 δ.

Example 54

Methyl 3-(1-Methoxy)phthalanyl Acetate (XCIV)

A mixture of methyl 3-(1-hydroxy)phthalanyl acetate (XCIII, EXAMPLE 53 crude product, 12.5 g, 60 mmol), p-toluenesulfonic acid (0.23 g, 1.2 mmol) and trimethylorthoformate (50 ml) in methanol is stirred at 20°–25° for 3 hr. The solvent is then removed under reduced pressure and diluted with methylene chloride (2×800 ml). The organic phase is separated, washed with saturated sodium bicarbonate, water, saline, dried (magnesium sulfate), filtered and concentrated. The concentrate is purified by liquid chromatography on silica gel 60 (800 g, 230–400 mesh), eluting with hexane/ethyl acetate (4/1). The appropriate fractions homogeneous by TLC are combined and concentrated to give the title compound, NMR (CDCl$_3$ TMS) 7.40–7.22, 6.19/6.10, 5.76/5.60, 3.77/3.75, 3.48/3.44, 2.90–2.72 δ.

Example 55

Methyl 1-Phthalanyl Acetate (XCV)

A mixture of methyl 3-(1-methoxy)phthalanyl acetate (XCIV, EXAMPLE 54, 4.0 g, 18 mmol) and triethylsilane (29 ml, 180 mmol) in methylene chloride (100 ml) is cooled to −78° under the nitrogen atmosphere. Trimethylsilyl trifluoromethanesulfonate (3.5 ml, 18 mmol) is added over a period of 5 min. The mixture is allowed to warm to 20°–25° and stirred for 1 hr. The reaction is quenched with saturated sodium bicarbonate and extracted with methylene chloride (800 ml). The organic phase is separated, washed with saline, dried (magnesium sulfate), filtered and concentrated under reduced pressure. The concentrate is purified by liquid chromatography on silica gel 60 (400 g, 230–400 mesh), eluting with hexane/ethyl acetate (4/1). The appropriate fractions homogeneous by TLC are combined and concentrated under reduced pressure to give the title compound, NMR (CDCl$_3$, TMS) 7.33–7.17, 5.70–5.62, 5.12, 3.74 and 2.88–2.68 δ.

Example 56

1-Phthalanylacetic Acid (XCVI)

A mixture of methyl 1-phthalanyl acetate (XCV, EXAMPLE 55, 3.84 g, 20 mmol) and sodium hydroxide (6N, 16.7 ml, 100 mmol) in methanol (50 ml) is stirred at 20°–25° for 4 hr. Methanol is removed under reduced pressure and the concentrate is acidified with hydrochloric acid (6N) to pH<3. The mixture is extracted with ethyl acetate (800 ml). The organic phase is separated, washed with saline, dried over sodium sulfate, filtered, and concentrated under reduced pressure to give the title compound, NMR (CDCl$_3$, TMS) 7.34–7.21, 5.70–5.62, 5.17 and 2.88–2.62 δ.

Example 57

4-[(Phthalan-1-yl)acety]-1-(4-methoxyphenyl) piperazine (XCVII)

A mixture of 1-phthalanyl acetic acid (XCVI, EXAMPLE 56, 3.56 g, 18 mmol) and triethylamine (14 ml, 100 mmol) and 1-(4-methoxyphenyl)piperazine dihydrochloride (LXV, 6.3 g, 24 mmol) in methylene chloride (200 ml) is stirred at 20°–25° under a nitrogen atmosphere. Diethylcyanophosphonate (6 ml, 40 mmol) is added over a period of 10 min and the mixture is stirred for 3 hr. The reaction is quenched with sodium hydroxide (20%) and extracted with methylene chloride (800 ml). The organic phase is washed with saline, dried (magnesium sulfate), filtered and concentrated under reduced pressure. The concentrate is purified by liquid chromatography on silica gel 60 (230–400 mesh, 400 g), eluting with hexane/ethyl acetate (1/4). The appropriate fractions homogeneous by TLC are combined and concentrated under reduced pressure to give the title compound which is crystallized from hexane/ethyl acetate, mp 103°–104°, NMR (CDCl$_3$, TMS) 7.30–6.85, 5.78, 5.12, 3.78 and 3.95–2.68 δ.

Example 58

4-[2-(Phthalan-1-yl)ethyl]-1-(4-methoxyphenyl) piperazine dihydrochloride (XCVIII)

A suspension of lithium aluminum hydride (1.0 g, 27 mmol) in THF (200 ml) is cooled to −20° under a nitrogen atmosphere. Aluminum chloride (3.6 g, 27 mmol) is added slowly via a powder funnel and the mixture is stirred for 10 min. A solution of 4-[(phthalan-1-yl)acetyl]-1-(4-methoxyphenyl)piperazine (XCVII, EXAMPLE 57, 4.76 g, 13.5 mmol) in THF (100 ml) is added dropwise over 10 min. The mixture is allowed to warm to 0°–5° and stirred for 1 hr. The reaction is quenched with sodium hydroxide (20%) and extracted with methylene chloride (800 ml). The organic phase is washed with water, saline, dried (magnesium sulfate), filtered and concentrated under reduced pressure. The concentrate is purified by liquid chromatography on silica gel 60 (230–400 mesh, 400 g), eluting with hexane/acetone (4:1). The appropriate fractions homogeneous by TLC are combined and concentrated under reduced pressure to give the free base of the title compound. This material is crystallized from ethyl acetate/methanol to give the title compound, mp=190°–191°, NMR (CDCl$_3$, TMS) 7.78–6.88, 5.32–5.40, 5.11, 3.83 and 4.70–2.20 δ.

Example 59

3-(1-Methoxy)phthalanylacetic Acid (CI)

A mixture of methyl 3-(1-methoxy)phthalanyl acetate (XCIV, EXAMPLE 54, 1.1 g, 5 mmol) and sodium hydroxide (6N, 10 ml, 60 mmol) in methanol (30 ml) is stirred at 20–°25° for 3 hr. Methanol is removed under reduced pressure and the concentrate is acidified with hydrochloric acid (6N) to pH<3. The mixture is extracted with ethyl acetate (800 ml). The organic phase is separated, washed with saline, dried (sodium sulfate), filtered, and concentrated under reduced pressure to give the title compound, NMR (CDCl$_3$, TMS) 7.44–7.16, 6.19/6.10, 5.76/5.60, 3.48/3.44 and 2.82–2.70 δ.

Example 60

4-[2-(1-Methoxyphthalan-3-yl)acetyl]-1-(4-methoxyphenyl)piperazine (CII)

A mixture of 3-(1-methoxy)phthalanylacetic acid (CI, EXAMPLE 59, 1.1 g, 5 mmol), triethylamine (3.5 ml, 25 mmol) and 1-(4-methoxyphenyl)piperazine dihydrochloride (LXV, 1.6 g, 6 mmol) in methylene chloride (50 ml) is stirred under a nitrogen atmosphere. Diethylcyanophosphonate (1.5 ml, 10 mmol) added over a period of 10 min at 20°–25°. After the mixture is stirred for 3 hr, the reaction is quenched with sodium hydroxide (20%) and extracted with methylene chloride (500 ml). The organic phase is washed with saline, dried (magnesium sulfate), filtered, and concentrated under reduced pressure. The concentrate is purified by liquid chromatography on silica gel 60 (230–400 mesh, 400 g), eluting with ethyl acetate. The appropriate fractions homogeneous by TLC are combined and concentrated under reduced pressure to give the title compound, NMR (CDCl$_3$, TMS) 7.40–6.8, 6.19/6.05, 5.34/5.22, 3.79, 3.53/3.39 and 3.90–2.65 δ.

Example 61

4-[2-(1-methoxyphthalan-3-yl)ethyl]-1-(4-methoxyphenyl)piperazine dihydrochloride (CIII)

A suspension of lithium aluminum hydride (0.3 g, 7.8 mmol) in THF (50 ml) is cooled to –20° under a nitrogen atmosphere. Aluminum chloride (1.0 g, 7.8 mmol) is added slowly via a powder funnel and the mixture is stirred for 10 min. A solution of 4-[1-methoxyphthalan-3-yl)acetyl]1-(4-methoxyphenyl)piperazine (CII, EXAMPLE 60, 0.96 g, 2.6 mmol) in THF (20 ml) is added dropwise over 10 min. The mixture is allowed to warm to 0-5° and stirred for 1 hr. The reaction is quenched with sodium hydroxide (20%) and extracted with methylene chloride (800 ml). The organic phase is separated, washed with water, saline, dried (magnesium sulfate), filtered and concentrated under reduced pressure. The concentrate is purified by liquid chromatography on silica gel 60 (230–400 mesh, 400 g) eluting with hexane/ethyl acetone (1/4). The appropriate fractions homogeneous by TLC are combined and concentrated under reduced pressure to give the title compound, NMR (CDCl$_3$, TMS) 7.40–6.78, 6.18/6.10, 5.44–5.24, 3.76, 3.49/3.43 and 3.14–1.82 δ.

Example 62

(E)-1-Carbethoxymethyleneindan (CVII-A), Ethyl 1-indenylacetate (CVII-B) and (Z)-1-carbethoxymethyleneindan (CVII-C)

Sodium hydride (3.2 g, 80 mmol) in oil dispersion (60% active) is washed with hexane (2×100 ml) and suspended in THF (400 ml). A solution of triethylphosphonoacetate (17.9 ml, 90 mmol) is added dropwise over 10 min. The mixture is heated at 70° for 30 min and allowed to cool to 20°–25°. 1-Indanone (CVI, 6.6 g, 50 mmol) is added and the resulting mixture is heated at 70° for 18 hr. The mixture is quenched with hydrochloric acid (6N) until pH<3. The solvent is removed under reduced pressure and the concentrate is extracted with hexane/ethyl acetate (4/1, 800 ml). The organic phase is washed with saline, dried (magnesium sulfate), filtered and concentrated. The concentrate is purified by chromatography on silica gel 60 (230–400 mesh, 800 g) eluting with hexane/ethyl acetate (9/1). The appropriate fractions are pooled and concentrated to give the title compounds, NMR experiments confirmed that the esters are a mixture of three isomers: a narrow triplet at 6 6.43 for ene-isomer (XIVB), δ6.30 for E-isomer (XIVA), and 6 5.96 for Z-isomer (XIVC) in 4.7/3.0/1.0 ratio. These isomers can be separated by repeated liquid chromatography.

Example 63

(E)-1-Carbethoxymethylene-1,2,3,4-tetrahydronaphthalene (CVII-A), Ethyl 1-(3,4-Dihydronaphthyl)acetate (CVII-B) and (Z)-1-carbethoxymethylene-1,2,3,4-tetrahydronaphthalene (CVII-C)

Following the general procedure of EXAMPLE 62 and making non-critical variations but using 1-tetralone (CVI) in place of 1-indanone (CVI) the title compounds are obtained, NMR experiments confirmed that the esters are a mixture of three isomers: a narrow triplet at δ6.46 for E-isomer (CVII-A), δ5.93 for ene-isomer (CVII-B), and δ5.81 for Z-isomer (CVII-C) in 1.2/0.3/1.0 ratio. These isomers can be separated by repeated liquid chromatography.

Example 64

Ethyl 1-Indanylacetate (CVIII)

(E)-1-Carbethoxymethyleneindan, ethyl 1-indenylacetate and (Z)-1-carbethoxymethyleneindan (CVII-A+CVII-B+CVII-C, EXAMPLE 62, 7.8 g, 38.5 mmol) and palladium on carbon (10%, 0.8 g) in ethyl acetate (100 ml) are hydrogenated in a Parr shaker under 40 p.s.i. of hydrogen atmosphere at 20°–25° for 3 hr. The mixture is filtered through a folded filter paper and the filtrate is concentrated under reduced pressure to give the title compound, NMR (CDCl$_3$, TMS) 7.24–7.14, 4.17, 3.64–1.62 and 1.28 δ.

Example 65

Ethyl 1,2,3,4-Tetrahydro-1-naphthylacetate (CVIII)

Following the general procedure of EXAMPLE 64 and making non-critical variations but starting with (E)-1-carbethoxymethylene-1,2,3,4-tetrahydronaphthalene (CVII-A, EXAMPLE 63), ethyl 1-(3,4-dihydronaphthyl)acetate (CVII-B, EXAMPLE 63) and (Z)-1-carbethoxymethylene-1,2,3,4-tetrahydronaphthalene (CVII-C, EXAMPLE 63), the title compound is obtained, NMR (CDCl$_3$, TMS) 7.25–7.05, 4.16, 3.38–3.30, 2.83–1.64 and 1.27 δ.

Example 66

1-Indanylacetic Acid (CIX)

A mixture of ethyl 1-indanylacetate (CVIII, EXAMPLE 64, 8.6 g, 42 mmol) and sodium hydroxide (6N. 35 ml, 210 mmol) in methanol (105 ml) is stirred at 20– 25°for 3 hr.

Methanol is removed under reduced pressure and the concentrate is acidified with hydrochloric acid (6N) to pH<3. The mixture is extracted with ethyl acetate (800 ml). The organic phase is separated, washed with saline, dried (sodium sulfate), filtered and concentrated under reduced pressure to give the title compound, NMR (CDCl$_3$, TMS) 7.28–7.15 and 3.68–1.62 δ.

Example 67

1,2,3,4-Tetrahydro-1-naphthylacetic acid (CIX)

Following the general procedure of EXAMPLE 66 and making non-critical variations but starting with ethyl 1,2,3,4-Tetrahydro-1-naphthylacetate (CVIII, EXAMPLE 65), the title compound is obtained, NMR (CDCl$_3$, TMS) 7.24–7.14 and 3.42–1.62 δ.

Example 68

4-[2-(Indan-1-yl)acetyl]-1-(4-methoxyphenyl) piperazine (CXI)

A mixture of 1-indanylacetic acid (CIX, EXAMPLE 66, 7.4 g, 42 mmol) and triethylamine (29.3 ml, 210 mmol), and 1-(4-methoxyphenyl)piperazine dihydrochloride (LXV, 13.3 g, 50.4 mmol) in methylene chloride (420 ml) is stirred at 20°–25° under a nitrogen atmosphere. Diethylcyanophosphonate (12.7 ml, 84 mmol) is added over a period of 10 min at 20°–25°. After the stirring for 3 hr, the reaction is quenched with sodium hydroxide (20%) and extracted with methylene chloride (2×500 ml). The organic phase is washed with saline, dried (magnesium sulfate), filtered and concentrated under reduced pressure. The crude product is purified by crystallization from ethyl acetate/methanol. The mother liquor is purified by liquid chromatography on silica gel 60 (230–400 mesh, 400 g), eluting with hexane/ethyl acetate (1/2). The appropriate fractions homogeneous by TLC are combined and concentrated under reduced pressure to give a solid. Both solids are combined to give the title compound, mp=111°–112°; NMR (CDCl$_3$, TMS) 7.26–6.83, 3.77 and 3.85–1.54 δ.

Example 69

4-[2-(1,2,3,4-Tetrahydronaphthalen-1-yl)acetyl]-1-(4-methoxyphenyl)piperazine (CXI)

Following the general procedure of EXAMPLE 68 and making non-critical variations but starting with 1,2,3,4-tetrahydro-1-naphthylacetic acid (CIX, EXAMPLE 67), the title compound is obtained, mp=133°–134°, NMR (CDCl$_3$, TMS) 7.24–7.14, 4.17, 3.64–1.62 and 1.28 δ.

Example 70

4-[2-(Indan-1-yl)ethyl]-1-(4-methoxyphenyl) piperazine dihydrochloride (CXII)

A suspension of lithium aluminum hydride (1.9 g, 50 mmol) in THF (250 ml) is cooled to −20° under a nitrogen atmosphere. Aluminum chloride (6.7 g, 50 mmol) is added slowly via a powder funnel and the mixture is stirred for 10 min. A mixture of 4-[(indan-1-yl)acetyl]-1-(4-methoxyphenyl)piperazine (CXI, EXAMPLE 68, 8.76 g, 25 mmol) in THF (100 ml) is added dropwise over 10 min. The mixture is allowed to warm to 0°–5° and stirred for 1 hr. The reaction is quenched with sodium hydroxide (20%) and extracted with methylene chloride (2×800 ml). The organic phase is washed with water, saline, dried (magnesium sulfate), filtered and concentrated under reduced pressure. The concentrate is purified by liquid chromatography on silica gel 60 (230–400 mesh, 400 g), eluting with hexane/ ethyl acetate (1/2). The appropriate fractions homogeneous by TLC are combined and concentrated under reduced pressure to give the free base of the title compound, which is converted into the hydrochloric acid salt and crystallized from ethyl acetate/methanol to give the title compound, mp 237°–239°; NMR (CDCl$_3$, TMS) 7.80–6.92, 3.84 and 4.82–1.50 δ.

Example 71

4-[2-(1,2,3,4-Tetrahydronaphthalen-1-yl)ethyl]-1-(4-methoxyphenyl)piperazine dihydrochloride (CXII)

Following the general procedure of EXAMPLE 70 and making non-critical variations but starting with 4-[1-(1,2,3,4-tetrahydronaphthyl)acetyl]-1-(4-methoxyphenyl) piperazine (CXI, EXAMPLE 69), the title compound is obtained, mp 231°–233°; NMR (CDCl$_3$, TMS) 7.82–6.92, 3.83 and 4.80–1.60 δ.

Example 72

4-[2-(Indan-1-yl)ethyl]-1-(4-hydroxyphenyl) piperazine dihydrochloride (CXII)

A solution of diphenylphosphine (8.7 ml, 50 mmol) in THF (60 ml) is cooled to 0° under a nitrogen atmosphere and treated with n-butyllithium in hexane (1.6M, 31.3 ml, 50 mmol). After stirring for 10 min, a solution of 4-[2-(indan-1-yl)ethyl]-1-(4-methoxyphenyl)piperazine (CXII, EXAMPLE 70, 6.73 g, 20 mmol) in THF (20 ml) is added. The mixture is refluxed for 24 hr, quenched with water and extracted with ethyl acetate (2×800 ml). The organic phase is washed with water, saline, dried (magnesium sulfate), filtered and concentrated under reduced pressure. The concentrate is purified by liquid chromatography on silica gel 60 (230–400 mesh, 400 g), eluting with hexane/acetone (2/1). The appropriate fractions homogeneous by TLC are combined and concentrated to give the free base of the title compound. This free base is converted into the hydrochloric acid salt and recrystallized from ethyl acetate/methanol to give the title compound, mp 215°–216°, NMR (DMSO-d$_6$, TMS) 7.30–6.68 and 3.68–1.60 δ.

Example 73

4-[2-(1,2,3,4-Tetrahydronaphthalen-1-yl)ethyl]-1-(4-hydroxyphenyl)piperazine dihydrochloride (CXII)

Following the general procedure of EXAMPLE 72 and making non-critical variations but starting with 4-[2-(1,2,3,4-tetrahydronaphthalen-1-yl)ethyl]1-(4-methoxyphenyl) piperazine dihydrochloride (CXII, EXAMPLE 71), the title compound is obtained, mp 263°–265°; NMR (DMSO-d$_6$, TMS) 7.28–6.68 and 3.64–1.55 δ.

Example 74

4-[2-(Indan-1-yl)ethyl]-1-[(4-trifluoromethanesulfonyloxy)phenyl]piperazine hydrochloride (CXII)

A mixture of 4-[2-(1,2,3,4-tetrahydronaphthalen-1-yl) ethyl]-1-(4-hydroxyphenyl)piperazine dihydrochloride (CXII, EXAMPLE 73, 0.97 g, 3 mmol), dimethylaminopyridine (0.04 g, 0.3 mmol), pyridine (6 ml) in methylene chloride (30 ml) is cooled to −20° and triflic anhydride (1.5 ml) is added dropwise over a period of 5 min. The mixture is then allowed to warm to 0° and stirred for 1 hr. The reaction is quenched with methanol (5 ml) and stirred for 1 hr. The mixture is extracted with methylene chloride (800 ml). The organic phase is washed with saline, dried (magnesium sulfate), filtered and concentrated. The concentrate purified by liquid chromatography on silica gel on silica gel 60 (230–400 mesh, 400 g), eluting with hexane/acetone (2/1). The appropriate fractions homogeneous on TLC are combined and concentrated under reduced pressure to yield the free base of title compound. The free base is converted into the hydrochloric acid salt and crystallized from ethyl acetate/methanol to give the title compound, mp 198°–199°, NMR (CDCl$_3$, TMS) 7.26–6.94 and 3.90–1.60 δ.

Example 75

4-[2-(1,2,3,4-Tetrahydronaphthalen-1-yl)ethyl]-1-[(4-trifluoromethanesulfonyloxy)phenyl]piperazine hydrochloride (CXII)

Following the general procedure of EXAMPLE 74 and making non-critical variations but starting with 4-[2-(1,2,3,4-tetrahydronaphthalen-1-yl)ethyl]-1-(4-hydroxyphenyl) piperazine dihydrochloride (CXII, EXAMPLE 73), the title compound is obtained, mp 188°–189°, NMR (DMSO-d$_6$, TMS) 7.37–7.00 and 3.85–1.52 δ.

Example 76

4-[2-(Indan-1-yl)ethyl]-1-(4-methoxycarbonyl)phenylpiperazine hydrochloride (CXII)

A mixture of 4-[2-(indan-1-yl)ethyl]-1-[(4-trifluoromethanesulfonyloxy)phenyl]piperazine hydrochloride (CXII, EXAMPLE 74, 6.5 g, 14.3 mmol), triethylamine (5 ml, 35.8 mmol), bis-(diphenylphosphino)propane (0.78 g, 1.9 mmol), and palladium acetate (0.31 g, 1.4 mmol) in dimethylformamide-methanol (10/1) is bubbled through with carbon monoxide gas at 60° for 24 hr. The reaction is then quenched with saturated sodium bicarbonate and extracted with tert-butylmethyl ether/ethyl acetate (1/1). The organic phase is separated, washed with saline, dried (magnesium sulfate), filtered, and concentrated. The concentrate is purified by liquid chromatography on silica gel on silica gel 60 (230–400 mesh, 800 g), eluting with hexane/ethyl acetate (2/1). The appropriate fractions homogeneous by TLC are combined and concentrated under reduced pressure to give the free base which is converted into the hydrochloric acid salt and crystallized from ethyl acetate/methanol to give the title compound, mp 220°–221°, NMR (DMSO-D$_6$, TMS) 7.85–7.07, 3.79 and 4.03–1.62 δ.

Example 77

4-[2-(Indan-1-yl)ethyl]-1-(4-aminocarbonylphenyl)piperazine (CXII)

A mixture of 4-[2-(indan-1-yl)ethyl]-1-(4-carbomethoxy)phenylpiperazine hydrochloride (CXII, EXAMPLE 76, 1.46 g, 4 mmol), formamide (0.64 ml, 16 mmol) in dimethylformamide (20 ml) is heated at 100°. Sodium methoxide in methanol (1.84 ml, 8 mmol) is added dropwise over a period of 5 min. The mixture is stirred for 3 hr and quenched with sodium hydroxide (20%, 10 ml) and then diluted with water (100 ml). The mixture is extracted with methylene chloride (800 ml), and the organic phase is separated, washed with saline, dried (magnesium sulfate), filtered and concentrated. The solid is crystallized from ethyl acetate/methanol to give the title compound, mp 204°–205°, NMR (DMSO-D$_6$, TMS) 7.76–6.92 and 3.26–1.46 δ.

Example 78

4-[2-(Indan-1-yl)ethyl]-1-(4-cyanophenyl)piperazine (CXII)

A mixture of 4-[2-(indan-1-yl)ethyl]-1-(4-carboxamido) phenylpiperazine (CXII, EXAMPLE 77, 0.7 g, 2 mmol), phosphorus oxychloride (0.93 ml, 10 mmol) in dimethylformamide (20 ml) is heated at 80° for 2 hr. The mixture is stirred for 2 hr and quenched with sodium hydroxide (20%) until the pH>13. The mixture is extracted with ethyl acetate (800 ml), and the organic phase is washed with saline, dried (magnesium sulfate), filtered and concentrated. The concentrate is purified by liquid chromatography on silica gel 60 (400 g), eluting with hexane/ethyl acetate (1/1). The appropriate fractions homogeneous by TLC are combined and concentrated to give the free base of title compound, which is converted into the hydrochloric acid salt and crystallized from hexane/ethyl acetate to give the title compound, mp 157°–158°, NMR (CDCl$_6$, TMS) 7.62–6.92 and 3.94–1.46 δ.

Example 79

(E)-4-[1-(1,2,3,4-Tetrahydronaphthyl) methylidenecarbonyl]-1-(4-methoxyphenyl) piperazine (CXIV-A), 4-[1-(3,4-Dihydronaphthyl) acetyl]-1-(4-methoxyphenyl)piperazine (CXIV-B) and (Z)-4-[1-(1,2,3,4-Tetrahydronaphthyl) methylidenecarbonyl]-1-(4-methoxyphenyl) piperazine (CXIV-C)

A mixture of (E)-1-carbethoxymethylene-1,2,3,4-tetrahydronaphthalene (CVII-A), ethyl 1-(3,4-dihydronaphthyl)acetate (CVII-B) and (Z)-1-carbethoxymethylene-1,2,3,4-tetrahydronaphthalene (CVII-C) [EXAMPLE 63, 2:1:2, 2.16 g, 10 mmol] in methanol (25 ml) and add sodium hydroxide (6N, 8.3 ml). The mixture is stirred for 3 hr. Methanol is removed under reduced pressure and the concentrate is acidified with hydrochloric acid (6N) to pH<3. The mixture is extracted with ethyl acetate (800 ml). The organic phase is separated, washed with saline, dried (sodium sulfate), filtered and concentrated under reduced pressure. The concentrate (2.0 g), triethylamine (7 ml, 50 mmol), and 1-(4-methoxyphenyl)piperazine dihydrochloride (LXV, 3.17 g, 12 mmol) in methylene chloride (200 ml) is stirred at 20°–25° under the nitrogen atmosphere. Diethylcyanophosphonate (3 ml, 20 mmol) is added over a period of 10 min and stirred for 3 hr. The reaction is quenched with sodium hydroxide (20%) and extracted with methylene chloride (800 ml). The organic phase is washed with saline, dried (magnesium sulfate), filtered and concentrated under reduced pressure. The crude product is purified by liquid chromatography on silica gel 60 (230–400 mesh, 800 g), eluting with hexane/acetone (2/1). The appropriate fractions homogeneous by TLC are combined and concentrated under reduced pressure. The least polar fraction, after crystallization from hexane/ethyl acetate gives the E-isomer (CXIV-A), mp 107°–108°, NMR (CDCl$_3$, TMS) 7.63–6.82, 6.46, 3.77, 3.86/3.71, 2.86–2.74 and 1.92–1.84 δ. The next polar fraction, after crystallization from hexane/ethyl acetate, gives the ene-isomer (CXIV-B), mp 133°–134°, NMR (CDCl$_3$, TMS) 7.21–5.82, 5.93, 3.77, 3.83/3.59, 3.54 and 3.03–2.28 δ. The most polar fraction, after crystallization from hexane/ethyl acetate, gives the Z-isomer (CXIV- C), mp 128°–129°, NMR (CDCl₃, TMS) 7.48–6.72, 5.81, 3.79/3.38, 3.75, 3a.38–2.48 and 2.03–1.94 δ.

Example 80

(E)-4-[1-(1,2,3,4-Tetrahydronaphthenyl) methylidenemethyl]-1-(4-methoxyphenyl)piperazine (CXV-A)

A suspension of lithium aluminum hydride (0.15 g, 4 mmol) in THF (20 ml) is cooled to –20° under a nitrogen atmosphere. Aluminum chloride (0.53 g, 4 mmol) is added slowly via a powder funnel and the mixture is stirred for 10 min. A solution of (E)-4-[1-(1,2,3,4-tetrahydronaphthyl) methylidenecarbonyl]-1-(4-methoxyphenyl)piperazine (CXIV-A, EXAMPLE 79, 0.73 g, 2 mmol) in THF (10 ml) is added dropwise over 10 min. The mixture is allowed to warm to 0°–5° and stirred for 1 hr. The reaction is quenched with sodium hydroxide (20%) and extracted with methylene chloride (2×800 ml). The organic phase is washed with water, saline, dried (magnesium sulfate), filtered and concentrated under reduced pressure. The concentrate is purified by liquid chromatography on silica gel 60 (230–400 mesh, 400 g), eluting with hexane/acetone (4/1). The appropriate fractions homogeneous by TLC are combined and concentrated under reduced pressure to give the free base of the title compound, is converted into the hydrochloric acid salt and crystallized from ethyl acetate/methanol to give the title compound, mp 215°–216°, NMR (CDCl₃, TMS) 7.84–6.90, 6.27, 4.73, 3.84 and 4.34–1.85 δ.

Example 81

4-[2-(3,4-Dihydronaphthalen-1-yl)ethyl]-1-(4-methoxyphenyl)piperazine (CXV-B)

Following the general procedure of EXAMPLE 80 and making non-critical variations but starting with 4-[1-(3,4-dihydronaphthyl)acetyl]-1-(4-methoxyphenyl)piperazine (CXIV-B, EXAMPLE 79), the title compound is obtained, mp 221°–222°; NMR (CDCl₃, TMS) 7.92–6.90, 6.07, 4.77, 3.84 and 4.42–2.22 δ.

Example 82

(Z)-4-[1-(1,2,3,4-Tetrahydronaphthyl) methylidenecarbonyl]-1-(4-methoxyphenyl) piperazine (CXV-C)

Following the general procedure of EXAMPLE 80 and making non-critical variations but starting with (Z)-4-[1-(1,2,3,4-tetrahydronaphthyl)methylidenecarbonyl]-1-(4-methoxyphenyl)piperazine (CXIV-C, EXAMPLE 79), the title compound is obtained, mp 211°–212°; NMR (CDCl₃, TMS) 7.80–6.90, 5.82, 4.77, 3.82 and 4.20–1.92 δ.

Example 83

(–)-(Isochroman-1-yl)acetic acid (LV) Obtained By Using *Pseudomonas cepaica* Lipase To a suspension of ethyl (±)-(isochroan-1-yl)acetate (LIV) in pH 7 phosphate buffer solution (0.048 g/ml) is added an equal weight of PS-30 (*Pseudomonas cepaica*, Amano Corporation) lipase. The contents are shaken at 28° and at 180 rpm for 24 hr. At the end of this period, the reaction mixture is acidified to pH<4 with hydrochloric acid (10%), and extracted with ethyl acetate. The ethyl acetate solution is washed two times with saturated sodium carbonate solution, the combined base washings are acidified with hydrochloric acid (10%), and the acid solution thoroughly extracted with ethyl acetate. The ethyl acetate extract is dried over magnesium sulfate and concentrated to give crude (–)-acid. Recrystallization of the crude (–)-acid from methyl-tert-butyl ether give the title compound, $[\alpha]^{25}$ –132°, c=0.8 in methylene chloride.

Example 84

4-[2-(Inden-1-yl)acetyl]-1-(4-methoxyphenyl) piperazine (CXIV-B)

Following the general procedure of EXAMPLE 79 and making non-critical variations but starting with ethyl 1-indenylacetate (CVII-B, EXAMPLE 62), the title compound is obtained, mp 123°–125°; NMR (CDCl₃, TMS) 7.48–6.81, 6.34, 3.84, 3.76, 3.69, 3.60–2.95 δ.

Example 85

4-[2-(Inden-1-yl)ethyl]-1-(4-hydroxyphenyl) piperazine (CXV-B)

Following the general procedure of EXAMPLE 72 and making non-critical variations but starting with 4-[(inden-1-yl)ethyl]-1-(4-methoxyphenyl)piperazine (CXV-B, EXAMPLE 89), the title compound is obtained, mp 228°; NMR (DMSO-d₆) 7.39–6.54, 6.23 and 3.60–2.78 δ.

Example 86

2-(Inden-1-yl)ethanol (CXVI-B)

A suspension of lithium aluminum hydride (2.8 g, 74 mmol) in THF (75 ml) is cooled to 0°–5° and a solution of ethyl 1-indenylacetate (CVII-B, EXAMPLE 62) in THF (75 ml) is added dropwise over 5 min. The mixture is stirred for 3 hr. The reaction is quenched with hydrochloric acid (6N) and extracted with ethyl acetate. The organic layer is washed with water, saline, dried (magnesium sulfate), filtered and concentrated. The concentrate is purified by liquid chromatography on silica gel 60 (230–400 mesh, 400 g), eluting with hexane/ethyl acetate (2/1). The appropriate fractions are pooled and concentrated to give the title compound, NMR (CDCl₃, TMS) 7.48–7.14, 6.33, 3.92–3.89, 3.35 and 3.04–2.99 δ.

Example 87

4-[2-(Inden-1-yl)ethyl]-1-(4-aminocarbonylphenyl) piperazine (CXV-B)

A mixture of 2-(inden-1-yl)ethanol (CXVI-B, EXAMPLE 86, 0.8 g, 5 mmol), dimethylaminopyridine (0.02 g, 0.2 mmol) and triethylamine (1.7 ml, 12.5 mmol) in tetrahydrofuran (10 ml) is cooled to 0° and methanesulfonyl chloride (0.43 ml, 5.5 mmol) is added dropwise. After 45 min, 4-(piperazinyl)benzenecarboxamide (LXV, 1.23 g, 6 mmol), diisopropylethylamine (1.0 ml, 6 mmol) and ethyleneglycol (10 ml) are added and heated at 85° for 60 hr. The mixture is diluted with water and extracted with methylene chloride. The organic phase is separated, washed with saline, dried (magnesium sulfate), filtered and concentrated. Crystallization from ethyl acetate gives the title compound, mp 207°; NMR (CDCl₃, TMS) 7.75–6.90, 6.28 and 3.39–2.68 δ.

Example 88

4-[1-Methyl-2-(1,2,3,4-tetrahydronaphthalen-1-yl) ethyl]-1-(4-methoxyphenyl)piperazine dihydrochloride (CXII)

A solution of 4-[1-(1,2,3,4-tetrahydronaphthyl)acetyl]-1-(4-methoxyphenyl)piperazine (CXI, EXAMPLE 69, 0.55 G, 1.5 mmol) in THF/ether (3/1, 40 ml) is cooled to 0°–5° under a nitrogen atmosphere. Methylmagnesium bromide in ether (3M, 5 ml, 15 mmol) is added dropwise over 2 min. The mixture is allowed to warm to 20°–25° and stirred for 18 hr. The mixture is then cooled again to 0°–5° and sodium cyanoborohydride (1.4 g, 15 mmol) is added in one portion. The mixture is then treated with a mixture os acetic acid (5 ml) and methanol (30 ml) and stirred at 20°–25° for 18 hr. The mixture is then cooled again to 0°–5° and sodium cyanoborohydride (1.4 g, 15 mmol) is added in one portion. The mixture is then treated with a mixture os acetic acid (5 ml) and methanol (30 ml) and stirred at 20°–25° for 18 hr. The reaction is quenched with sodium hydroxide (20%) until the pH is 13 and then extracted with methylene chloride (2×800 ml). The organic phase is washed with water, saline, dried (magnesium sulfate), filtered and concentrated under reduced pressure. The concentrate is purified by liquid chromatography on silica gel 60 (230–400 mesh, 600 g), eluting with hexane/ethyl acetate (2/1). The appropriate fractions are pooled and concentrated under reduced pressure to give the free base of the title compounds. The two diastereomers are isolated with different Rf's. These diastereomers are converted into the hydrochloric salt and crystallized from ethyl acetate/methanol to give the title compounds: diastereomer A, mp 224°–225°; NMR (CDCl$_3$, TMS) 7.86–6.97, 3.83, 5.10–1.68 and 1.62 δ: diastereomer B, mp 228°–229°; NMR (CDCl$_3$, TMS) 7.88–6.95, 3.84, 5.02–1.78 and 1.64 δ.

Example 89

4-[2-(Inden-1-yl)ethyl]-1-(4-methoxyphenyl) piperazine (CXV-B

Following the general procedure of EXAMPLE 80 and making non-critical variations but starting with 4-[(inden-1-yl)acetyl]-1-(4-methoxyphenyl)piperazine (CXIV-B, EXAMPLE 84), the title compound is obtained, mp 220°–221°; NMR (DMSO-d$_6$, TMS) 7.61–6.92, 6.44, 3.75 and 3.82–3.10 δ.

Example 91

1-(4-Fluorophenyl)-4-[2-(4-methyl-7-phenylisochroman-1-yl)ethyl]piperazine (LXVI)

A mixture of 2-(4-phenyl)phenyl-1-propanol (1.49 g) and 3-chloropropionaldehyde diethyl acetal (1 eq) in nitromethane (0.1M) is cooled to 0° and treated dropwise with titanium tetrachloride (2 eqs, 1.0M solution in dichloromethane). The reaction is warmed to 60° and maintained at that temperature until the absence of starting phenethanol is apparent by TLC (2–18 hrs). The reaction is then poured into hydrochloric acid (1N), saline is added and the product is extract with dichloromethane (2×). The combined organic extracts are washed with saline, dried over magnesium sulfate, filtered, and concentrated to a crude material which is purified by silica gel chromatography to give 2-(4-methyl-7-phenylisochroman-1-yl ethyl chloride (LXIV).

Following the general procedure of EXAMPLE 1 and making non-critical variations but alkylation of p-fluorophenylpiperazine with 2-(4-methyl-7-phenylisochroman-1-yl ethyl chloride (LXIV, 286 mg) gives the title compound. The bis hydrochloride salt of the title compound is obtained, mp 182°–184°

Example 92

1-(4-Methoxyphenyl)-4-[2-(4-methyl-7-phenylisochroman-1-yl)ethyl]piperazine (LXVI)

Following the general procedure of EXAMPLE 1 and making non-critical variations but alkylating p-methoxyphenylpiperazine (V) with 2-(4-methyl-7-phenylisochroman-1-yl ethyl chloride (LXIV, EXAMPLE 91, 286 mg) gives the title compound. The bis hydrochloride salt of the title compound is obtained, mp 181°–183°.

Example 93 cis-1-(4-Fluorophenyl)-4-[2-(3-methylisochroman-1-yl)ethyl]piperazine (LXVI)

Following the general procedure of EXAMPLE 91 and making non-critical variations but using 1-phenyl-2-propanol (XLIX, 409 mg) is converted to a mixture of separable, diastereomeric isochroman chlorides 2-(3-methylisochroman-1-yl) ethyl chloride (LXIV). The major isomer cis-2-(3-methylisochroman-1-yl)ethyl chloride (LXIV, 237 mg) is used to alkylate p-fluorophenylpiperazine (V) according to the general procedure of EXAMPLE 1 (making non-critical variations) to give the title compound. The bis hydrochloride salt of the title compound is obtained, mp 220°–221.5°.

Example 94 trans-1-(4-Fluorophenyl)-4-[2-(3-methylisochroman-1-yl)ethyl]piperazine (LXVI)

The minor isomer of the isochroman chloride prepared in EXAMPLE 93, trans-2-(3-methylisochroman-1-yl)ethyl chloride (LXIV, 146 mg) is used to alkylate p-fluorophenylpiperazine (V) according to the general procedure of EXAMPLE 1 (making non-critical variations) to give the title compound. The bis hydrochloride salt of the title compound is obtained, mp 237°–238°.

Example 95

1-(4-Fluorophenyl)-4-[2-(4-phenylisochroman-1-yl) ethyl]piperazine (LXVI)

Following the general procedure of EXAMPLE 91 and making non-critical variations but using 2,2-diphenyl-1-ethanol (XLIX, 595 mg) is converted to the isochroman chloride, 2-(4-phenylisochroman-1-yl)ethyl chloride (LXIV). Following the general procedure of EXAMPLE 1 and making non-critical variations, this isochroman chloride, 2-(4-phenylisochroman-1-yl)ethyl chloride (LXIV, 200 mg) is used to alkylate p-fluorophenylpiperazine (V) to give the title compound. The bis hydrochloride salt of the title compound is obtained, mp 220°–221° (turns dark at 177°).

Example 96 cis-1-(4-Fluorophenyl)-4-[2-(1,2,3,4,6,10b-hexahydro-4aH-benzo[c]chromen-6-yl)ethyl] piperazine (LXVI)

Following the general procedure of EXAMPLE 91 and making non-critical variations trans-2-phenylcyclohexanol (1.41 g) is converted to a mixture of separable, diastereomeric isochroman chlorides, 2-(1,2,3,4,6,10b-hexahydro-4aH-benzo[c]chromen-6-yl)ethyl chloride (LXIV). Following the general procedure of EXAMPLE 1 and making non-critical variations the resulting major isomer (693 mg) is used to alkylate p-fluorophenylpiperazine (V) to give the title compound. The bis hydrochloride salt of the title compound is obtained, mp 220°–223°.

Example 97 trans-1-(4-Fluorophenyl)-4-[2-(1,2,3,4,6,10b-hexahydro-4aH-benzo[c]chromen-6-yl)ethyl] piperazine (LXVI)

Following the general procedure of EXAMPLE 6 and making non-critical variations, trans-2-(1,2,3,4,6,10b- hexahydro-4aH-benzo[c]chromen-6-yl)ethyl chloride (LXIV, EXAMPLE 96, the minor isochroman chloride isomer) is used to alkylate p-fluorophenylpiperazine (V) to give the title compound. The bis hydrochloride salt of the title compound is obtained, mp 246°–248°.

Example 98

1-(4-Fluorophenyl)-4-[2-(3,7,8,9,10,10a-hexahydro-1H-2-oxacyclohepta[d,e]naphthalen-3-yl)ethyl] piperazine (LXVI)

Following the general procedure of EXAMPLE 91 and making non-critical variations 1-hydroxymethylbenzocycloheptane (XLIX, 1.76 g) is converted to the corresponding isochroman chloride, 2-(3,7,8, 9,10,10a-hexahydro-1H-2-oxacyclopepta[d,e]naphthalen-3-yl)ethyl chloride (LXIV). Following the general procedure of EXAMPLE 1 and making non-critical variations 2-(3,7, 8,9,10,10a-hexahydro-1H-2-oxacyclopepta[d,e]naphthalen-3-yl)-ethyl chloride (LXIV, 450 mg) is used to alkylate p-fluorophenylpiperazine (V) to give the title compound. The bis hydrochloride salt of the title compound is obtained, mp 237°–240°.

Example 99

1-(4-Methoxyphenyl)-4-[2-(3,7,8,9,10,10 a-hexahydro-1H-2-oxacyclohepta[de]naphthalen-3-yl)ethyl]piperazine (LXVI)

Following the general procedure of EXAMPLE 1 and making non-critical variations 2-(3,7,8,9,10,10a-hexahydro-1H-2-oxacyclopepta[d,e]naphthalen-3-yl)ethyl chloride (LXIV, EXAMPLE 98, 450 mg) is used to alkylate p-methoxyphenylpiperazine (V) to give the title compound. The bis hydrochloride salt of the title compound is obtained, mp 213°–216°.

Example 100

1-(4-Methoxyphenyl)-4-[2-(5-bromoisochroman-1-yl)ethyl]piperazine (LXXIV)

Following the general procedure of EXAMPLE 45 (step 1) and making non-critical variations 2-(o-bromophenyl)-1-ethanol (XLIX, 3.3 g) is converted to ethyl 2-(5-bromoisochroman-1-yl)acetate (LXXI). Following the general procedure of EXAMPLE 45 (Step 2) and making non-critical variations ethyl 2-(5-bromoisochroman-1-yl) acetate (LXXI, 1.0 g) is hydrolyzed to the corresponding acid, 2-(5-bromoisochroman-1-yl)acetic acid (LXXII). This acid (LXXII, 740 mg) is coupled with p-methoxyphenylpiperazine (V) and the resulting amide, 1-(4-methoxyphenyl)-4-[2-(5-bromoisochroman-1-yl)] acetyl piperazine (LXXIII, 1.10 g) is reduced according to the general procedure described in EXAMPLE 50 (making non-critical variations) to give the title compound, mp 105°–106°.

Example 101

1-(4-Methoxyphenyl)-4-[2-(7-bromoisochroman-1-yl)ethyl]piperazine (LXXIV)

Following the general procedure of EXAMPLE 100 and making non-critical variations but starting with 2-(p-bromophenyl)-1-ethanol (XLIX, 2.0 g), the title compound is obtained, mp 78°–79°; HRMS 430.1248 (theory 430.1256).

Example 102

1-(4-Methoxyphenyl)-4-[2-(5-aminocarbonylisochroman-1-yl)ethyl]piperazine (CXXVII)

A mixture of t-butyl lithium (2 eqs, 1.7M in hexane) in THF (2 ml/mmol bromide) is cooled to −78° for 10 minutes before adding the 1-(4-methoxyphenyl)-4-[2-(5-bromoisochroman-1-yl)ethyl]piperazine (LXXIV, EXAMPLE 100) in THF (4 ml/mmol) dropwise over 10 minutes. A freshly distilled solution of trimethylsilylisocyanate (1.5 eqs) is added via syringe as a solution in dioxane (4 volume equivalents) at once. After 15 minutes, the cooling bath is removed and the mixture allowed to warm to 20°–25°. The reaction mixture is quenched with ammonium chloride, the organics are removed under reduced pressure, and the aqueous residue is extracted two times with methylene chloride, dried over sodium sulfate, filtered and concentrated. The crude material is purified by flash chromatography on silica gel. In this manner, 1-(4-methoxyphenyl)-4-[2-(5-bromoisochroman-1-yl)ethyl]piperazine (LXXIV, EXAMPLE 100, 345 mg) is converted to the corresponding amide, the title compound, mp 185°–186°.

Example 103

1-(4-Methoxyphenyl)-4-[2-(6-aminocarbonylisochroman-1-yl)ethyl]piperazine (CXXVII)

Following the general procedure of EXAMPLE 102 and making non-critical variations 1-[2-(6-bromoisochroman-1-yl)ethyl]-4-(4-methoxyphenyl)piperazine dihydrochloride (LXXXI, EXAMPLE 22, 335 mg) is converted to the title compound, mp 180°–182°.

Example 104

1-(4-Methoxyphenyl)-4-[2-(6-trimethylsilylisochroman-1-yl)ethyl]piperazine (LXXIV)

When the reaction described in EXAMPLE 103 is performed (295 mg scale) but with the omission of dioxane as a co-solvent, two other compounds are obtained. One of these is the title compound (trimethylsilyl derivative), mp 78°–80°.

Example 105

1-(4-Methoxyphenyl)-4-[2-(6-cyanoisochroman-1-yl)ethyl]piperazine (LXXIV)

When the reaction described in EXAMPLE 103 is performed (295 mg scale) but with the omission of dioxane as a co-solvent, two other compounds are obtained. One of these is the title compound (nitrile derivative), mp 86°–88°.

Example 106

1-(4-Methoxyphenyl)-4-[2-(7-aminocarbonylisochroman-1-yl)ethyl]piperazine (CXXVII)

Following the general procedure of EXAMPLE 102 and making non-critical variations but using 1-(4-methoxyphenyl)-4-[2-(7-bromoisochroman-1-yl)ethyl] piperazine (LXXIV, EXAMPLE 101), the title compound is obtained, mp 178°–180°.

Example 107

1-(4-Methoxyphenyl)-4-[2-(1,3,4,5-tetrahydrobenzo[c]oxepin-1-yl)-ethyl]-piperazine hydrochloride (CXXV)

Step 1—A mixture of methyl o-iodobenzoate (9.17 g), propargyl alcohol (3.06 ml) and diethyl amine (90 ml) is treated with bis(triphenylphosphine)palladium chloride (1.23 g) and copper iodide (333 mg) and the reaction is stirred at 20°–25° under nitrogen for 18 hrs. The reaction is then filtered through a filter agent and concentrated. The resulting residue is partitioned between water and dichloromethane. The combined organic phases are washed once with saline, dried over magnesium sulfate, filtered and concentrated to an oil. Purification by silica gel chromatography gives methyl o-(1-hydroxy-2-propyn-3-yl)benzoate (CXIX).

Step 2—A mixture of methyl o-(1-hydroxy-2-propyn-3-yl)benzoate (CXIX, 5.91 g) in methanol (60 ml) is hydrogenated at 40 psi hydrogen for 9 hrs using a total of 900 mg. Palladium on carbon (10%) is added in equal portions three times during the course of the reaction. The reaction is filtered and concentrated to give the saturated ester, methyl o-(1-hydroxyprop-3-yl)benzoate (CXXI).

Step 3: A mixture of methyl o-(1-hydroxyprop-3-yl)benzoate (CXXI, 1.94 g) in THF is cooled to −78° and treated dropwise with three equivalents of the lithium enolate of tert-butyl acetate (generated with lithium diisopropylamide). The reaction is warmed to 0° for 2.5 hrs before being quenched with cold aqueous hydrochloric acid and partitioned into ethyl acetate. The combined organic phases are washed once with saline, dried over magnesium sulfate, filtered and concentrated to give an oil which is purified by silica gel chromatography. The appropriate fractions are pooled and concentrated to give ε-butyl o-(3-hydroxypropyl)benzo acetate (CXII).

Step 4—A mixture of ε-butyl o-(3-hydroxypropyl)benzo acetate (CXII, 14.56 g) in dichloromethane is cooled to −78° and treated with triethylsilane (83.5 ml) followed by the dropwise addition of trimethylsilyl trifluoromethane sulfonate (10.1 ml). The reaction is warmed to 0° for 20 min, treated with trifluoroacetic acid (8.06 ml), and stirred for an additional 20 min at 20°–25°, at which point the reaction is transferred to a separatory funnel and washed three times with sodium hydroxide (1M). The combined base phases are adjusted to pH=1 with concentrated hydrochloric acid and extracted with dichloromethane. The combined organic layers were washed with saline, dried over magnesium sulfate, filtered and concentrated to an oil which is purified by silica gel chromatography to give (1,3,4,5-tetrahydrobenzo[c]oxepin-1-yl)acetic acid (CXXIII).

Step 5—Following the general procedure of EXAMPLE 50 and making non-critical variations p-methoxyphenylpiperazine is acylated with (1,3,4,5-tetrahydrobenzo[c]oxepin-1-yl)acetic acid (CXXIII, 619 mg) and the resulting amide, 1-(4-methoxyphenyl)-4-(1,3,4,5-tetrahydrobenzo[c]oxepin-1-yl)acetyl piperazine (CXXIV, 1.07 g) is reduced according to the general procedure described in EXAMPLE 50 (making non-critical variations) to give crude product. This crude material is dissolved in ether (30 ml) and methanol (3 ml) and treated with gaseous hydrochloric acid resulting in the formation of a salt. This crude salt is recrystallized from methanol/ethyl acetate to give the title compound, mp 217.0°–219.0° (uncorrected, decomp.).

Example 108

1-(4-Fluorophenyl)-4-[2-(1,3,4,5-tetrahydrobenzo[c]oxepin-1-yl)ethyl]-piperazine (CXXV)

Following the general procedure of EXAMPLE 50 and making non-critical variations p-fluorophenylpiperazine is acylated with (1,3,4,5-tetrahydrobenzo[c]oxepin-1-yl)acetic acid (CXXIII, EXAMPLE 107—step 4, 619 mg) and the resulting amide 1-(4-fluorophenyl)-4-(1,3,4,5-tetrahydrobenzo[c]- oxepin-1-yl)acetyl piperazine (CXXIV, 368 mg) is reduced according to the general procedure of Example 50. The crude product is dissolved in ether (30 ml) and methanol (3 ml) and treated with gaseous hydrochloric acid. This crude salt is recrystallized from methanol/ethyl acetate to give the title compound, mp 204.5°–205.5° (uncorrected, decomp.).

Example 109

(−)-1-[2-(Isochroman-1-yl)ethyl]-4-(4-methoxyphenyl)piperazine dihydrochloride (LXXXI)

Following the general procedure of EXAMPLE 48 and making non-critical variations but using 1-(4-methoxyphenyl)piperazine dihydrochloride (XI) in place of 4-(piperazin-1-yl)benzamide (IV), the title compound is obtained, mp 218°–223°; [α]–50 (c 0.95, $CH_2Cl_2$).

Example 110

(+)-1-[2-(Isochroman-1-yl)ethyl]-4-(4-methoxyphenyl)piperazine dihydrochloride (LXXXI)

Following the general procedure of EXAMPLE 48 and making non-critical variations but using (+)-(isochroman-1-yl)acetic acid (prepared in the same manner as for EXAMPLE 45, Step 3, but using S-(−)-α-methylbenzylamine in place of R-(+)-α-methylbenzylamine), containing some (−)-(isochroman-1-yl)acetic acid as an impurity, in place of (−)-(isochroman-1-yl)acetic acid (LXI, EXAMPLE 45—Step 3), and using 1-(4-methoxyphenyl)piperazine dihydrochloride (XI) in place of 4-(piperazin-1-yl)benzamide (IV), the title compound is obtained, mp 210°–216°; [α]+42 (c 0.99, $CH_2Cl_2$).

Example 111

2-Bromophenethanol (CXXXIX)

2-Bromophenylacetic acid (CXXXVIII, 34.7 g, 161 mmol) is dissolved in THF (200 ml) and cooled to 0°. Borane-methyl sulfide (1.5 eq., 24 ml of a 10M solution) is slowly added. After the gas evolution subsided, the ice bath is removed and the mixture is stirred overnight at 25°. The mixture is then placed in an ice bath and carefully quenched with aqueous hydrochloric acid (2N, 150 ml). Water (200 ml) is added and the mixture stirred 30 min, and then extracted with ether (250 ml). The organic phase is washed with water (2×150 ml), saturated aqueous sodium bicarbonate and saline. Drying over anhydrous sodium sulfate followed by filtration and solvent removal under reduced pressure gives the title compound, single peak via HPLC (8.23 min retention); NMR (300 MHz, $CDCl_3$) 7.55, 7.26, 7.09, 3.88, 3.03, 1.53; IR (thin film) 3350, 1471, 1439, 1040 $cm^{-1}$; high resolution MS calculated for 199.9837, found 199.9873.

Example 112

Ethyl 2-(2-hydroxyethyl)cinnamate (CXXX)

Triphenylphosphine (9 mol %, 44.8 g, 171 mmol) and palladium acetate (4 mole %, 17.0 g, 76 mmol) are weighed out in open air and added to 2-bromophenethanol (CXXIX, EXAMPLE 111, 383 g, 1.9 moles). The reaction flask is flushed thoroughly with nitrogen, after which the reaction flask was kept under mineral oil bubbler positive nitrogen pressure. DMF (1 ml/6 mmol substrate, 316 ml) is added, followed by triethylamine (1.1 eq., 290.7 ml, 2.1 moles) and ethyl acrylate (1.1 eq., 283 ml, 2.1 moles), all via syringe. The well wrapped reaction flask is heated on a steam bath. An initial vigorous reflux slowly subsides as the reaction progresses, mirroring a gradual increase in solution temperature from <100° to 110°. After 4 hr, the reaction is complete as measured by HPLC. The mixture is allowed to cool and stir overnight. After cooling the mixture crystallized in appearance. Methyl-t-butyl ether (MTB, 400 ml) is added with stirring, followed by hexane (600 ml) and diatomaceous earth (100 g). The slurry is filtered through a sintered glass funnel and the solids are washed with MTB/hexane (1/2). After solvent removal under reduced pressure, this product which possessed only very small amounts of impurities in the aromatic region of the proton NMR is combined with a separate 497 mmol run and dissolved in MTB (1.5 liters) and washed with aqueous hydrochloric acid (1N, 800 ml), water (2×800 ml), saturated aqueous sodium bicarbonate and saline. Drying over anhydrous sodium sulfate (30 min) followed by filtration directly through 200 mesh silica gel (800 g) using a sintered glass funnel, washing the silica gel with additional MTB until TLC shows no more product. Toluene (100 ml) is added to azetrope and remaining water and the solvents removed under reduced pressure. An analytical sample is more carefully filtered through silica gel to give the title compound, NMR (300 MHz, CDCl$_3$) 8.0, 7.59, 7.31, 6.38, 4.27, 3.83, 3.04, 1.34; IR (thin film) 3417, 1712, 1632, 1316, 1179 cm$^{-1}$; high resolution MS calculated for 220.1099, found 220.1105.

Example 113

Ethyl 2-(Isochroman-1-yl)acetate (CXXXI)

Ethyl 2-(2-hydroxyethyl)cinnamate (CXXX, EXAMPLE 112, theoretically 2.40 moles) is dissolved in THF (2.4 liters) and cooled to 0°. Potassium t-butoxide (5 mol %, 120 ml of a 1 molar THF solution) is added via syringe. After 5 min HPLC shows the cyclization is completed. Acetic acid (6 mol %, 8.2 ml, 144 mmol) is added. The slurry is filtered through approximately 300 g of 200 mesh silica gel. The solvent is removed under reduced pressure until approximately 0.5 liter of THF remained. Diatomaceous earth (100 g) is added followed by hexane (4.5 liters). This slurry is filtered through 200 mesh silica gel (400 g), washing with THF/hexane (1/9) until TLC shows no remaining product. Solvent removal gives the title compound. This material is filtered through silica gel more carefully, giving an analytical sample of the title compound, NMR (300 MHz, CDCl$_3$) 7.1–7.2, 7.05, 5.26, 4.23, 4.12, 3.83, 3.0–2.7, 1.28; high resolution MS calculated for 220.1099, found 220.1105.

Example 114

Racemization of (+)-ethyl (isochroman-1-yl)acetate (LVI)

Crude (+)-ethyl (isochroman-1-yl)acetate (LVI, 21.4 g, 97.2 mmol) recovered as a 92/8 ratio of enantiomers from a *Pseudomonas cepaica* catalyzed kinetic resolution (see EXAMPLE 83) which assayed to be approximately 81% pure by HPLC (although almost baseline purity by proton NMR) is dissolved in THF (97 ml) and cooled to 0°. Potassium t-butoxide (5 mol %, 4.8 ml) is added via syringe and the solution stirred 10 min. The solution was quenched with acetic acid (6 mol %, 0.33 ml) and the solvent removed under reduced pressure. THF (25 ml) is added followed by hexane (200 ml). The slurry is filtered through 200 mesh silica gel (100 g), washing with THF/hexane (1/9) until TLC showed no remaining product which assays to 86% purity by HPLC. An aliquot is removed and reduced to the carbinol with lithium aluminum hydride in THF at 25°. Analysis of this carbinol on a HPLC fitted with a chiral stationary phase column eluting with isopropanol/hexane (10/90) demonstrates a 1/1 ratio of enantiomers. The carbinol deriving from the (+)-isochroman ester elutes at 9.07 min, while the carbinol deriving from the (−)-isochroman ester elutes at 11.35 min.

Example 115

(−)-(Isochroman-1-yl)acetic acid (LV) Obtained By Using *Pseudomonas cepaica* Lipase To a suspension of ethyl (+)-(isochroan-1-yl)acetate (LIV) in pH 7 phosphate buffer solution (0.048 g/ml) is added 10% by weight of PS-30 (*Pseudomonas cepaica*, Amano Corporation) lipase. The contents are shaken at 28° and at 180 rpm for 24 hr. At the end of this period, the reaction mixture is acidified to pH<4 with hydrochloric acid (10%), and extracted with ethyl acetate. The ethyl acetate solution is washed two times with saturated sodium carbonate solution, the combined base washings are acidified with hydrochloric acid (10%), and the acid solution thoroughly extracted with ethyl acetate. The ethyl acetate extract is dried over magnesium sulfate and concentrated to give crude (−)-acid. Recrystallization of the crude (−)-acid from methyl-tert-butyl ether give the title compound.

Example 116

(+)-1,2,3,4-Tetrahydro-1-naphthalenylacetic Acid (CIX)

Following the general procedure of EXAMPLE 83 and making non-critical variations but starting with (±)-ethyl 1,2,3,4-tetrahydro-1-naphthalenylacetate (CVIII, EXAMPLE 65), the title compound is obtained, $[\alpha]^{25}$+2° (c=2.5 in methanol).

Example 117

(−)-Ethyl 1,2,3,4-Tetrahydro-1-naphthalenylacetate (CVIII)

The unhydrolyzed ester recovered from the hydrolysis with lipase (EXAMPLE 116), the ethyl acetate layer after aqueous sodium carbonate wash, is recovered and purified to give the ester enriched with (−) enantiomer of the title compound, $[\alpha]^{25}$−2° (c=1.38 in methanol).

Example 118

(±)-, (+)-, and (−)-4-[4-[2-(1,2,3,4-Tetrahydro-1-naphthalenyl)ethyl]-1-piperazinyl]benzamide, -hydrochloride, -maleate, -fumarate, and -mesylate (CXII)

Following the general procedure of EXAMPLE 86 and making non-critical variations but starting with (±)-ethyl 1,2,3,4-tetrahydro-1-naphthalenylacetate (CVIII, EXAMPLE 65), (±)-2-(1,2,3,4-tetrahydro-1-naphthalenyl) ethanol (CX) is obtained.

Following the general procedure of EXAMPLE 87 and making non-critical variations but starting with this alcohol (CX), it is converted into the corresponding mesylate (CXIII).

This mesylate (2.5 g, 10 mmol) in a mixture of 4-(piperazin-1-yl)benzamide (IV, EXAMPLE 47, 2.5 g, 12 mmol), diisopropylethylamine (3.5 ml, 20 mmol), ethyleneglycol (30 ml), and tetrahydrofuran (30 ml) is heated at 90° for 18 hr. The mixture is cooled to 20°–25°, diluted with water, and the resulting solid is separated. Crystallization from methanol/tetrahydrofuran/ethyl acetate gives the title compound as a racemate, mp 217°; NMR (DMSO-$d_6$, TMS) 7.73–6.89, 3.25 and 2.92–1.62 δ.

The salts are prepared according to the procedure of EXAMPLE 49; hydrochloride salt mp 233°, maleate mp 231°, fumarate mp 193°, mesylate mp 212°.

Following the general procedure described above and making non-critical variations but starting with (+)-1,2,3,4-tetrahydro-1-naphthalenylacetic acid (CIX, EXAMPLE 116), the (+)-enantiomer is obtained, mp 211°. The salts are prepared according to the procedure of EXAMPLE 49, the mesylate shows $[\alpha]_D^{25}+3°$ (c=0.87, methanol).

Following the general procedure described above and making non-critical variations but starting with (−)-ethyl 1,2,3,4-tetrahydro-1-naphthalenylacetate (CVIII, EXAMPLE 117), the (−)-enantiomer is obtained, mp 211°. The salts are prepared according to the procedure of EXAMPLE 49: the mesylate shows $[\alpha]_D^{25}-4°$ (c=0.98, methanol).

Example 119

(±)-, (+)-, and (−)-4-[4-[2-(1,2,3,4-Tetrahydro-1-naphthalenyl)ethyl]-1-piperazinyl]benzenesulfonamide, -hydrochloride, -maleate, -fumarate, -mesylate, malonate, lactate, tosylate, tartrate, and citrate (CXII)

Following the general procedure of EXAMPLE 118 and making non-critical variations but starting with (±)-ethyl 1,2,3,4-tetrahydro-1-naphthalenylacetate (CVIII, EXAMPLE 65), and using 4-(piperazin-1-yl)benzenesulfonamide (IV) in place of 4-(piperazin-1-yl)benzamide (IV), the title compound is obtained as a racemate, mp 221°; NMR (DMSO-$d_6$, TMS) 7.61–7.00, 3.32–3.24, 2.92–1.60 δ.

The salts are prepared according to the procedure of EXAMPLE 49; hydrochloride salt mp 284°, maleate mp 133°, fumarate mp 221°, mesylate mp 162°.

Following the general procedure described above and making non-critical variations but starting with (+)-1,2,3,4-tetrahydro-1-naphthalenylacetic acid (CIX, EXAMPLE 116), the (+)-enantiomer is obtained, mp 197°. The salts are prepared according to the procedure of EXAMPLE 49: maleate mp 177°, fumarate mp 221°, mesylate mp 194° shows $[\alpha]_D^{25}+3.3°$ (c=2.7, methanol, malonate mp 158°, lactate mp 174°, tosylate mp 278°, tartrate mp>240° (decomp), citrate mp 152°.

Following the general procedure described above and making non-critical variations but starting with (−)-ethyl 1,2,3,4-tetrahydro-1-naphthalenylacetate (CVIII, EXAMPLE 117), the (−)-enantiomer is obtained, mp 196°. The salts are prepared according to the procedure of EXAMPLE 49: the mesylate shows $[\alpha]_D^{25}-3°$ (c=0.95, methanol).

Example 120

4-[4-[2-(3,4-Dihydro-1-naphthalenyl)ethyl]-1-piperazinyl]benzamide (CXV-B)

A mixture of (E)-1-Carbethoxymethylene-1,2,3,4-tetrahydronaphthalene (CVII-A), Ethyl (3,4-Dihydro-1-naphthalenyl)acetate (CVII-B) and (Z)-1-carbethoxymethylene-1,2,3,4-tetrahydronaphthalene (CVII-C, EXAMPLE 63, 10.8 g, 50 mmol) in sodium methoxide (250 mmol/methanol, 300 ml) is refluxed for 24 hr. The reaction is quenched with water (50 ml) and stirred for 5 hr. The mixture is then acidified with hydrochloric acid (6N) to pH<3, concentrated, and extracted with ethyl acetate. The crude product is crystallized from ethyl acetate/hexane, mp. 104°–105°, NMR (CDCl$_3$, TMS) 6.0 δ confirmed this compound as 3,4-dihydro-1-naphthalenylacetic acid.

Following the general procedure of EXAMPLE 86 and making non-critical variations but starting with this acid, 2-(3,4-dihydro-1-naphthalenyl)ethanol (CXVI-B) is obtained.

Following the general procedure of EXAMPLE 87 and making non-critical variations but starting with this alcohol, it is converted into the mesylate (CXVII-B).

Following the general procedure of EXAMPLE 118, the title compound is obtained, mp 216°.

Example 121

4-[4-[2-(3,4-Dihydro-1-naphthalenyl)ethyl]-1-piperazinyl]benzenesulfonamide (CXV-B)

Following the general procedure described in EXAMPLE 119 and making non-critical variations but starting with 2-(3,4-dihydro-1-naphthalenyl)ethanol (CXVI-B) (EXAMPLE 120), the title compound is obtained, mp 222°.

Example 122

4-[4-[2-(Inden-1-yl)ethyl]piperazin-1-yl]benzenesulfonamide (CXV-B)

Following the general procedure described in EXAMPLE 87, and using 4-(piperazin-1-yl)benzenesulfonamide (IV) in place of 4-(piperazin-1-yl)benzamide (IV), the title compound is obtained, mp 181°.

Example 123

4-[4-[2-(Indan-1-yl))ethyl]piperazin-1-yl]benzenesulfonamide (CXII)

Following the general procedure of EXAMPLE 86, and making non-critical variations but staring with ethyl 1-indanylacetate (CVIII, EXAMPLE 64), 2-(indan-1-yl)ethanol (CX) is obtained.

Following the general procedure of EXAMPLE 87 and making non-critical variations and using 4-(piperazin-1-yl)benzenesulfonamide (IV) in place of 4-(piperazin-1-yl)benzamide (IV), the title compound is obtained, mp 224°.

Example 124

1-(3,4-Dichlorophenyl)-4-[2-(6-bromoisochroman-1-yl)ethyl]piperazine (CXVI)

(6-Bromoisochroman-1-yl)acetic acid (EXAMPLE 22, LXVIII) is coupled with 3,4-dichlorophenylpiperazine (XI) and the resulting amide, 1-(3,4-dichlorophenyl)-4-[2-(6-bromoisochroman-1-yl)]acetyl piperazine (LXIII, 1.66 mmol) is reduced following the general procedure of EXAMPLE 50 and making non-critical variations, to give the title compound, HRMS Calcd for $C_{21}H_{23}N_2O_1Br_1Cl_2$= 468.0371, found=418.0363.

Example 125

1-(4-Fluorophenyl)-4-[2-(6-bromoisochroman-1-yl)ethyl]piperazine (CXXVI)

(6-Bromoisochroman-1-yl)acetic acid (EXAMPLE 22, LXVIII) is coupled with 4-fluorophenylpiperazine (XI) and the resulting amide, 1-(4-fluorophenyl)-4-[2-(6-bromoisochroman-1-yl)]acetyl piperazine (LXIII, 1.64 mmol) is reduced following the general procedure of EXAMPLE 50 and making non-critical variations, to give the title compound, HRMS Calcd for $C_{21}H_{24}N_2O_1Br_1F_1$= 418.1056, found=418.1057.

Example 126

1-(2-Ethoxyphenyl)-4-[2-(6-bromoisochroman-1-yl) ethyl]piperazine (CXXVI)

(6-Bromoisochroman-1-yl)acetic acid (EXAMPLE 22, LXVIII) is coupled with 2-ethoxyphenylpiperazine (XI) and the resulting amide, 1-(2-ethoxyphenyl)-4-[2-(6-bromoisochroman-1-yl)]acetyl piperazine (LXIII, 3.7 mmol) is reduced following the general procedure of EXAMPLE 50 making non-critical variations, to give the title compound, IR (neat) 2816, 1501, 1480, 1448, 1240, 1143, 1124, 1046, 1110 and 748 cm$^{-1}$; NMR (300 MHz, CDCl$_3$) 7.31–7.26, 7.00–6.90, 6.85°6.83, 4.78, 4.14–4.03, 3.78–3.70, 3.13, 3.00–2.90, 2.13, 1.99, 1.45; CMR (75 MHz, CDCl$_3$) 151.37, 141.19, 137.0, 136.1, 131.5, 129.1, 126.4, 122.5, 120.8, 119.8, 117.9, 112.2, 74.2, 63.4, 62.6, 54.6, 53.5, 50.4, 33.0, 28.7 and 14.8δ; HRMS Calcd for $C_{23}H_{29}N_2O_2Br_1$=444.1413, found=444.1400.

Example 127

1-(4-Methylphenyl)-4-[2-(6-bromoisochroman-1-yl) ethyl]piperazine (CXXVI)

(6-Bromoisochroman-1-yl)acetic acid (EXAMPLE 22, LXVIII) is coupled with 4-methylphenylpiperazine (XI) and the resulting amide, 1-(4-methylphenyl)-4-[2-(6-bromoisochroman-1-yl)]acetyl piperazine (LXIII, 1.49 mmol) is reduced according to the general procedure of EXAMPLE 50 making non-critical variations, to give the title compound, NMR (300 MHz, CDCl$_3$) 7.32–7.26, 7.07, 6.97, 6.84, 4.78, 4.14–3.07, 3.78–3.69, 3.16, 2.94, 2.7–2.48, 2.26, 2.15–1.90 δ; CMR (75 MHz, CDCl$_3$) 149.0, 136.9, 136.1, 131.4, 129.4, 129.0, 128.9, 126.3, 119.8, 116.1, 74.1, 62.6, 54.4, 53.2, 49.5, 33.0, 28.6 and 20.2 δ.

Example 128

1-(4-Chlorophenyl)-4-[2-(6-bromoisochroman-1-yl) ethyl]piperazine (CXXVI)

(6-Bromoisochroman-1-yl)acetic acid (EXAMPLE 22, LXVIII) is coupled with 4-chlorophenylpiperazine (XI) and the resulting amide, 1-(4-chlorophenyl)-4-[2-(6-bromoisochroman-1-yl)]acetyl piperazine (LXIII, 1.39 mmol) is reduced according to the general procedure of EXAMPLE 50 making non-critical variations, to give the title compound, mp 94°–96°; IR (mull) 1500, 1483, 1448, 1248, 1242, 1152, 1144, 1113, 1102, 815 cm$^{-1}$; NMR (300 MHz, CDCl$_3$) 7.32–7.26, 7.19, 6.97, 6.83, 4.78, 4.14–4.07, 3.78–3.69, 3.16, 3.00–2.90, 2.7–2.48, 2.15–1.90 δ; CMR (75 MHz, CDCl$_3$) 149.6, 137.1, 136.0, 131.4, 129.1, 128.7, 126.3, 124.6, 120.0, 116.9, 74.0, 62.6, 54.3, 53.3, 53.0, 48.9, 33.0 and 28.6 δ.

Example 129

1-(4-Benzyloxyphenyl)-4-[2-(6-bromoisochroman-1-yl)ethyl]piperazine (CXXVI)

(6-Bromoisochroman-1-yl)acetic acid (EXAMPLE 22, LXVIII) is coupled with 4-benzyloxyphenylpiperazine (XI) and the resulting amide, 1-(4-benzyloxyphenyl)-4-[2-(6-bromoisochroman-1-yl)]acetyl piperazine (LXIII, 7.23 mmol) is reduced according to the general procedure of EXAMPLE 50 making non-critical variations to give the title compound, mp 87°–90°.

Example 130

1-(4-Butyloxyphenyl)-4-[2-(6-bromoisochroman-1-yl)ethyl]piperazine (CXXVI)

(6-Bromoisochroman-1-yl)acetic acid (EXAMPLE 22, LXVIII) is coupled with 4-butyloxyphenylpiperazine (XI) and the resulting amide, 1-(4-butyloxyphenyl)-4-[2-(6-bromoisochroman-1-yl)]acetyl piperazine (LXIII, 4.2 mmol) is reduced according to the general procedure of EXAMPLE 50 making non-critical variations, to give the title compound, NMR (300 MHz, CDCl$_3$) 7.32, 7.06, 6.85, 4.80, 4.13–4.08, 3.71, 3.28, 3.10–2.72, 2.65, 2.40, 2.22, 1.74, 1.46, 1.25 and 0.96 δ.

Example 131

1-(3,4-Dichlorophenyl)-4-[2-(6-aminocarbonylisochroman-1-yl)ethyl]piperazine (CXVII)

Following the general procedure of EXAMPLE 102 and making non-critical variations but using 1-(3,4-dichlorophenyl)-4-[2-(6-bromoisochroman-1-yl)ethyl] piperazine (CXXVI, EXAMPLE 124, 0.63 mmol), the title compound is obtained, HRMS Calcd for $C_{22}H_{26}N_3F_1O_2$= 433.1324, found=433.1325.

Example 132

1-(4-Fluorophenyl)-4-[2-(6-aminocarbonylisochroman-1-yl)-ethyl]piperazine (CXVII)

Following the general procedure of EXAMPLE 102 and making non-critical variations but using 1-(4-fluorophenyl)-4-[2-(6-bromoisochroman-1-yl)ethyl]piperazine (CXXVI, EXAMPLE 125, 0.62 mmol), the title compound is obtained, HRMS Calcd for $C_{22}H_{26}N_3F_1O_2$=383.2009, found=383.2010.

Example 133

1-(2-Ethoxyphenyl)-4-[2-(6-aminocarbonylisochroman-1-yl)ethyl]piperazine (CXVII)

A dry 25 ml round bottom flask is charged with THF (2 ml) and cooled to −78°. t-butyllithium in hexanes (1.6M, 1.18 ml, 2 mmol) is added at once via syringe and stirred for 5 min. A solution of 1-(2-ethoxyphenyl)-4-[2-(6-bromoisochroman-1-yl)-ethyl]piperazine (CXXVI, EXAMPLE 126) in THF (3 ml) is added via canula, and stirred for another 10 min. Dry carbon dioxide gas is bubbled through the reaction mixture for 10 min, while maintaining the dry ice/acetone cooling bath. The reaction mixture is warmed to 20°–25°. When the gas evolution stopped, oxalyl chloride (0.13 ml, 1.5 mmol) is added dropwise via syringe, followed by DMF (4 drops). After two hours of stirring, the reaction mixture is poured into ammonium chloride (40 ml), extracted two times with equal volumes of methylene chloride (which are combined), dried with sodium sulfate, filtered and concentrated. The concentrate is purified by flash chromatography (silica gel, 25 g;

eluting with methanol/ethyl acetate (10/90) to give the impure product. The impurity is removed by triturating with methylene chloride and hexane to leave an oil which is converted into the hydrochloride salt using ethereal hydrochloric acid to give the title compound, mp 208°–210°; HRMS Calcd for $C_{24}H_{31}N_{3O3}$=409.2365, found=409.2364.

Example 134

1-(4-Methylphenyl)-4-[2-(6-aminocarbonylisochroman-1-yl)ethyl]piperazine (CXVII)

An oven dried 5 ml micro vial, equipped with a Claisen condenser, water cooled condenser, and hose adapter, is charged with 1-(4-methylphenyl)-4-[2-(6-bromoisochroman-1-yl)-ethyl]piperazine (CXXVI, EXAMPLE 127, 103 mg, 0.25 mmol), palladium acetate (98%, 2.9 mg, 0.012 mmol) and 1,3-bis-diphenylphosphinopropane (97%, 6.4 mg, 0.015 mmol). Carbon monoxide atmosphere is established in the vial. To the reaction vessel is introduced via syringe DMF (0.62 ml), 1,1,1,3,3,3-hexamethyldisilazane (98%, 0.38 ml, 1.8 mmol), and diisopropylethylamine (0.087 ml, 0.5 mmol). The mixture is heated to 100° over 18 hr. After cooling to 20°–25°, the reaction mixture separates into two phases. The reaction mixture is poured into methylene chloride (pH=12). The mixture is washed one time with aqueous sodium hydroxide (1N). The organic phase is then concentrated under reduced pressure to remove excess solvents and reactants. The residue is dissolved in methylene chloride again and the mixture is washed twice with aqueous hydrochloric acid (1N). The aqueous acidic phases are combined, made basic with concentraged aqueous sodium hydroxide (pH>14). The basic mixture is extracted four times with methylene chloride, the organics phases are combined and concentrated. The product crystallized out of the crude and the mother liquor is purified by flash chromatography (silica gel, 13 g; eluting with methanol/ethyl acetate (10/90) to give additional title compound, HRMS Calcd for $C_{23}H_{29}N_3O_2$=379.2260, found=379.2269.

Example 135

1-(4-Chlorophenyl)-4-[2-(6-aminocarbonylisochroman-1-yl)ethyl]piperazine (CXVII)

Following the general procedure of EXAMPLE 134 and making non-critical variations but using 1-(4-chlorophenyl)-4-[2-(6-bromoisochroman-1-yl)ethyl]piperazine (CXXVI, EXAMPLE 128, 108 mg, 0.25 mmol), the title compound is obtained, mp 169°–171°.

Example 136

1-(4-Benzyloxyphenyl)-4-[2-(6-aminocarbonylisochroman-1-yl)ethyl]piperazine (CXVII)

Following the general procedure of EXAMPLE 134 and making non-critical variations but using 1-(4-benzyloxyphenyl)-4-[2-(6-bromoisochroman-1-yl)ethyl] piperazine (CXXVI, EXAMPLE 129, 108 mg, 0.25 mmol), the title compound is obtained, NMR (300 MHz, CDCl$_3$) 7.58, 7.43–7.30, 7.15, 6.90, 6.20–5.80, 5.0, 4.87, 4.18–4.10, 3.81–3.73, 3.10, 3.0, 2.75, 2.65–2.54, 2.15, 2.05; CMR (75 MHz, CDCl$_3$) 169.0, 152.9, 145.8, 142.3, 137.3, 134.5, 131.3, 128.5, 128.1, 127.8, 127.4, 125.0, 124.9, 118.0, 115.5, 74.5, 70.4, 62.8, 54.6, 53.4, 50.4, 33.1 and 29.0 δ.

Example 137

1-(4-Butyloxyphenyl)-4-[2-(6-aminocarbonylisochroman-1-yl)ethyl]piperazine (CXVII)

Following the general procedure of EXAMPLE 134 and making non-critical variations but using 1-(4-butyloxyphenyl)-4-[2-(6-bromoisochroman-1-yl)ethyl] piperazine (CXXVI, EXAMPLE 130, 108 mg, 0.25 mmol), the title compound is obtained, NMR (300 MHz, CDCl$_3$) 7.60, 7.18, 6.86, 6.20–5.80, 4.85, 4.15, 3.90, 3.77, 3.10, 2.96, 2.80–2.50, 2.15, 2.05, 1.74, 1.48 and 0.96 δ; CMR (75 MHz, CDCl$_3$) 169.1, 160.8, 153.4, 145.6, 142.4, 134.6, 131.3, 130.3, 128.2, 127.6, 125.1, 125.0, 118.1, 115.1, 74.5, 68.1, 62.9, 54.7, 53.5, 50.6, 41.4, 33.2, 31.5, 29.0, 19.3 and 13.9 δ.

Example 138

1-(4-Methoxyphenyl)-4-[2-(6-methylaminocarbonylisochroman-1-yl)-ethyl] piperazine (LXXIV)

Following the general procedure of EXAMPLE 133 and making non-critical variations but starting with 1-(4-methoxyphenyl)-4-[2-(6-bromoisochroman-1-yl)ethyl] piperazine (LXXI, EXAMPLE 22, 1.08 g) and using methylamine gas instead of aqueous ammonium chloride, the title compound is obtained, mp 174°–176°.

Example 139

1-(4-Methoxyphenyl)-4-[2-(6-dimethylaminocarbonylisochroman-1-yl)-ethyl] piperazine (LXXIV)

Following the general procedure of EXAMPLE 133 and making non-critical variations but starting with 1-(4-methoxyphenyl)-4-[2-(6-bromoisochroman-1-yl)ethyl] piperazine (LXXI, EXAMPLE 22, 1.08 g) and using dimethylamine gas instead of aqueous ammonium chloride, the title compound is obtained, mp 94°–96°.

Example 140

(S)-(−)-3-Bromo-4-[4-[2-(6-bromoisochroman-1-yl) ethyl]piperazin-1-yl]benzenesulfonamide (LXXXI)

Following the general procedure of EXAMPLE 49 and making non-critical variations, 2-(6-bromoisochroman-1-yl) ethanol (LXXIX, 0.399 g) and 3-bromo-4-(piperazin-1-yl)-benzenesulfonamide hydrochloride (VIII, Chart C, 0.544 g; prepared by the method of EXAMPLE 37 but using 4-(piperazin-1-yl)benzenesulfonamide (IV) in place of 1-(4-methoxyphenyl)piperazine) are combined to give the title compound; mp 206°–208°; MS (m/z) 557 and 559; IR (mineral oil) 1165, 1338, 1450, 616, 1586 and 731 cm$^{-1}$.

Example 141

N-Acetyl-(S)-(−)-4-[4-[2-(isochroman-1-yl)ethyl] piperazin-1-yl]benzenesulfonamide (LXXXI)

(S)-(−)-4-[4-[2-(Isochroman-1-yl)ethyl]piperazin-1-yl] benzenesulfonamide (EXAMPLE 49, 0.203 g) is stirred in DMF (2 ml) and triethylamine (0.211 ml) and acetyl chloride (0.108 ml) is added. The mixture is stirred at 20°–25° for one hr and then at 50° for 4 days. After cooling, the mixture is partitioned between dichloromethane and aqueous sodium

Example 142

(S)-(−)-4-[4-[2-(Isochroman-1-yl)ethyl]-cis-3,5-dimethylpiperazin-1-yl]benzamide (LXXXI)

Following the general procedure of EXAMPLE 48 and making non-critical variations (−)-isochromanylacetic acid (LXI, EXAMPLE 45, 0.346 g) and 4-(3,5-dimethylpiperazin-1-yl)benzamide [(IV), 0.462 g; prepared from 4-fluorobenzamide (III) and cis-2,6-dimethylpiperazine (II, Aldrich) by the procedure of EXAMPLE 47, Step 1] gives the title compound, mp 206°–207°; MS (m/z) 393; IR (mineral oil) 1640, 1607, 1246, 3383, 1402, 1395, 1422, 1112 and 1332 cm$^{-1}$.

Example 143

(S)-(−)-4-[4-[2-(Isochroman-1-yl)ethyl]-cis-3,5-dimethylpiperazin-1-yl]benzenesulfonamide (LXXXI)

Following the general procedure of EXAMPLE 49 and making non-critical variations 2-(isochroman-1-yl)ethanol-O-methanesulfonate (LXXX, 0.412 g) and 4-(3,5-dimethylpiperazin-1-yl)benzenesulfonamide [(IV), 0.433 g; prepared from 4-fluorobenzenesulfonamide, III, and cis-2,6-dimethylpiperazine, II (Aldrich), by the method of EXAMPLE 47] gives the title compound; mp 170°–175° (decomp)°; MS (m/z) 429; IR (mineral oil) 1153, 1596, 1325, 1162 and 1096 cm$^{-1}$.

Example 144

(±)-4-[4-[2-(6-Fluoroisochroman-1-yl)ethyl]piperazin-1-yl]benzenesulfonamide (LXXXI)

Following the general procedure for EXAMPLE 49 and making non-critical variations but starting with (±)-(6-fluoroisochroman-1-yl)ethanol (LXXIX, 1.61 g) and extracting the product with dichloromethane rather than precipitating it with water, the title compound is obtained. For the free base mp 229°–232°; MS (m/z) 419; IR (mineral oil) 1156, 1334, 1499, 1234 and 1595 cm$^{-1}$ and for the methanesulfonate salt mp 200°–203°; IR (mineral oil) 1155, 1042, 1218, 1323 and 1105 cm$^{-1}$.

Example 145

(±)-4-[4-[2-(7-Methylisochroman-1-yl)ethyl]piperazin-1-yl]benzenesulfonamide (LXXXI)

Following the general procedure for EXAMPLE 49 and making non-critical variations but starting with (±)-(7-methylisochroman-1-yl)ethanol (LXXIX, 2.20 g) and extracting the product with dichloromethane rather than precipitating it with water, the title compound is obtained. For the free base mp 228°–229°; MS (m/z) 415; IR (mineral oil) 1155, 1332, 829, 1596 and 1114 cm$^{-1}$ and methanesulfonate salt mp 227°–229°.

Example 146

(±)-4-[4-[2-(6-Methylisochroman-1-yl)ethyl]piperazin-1-yl]benzenesulfonamide (LXXXI)

Following the general procedure for EXAMPLE 49 and making non-critical variations but starting with (±)-(6-methylisochroman-1-yl)ethanol (LXXIX, 2.20 g) and extracting the product with dichloromethane rather than precipitating it with water, the title compound is obtained, mp 221°–222°; MS (m/z) 415; IR (mineral oil) 1157, 1334, 1596, 1096 and 831 cm$^{-1}$.

Example 147

(R)-(+)-2-[4-[2-(Isochroman-1-yl)ethyl]piperazin-1-yl]benzamide (LXXXI)

Following the general procedure for EXAMPLE 49 and making non-critical variations 2-(isochroman-1-yl)ethanol (LXXIX, (+)-enantiomer, 0.6032 g) and 2-(piperazin-1-yl)benzamide (IV, 0.8375 g) are combined to give the title compound. A portion is recrystallized from dichloromethane/ether, mp 156.75°–158°; MS (m/z) 365; [α]$_D$+59° (c 1.02, methylene chloride); IR (mineral oil) 1663, 1451, 3276, 1109 and 3305 cm$^{-1}$.

Example 148

(R)-(+)-4-[4-[2-(Isochroman-1-yl)ethyl]piperazin-1-yl]benzenesulfonamide (LXXXI)

Following the general procedure for EXAMPLE 49 and making non-critical variations 2-(isochroman-1-yl)ethanol (LXXIX, (+)-enantiomer, 0.6045 g) and 4-(piperazin-1-yl)benezenesulfonamide (IV, 0.9824 g ) are combined to give the title compound, mp 189°–190°; MS (m/z) 401; [α]$_D$+48 (c 0.877, DMF); IR (mineral oil) 1162, 1594, 1150, 1101, 614 cm$^{-1}$.

Example 149

N-(3-Ethoxypyridin-2-yl)-N-[1-[2-(isochroman-1-yl)ethyl]piperidin-4-yl]methylamine methanesulfonate (LXXXI)

Step 1

A mixture of 1-benzyl-4-piperidone (XXV, Chart G, 24.5 mL, 0.1295 mol), N-methylamine hydrochloride (44.75 g, 0.6628 mol) and methanol (50 ml) is stirred for 35 minutes at 20°–25°, at which time additional methanol (10 ml) is added. The mixture is then cooled in an ice bath and a solution of sodium cyanoborohydride (9.1749 g, 0.1460 mol) in methanol (68 ml) is added to the mixture. The mixture is stirred for 5 min and then is allowed to warm to 20°–25°. After 1.25 hr the mixture is concentrated under reduced pressure and saturated aqueous sodium bicarbonate is added. After stirring for 1 hr, the mixture is extracted with dichloromethane and the organic phases are combined, backwashed with saline, dried with magnesium sulfate and concentrated under reduced pressure to give (XXVII). The material is upgraded by forming the dihydrochloride salt and collecting the resulting solids. The dihydrochloride salt is further upgraded by trituration with dichloromethane. The free base (XXVII) is recovered by slurrying the dihydrochloride salt (7.5204 g, 0.02713 mol) in dichloromethane and adding enough saturated sodium bicarbonate to dissolve all the solids and then extracting the aqueous layer exhaustively with dichloromethane to obtain N-(1-benzylpiperidin-4-yl)-N-methylamine (XXVII), MS (m/z) 204; IR (neat) 2942, 2796, 2775, 743 and 2749 cm$^{-1}$.

Step 2

Iodoethane (26 ml) is added to a mixture of 2-bromo-3-pyridinol (Aldrich, 22.75 g), potassium carbonate anhydrous (32.541 g) and DMF (258 ml). The mixture is stirred at 80°–85° for 3.25 hr, at which time the mixture is cooled in an ice water bath and potassium carbonate is then filtered off and washed with dichloromethane. The filtrate is concentrated under reduced pressure and the residue is dissolved in ethyl acetate (570 ml) and washed with water (300 ml). The aqueous layer is backwashed with ethyl acetate (500 ml) and each of the organic phases are washed with saline (114 ml). The organic phases are combined, dried with magnesium sulfate and concentrated under reduced pressure. The crude material is chromatographed (silica gel; eluting with ethyl acetate/hexane (20/80) to give 2-bromo-3-ethoxypyridine (XXVIIIa, Chart G), MS (m/z) 201, 203; IR (neat) 1448, 1294, 1389, 1420 and 1205 cm$^{-1}$.

Step 3

A mixture of N-(1-benzylpiperidin-4-yl)-N-methylamine (XXVII, 4.80 g) and 2-bromo-3-ethoxypyridine (XXVIIIa, 2.3805 g) is placed in a metal, screw cap reaction vessel using dichloromethane as the transfer solvent. Reduced pressure is applied to the vessel with heating at 50° to 60° for 45 min to remove dichloromethane. The vessel is then sealed and heated at 160° to 165° for 2 days. After cooling, the resulting solids are dissolved in dichloromethane and washed with water and saline. The organic phases are dried over magnesium sulfate and concentrated under reduced pressure to give the product, which is chromatographed (silica gel; eluting with ethyl acetate/hexane (30/70) followed by ethyl acetate/hexane (50/50)), to give N-(1-benzylpiperidin-4-yl)-N-(3-ethoxypyridin-2-yl)-methylamine (XXVIII, Chart G); MS (m/z) 325; IR (neat) 1462, 1211, 1481, 1589 and 1450 cm$^{-1}$.

Step 4

A mixture of N-(1-benzylpiperidin-4-yl)-N-(3-ethoxypyridin-2-yl)-methylamine (XXVIII, Chart G, 1.0374 g), ammonium formate (1.0758 g, 17.1 mmol), palladium on carbon (10%, 0.1043 g) and methanol (7.4 ml) is heated at reflux for 37 min. After cooling, the palladium on carbon catalyst is filtered off and washed with methanol. The filtrate is concentrated under reduced pressure to an oil, which is then partitioned between dichloromethane and saturated aqueous sodium bicarbonate. The combined the organic phases are dried with magnesium sulfate and concentrated under reduced pressure to give N-(piperidin-4-yl)-N-(3-ethoxypyridin-2-yl)methylamine (XXIX, Chart G), MS (m/z) 235; IR (neat) 1211, 1462, 1481, 1589 and 1449 cm$^{-1}$.

Step 5

Following the general procedures of EXAMPLES 57 and 58 and making non-critical variations (but using borane-methyl sulfide in place of lithium aluminum hydride and including treatment with acetone/aqueous hydrochloric acid in the workup), 2-(isochroman-1-yl)acetic acid (LXXVIII) and N-(piperidin-4-yl)-N-(3-ethoxypyridin-2-yl)-methylamine (XXIX, Chart G) are combined to give the free base of the title compound (LXXXI). The methansulfonate salt is formed using methanesulfonic acid, MS (m/z) 395; IR (neat) 1218, 1037, 1194, 1164 and 1462 cm$^{-1}$.

Example 150

(S)-(−)-4-[4-[2-(Isochroman-1-yl)ethyl] homopiperazin-1-yl]benzenesulfonamide (LXXXI)

Following the general procedure for EXAMPLE 48 and making non-critical variations (−)-2-(isochroman-1-yl) ethanol (LXXIX) and 4-(homopiperazin-1-yl) benzenesulfonamide (IV; prepared from 4-fluorobenzenesulfonamide (III) and homopiperazine (II, Aldrich) by the method of EXAMPLE 47 Step 1) give the title compound, MS (m/z) 415; [α]$_D$ −50° (c 0.9996, methylene chloride); IR (mineral oil) 1153, 1595, 1102, 1511 and 1316 cm$^{-1}$.

Example 151

4-[4-[2-((−)-Isochroman-1-yl)ethyl]-3-(RS)-3-methylpiperazin-1-yl]benzenesulfonamide (LXXXI)

Following the general procedure for EXAMPLE 48 and making non-critical variations (−)-2-(isochroman-1-yl) ethanol (LXXIX) and 4-(3-methylpiperazin-1-yl) benzenesulfonamide (IV; prepared from 4-fluorobenzenesulfonamide (III) and 2-methylpiperazine (II, Aldrich) by the method of EXAMPLE 47) give the title compound, 174°–174.75°; MS (m/z) 415; IR (mineral oil) 1154, 1334, 830, 1111 and 1116 cm$^{-1}$.

Example 152

N-Methyl-(S)-(−)-4-[4-[2-(isochroman-1-yl)ethyl] piperazin-1-yl]benzenesulfonamide N-Methyl-4-fluorobenzenesulfonamide (III)

A mixture of 4-fluorobenzenesulfonyl chloride (III, Aldrich, 3.12 g), methylamine hydrochloride (1.17 g), triethylamine (4.8 ml) and THF (25 ml) are stirred at 20°–25° for five days. The mixture is then partitioned between dichloromethane, aqueous sodium bicarbonate, and saline. The organic phases are dried over magnesium sulfate and concentrated. The resulting solid is crystallized from dichloromethane/hexane and then recrystallized from methanol/dichloromethane to give N-methyl-4-fluorobenzenesulfonamide, NMR 2.67, 4.55, 7.21, 7.89 δ.

Following the general procedure for EXAMPLE 48 and making non-critical variations (−)-2-(isochroman-1-yl) ethanol (LXXIX) and N-methyl-4-(piperazin-1-yl) benzenesulfonamide (IV; prepared from N-methyl-4-fluorobenzenesulfonamide (III) and piperazine (II) by the method of EXAMPLE 47) give the title compound, MS (m/z) 415; [α]$_D$ −49° (c, 0.932, methylene chloride), IR(mineral oil) 1158, 1310, 1099, 1317 and 1149 cm$^{-1}$.

Example 153

(+)-1-(4-Fluorophenyl)-4-[2-(isochroman-1-yl)ethyl] piperazine methanesulfonate (LXXI)

Following the general procedure for EXAMPLE 49 and making non-critical variations, but extracting the final product with dichloromethane rather than precipitating it with water, (−)-2-(isochroman-1-yl)ethanol (LXXIX, 0.5565 g) and 1-(4-fluorophenyl)piperazine (0.6857 g) are combined to give the title compound, MS (m/z) 340; [α]$_D$ +42° (c, 0.828, DMF); IR(mineral oil) 1233, 1509, 1158, 1151 and 1030 cm$^{-1}$.

Example 154

(S)-(−)-4-[4-[2-(Isochroman-1-yl)ethyl] homopiperazin-1-yl]benzamide methanesulfonate (LXXXI)

Following the general procedure for EXAMPLE 49 and making non-critical variations (−)-2-(isochroman-1-yl) ethanol (LXXIX, 0.394 g) and 4-(homopiperazin-1-yl)

benzamide (IV; 0.601 g prepared by the method of EXAMPLE 47, Step 1 from 4-fluorobenzamide, III, and homopiperazine, II) are combined to give the title compound, mp 163.75°–165°; MS (m/z) 379; [α]$_D$–41° (c, 0.975, DMF); IR(mineral oil) 1609, 1043, 1662, 1167 and 1216 cm$^{-1}$.

Following the general procedures of EXAMPLES 9 and 19 and making non-critical variations the compounds of EXAMPLES 155 thru 159 are prepared:

Example 155

N-(3-Ethoxypyridin-2-yl)-N-[(isochroman-1-yl)methyl]piperidin-4-yl]methylamine maleate hemihydrate Following the general procedure of EXAMPLE 9 and making non-critical variations but using N-(piperidin-4-yl)-N-(3-ethoxypyridin-2-yl)methylamine (XXIX, EXAMPLE 149 Step 4) the title compound is obtained, mp 145.5°–146.5°, MS (m/z) 381; IR (mineral oil) 1451, 1481, 1356, 1589 and, 1580 cm$^{-1}$.

Example 156

(RS)-4-[4-[(Isochroman-1-yl)methyl]piperazin-1-yl]benzamide maleate

Following the general procedure of EXAMPLE 9 and making non-critical variations but using 4-(piperazin-1-yl)benzamide (IV, EXAMPLE 47 Step 1), the title compound is obtained, mp 191.25°–191.75°; MS (m/z) 351; IR (mineral oil) 1610, 1394, 1353, 1493 and 1663 cm$^{-1}$.

Example 157

(RS)-4-[4-[(Isochroman-1-yl)methyl]piperazin-1-yl]benzenesulfonamide

Following the general procedure of EXAMPLE 9 and making non-critical variations but using 4-(piperazin-1-yl)benzenesulfonamide (EXAMPLE 49 Step 1), the title compound is obtained, mp 217.5°–218.5°; MS (m/z) 387; IR (mineral oil) 1151, 1321, 1594, 1161 and 1101 cm$^{-1}$.

Example 158

(RS)-4-[4-[3-(Isochroman-1-yl)propyl]piperazin-1-yl]benzamide

Following the general procedure of EXAMPLE 19 and making non-critical variations but using 4-(piperazin-1-yl)benzamide (IV, EXAMPLE 47 Step 1), the title compound is obtained, mp 185°–185.25°; MS (m/z) 379; IR (mineral oil) 1643, 1611, 3402, 1393 and 3183 cm$^{-1}$.

Example 159

(RS)-4-[4-[3-(Isochroman-1-yl)propyl]piperazin-1-yl]benzenesulfonamide

Following the general procedure of EXAMPLE 19 and making non-critical variations but using 4-(piperazin-1-yl)benzenesulfonamide (EXAMPLE 49 Step 1), the title compound is obtained, mp 177°–177.5°; MS (m/z) 415; IR (mineral oil) 1155, 1332, 819, 1309 and 3266 cm$^{-1}$.

Example 160

1-(2-(Isochroman-1-yl)ethyl)-piperazine

Methanesulfony chloride (524 ml, 6.77 mol) is added to a cooled mixture of (–)-2-(isochroman-1-yl)ethanol (EXAMPLE 48, LXXIX, 940 g, 5.2 mol), diisopropylethylamine (1.27 1, 7.29 mol) in tetrahydrofuran (5.6 l). After 4 hr, aqueous hydrochloric acid (1N, 8 l) is added and the mixture extracted with ethyl acetate (17 1). The organic phase is washed with saturated aqueous sodium chloride (2 l) and concentrated under reduced pressure. The concentrate is dissolved in pyridine (4 l) and added to a mixture of piperazine (2.71 kg, 31.5 mol) in pyridine (6.88 l). After 21 hr, the mixture is concentrated under reduced pressure to a slurry and the solids filtered off and washed with ethyl acetate (10 l). The filtrate is concentrated under reduced pressure to an oil and azeotroped with heptane (8 l). The oil is dissolved in ethyl acetate (20 l) and washed with saturated aqueous sodium bicarbonate (2.4 l). The organic phase is concentrated under reduced pressure and the oil azeotroped with toluene (4 l) to give 1.28 kg of the title compound; HPLC retention time=7.3 min (Column=Zorbax C-8; Injection vol.=10 μl; Mobile phase=water (1100 ml)/acetonitrile (500 ml)/methanol (400 mm)/potassium phosphate, monobasic (15 g); Detector=254 nm; Flow rate=0.5 ml/min).

Example 161

(–)-4-[4-[2-(Isochroman-1-yl)ethyl]piperazin-1-yl]benzenesulfonamide hydrochloride and methanesulfonate (LXXXI)

Step 1

To a mixture of 1-(2-(isochroman-1-yl)ethyl)-1-piperazine (example 160, 1.28 kg, 5.2 mol), tetrahydrofuran (800 ml) in ethylene glycol (1.33 l) is added 4-fluorobenzenesulfonamide (1.05 kg, 5.99 mol) followed by diisopropylethylamine (1.89 l, 10.85 mol). The mixture is heated to 110° while driving off the tetrahydrofuran. After stirring for 21 hr between 100° and 126°, the mixture is cooled to 95° and tetrahydrofuran (2.6l) is added followed by water (2.65 l). The mixture is cooled to 20°–25° and the resulting solids collected and washed with water (2.5 l). The solid (1.069 kg) is dried under reduced pressure, mixed with dry silica gel (3 kg) and wetted with methanol/methylene chloride (4/96) and chromatographed (silica gel, 27 kg; eluting with methanol/methylene chloride (4/96), to give the title compound, as the free base; HPLC retention time 9.1 min.

Step 2

To a suspension of (–)-4-[4-[2-(3,4-dihydro-1H-2-benzopyran-1-yl)ethyl]-1-piperazinyl]benzenesulfonamide (EXAMPLE 160, 770 g, 1.92 mol) in methanol (7.7 L) is added all at once methanesulfonic acid (138 mL, 2.13 mol). After 1 hr, the 2suspension is concentrated under reduced pressure to a volume of 4 l and ethyl acetate (7.7 l) added. After stirring at 20°–26° for 17 hr, the suspension is cooled to 3° and the solids collected and washed with ethyl acetate (1 l). The solid is dried under reduced pressure to give the title compound. The solid is dissolved methanol (7 l) and acetonitrile (7 l), clarified, and concentrated under nitrogen until solids appear. The suspension is cooled to 20°–25°, diluted with ethyl acetate (8 l) and the solids collected and washed with ethyl acetate (3 l). The solid is dried under reduced pressure to give the title compound; HPLC retention time 9.1 min.

FORMULAS OF THE EXAMPLES (E-#)
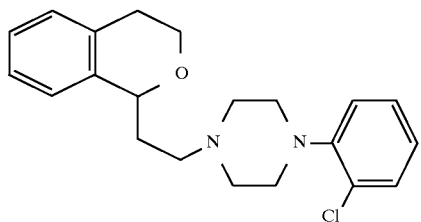
E-1
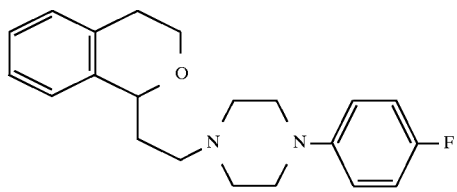
E-2
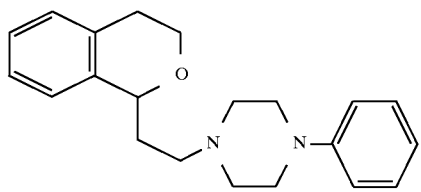
E-3
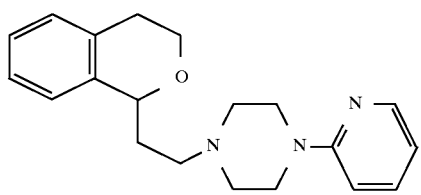
E-4
—
E-5
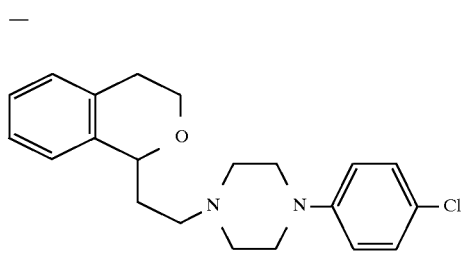
E-6
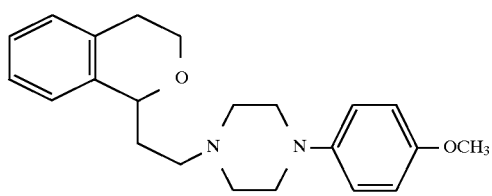
E-7
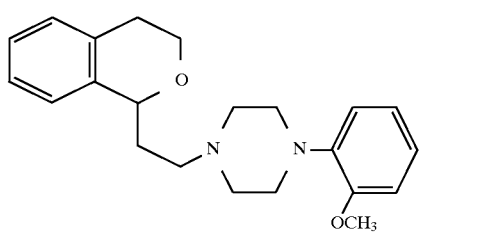
E-8

-continued
FORMULAS OF THE EXAMPLES (E-#)
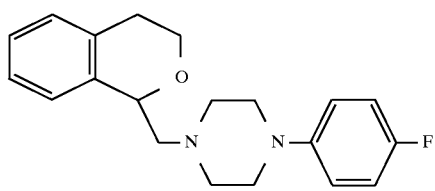
E-9
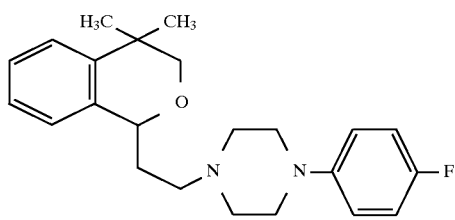
E-10
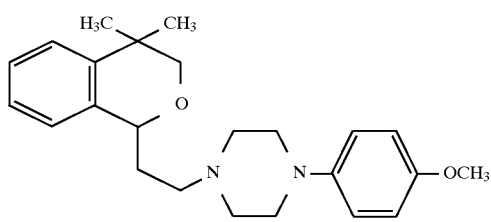
E-11
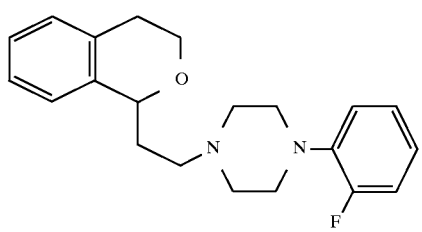
E-12
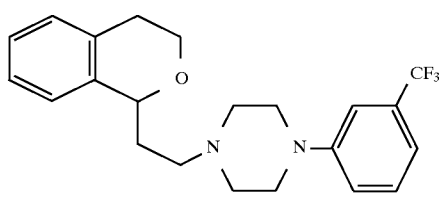
E-13
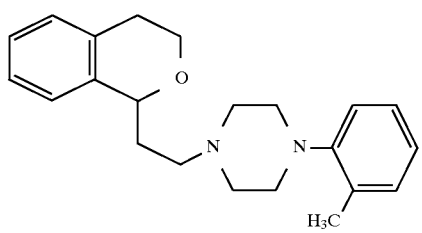
E-14
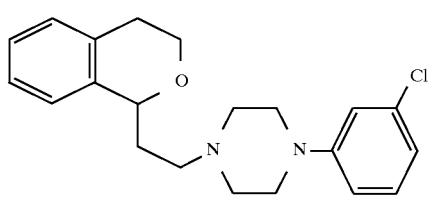
E-15

-continued
FORMULAS OF THE EXAMPLES (E-#)
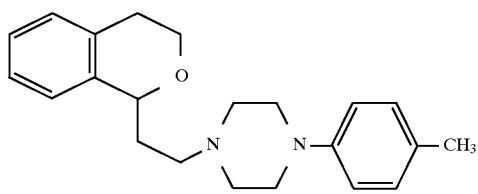
E-16
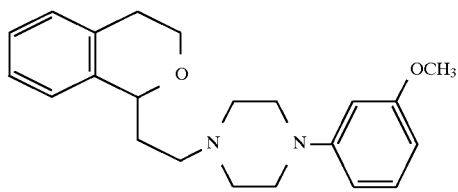
E-17
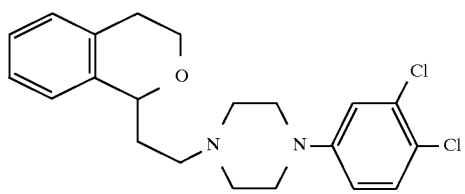
E-18
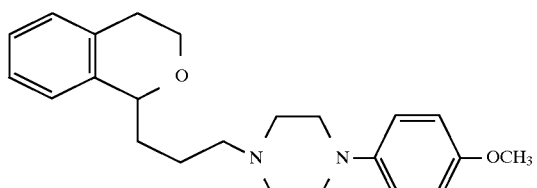
E-19
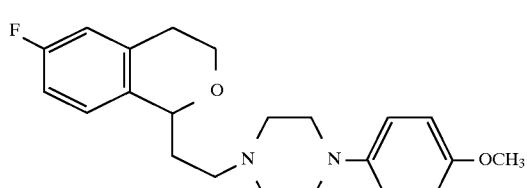
E-20
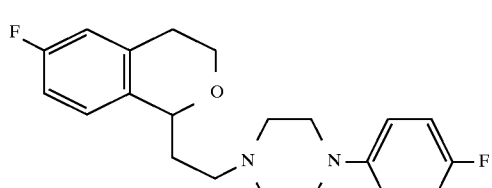
E-21
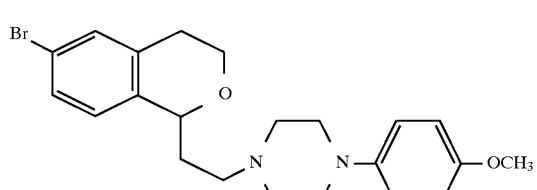
E-22
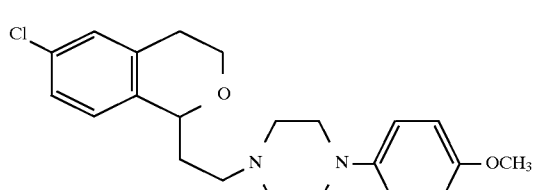
E-23

-continued
FORMULAS OF THE EXAMPLES (E-#)
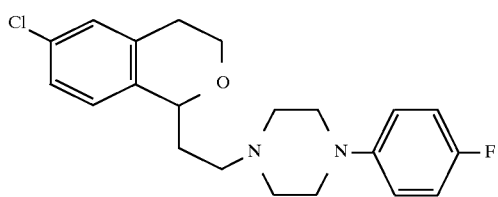 E-24
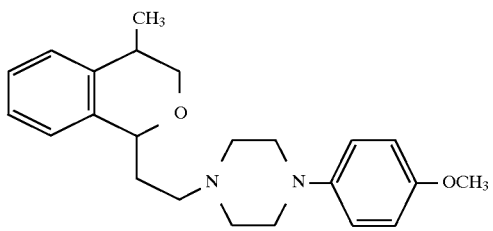 E-25
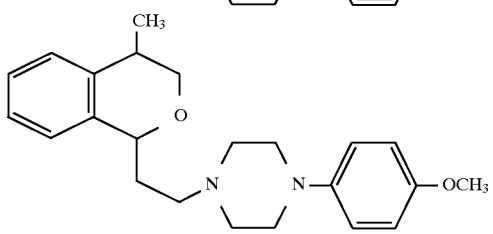 E-26
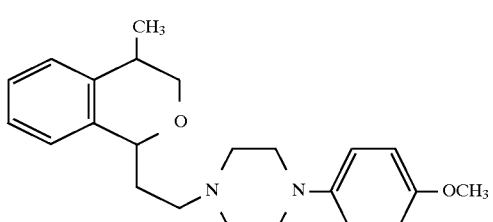 E-27
ISOMER C
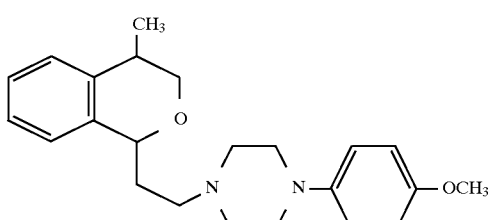 E-27 (E-28)
Isomer D
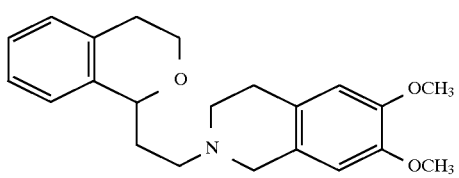 E-29
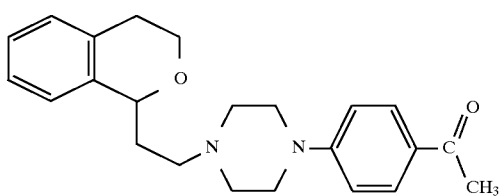 E-30

-continued
FORMULAS OF THE EXAMPLES (E-#)
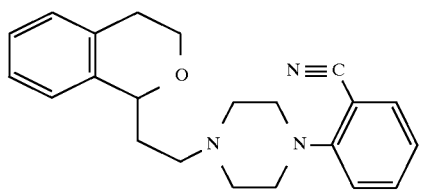  E-31
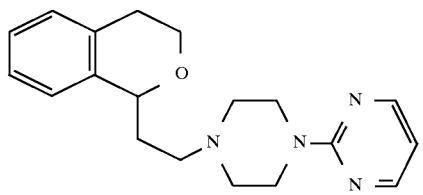  E-32
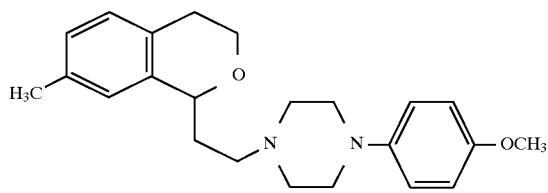  E-33
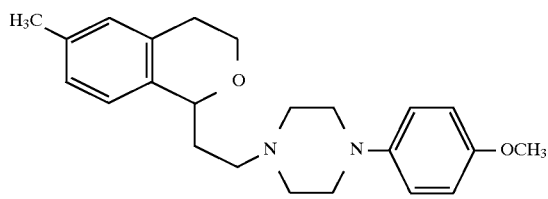  E-34
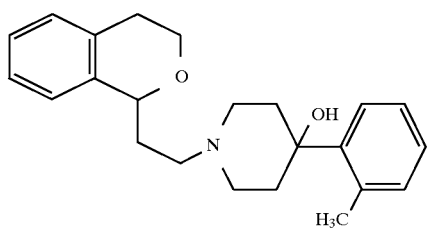  E-35
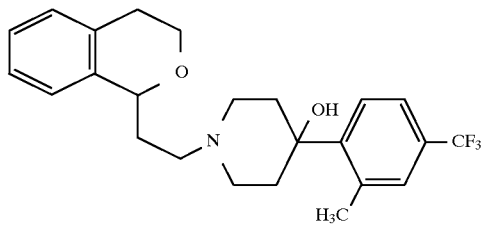  E-36
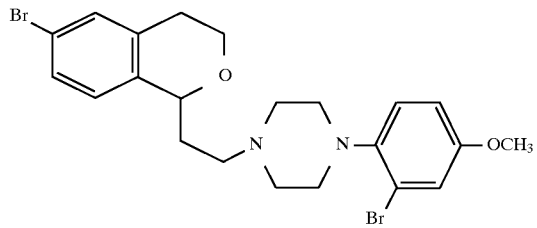  E-37

-continued
FORMULAS OF THE EXAMPLES (E-#)
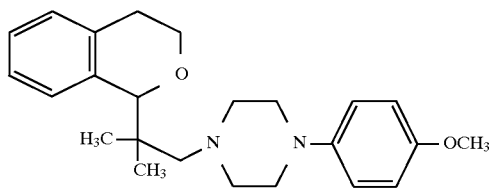
E-38
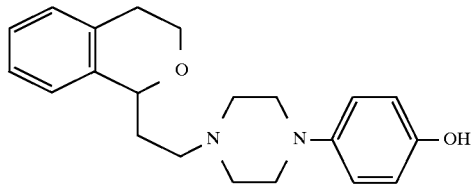
E-39
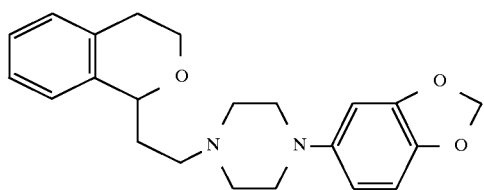
E-40
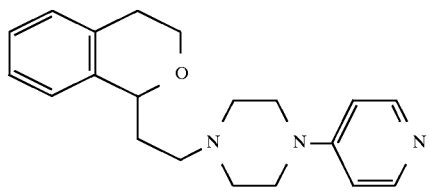
E-41
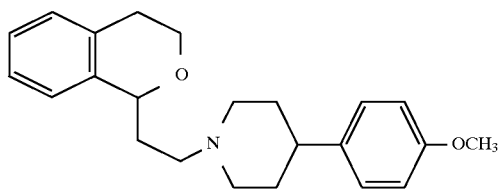
E-42
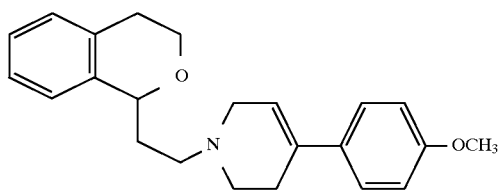
E-43
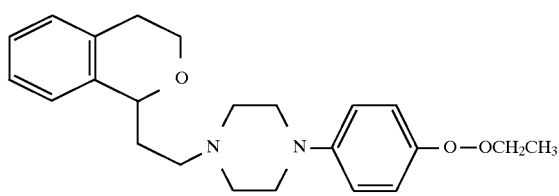
E-44
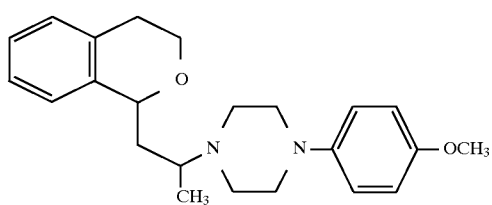
E-45
(−)-isomer at isochroman ring
Isomer C -continued
FORMULAS OF THE EXAMPLES (E-#)
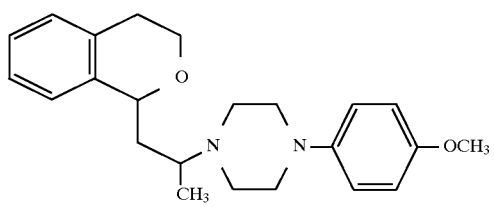
Isomer D
(−)-isomer at isochroman ring
E-45
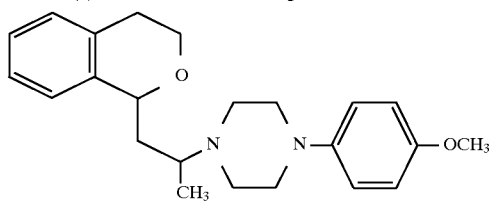
Isomer A (racemic pair)
E-46
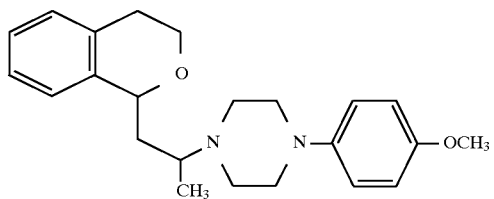
Isomer B (racemic pair)
E-46
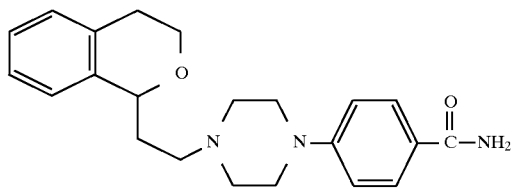
E-47
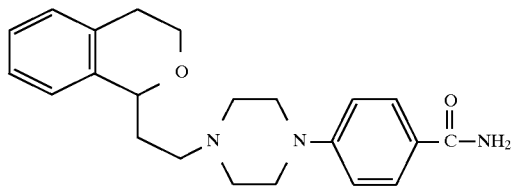
(−)-enantiomer
E-48
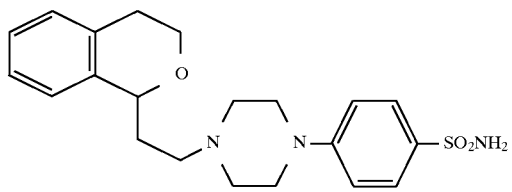
(−)-enantiomer
E-49

-continued
FORMULAS OF THE EXAMPLES (E-#)
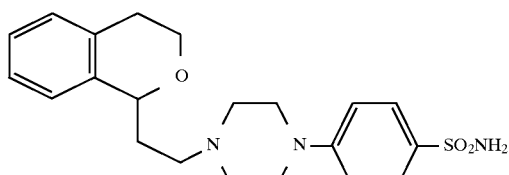
(−)-enantiomer
E-49
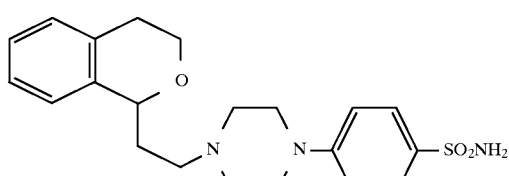
(−)-enantiomer
E-49
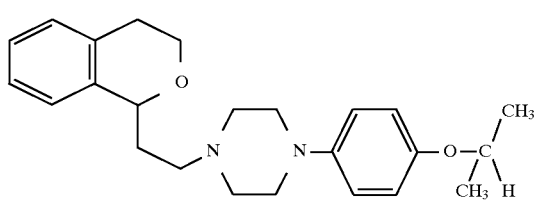
(−)-enantiomer
E-50
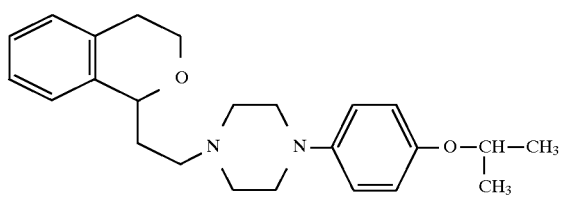
E-51
— E-52
— E-53
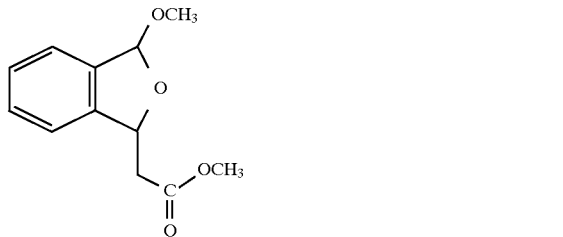
E-54
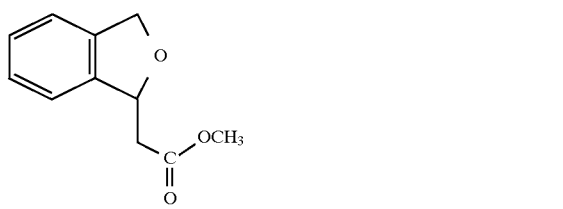
E-55
— E-56
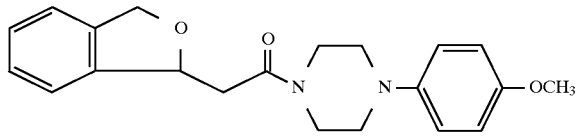
E-57

-continued
FORMULAS OF THE EXAMPLES (E-#)
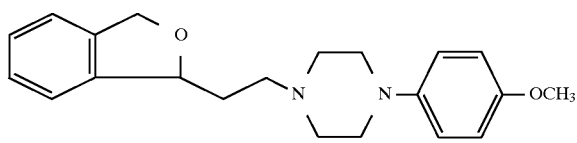
E-58
— E-59
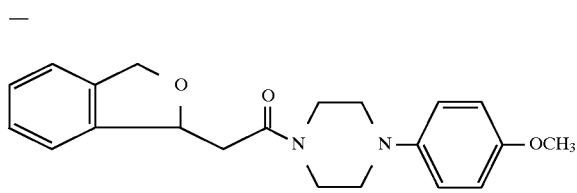
E-60
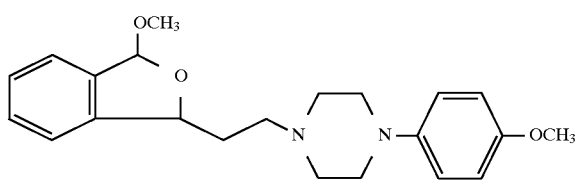
E-61
— E-62
— E-63
— E-64
— E-65
— E-66
— E-67
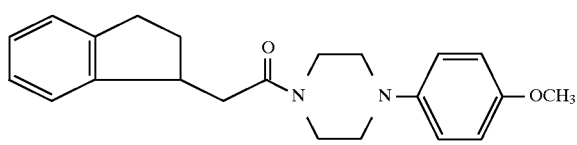
E-68
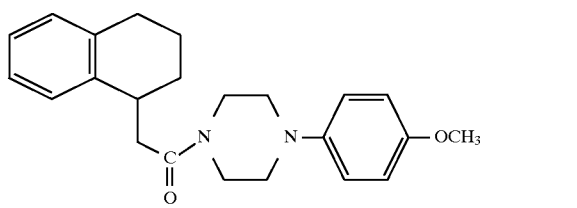
E-69
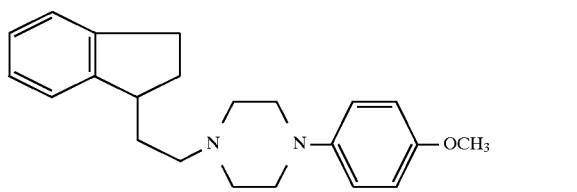
E-70
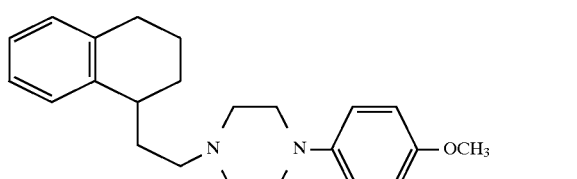
E-71

-continued
FORMULAS OF THE EXAMPLES (E-#)
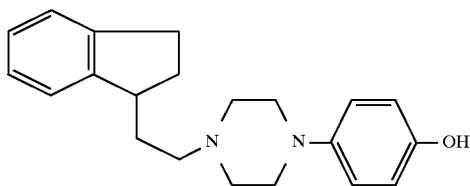
E-72
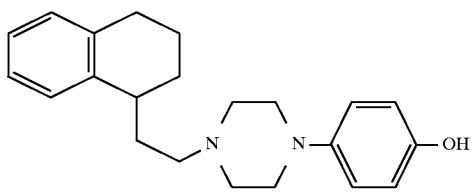
E-73
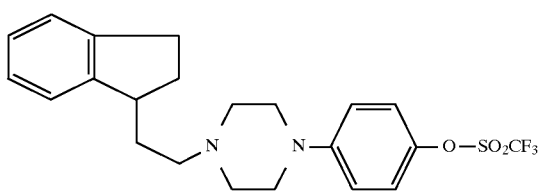
E-74
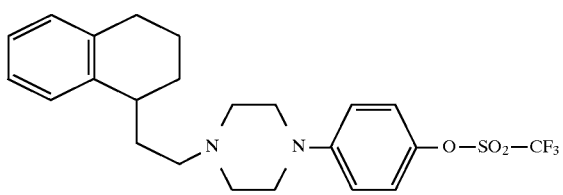
E-75
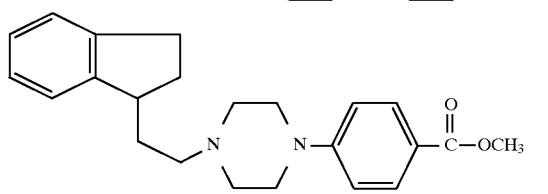
racemate
E-76
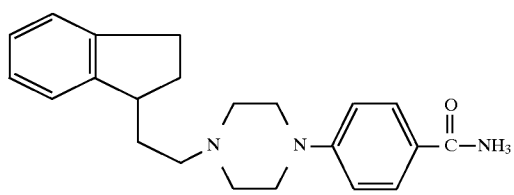
racemate
E-77
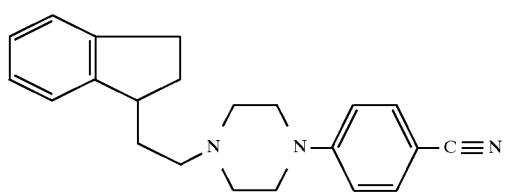
racemate
E-78
—
E-79

-continued
FORMULAS OF THE EXAMPLES (E-#)
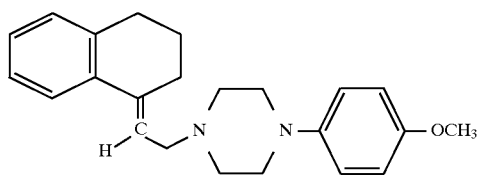
E Isomer
E-80
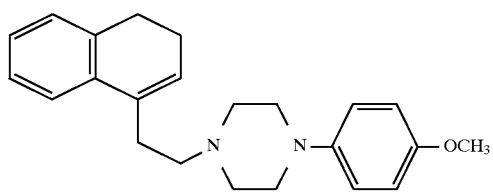
E-81
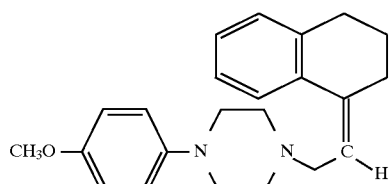
Z Isomer
E-82
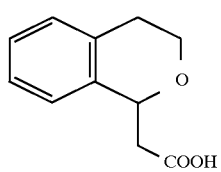
(−)-enantiomer
E-83
—
E-84
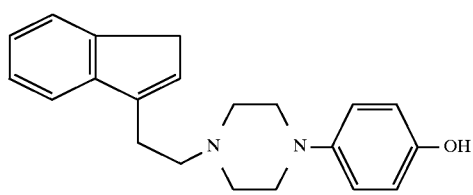
E-85
—
E-86
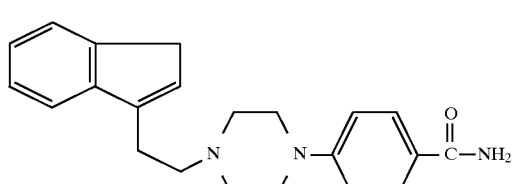
E-87
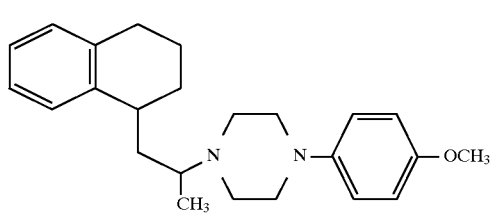
Diastereomer "A"
E-88

-continued
FORMULAS OF THE EXAMPLES (E-#)
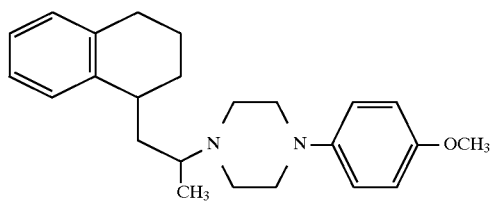
Diastereomer "B"
E-88
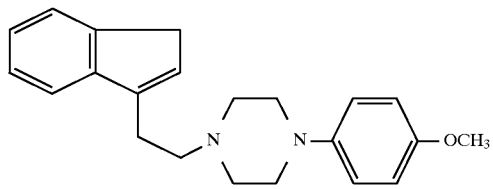
E-89
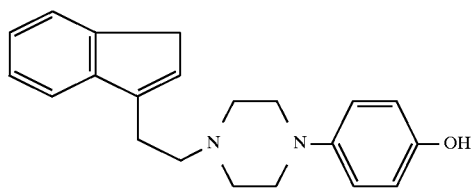
E-90
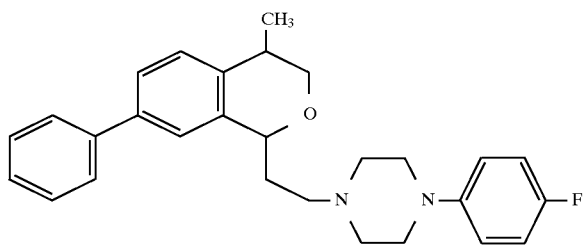
MIXED ISOMERS
E-91
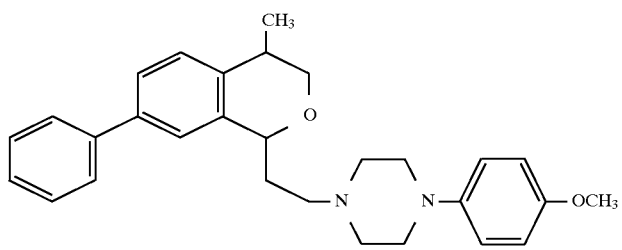
MIXED ISOMERS
E-92
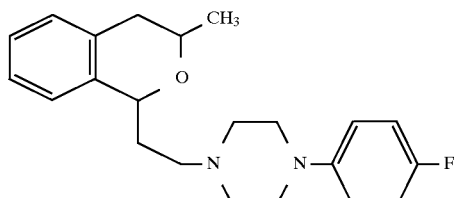
MAJOR ISOMER
E-93

-continued
FORMULAS OF THE EXAMPLES (E-#)
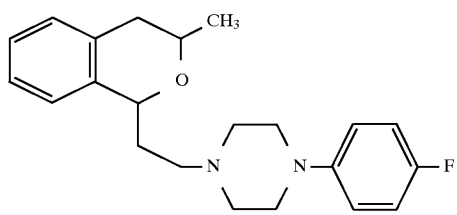
MINOR ISOMER
E-94
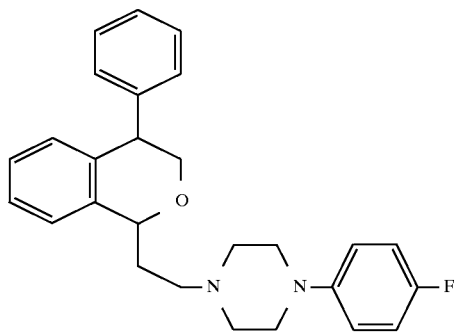
E-95
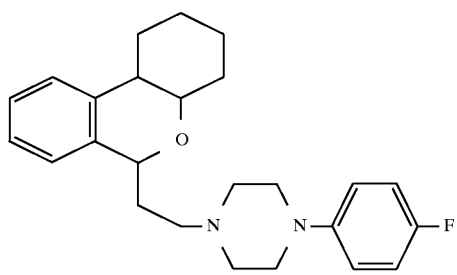
MAJOR ISOMER
E-96
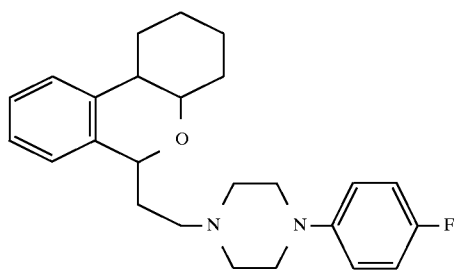
MINOR ISOMER
E-97
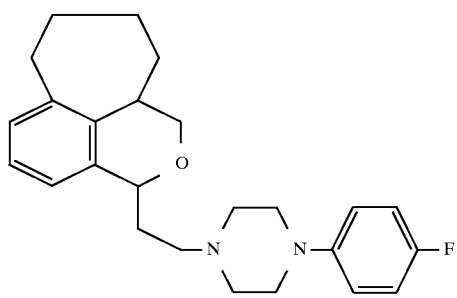
E-98

-continued
FORMULAS OF THE EXAMPLES (E-#)
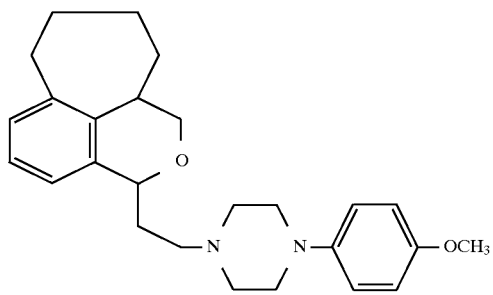
E-99
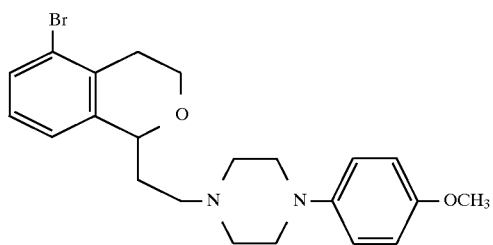
E-100
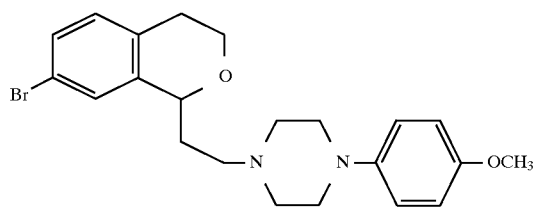
E-101
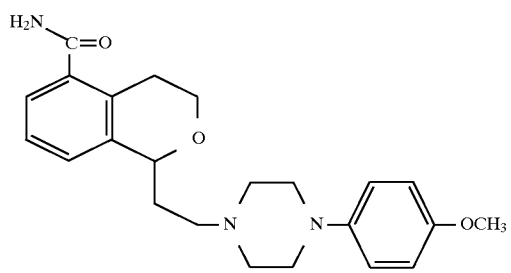
E-102
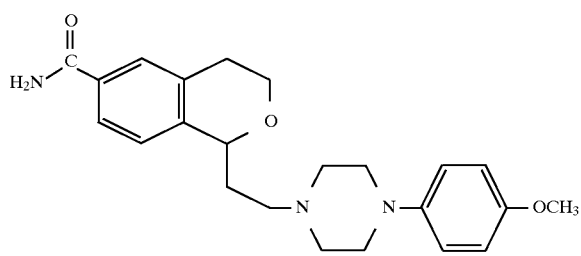
E-103
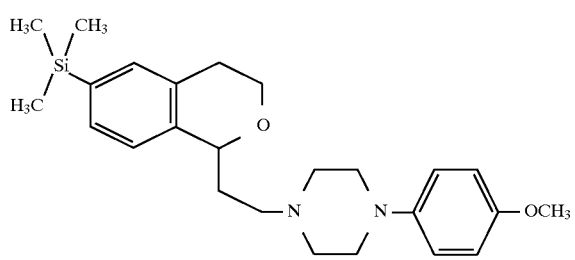
E-104

-continued
FORMULAS OF THE EXAMPLES (E-#)
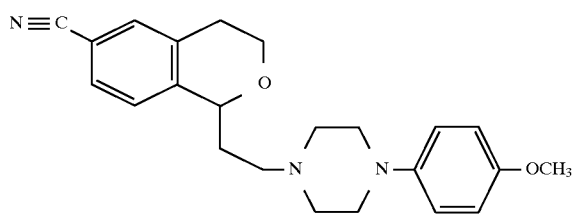 E-105
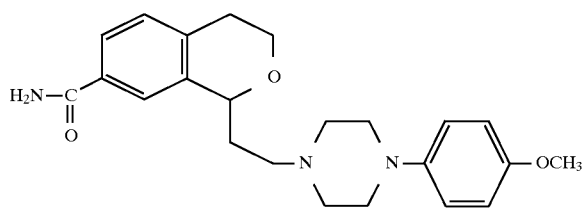 E-106
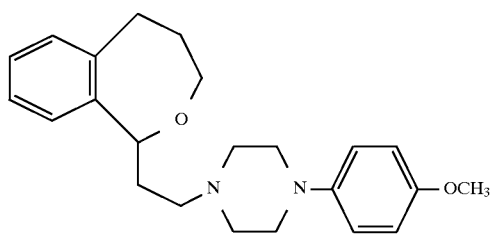 E-107
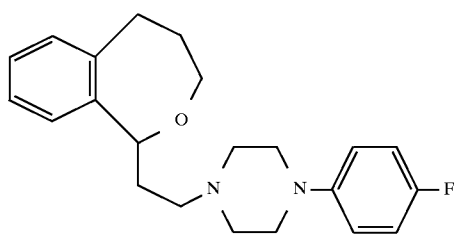 E-108
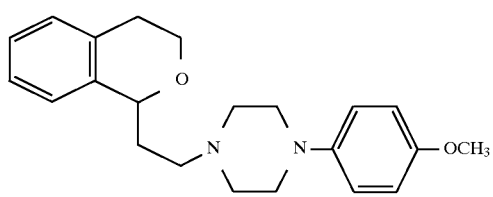 E-109
(−)-isomer
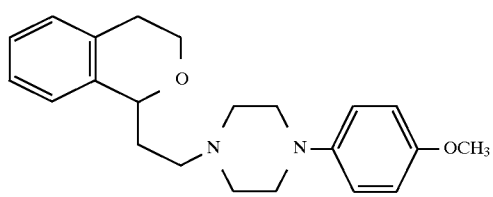 E-110
(+)-isomer
— E-111
— E-112

-continued
FORMULAS OF THE EXAMPLES (E-#)
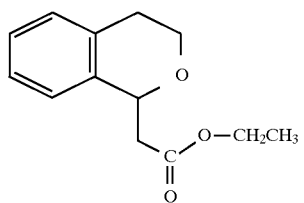
racemate
E-113
— E-114
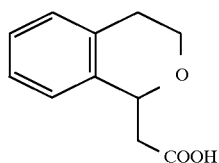
(−)-enantiomer
E-115
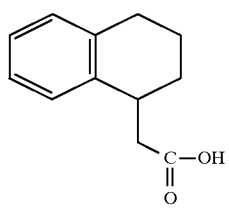
(+)-enantiomer
E-116
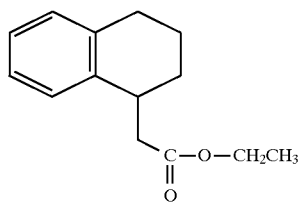
(−)-enantiomer
E-117
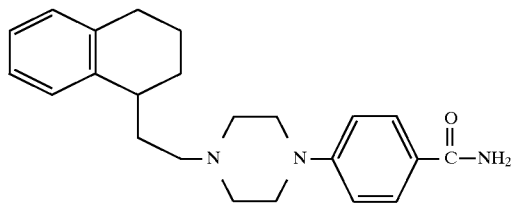
E-118
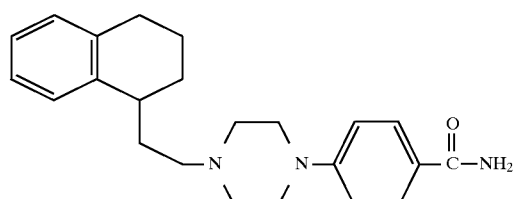
(+)-enantiomer
E-118

-continued
FORMULAS OF THE EXAMPLES (E-#)
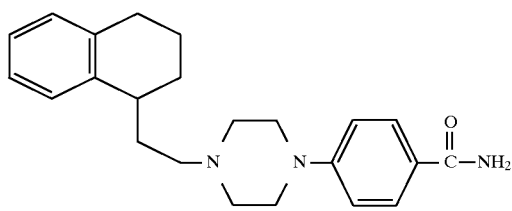
(−)-enantiomer
E-118
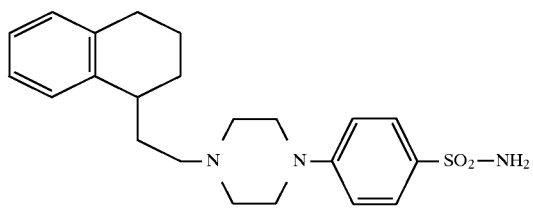
E-119
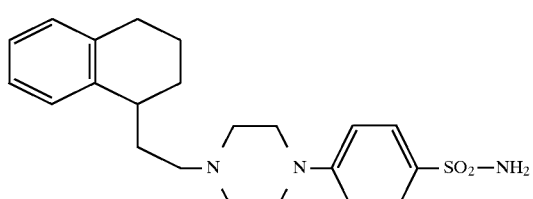
(+)-enantiomer
E-119
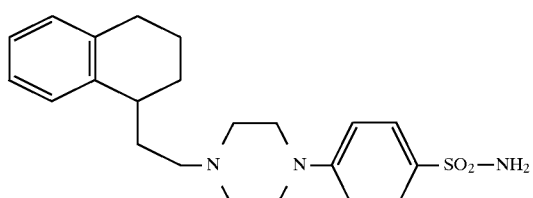
(−)-enantiomer
E-119
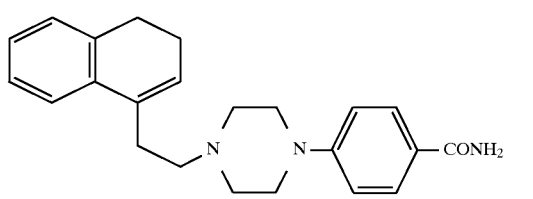
E-120
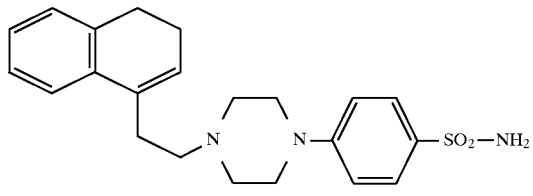
E-121
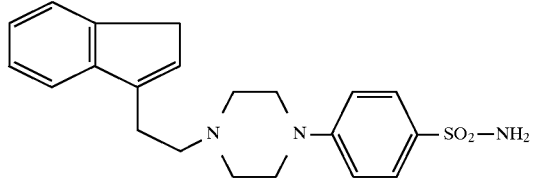
E-122

117
-continued
FORMULAS OF THE EXAMPLES (E-#)
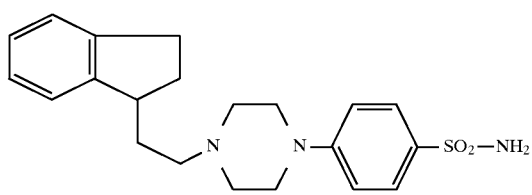  E-123
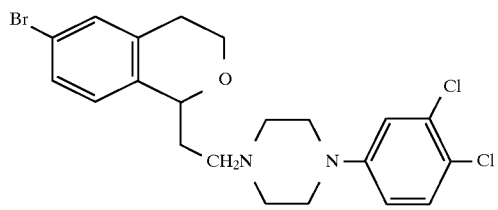  E-124
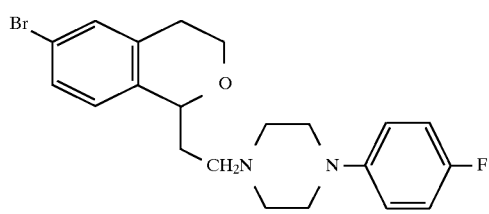  E-125
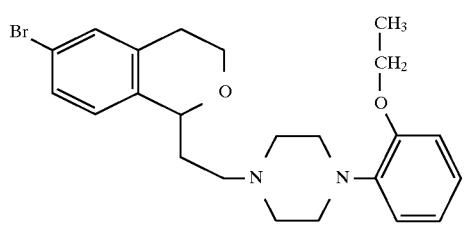  E-126
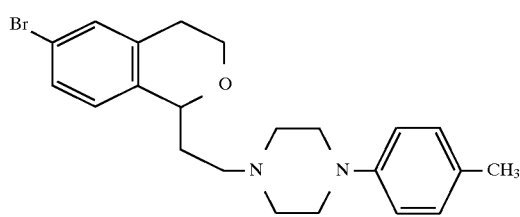  E-127
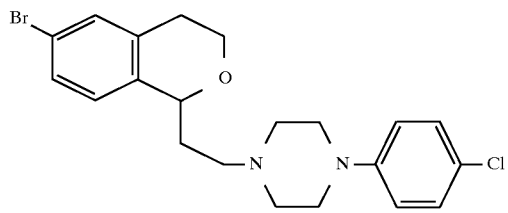  E-128
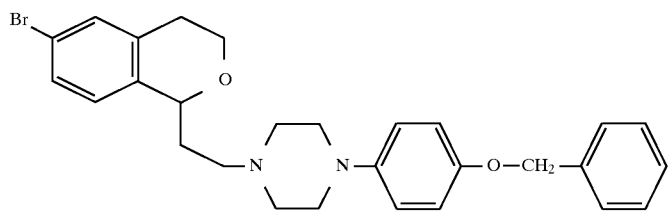  E-129

-continued
FORMULAS OF THE EXAMPLES (E-#)
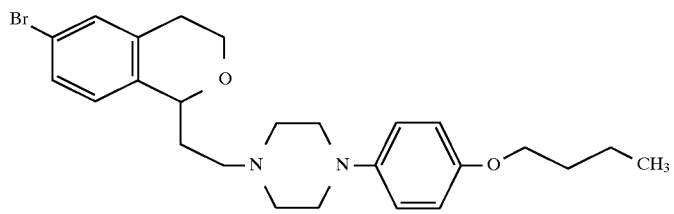
E-130
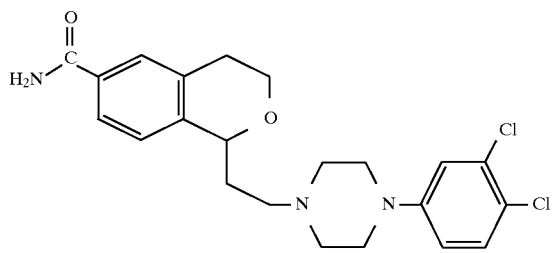
E-131
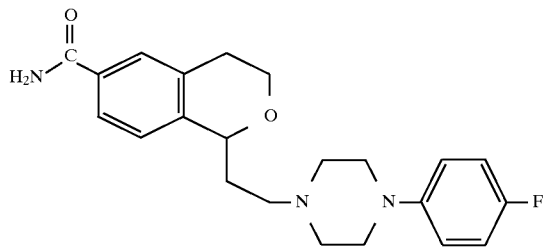
E-132
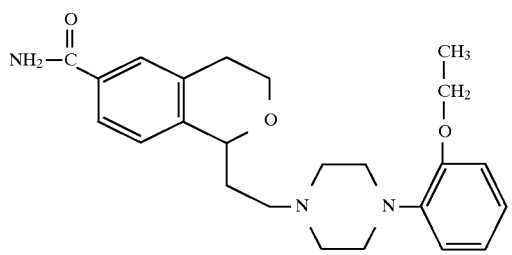
E-133
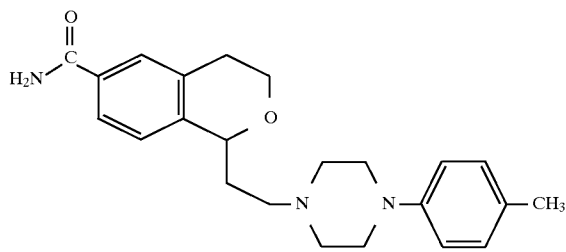
E-134
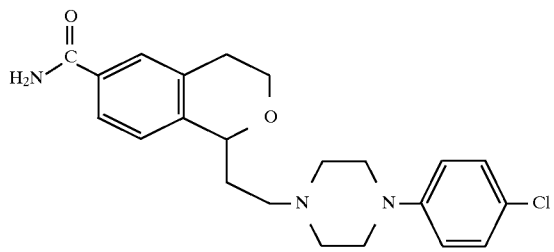
E-135

-continued
FORMULAS OF THE EXAMPLES (E-#)
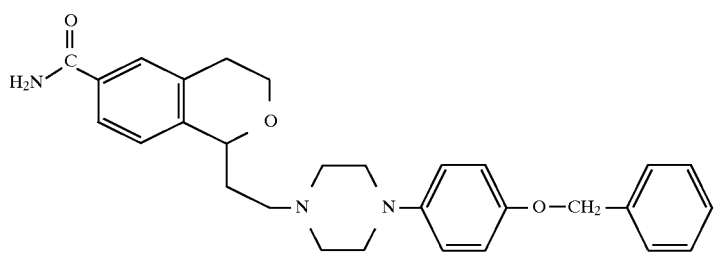
E-136
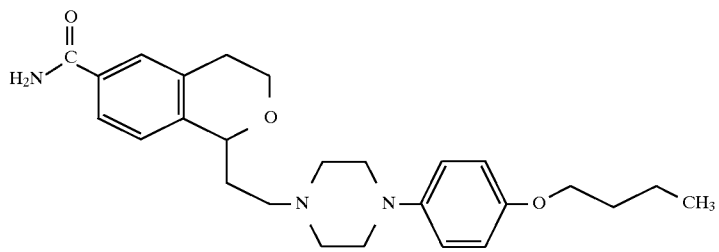
E-137
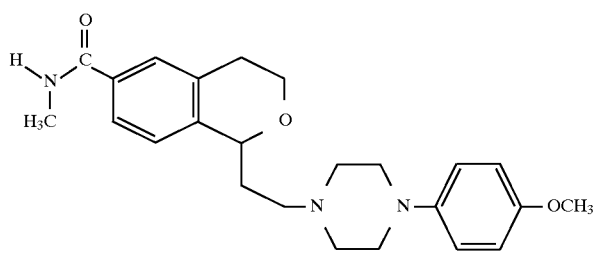
E-138
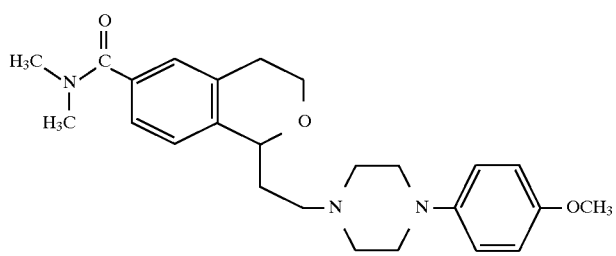
E-139
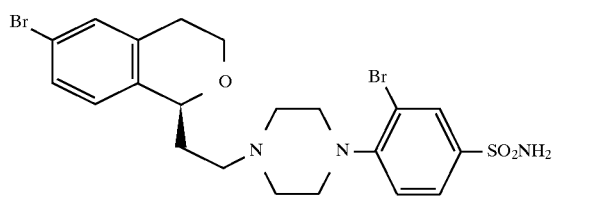
E-140
S-(−)-enantiomer
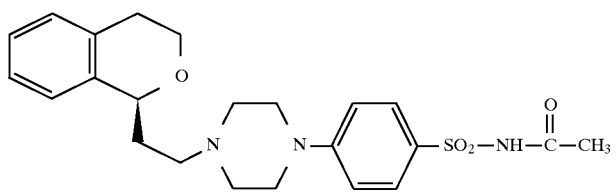
E-141
S-(−)-enantiomer -continued
FORMULAS OF THE EXAMPLES (E-#)
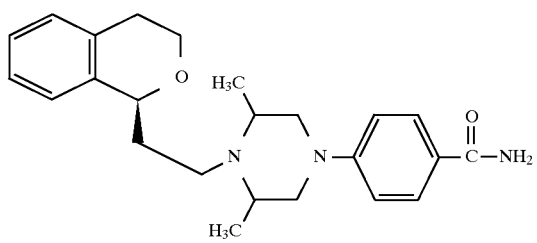
S-(−)-enantiomer
(cis-dimethylpiperazine)
E-142
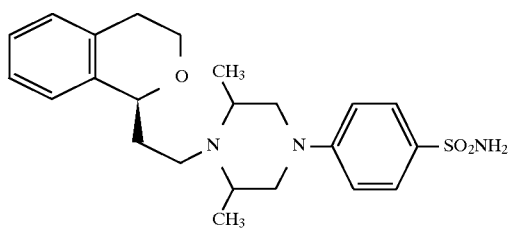
S-(−)enantiomer
E-143
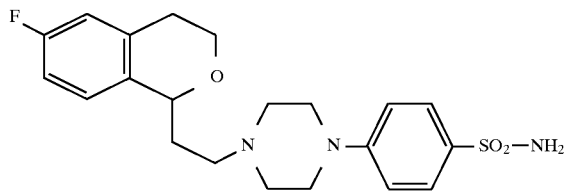
(−/+)
E-144
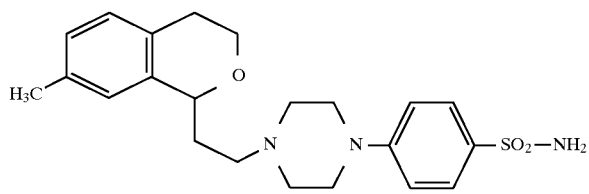
(−/+)
E-145
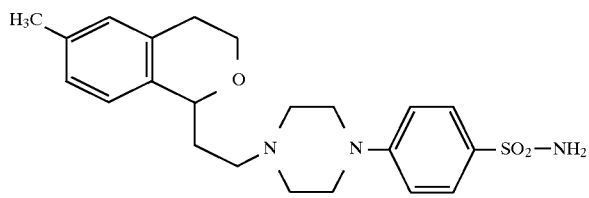
(−/+)
E-146

-continued
FORMULAS OF THE EXAMPLES (E-#)
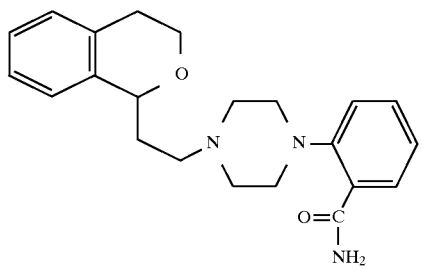
(+) enantiomer
E-147
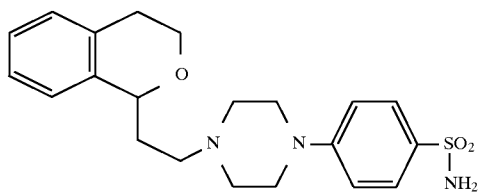
(+) enantiomer
E-148
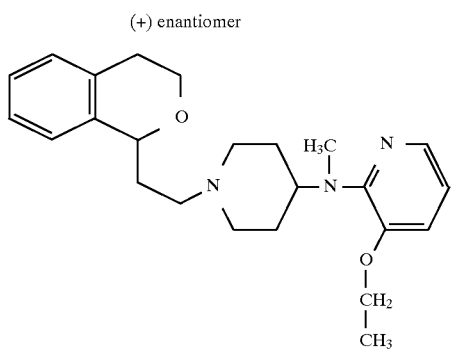
E-149
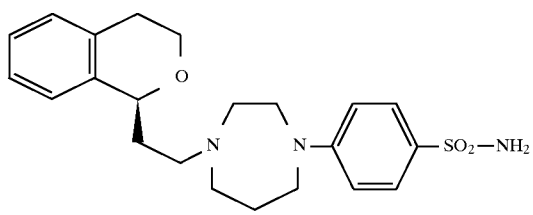
s(−)enantiomer
E-150
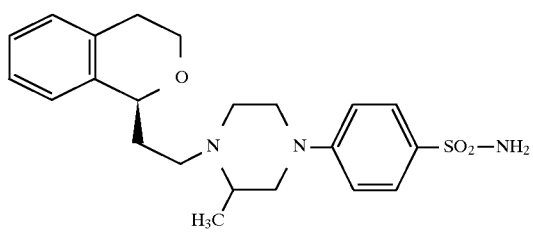
s(−)enantiomer
E-151
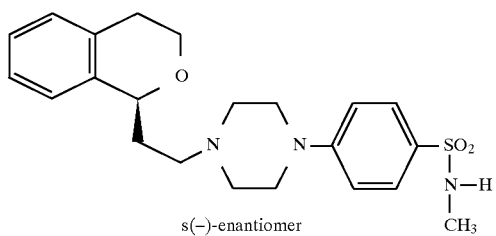
s(−)-enantiomer
E-152

-continued
FORMULAS OF THE EXAMPLES (E-#)
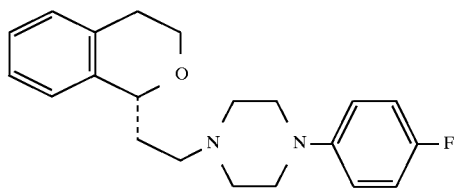
R-(+)-enantiomer
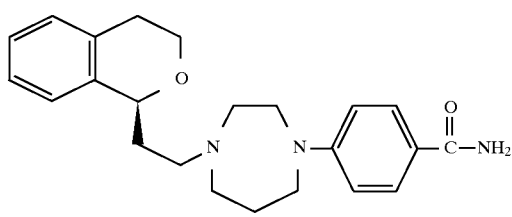
s(−)enantiomer
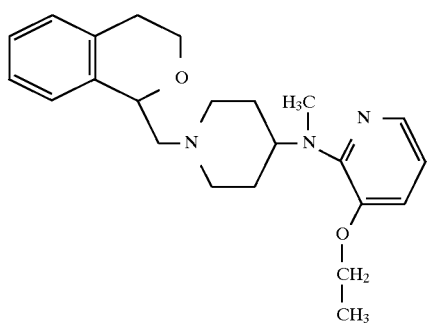
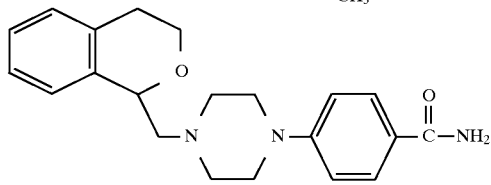
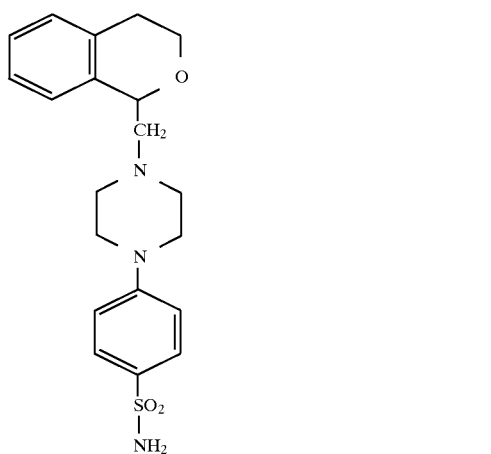
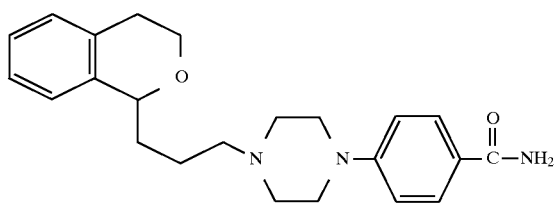
E-153
E-154
E-155
E-156
E-157
E-158

-continued
FORMULAS OF THE EXAMPLES (E-#)
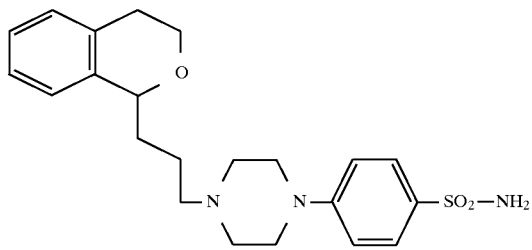
E-159
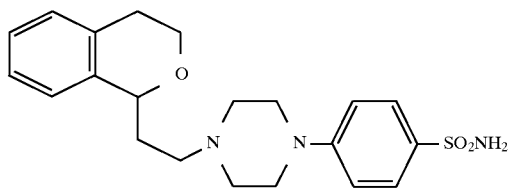
E-160
(−) enantiomer
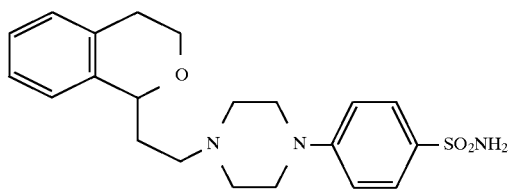
E-161
(−) enantiomer
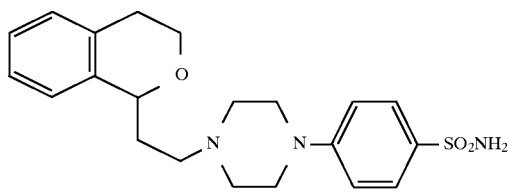
E-162
(−) enantiomer
CHART A
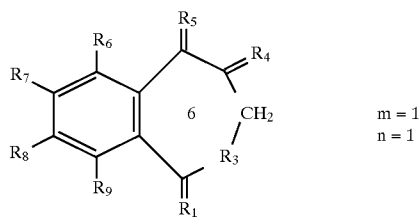
(I)
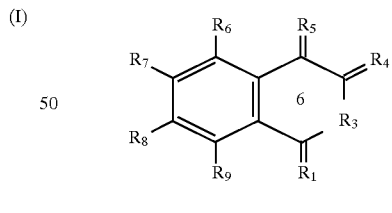
m = 0
n = 1
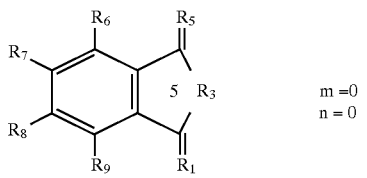
m = 1
n = 1
-continued
CHART A
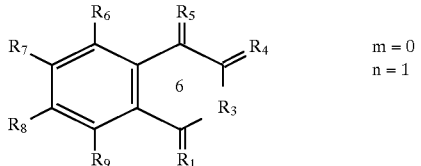
m = 0
n = 0

CHART B
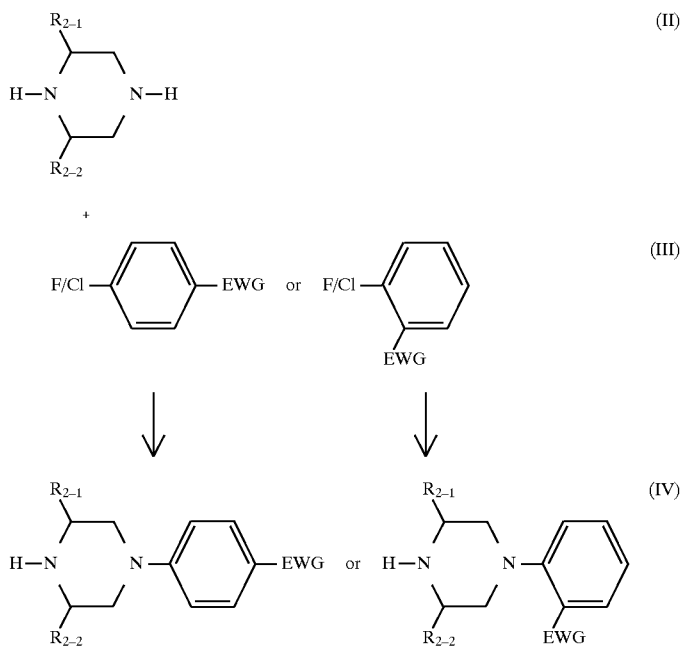
CHART C
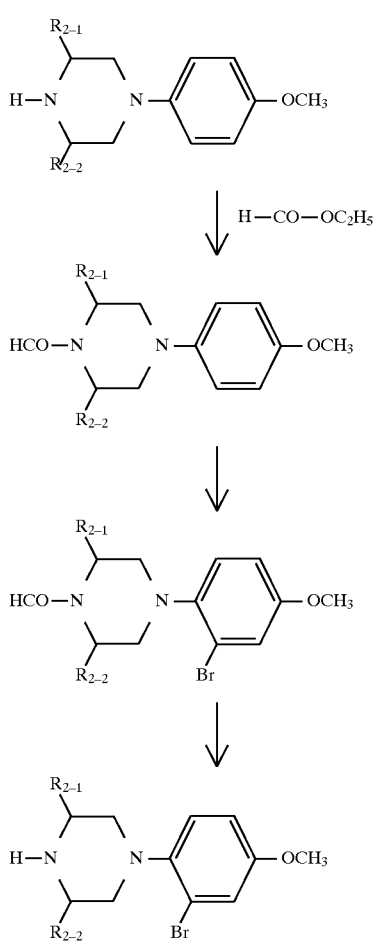
CHART D
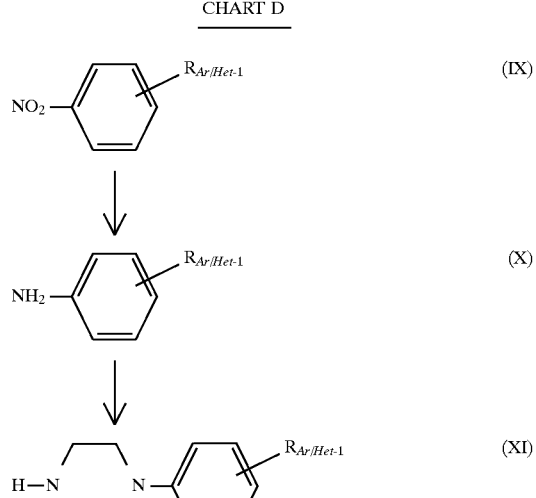
CHART E
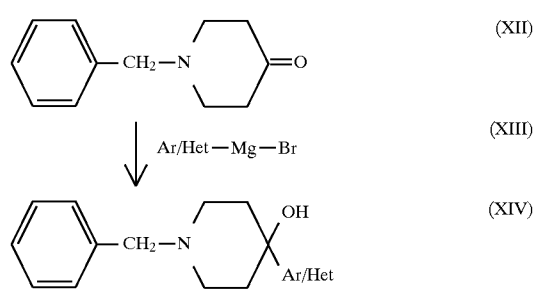

5,877,317
133
-continued
CHART E
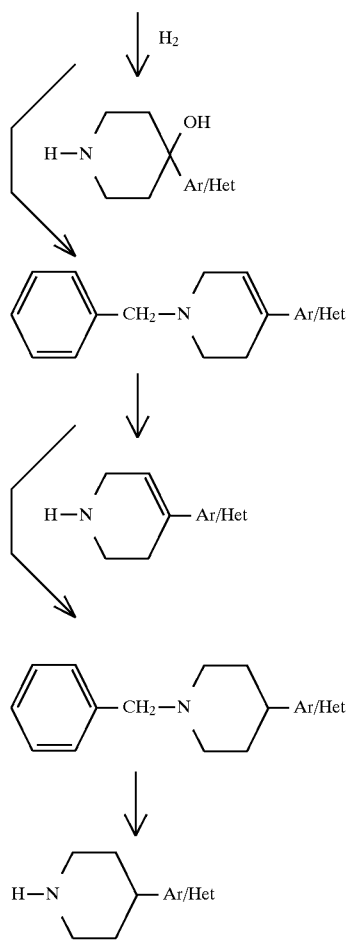
CHART F
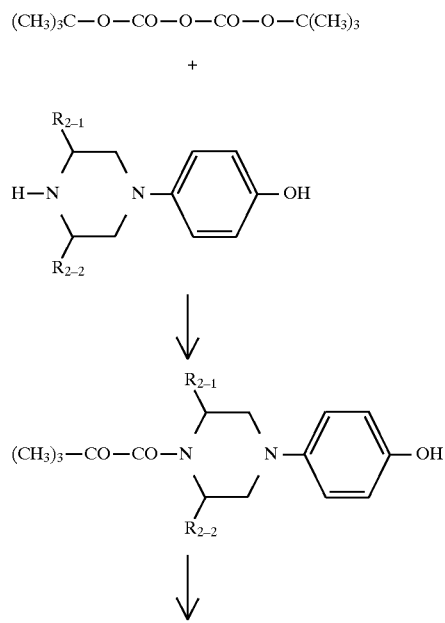
CHART F
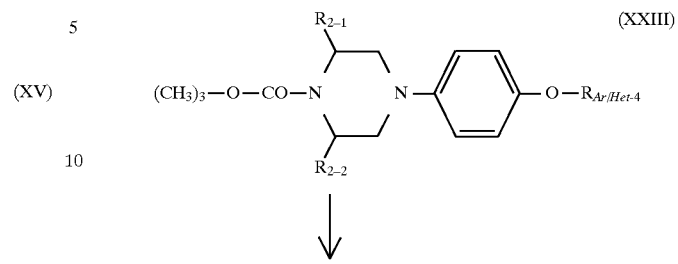
(XXIII)
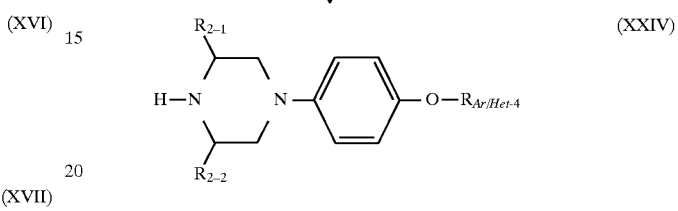
(XXIV)
CHART G
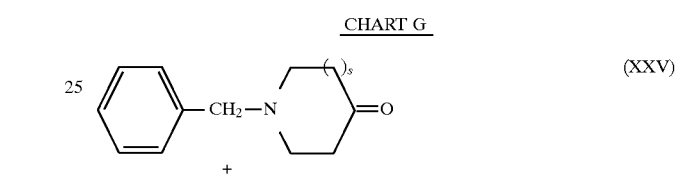
(XXV)
$H_2N-R_{2-4}$ (XXVI)
↓ NaCNBH₃
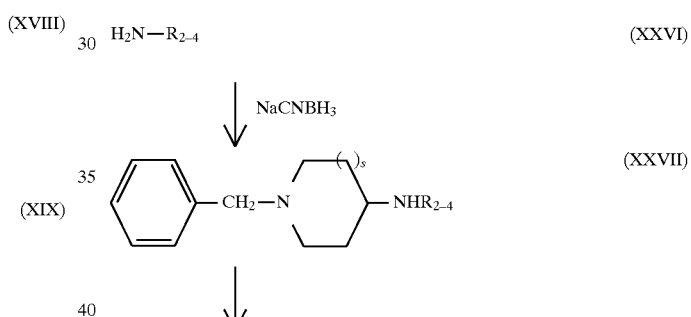
(XXVII)
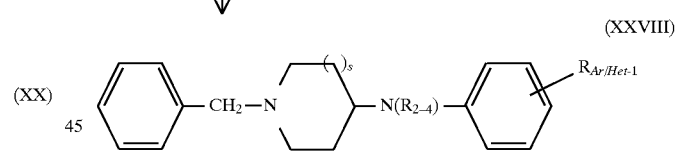
(XXVIII)
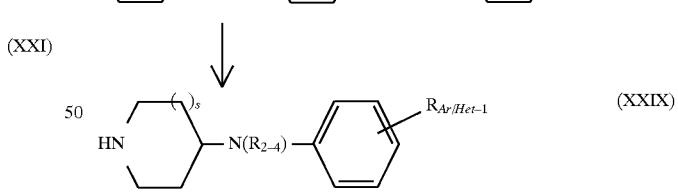
(XXIX)
CHART H
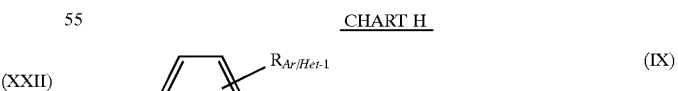
(IX)
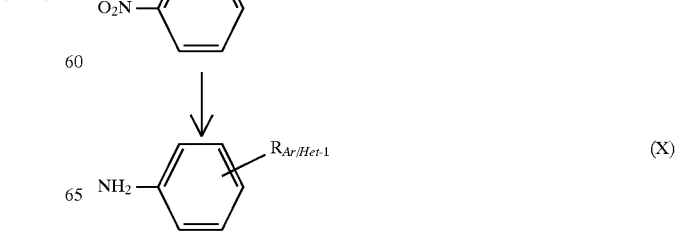
(X)

CHART H -continued
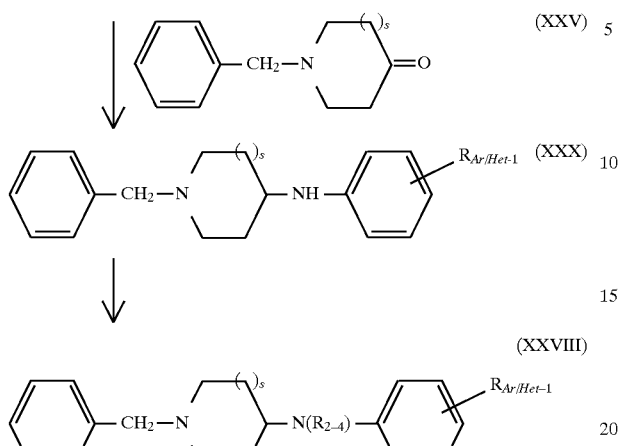
CHART I
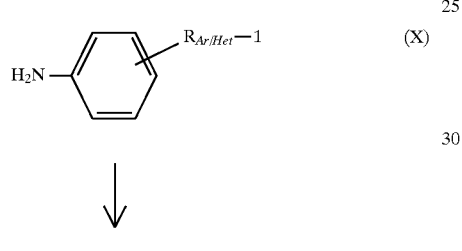
CHART I -continued
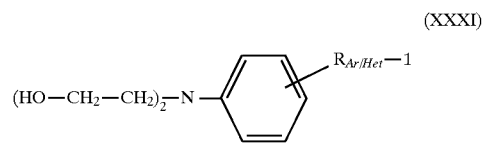
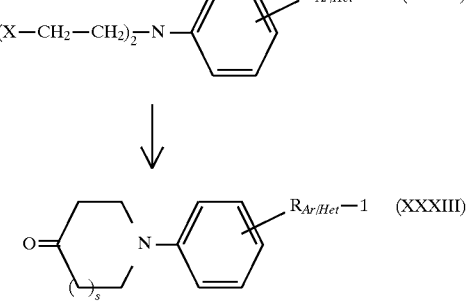
CHART J
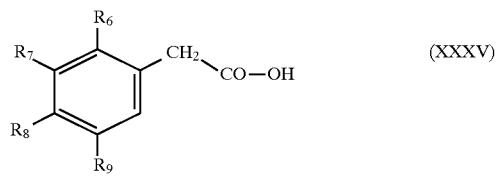
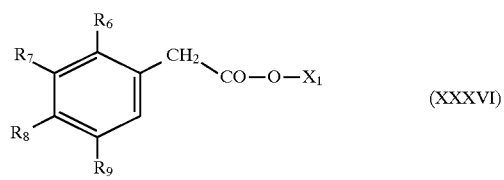

-continued
CHART J
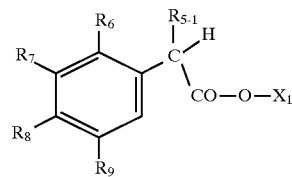 (XXXVII)
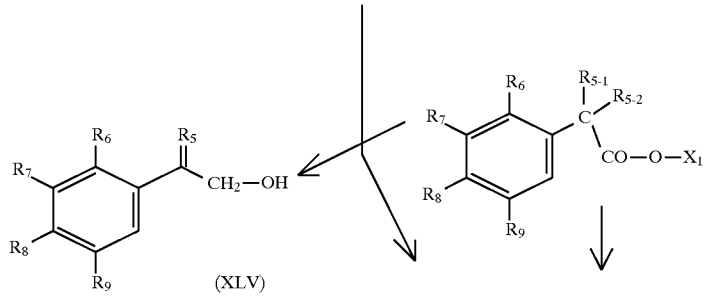 (XXXVIII)
(XLV)
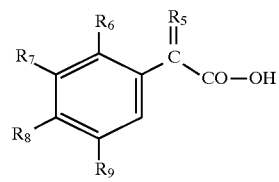 (XXXIX)
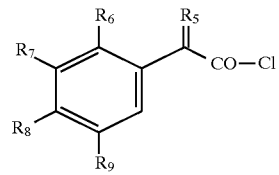 (XL)

-continued
CHART J
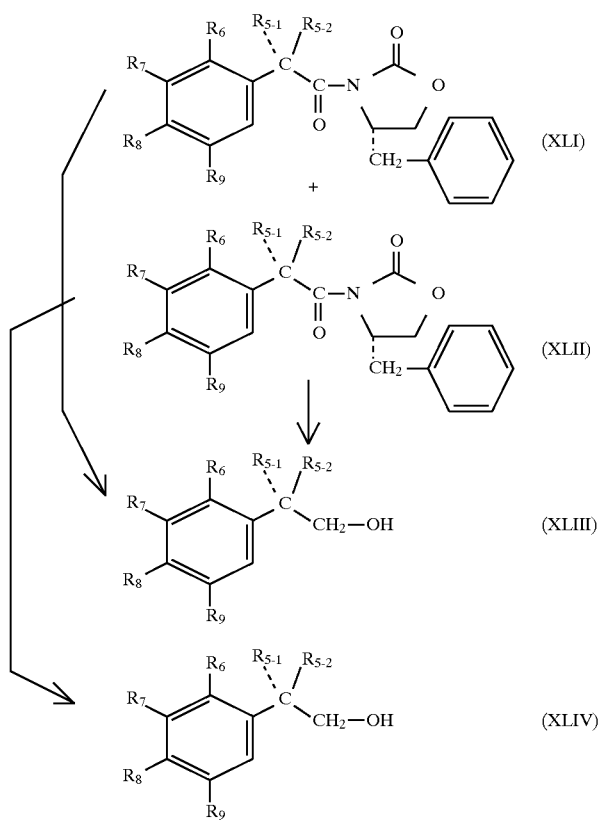
CHART K
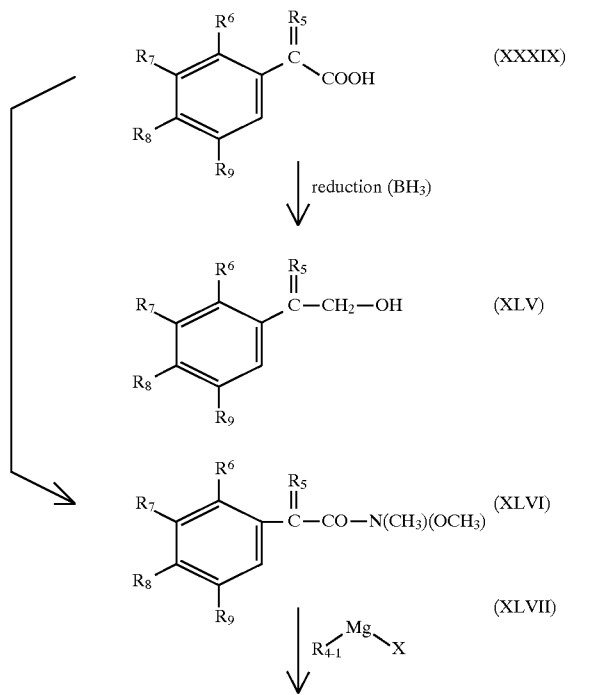

-continued
CHART K
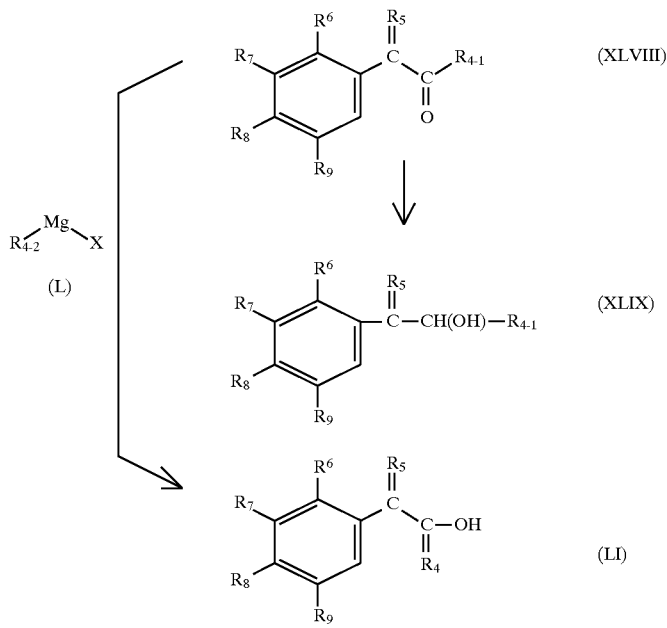
CHART L
(XLV), (XLIX) or (LI)
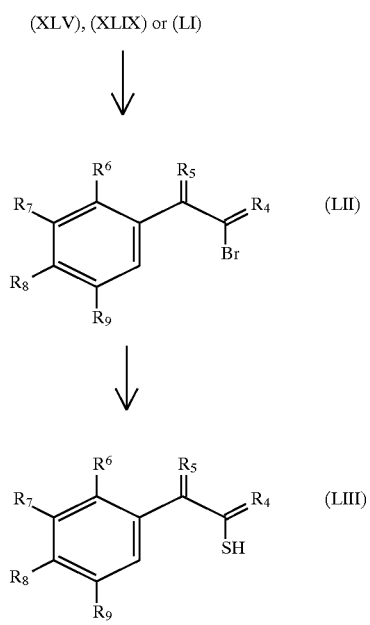
CHART M
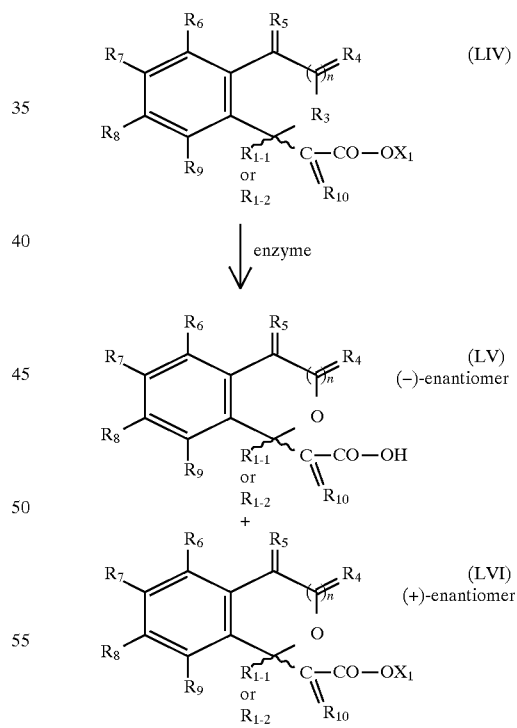

CHART N
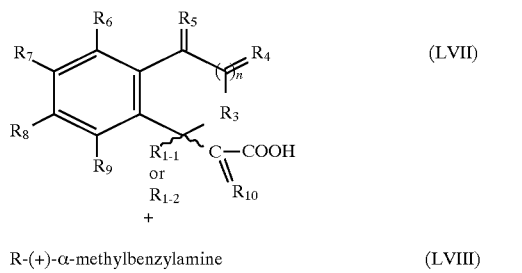
R-(+)-α-methylbenzylamine         (LVIII)
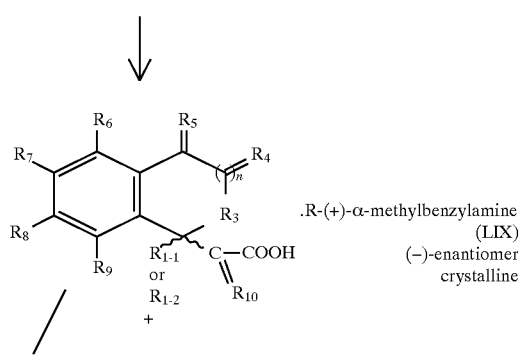
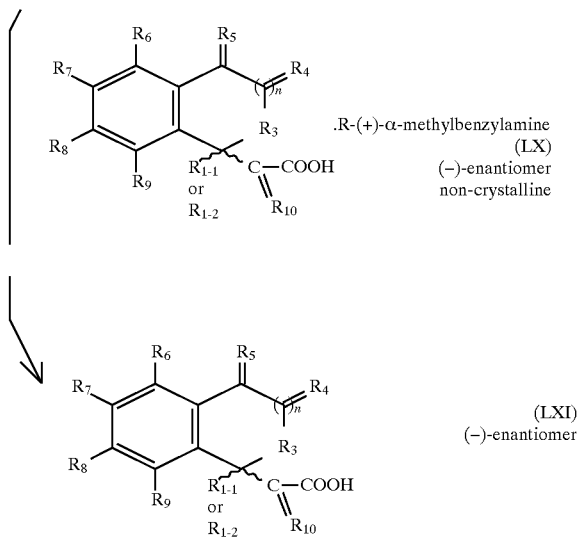
CHART O
(XLIII), (XLIV), (XLV), (XLIX), (LI) or (LIII)
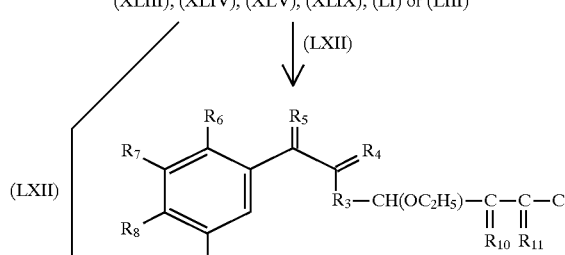
CHART O
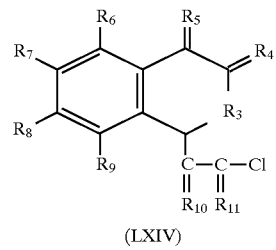
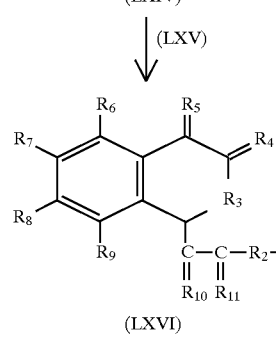
CHART P
(XLIII), (XLIV), (XLV), (XLIX), (LI) or (LIII)
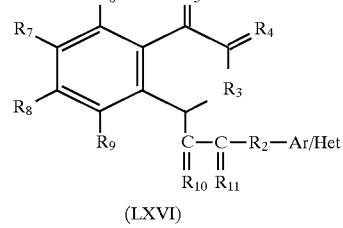

CHART Q
(CXXXIV)
+
(XLIII), (XLIV), (XLV), (XLIX), (LI) or (LIII)
↓
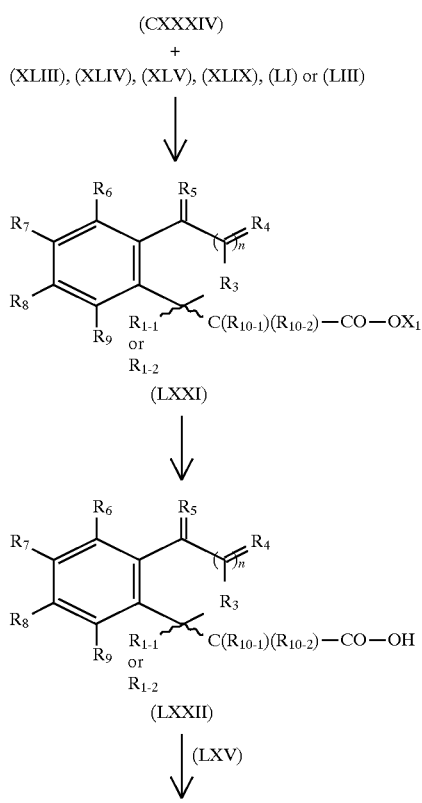
(LXXI)
↓
(LXXII)
↓ (LXV)
-continued
CHART Q
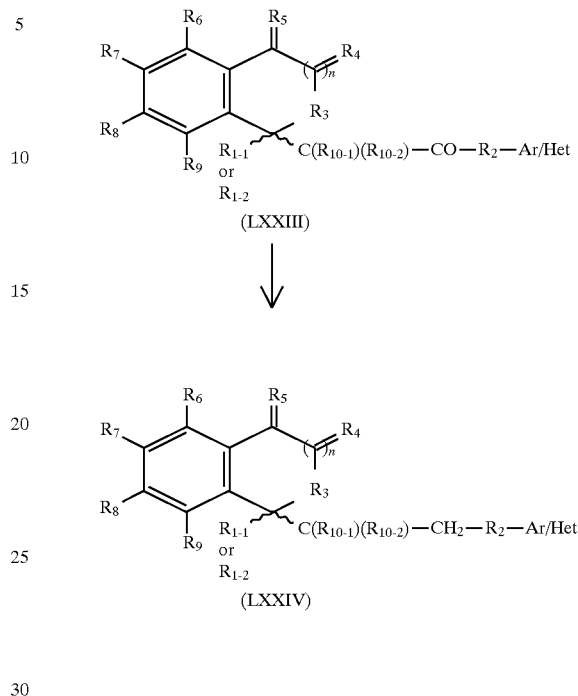
(LXXIII)
↓
(LXXIV)
CHART R
(XLIII, (XLIV), (XLV), (XLIX), (LI) OR (LIII)
+
$(C_2H_5O)_2CH-CH_2-CO-OC_2H_5$ (LXXV) or $R_1-CO-CH_2-CO-OC_2H_5$ (LXXVI)
↓
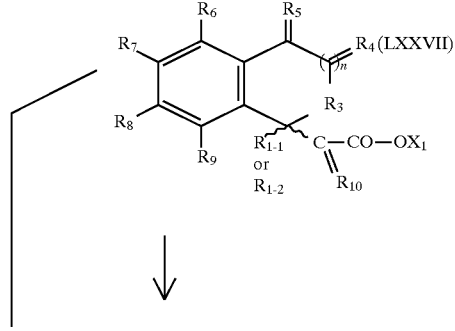
↓

-continued
CHART R
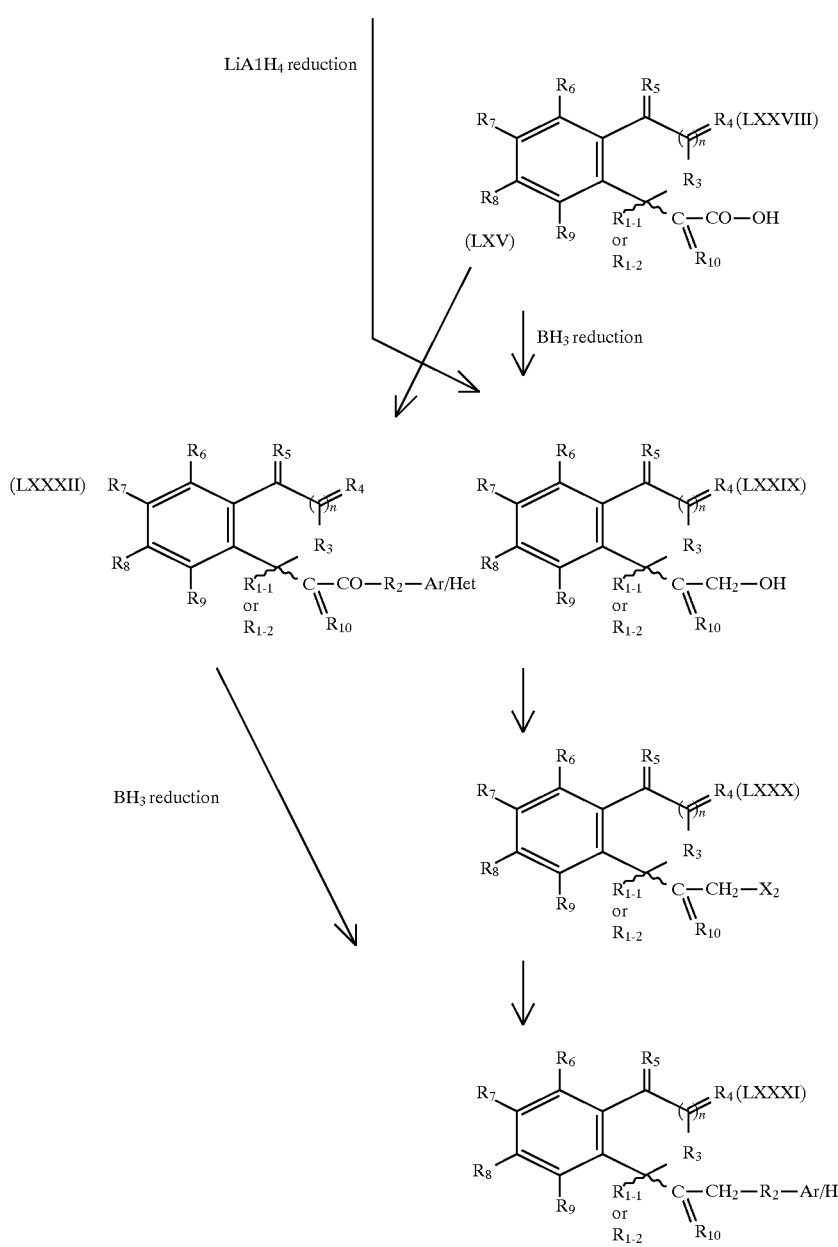
CHART S
(LXI), (LXXVIII)
-continued
CHART S
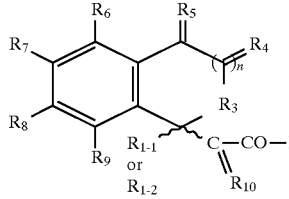
(LXXXIII)
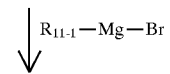

-continued
CHART S
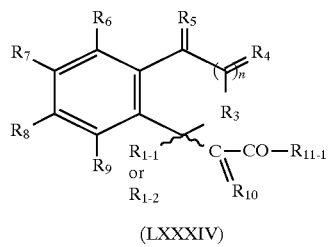
(LXXXIV)
↓
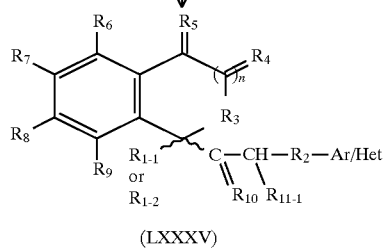
(LXXXV)
CHART T
(LXIV)
↓
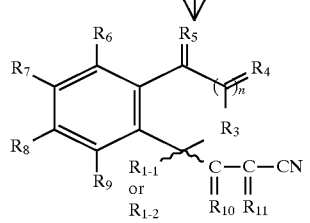
(LXXXVI)
↓
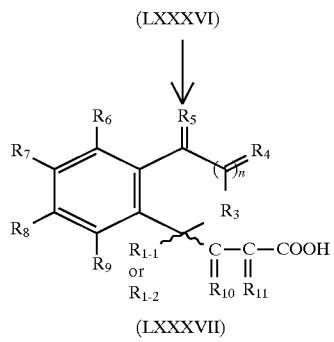
(LXXXVII)
↓
(LXXXVIII)
↓
-continued
CHART T
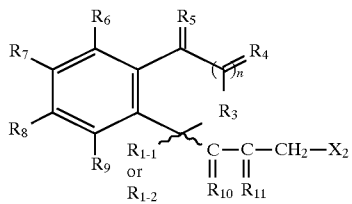
(LXXXIX)
↓ (LXV)
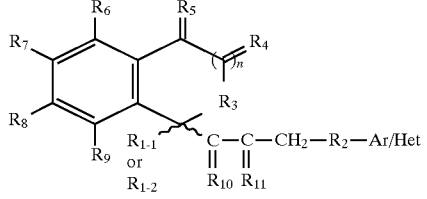
(XC)
CHART U
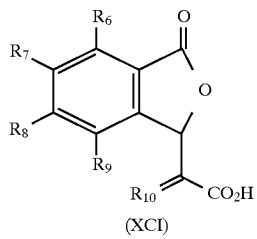
(XCI)
↓
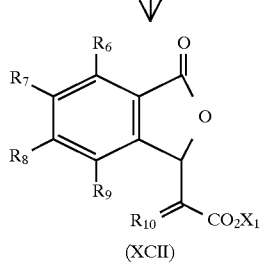
(XCII)
↓
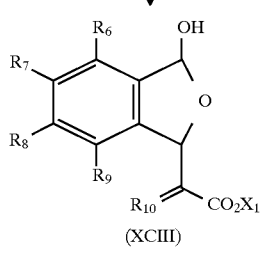
(XCIII)
↓

-continued
CHART U
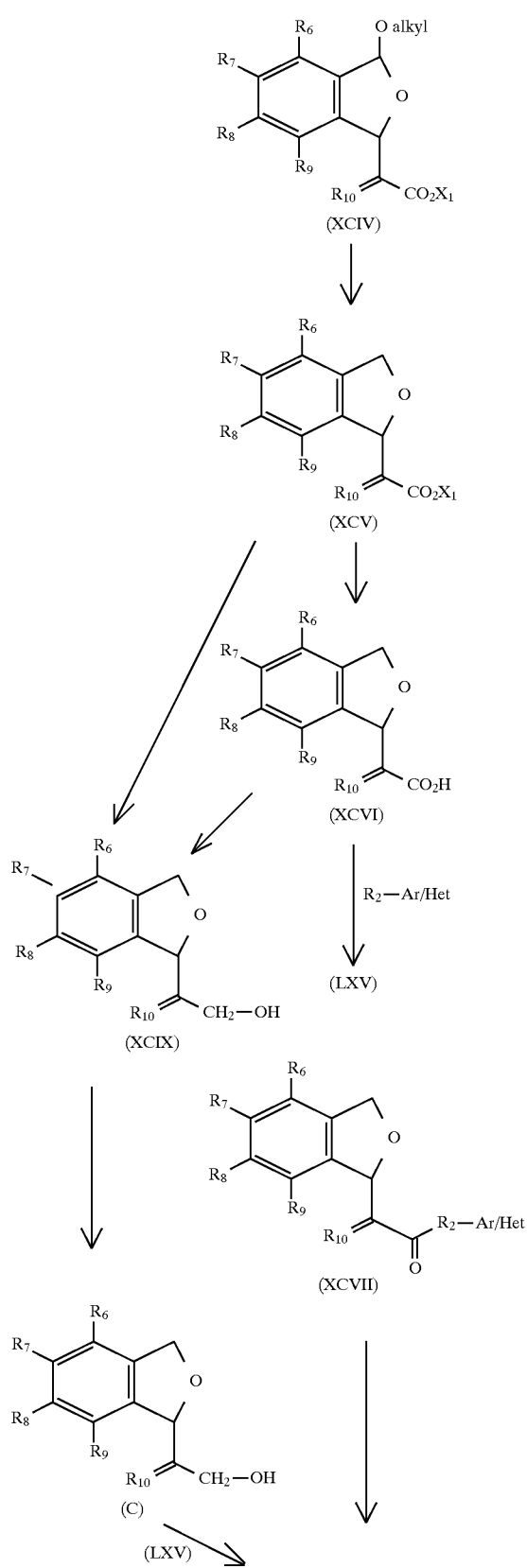
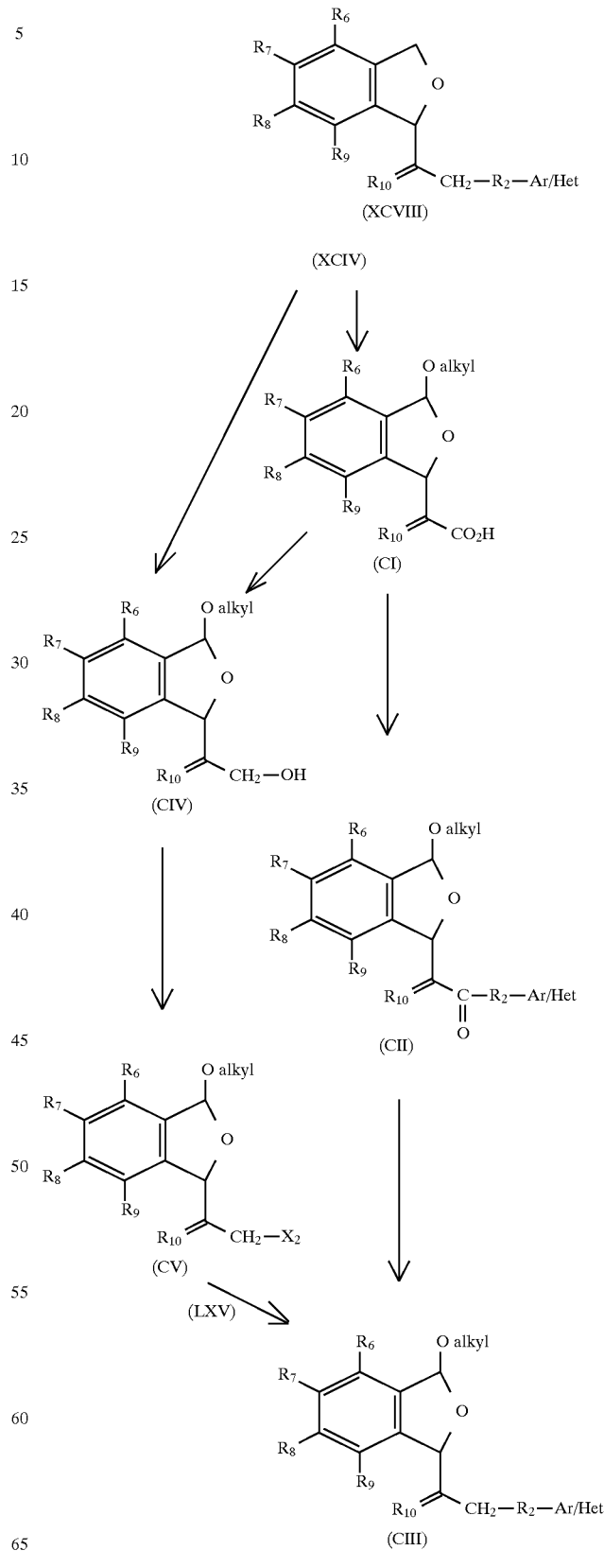

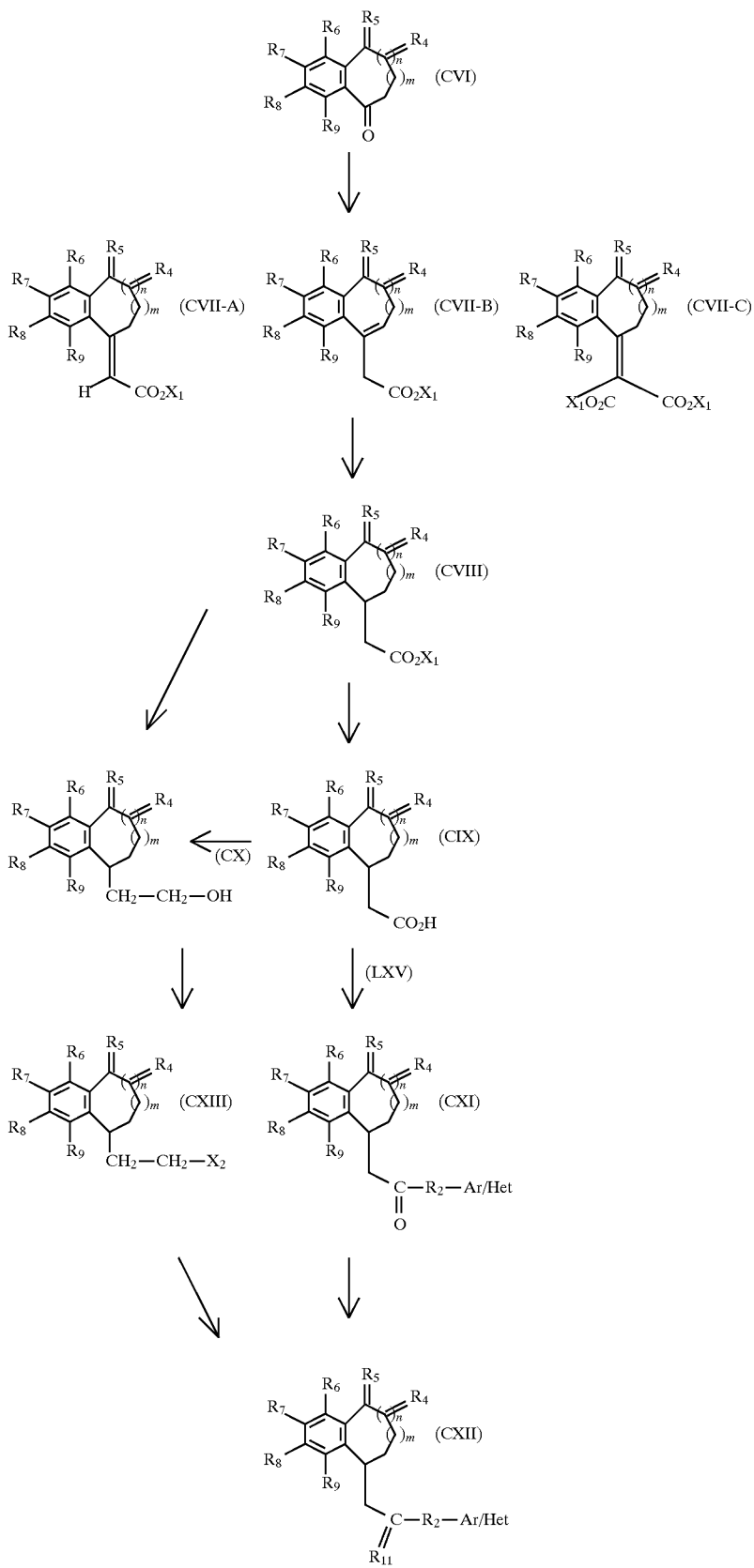
CHART V

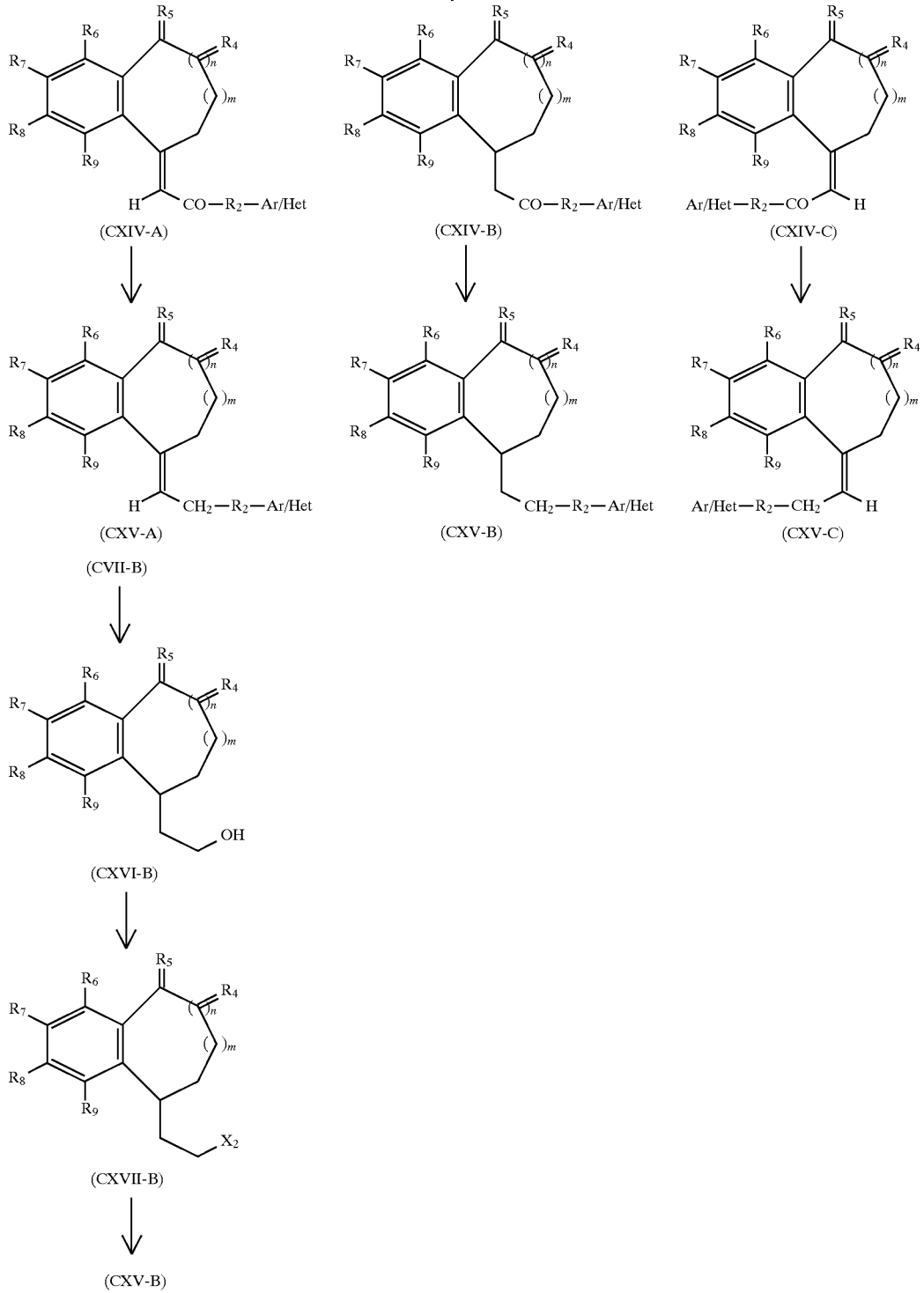

CHART X
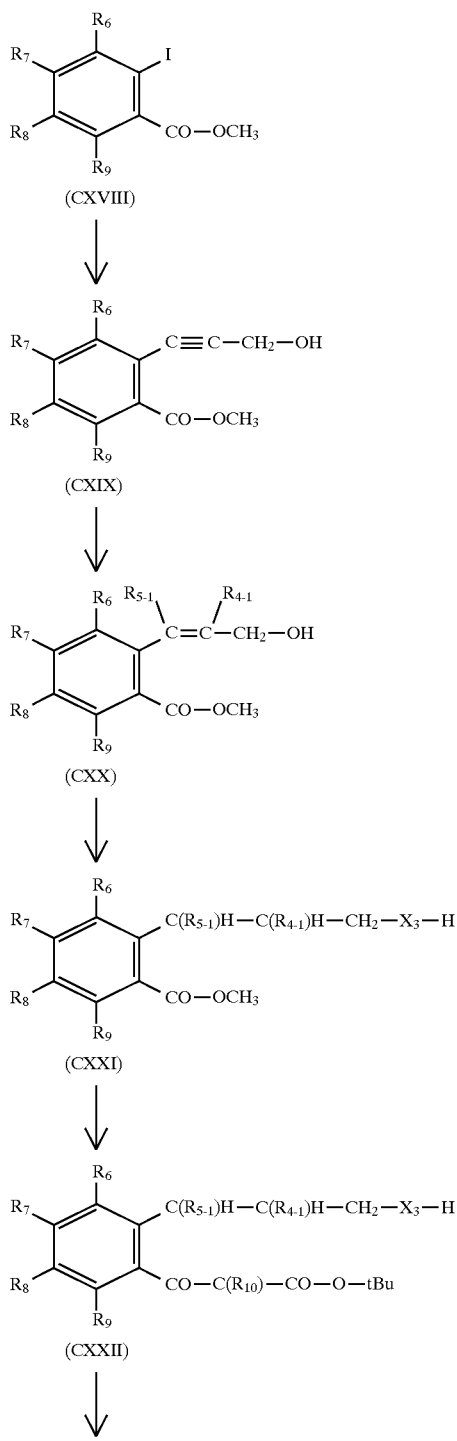
(CXVIII) → (CXIX) → (CXX) → (CXXI) → (CXXII)
-continued
CHART X
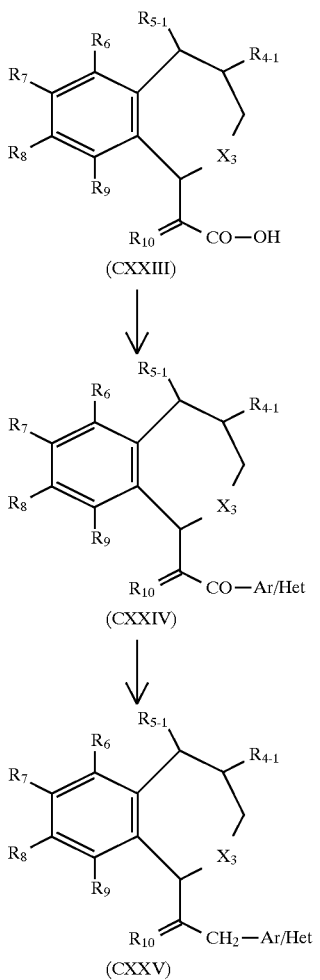
(CXXIII) → (CXXIV) → (CXXV)
CHART Y
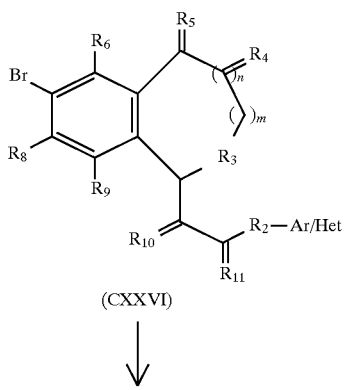
(CXXVI)

-continued

CHART Y (CXXVII)

CHART Z (CXXVIII)

↓

(CXXIX)

↓

(CXXX)

↓

(CXXXI)

CHART AA

HO—CH₂—C(CH₃)₂—CO—OH
(CXXXII)

↓

HO—CH₂—C(CH₃)₂—CO—OX₁
(CXXXIII)

↓

HO—CO—C(CH₃)₂—CO—OX₁
(CXXXIV)

We claim:
1. An aromatic bicyclic amines of formula (I)

(I)

where m is 0 or 1;
where n is 0 or 1;
where $R_1$ (1) is $\alpha$-$R_{1-1}$:$\beta$-$R_{1-2}$ where one of $R_{1-1}$ or $R_{1-2}$ is —H or $C_1$–$C_6$ alkyl and the other of $R_{1-1}$ or $R_{1-2}$ is —$CR_{10-1}R_{10-2}$—$CR_{11}$—$R_2$—Ar/Het
where $R_{10-1}$ and $R_{10-2}$ are the same or different and are —H or $C_1$–$C_6$ alkyl,
where $R_{11}$ is =O or $R_{11-1}$:$R_{11-2}$ where $R_{11-1}$ and $R_{11-2}$ are the same or different and are —H or $C_1$–$C_6$ alkyl;
where $R_2$ is selected from the group consisting of (XXV-A)

where $R_{2-1}$ and $R_{2-2}$ are —H or $C_1$–$C_6$ alkyl,
where $R_{2-3}$ is nitrogen (N—),
where q is 1,
where $R_3$ is —O— or —S—;
where $R_4$ is $\alpha$-$R_{4-1}$:$\beta$-$R_{4-2}$ where one of $R_{4-1}$ and $R_{4-2}$ is:
—H,
$C_1$–$C_6$ alkyl, and where the other of $R_{4-1}$ or $R_{4-2}$ is
—H,
$C_1$–$C_6$ alkyl,
—φ,
—OH,
—O—($C_1$–$C_3$)alkyl;
where $R_5$ is is $\alpha$-$R_{5-1}$:$\beta$-$R_{5-2}$ where one of $R_{5-1}$ and $R_{5-2}$ is:
—H,
$C_1$–$C_6$ alkyl, and where the other of $R_{5-1}$ or $R_{5-2}$ is
—H, $C_1$–$C_6$ alkyl,
—φ,
—OH,
—O—($C_1$–$C_3$)alkyl;
and when n is 1, one of $R_{4-1}$ or $R_{4-2}$ and one of $R_{5-1}$ or $R_{5-2}$ can be taken together with the carbon atoms to which they are attached to form a carbon ring of 5-, 6- or 7-members;
where $R_6$ is —H
—F,
—Cl,
—Br,
—I,
—CO—$NR_{6-1}R_{6-2}$ where $R_{6-1}$ and $R_{6-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{6-1}R_{6-2}$ where $R_{6-1}$ and $R_{6-2}$ are as defined above,
—$CF_3$,
—φ optionally substituted with one or two
—F,
—Cl,
—Br,
—I,
—CO—$NR_{6-1}R_{6-2}$ where $R_{6-1}$ and $R_{6-2}$ are as defined above,
—$NR_{6-1}R_{6-2}$ where $R_{6-1}$ and $R_{6-2}$ are as defined above,
—$NO_2$,
—C≡N,
—N($R_{6-1}$)—CO—$R_{6-2}$ where $R_{6-1}$ and $R_{6-2}$ are as defined above,
—O—$SO_2$—$CF_3$,
$C_1$–$C_4$ alkyl,
—Si($CH_3$)$_3$,
and where $R_6$ and one of $R_{5-1}$ or $R_{5-2}$ are taken together with the carbon atoms to which they are attached to form a carbon ring of 5-, 6- or 7-members;
where $R_7$ is —H
—F,
—Cl,
—Br,
—I,
—CO—$NR_{7-1}R_{7-2}$ where $R_{7-1}$ and $R_{7-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{7-1}R_{7-2}$ where $R_{7-1}$ and $R_{7-2}$ are as defined above,
—$CF_3$,
—φ optionally substituted with one or two
—F,
—Cl,
—Br,
—I,
—CO—$NR_{7-1}R_{7-2}$ where $R_{7-1}$ and $R_{7-2}$ are as defined above,
—$NR_{7-1}R_{7-2}$ where $R_{7-1}$ and $R_{7-2}$ are as defined above,
—$NO_2$,
—C≡N,
—N($R_{7-1}$)—CO—$R_{7-2}$ where $R_{7-1}$ and $R_{7-2}$ are as defined above,
—O—$SO_2$—$CF_3$,
$C_1$–$C_4$ alkyl,
—Si($CH_3$)$_3$;
where $R_8$ is —H
—F,
—Cl,
—Br,
—I,
—CO—$NR_{8-1}R_{8-2}$ where $R_{8-1}$ and $R_{8-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{8-1}R_{8-2}$ where $R_{8-1}$ and $R_{8-2}$ are as defined above,
—$CF_3$,
—φ optionally substituted with one or two
—F,
—Cl,
—Br,
—I,
—CO—$NR_{8-1}R_{8-2}$ where $R_{8-1}$ and $R_{8-2}$ are as defined above,
—$NR_{8-1}R_{8-2}$ where $R_{8-1}$ and $R_{8-2}$ are as defined above,
—$NO_2$,
—C≡N,
—N($R_{8-1}$)—CO—$R_{8-2}$ where $R_{8-1}$ and $R_{8-2}$ are as defined above,
—O—$SO_2$—$CF_3$,
$C_1$–$C_4$ alkyl,
—Si($CH_3$)$_3$;
where $R_9$ is —H
—F,
—Cl,
—Br,
—I,
—CO—$NR_{9-1}R_{9-2}$ where $R_{9-1}$ and $R_{9-2}$ are the same or different and are
—H,
$C_1$–$C_6$ alkyl,
$C_3$–$C_7$ cycloalkyl,
—$C_1$–$C_3$ alkyl-[$C_3$–$C_7$ cycloalkyl],
—SO—$NR_{9-1}R_{9-2}$ where $R_{9-1}$ and $R_{9-2}$ are as defined above,
—$CF_3$,
—φ optionally substituted with one or two
—F,
—Cl,
—Br,
—I,
—CO—$NR_{9-1}R_{9-2}$ where $R_{9-1}$ and $R_{9-2}$ are as defined above,
—$NR_{9-1}R_{9-2}$ where $R_{9-1}$ and $R_{9-2}$ are as defined above,
—$NO_2$,
—C≡N,
—N($R_{9-1}$)—CO—$R_{9-2}$ where $R_{9-1}$ and $R_{9-2}$ are as defined above,
—O—$SO_2$—$CF_3$,
$C_1$–$C_4$ alkyl,
—Si($CH_3$)$_3$;
with the proviso that not more than two of $R_6$, $R_7$, $R_8$ and $R_9$ are other than —H;
where Ar/Het is
—φ optionally substituted with one or two $R_{Ar/Het-1}$ where $R_{Ar/Het-1}$ is selected from the group consisting of
—F,
—Cl, —Br,
—I,
—CO—NR$_{Ar/Het-2}$R$_{Ar/Het-3}$ where R$_{Ar/Het-2}$ and R$_{Ar/Het-3}$ are the same or different and are:
—H,
C$_1$–C$_6$ alkyl,
C$_3$–C$_7$ cycloalkyl,
—C$_1$–C$_3$ alkyl-[C$_3$–C$_7$ cycloalkyl],
—SO$_2$—NR$_{Ar/Het-2}$R$_{Ar/Het-3}$ where R$_{Ar/Het-2}$ and R$_{Ar/Het-3}$ are as defined above,
—OH,
—SH,
C$_1$–C$_6$ alkyl,
C$_3$–C$_6$ cycloalkyl,
—O—R$_{Ar/Het-4}$ where R$_{Ar-Het-4}$ is
—C$_1$–C$_6$ alkyl,
—CH$_2$–(C$_3$–C$_6$ cycloalkyl),
—CH$_2$—φ,
—(C$_3$–C$_6$ cycloalkyl),
—SO$_2$—CF$_3$,
—CH$_2$—CF$_3$,
—CF$_3$,
—CO—R$_{Ar/Het-2}$ where R$_{Ar/Het-2}$ is as defined above,
—CO—OR$_{Ar/Het-2}$ where R$_{Ar/Het-2}$ is as defined above,
—C≡N,
—NO$_2$,
—NR$_{Ar/Het-2}$—CO—R$_{Ar/Het-3}$ where R$_{Ar/Het-2}$ and R$_{Ar/Het-3}$ are as defined above,
—S—(C$_1$–C$_6$ alkyl),
—NR$_{Ar/Het-2}$R$_{Ar/Het-3}$ where R$_{Ar/Het-2}$ and R$_{Ar/Het-3}$ are as defined above,
2-, 3- and 4-pyridinyl optionally substituted with one or two R$_{Ar/Het-1}$
where R$_{Ar/Het-1}$ is as defined above,
2-, 4-, 5- pyrimidinyl optionally substituted with one or two R$_{Ar/Het-1}$
where R$_{Ar/Het-1}$ is as defined above, and enantiomers and diastereomers thereof where such exist and pharmaceutically acceptable salts thereof.

2. Aromatic bicyclic amines of formula (I) according to claim 1 where n is 0 and m is 0.

3. Aromatic bicyclic amines of formula (I) according to claim 1 where n is 1 and m is 0.

4. Aromatic bicyclic amines of formula (I) according to claim 1 where n is 1 and m is 1.

5. Aromatic bicyclic amines of formula (I) according to claim 1 where R$_1$ (1) is R$_{1-1}$:R$_{1-2}$ where one of R$_{1-1}$ or R$_{1-2}$ is —H and the other of R$_{1-1}$ or R$_{1-2}$ is —CR$_{10-1}$R$_{10-2}$—CR$_{11}$—R$_2$—Ar/Het.

6. Aromatic bicyclic amines of formula (I) according to claim 1 where R$_2$ is 1,4-piperazinyl.

7. Aromatic bicyclic amines of formula (I) according to claim 1 where R$_3$ is —O—.

8. Aromatic bicyclic amines of formula (I) according to claim 1 where R$_4$ is α-R$_{4-1}$:β-R$_{4-2}$ where R$_{4-1}$ and R$_{4-2}$ are —H or C$_1$ alkyl.

9. Aromatic bicyclic amines of formula (I) according to claim 1 where R$_5$ is α-R$_{5-1}$:β-R$_{5-2}$ where R$_{5-1}$ and R$_{5-2}$ are —H or C$_1$ alkyl.

10. Aromatic bicyclic amines of formula (I) according to claim 1 where R$_6$ is —H, —Br or —CO—NH$_2$.

11. Aromatic bicyclic amines of formula (I) according to claim 1 where R$_7$ is —H, —F, —Cl, —Br or —CO—NH$_2$.

12. Aromatic bicyclic amines of formula (I) according to claim 1 where R$_8$ is —H, —Br or C$_1$ alkyl.

13. Aromatic bicyclic amines of formula (I) according to claim 1 where R$_9$ is —H.

14. Aromatic bicyclic amines of formula (I) according to claim 1 where R$_{10-1}$ and R$_{10-2}$ are —H:—H.

15. Aromatic bicyclic amines of formula (I) according to claim 1 where R$_{11-1}$ and R$_{11-12}$ are —H or C$_1$ alkyl.

16. Aromatic bicyclic amines of formula (I) according to claim 1 where Ar/Het is —φ substituted with one R$_{Ar/Het-1}$ where R$_{Ar/Het-1}$ is selected from the group consisting of —CO—NH$_2$, —SO$_2$—NH$_2$, C$_1$ alkoxy and —F.

17. Aromatic bicyclic amines of formula (I) according to claim 1 where the aromatic bicyclic amine is selected from the group consisting of:
1-(2-chlorophenyl)-4-[2-(isochroman-1-yl)ethyl]piperazine,
1-(4-fluorophenyl)-4-[2-(isochroman-1-yl)ethyl]piperazine,
1-[2-(isochroman-1-yl)ethyl]-4-phenylpiperazine,
1-[2-(isochroman-1-yl)ethyl]-4-(2-pyridyl)piperazine,
1-(4-chlorophenyl)-4-[2-(isochroman-1-yl)ethyl]piperazine,
1-[2-(isochroman-1-yl)ethyl]-4-(4-methoxyphenyl)piperazine,
1-[2-(isochroman-1-yl)ethyl]-4-(2-methoxyphenyl)piperazine,
1-(4-fluorophenyl)-4-[2-(4,4-dimethylisochroman-1-yl)ethyl]piperazine,
1-(4-methoxyphenyl)-4-[2-(4,4-dimethylisochroman-1-yl)ethyl]piperazine,
1-(2-fluorophenyl)-4-[2-(isochroman-1-yl)ethyl]piperazine,
1-[3-(trifluoromethyl)phenyl]-4-[2-(isochroman-1-yl)ethyl]piperazine,
1-[2-(isochroman-1-yl)ethyl]-4-(2-methylphenyl)piperazine,
1-(3-chlorophenyl)-4-[2-(isochroman-1-yl)ethyl]piperazine,
1-[2-(isochroman-1-yl)ethyl]-4-(4-methylphenyl)piperazine,
1-[2-(isochroman-1-yl)ethyl]-4-(3-methoxyphenyl)piperazine,
1-(3,4-dichlorophenyl)-4-[2-(isochroman-1-yl)ethyl]piperazine,
1-[2-(6-fluoroisochroman-1-yl)ethyl]-4-(4-methoxyphenyl)piperazine,
1-[2-(6-Fluoroisochroman-1-yl)ethyl]-4-(4-fluorophenyl)piperazine,
4-[2-(6-bromoisochroman-1-yl)ethyl]-4-(4-methoxyphenyl)piperazine,
1-[2-(6-chloroisochroman-1-yl)ethyl]-4-(4-methoxyphenyl)piperazine,
1-[2-(6-chloroisochroman-1-yl)ethyl]-4-(4-fluorophenyl)piperazine,
1-(4-methoxyphenyl)-4-[2-(4-methylisochroman-1-yl)ethyl]piperazine,
1-(4-methoxyphenyl)-4-[2-(4-methylisochroman-1-yl)ethyl]piperazine,
1-(4-methoxyphenyl)-4-[2-(4-methylisochroman-1-yl)ethyl]piperazine,
4'-[4-[2-(isochroman-1-yl)ethyl]piperazin-1-yl]benzophenone,
1-(2-cyanophenyl)-4-[2-(isochroman-1-yl)ethyl]piperazine,
1-[2-(isochroman-1-yl)ethyl]-4-(2-pyrimidyl)piperazine,
1-(4-methoxyphenyl)-4-[2-(7-methylisochroman-1-yl)ethyl]piperazine,
1-(4-methoxyphenyl)-4-[2-(6-methylisochroman-1-yl)ethyl]piperazine,
1-[2-(6-bromoisochroman-1-yl)ethyl]-4-(2-bromo-4-methoxyphenyl)piperazine,
1-[2-(isochroman-1-yl)-2-methylpropyl]-4-(4-methoxyphenyl)piperazine,
1-(4-hydroxyphenyl)-4-[2-(isochroman-1-yl)ethyl]piperazine,
1-[2-(isochroman-1-yl)ethyl]-4-(4-pyridyl)piperazine,
1-(4-ethoxyphenyl)-4-[2-(isochroman-1-yl)ethyl]piperazine,
1-[2-[(−)-isochroman-1-yl]-1,1-dimethylethyl]-4-(methoxyphenyl)piperazine, 1-[2-(isochroman-1-yl)-1,1-dimethylethyl]-4-(methoxyphenyl)piperazine,
4-[4-[2-(isochroman-1-yl)ethyl]piperazin-1-yl]benzamide,
(−)-4-[4-[2-(isochroman-1-yl)ethyl]piperazin-1-yl]benzamide,
(−)-4-[4-[2-(isochroman-1-yl)ethyl]piperazin-1-yl]benzenesulfonamide,
(−)-1-[2-(isochroman-1-yl)ethyl]-4-(4-isopropoxyphenyl)piperazine,
(±)-1-[2-(isochroman-1-yl)ethyl]-4-(4-isopropoxyphenyl)piperazine,
4-[2-(phthalan-1-yl)ethyl]-1-(4-methoxyphenyl)piperazine,
4-[2-(1-methoxyphthalan-3-yl)ethyl]-1-(4-methoxyphenyl)piperazine,
1-(4-fluorophenyl)-4-[2-(4-methyl-7-phenylisochroman-1-yl)-ethyl]piperazine,
1-(4-methoxyphenyl)-4-[2-(4-methyl-7-phenylisochroman-1-yl)ethyl]-piperazine,
cis-1-(4-fluorophenyl)-4-[2-(3-methylisochroman-1-yl)-ethyl]piperazine,
trans-1-(4-fluorophenyl)-4-[2-(3-methylisochroman-1-yl)-ethyl]piperazine,
1-(4-fluorophenyl)-4-[2-(4-phenylisochroman-1-yl)-ethyl]piperazine,
cis-1-(4-fluorophenyl)-4-[2-(1,2,3,4,6,10b-hexahydro-4aH-benzo[c]chromen-6-yl)ethyl]piperazine,
trans-1-(4-fluorophenyl)-4-[2-(1,2,3,4,6,10b-hexahydro-4aH-benzo[c]chromen-6-yl)ethyl]piperazine,
1-(4-fluorophenyl)-4-[2-(3,7,8,9,10,10a-hexahydro-1H-2-oxacyclohepta[d,e]-naphthalen-3-yl)ethyl]piperazine,
1-(4-methoxyphenyl)-4-[2-(3,7,8,9,10,10a-hexahydro-1H-2-oxacyclohepta[de]-naphthalen-3-yl)ethyl]piperazine,
1-(4-methoxyphenyl)-4-[2-(5-bromoisochroman-1-yl)-ethyl]piperazine,
1-(4-methoxyphenyl)-4-[2-(7-bromoisochroman-1-yl)ethyl]piperazine,
1-(4-methoxyphenyl)-4-[2-(5-aminocarbonylisochroman-1-yl)-ethyl]piperazine,
1-(4-methoxyphenyl)-4-[2-(6-aminocarbonylisochroman-1-yl)-ethyl]piperazine,
1-(4-methoxyphenyl)-4-[2-(6-trimethylsilylisochroman-1-yl)-ethyl]piperazine,
1-(4-methoxyphenyl)-4-[2-(6-cyanoisochroman-1-yl)-ethyl]piperazine,
1-(4-methoxyphenyl)-4-[2-(7-aminocarbonylisochroman-1-yl)-ethyl]piperazine,
1-(4-methoxyphenyl)-4-[2-(1,3,4,5-tetrahydrobenzo[c]oxepin-1-yl)-ethyl]-piperazine,
1-(4-fluorophenyl)-4-[2-(1,3,4,5-tetrahydrobenzo[c]oxepin-1-yl)-ethyl]-piperazine,
(−)-1-[2-(isochroman-1-yl)ethyl]-4-(4-methoxyphenyl)piperazine,
(+)-1-[2-(isochroman-1-yl)ethyl]-4-(4-methoxyphenyl)piperazine,
1-(3,4-dichlorophenyl)-4-[2-(6-bromoisochroman-1-yl)ethyl]piperazine,
1-(4-fluorophenyl)-4-[2-(6-bromoisochroman-1-yl)ethyl]piperazine,
1-(2-ethoxyphenyl)-4-[2-(6-bromoisochroman-1-yl)ethyl]piperazine,
1-(4-methylphenyl)-4-[2-(6-bromoisochroman-1-yl)ethyl]piperazine,
1-(4-chlorophenyl)-4-[2-(6-bromoisochroman-1-yl)ethyl]piperazine,
1-(4-benzyloxyphenyl)-4-[2-(6-bromoisochroman-1-yl)ethyl]piperazine,
1-(4-butyloxyphenyl)-4-[2-(6-bromoisochroman-1-yl)ethyl]piperazine,
1-(3,4-dichlorophenyl)-4-[2-(6-aminocarbonylisochroman-1-yl)ethyl]piperazine,
1-(4-fluorophenyl)-4-[2-(6-aminocarbonylisochroman-1-yl)ethyl]piperazine,
1-(2-ethoxyphenyl)-4-[2-(6-aminocarbonylisochroman-1-yl)ethyl]piperazine,
1-(4-methylphenyl)-4-[2-(6-aminocarbonylisochroman-1-yl)ethyl]piperazine,
1-(4-chlorophenyl)-4-[2-(6-aminocarbonylisochroman-1-yl)ethyl]piperazine,
1-(4-benzyloxyphenyl)-4-[2-(6-aminocarbonylisochroman-1-yl)ethyl]piperazine,
1-(4-butyloxyphenyl)-4-[2-(6-aminocarbonylisochroman-1-yl)ethyl]piperazine,
1-(4-methoxyphenyl)-4-[2-(6-methylaminocarbonylisochroman-1-yl)ethyl]piperazine,
1-(4-methoxyphenyl)-4-[2-(6-dimethylaminocarbonylisochroman-1-yl)ethyl]piperazine,
(S)-(−)-3-bromo-4-[4-[2-(6-bromoisochroman-1-yl)ethyl]piperazin-1-yl]-benzenesulfonamide,
N-acetyl-(S)-(−)-4-[4-[2-(isochroman-1-yl)ethyl]piperazin-1-yl]benzenesulfonamide,
(S)-(−)-4-[4-[2-(isochroman-1-yl)ethyl]-cis-3,5-dimethylpiperazin-1-yl]benzamide,
(S)-(−)-4-[4-[2-(isochroman-1-yl)ethyl]-cis-3,5-dimethylpiperazin-1-yl]benzenesulfonamide,
(±)-4-[4-[2-(6-fluoroisochroman-1-yl)ethyl]piperazin-1-yl]benzenesulfonamide,
(±)-4-[4-[2-(7-methylisochroman-1-yl)ethyl]piperazin-1-yl]benzenesulfonamide,
(±)-4-[4-[2-(6-methylisochroman-1-yl)ethyl]piperazin-1-yl]benzenesulfonamide,
(R)-(+)-2-[4-[2-(isochroman-1-yl)ethyl]piperazin-1-yl]benzamide,
(R)-(+)-4-[4-[2-(isochroman-1-yl)ethyl]piperazin-1-yl]benzenesulfonamide,
4-[4-[2-(−)-isochroman-1-yl)ethyl]-3-(RS)-3-methylpiperazin-1-yl]benzenesulfonamide,
N-methyl-(S)-(−)-4-[4-[2-(isochroman-1-yl)ethyl]piperazin-1-yl]benzenesulfonamide,
(+)-1-(4-fluorophenyl)-4-[2-(isochroman-1-yl)ethyl]piperazine.

18. An aromatic bicyclic amine according to claim 17 which is:
1-(4-fluorophenyl)-4-[2-(isochroman-1-yl)ethyl]piperazine,
1-[2-(isochroman-1-yl)ethyl]-4-phenylpiperazine,
1-[2-(isochroman-1-yl)ethyl]-4-(4-methoxyphenyl)piperazine,
(−)-4-[4-[2-(isochroman-1-yl)ethyl]piperazin-1-yl]benzamide,
(−)-4-[4-[2-(isochroman-1-yl)ethyl]piperazin-1-yl]benzenesulfonamide,
(−)-1-[2-(isochroman-1-yl)ethyl]-4-(4-methoxyphenyl)piperazine.

19. An aromatic bicyclic amine according to claim 18 which is
(−)-4-[4-[2-(isochroman-1-yl)ethyl]piperazin-1-yl]benzenesulfonamide.

20. An aromatic bicyclic amine according to claim 16 which is
(−)-4-[4-[2-(isochroman-1-yl)ethyl]piperazin-1-yl]benzenesulfonamide methanesulfonate.

21. (−)-4-[4-[2-(Isochroman-1-yl)ethyl]piperazin-1-yl]benzenesulfonamide.

22. (−)-4-[4-[2-(Isochroman-1-yl)ethyl]piperazin-1-yl]benzenesulfonamide methanesulfonate.

* * * * *